US012661352B2

(12) United States Patent (10) Patent No.: US 12,661,352 B2
Bossard et al. (45) Date of Patent: Jun. 23, 2026

(54) COMBINATION THERAPY WITH CLK/DYRK INHIBITORS AND BCL2 INHIBITORS TO TREAT LEUKEMIA

(71) Applicants: Memorial Sloan-Kettering Cancer Center, New York, NY (US); Memorial Hospital for Cancer and Allied Diseases, New York, NY (US); Sloan-Kettering Institute for Cancer Research, New York, NY (US); Biosplice Therapeutics, Inc., San Diego, CA (US)

(72) Inventors: Carine Bossard, San Diego, CA (US); Omar Abdel-Wahab, New York, NY (US)

(73) Assignees: Memorial Shan-Ketering Cancer Center, New York, NY (US); Memorial Hospital for Cancer and Allied Diseases, New York, NY (US); Sloan-Kettering Institute for Cancer Research, New York, NY (US); Biosplice Therapeutics, Inc., San Diego, CA (US)

( * ) Notice: Subject to any disclaimer, the term of this patent is extended or adjusted under 35 U.S.C. 154(b) by 0 days.

(21) Appl. No.: 19/299,240

(22) Filed: Aug. 13, 2025

(65) Prior Publication Data

US 2025/0375442 A1     Dec. 11, 2025

Related U.S. Application Data

(63) Continuation of application No. PCT/US2023/085214, filed on Dec. 20, 2023.

(60) Provisional application No. 63/589,873, filed on Oct. 12, 2023.

(51) Int. Cl.
| | |
|---|---|
| *A61K 31/496* | (2006.01) |
| *A61K 31/404* | (2006.01) |
| *A61K 31/635* | (2006.01) |
| *A61P 35/02* | (2006.01) |

(52) U.S. Cl.
CPC .......... *A61K 31/496* (2013.01); *A61K 31/404* (2013.01); *A61K 31/635* (2013.01); *A61P 35/02* (2018.01)

(58) Field of Classification Search
CPC .. A61K 31/496; A61K 31/404; A61K 31/635; A61P 35/02
See application file for complete search history.

(56) References Cited

U.S. PATENT DOCUMENTS

2022/0305134 A1     9/2022  Boitano et al.

FOREIGN PATENT DOCUMENTS

| | | |
|---|---|---|
| CN | 113046441 A | 6/2021 |
| WO | WO-2022/104061 A1 | 5/2022 |
| WO | WO-2022/153161 A1 | 7/2022 |

OTHER PUBLICATIONS

Chung, "SM09419, a Novel, Small-Molecule CDC-like Kinase (CLK) Inhibitor, Demonstrates Strong Inhibition of the Wnt Signaling Pathway and Antitumor Effects in Tumor Protein p53 (TP53)-Mutant Acute Myeloid Leukemia Models", Blood (2019) 134 (Supplement_1): 3913.*
Murai, PLoS One, Oct. 16, 2020;15(10), pp. 1-15.*
International Search Report and Written Opinion for PCT Appl. No. PCT/US2023/085214 mailed Apr. 11, 2024, (12 pages).
Wang et al., Sequestration of RBM10 in Nuclear Bodies: Targeting Sequences and Biological Significance, Int J Mol Sci, Sep. 29, 2021, vol. 33, 10526, pp. 1-14; [retrieved on Apr. 3, 2024]. Retrieved from the internet: <URL: https:// www.mdpi.com/1422-0067/22/19/ 10526>. entire document.

* cited by examiner

*Primary Examiner* — Sahar Javanmard
(74) *Attorney, Agent, or Firm* — Foley & Lardner LLP

(57) ABSTRACT

The present disclosure provides methods for treating leukemia (e.g., AML) using a CLK/DYRK inhibitor and a B-cell lymphoma 2 (BCL2) inhibitor (e.g., venetoclax). Kits for use in practicing the methods are also provided.

19 Claims, 65 Drawing Sheets

Specification includes a Sequence Listing.

FIG. 2G
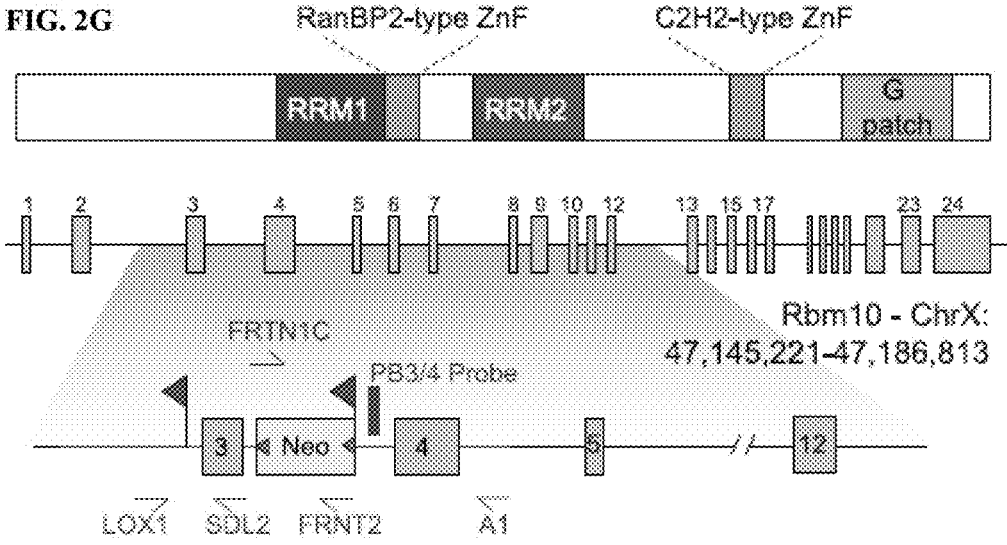
Rbm10 - ChrX: 47,145,221–47,186,813
FIG. 2H
FIG. 2I
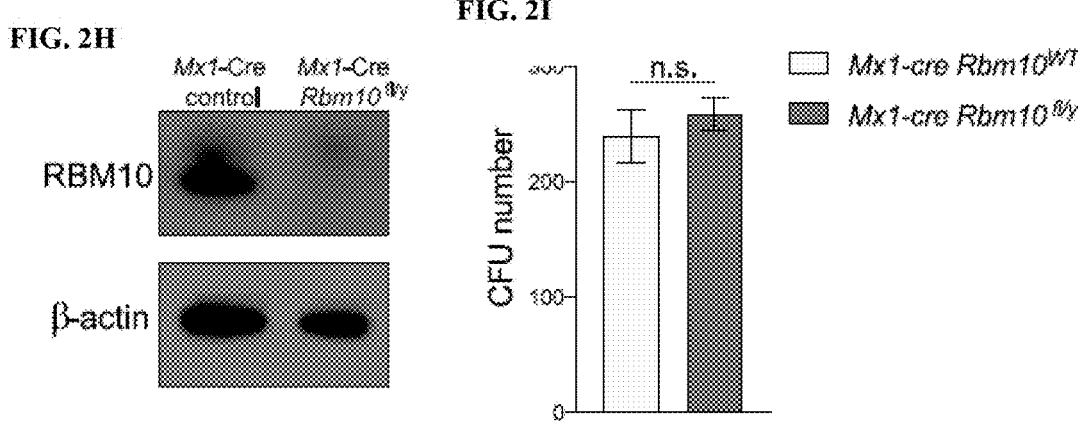

FIG. 3G
FIG. 3H
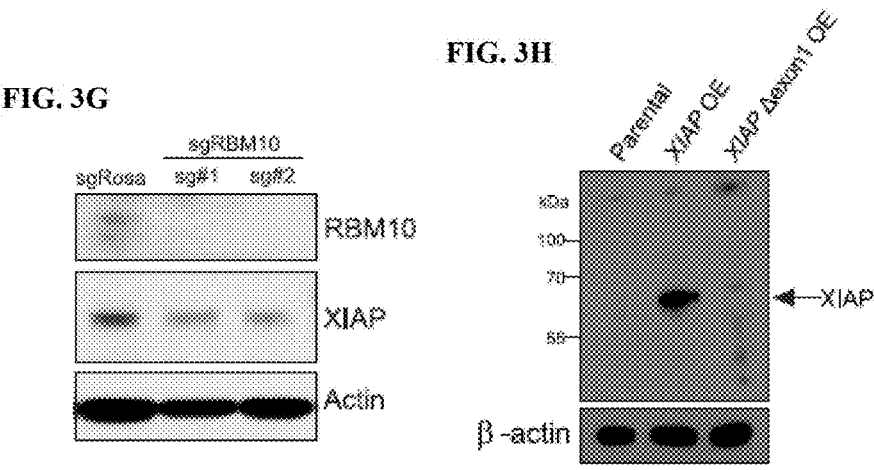
FIG. 3I
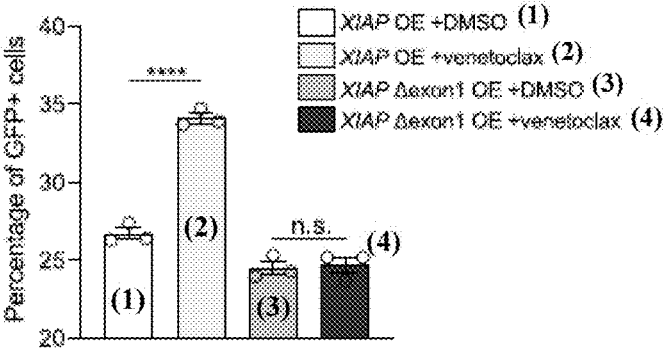
FIG. 3J
FIG. 3K
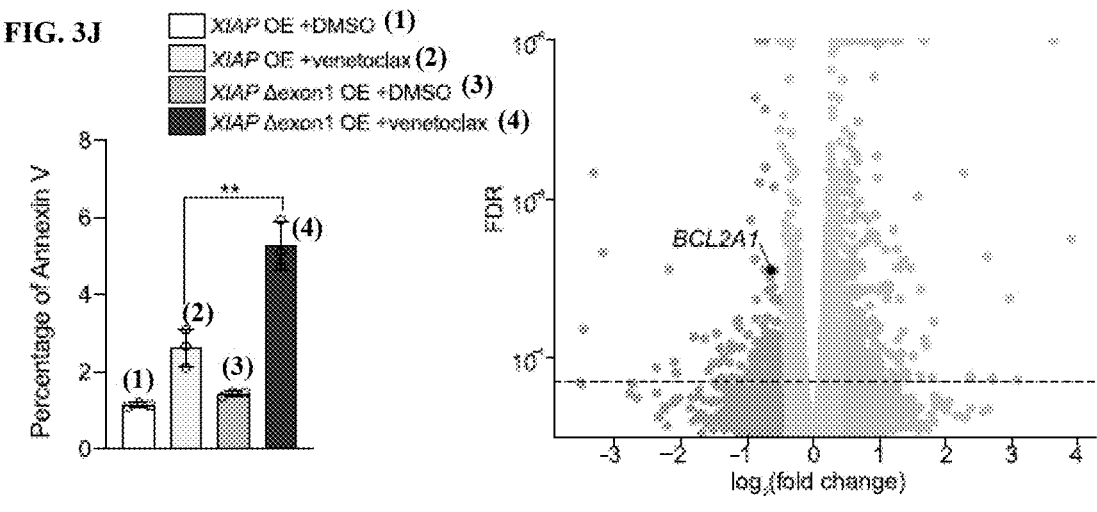

SM09419

IC$_{50}$ 0.001- 0.01uM

IC$_{50}$ 0.01- 0.1uM

| Kinase | IC$_{50}$ (nM) |
|--------|-----------|
| CLK1 | 20 |
| CLK2 | 5 |
| CLK3 | 19 |
| CLK4 | 2 |
| DYRK1A | 1 |
| DYRK1B | 4 |
| DYRK2 | 3 |
| DYRK3 | 11 |
| DYRK4 | 18 |

IC$_{50}$ SM09419 Cellular Target Engagement (nM)

| CLK1 | CLK2 | CLK3 | CLK4 | DYRK1A | DYRK1B | DYRK2 |
|------|------|------|------|--------|--------|-------|
| 1 | 6 | 42 | 1 | 16 | 77 | 62 |

(1) sgRosa (DMSO) vs. sgRBM10 (Venetoclax)

(2) DMSO vs. SM09419

(3) DMSO vs. SM09419 + Venetoclax

FIG. 6C

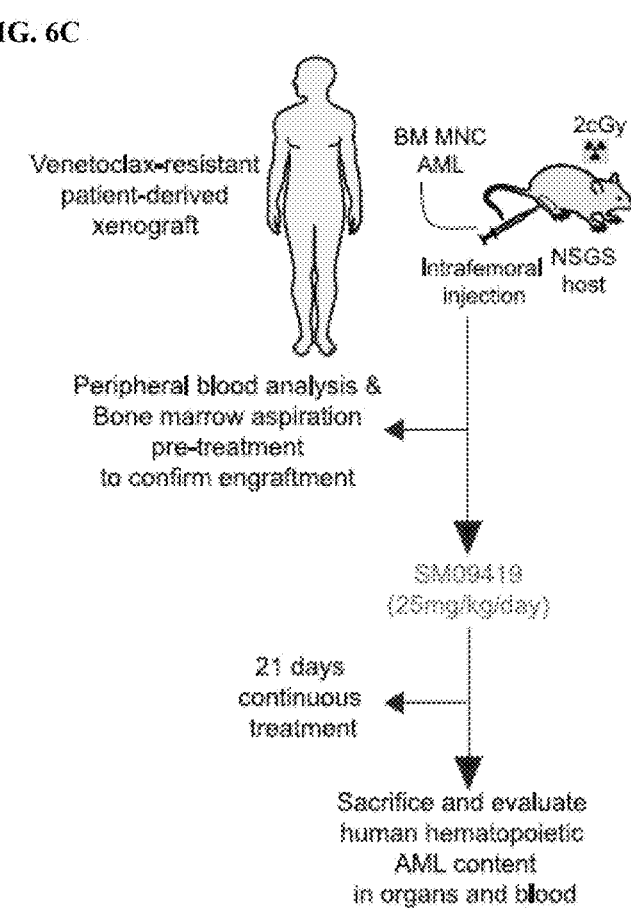

Venetoclax-resistant patient-derived xenograft

BM MNC AML

2cGy

Intrafemoral injection

NSGS host

Peripheral blood analysis & Bone marrow aspiration pre-treatment to confirm engraftment SM09419 (25mg/kg/day)

21 days continuous treatment

Sacrifice and evaluate human hematopoietic AML content in organs and blood

FIG. 6D

| Patient | Prior therapies | Reponse | Start of venetoclax | End of venetoclax | Sample date | Genetic alterations |
|---------|-----------------|---------|---------------------|-------------------|-------------|---------------------|
| 1 | VEN+Azacytidine | Primary refractory | 01/18/2019 | 02/27/2019 | 06/05/2020 | RUNX1, PTPN11, FLT3, SF3B1, STAG2 |
| 2 | VEN+Low-dose Cytarabine | Primary refractory | 01/03/2017 | 04/06/2017 | 04/10/2017 | RUNX1, DNMT3A, IDH2 |

FIG. 8G
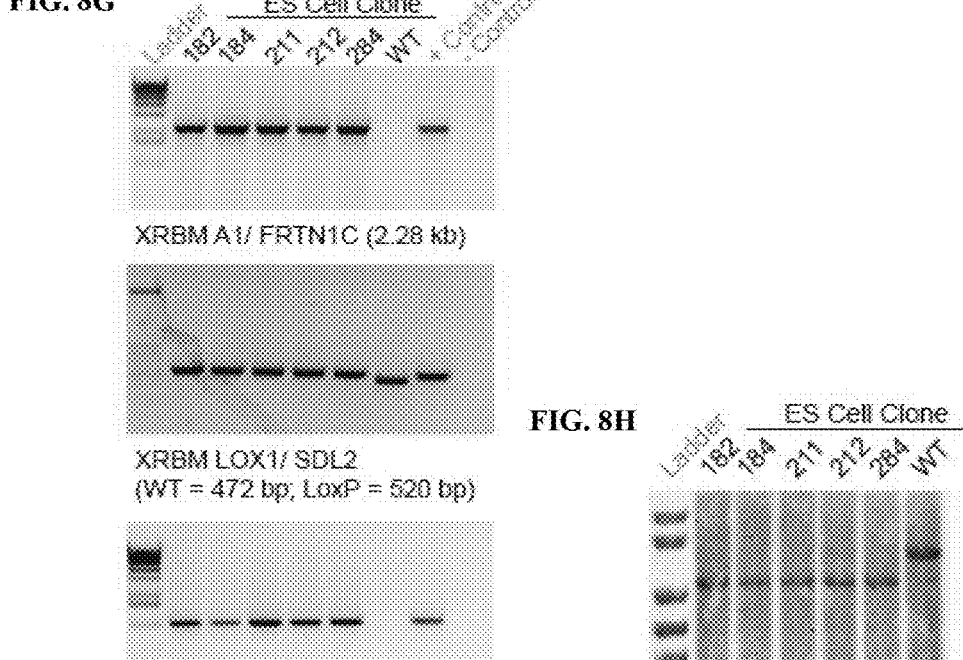
XRBM A1/ FRTN1C (2.28 kb)
XRBM LOX1/ SDL2
(WT = 472 bp; LoxP = 520 bp)
XRBM LOX1/ FRTN2C
(1.05 kb)
FIG. 8H
FIG. 8I
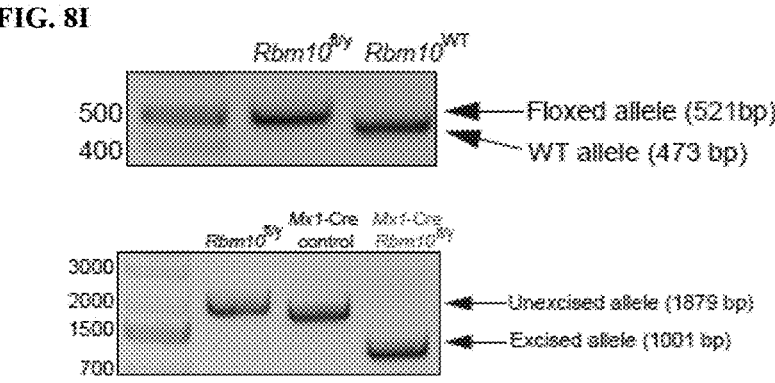

FIG. 10A
Top 10 Codependencies for
DYRK1A (DepMap)
| Gene | Correlations |
|------|--------------|
| AMBRA1 | 0.32 |
| EP300 | 0.26 |
| MNT | 0.26 |
| CLDN14 | 0.24 |
| CEP350 | 0.22 |
| BCL2 | 0.22 |
| PAPOLA | 0.21 |
| PDXK | 0.21 |
| PCBP3 | 0.21 |
| CDKN1A | 0.21 |
FIG. 10B
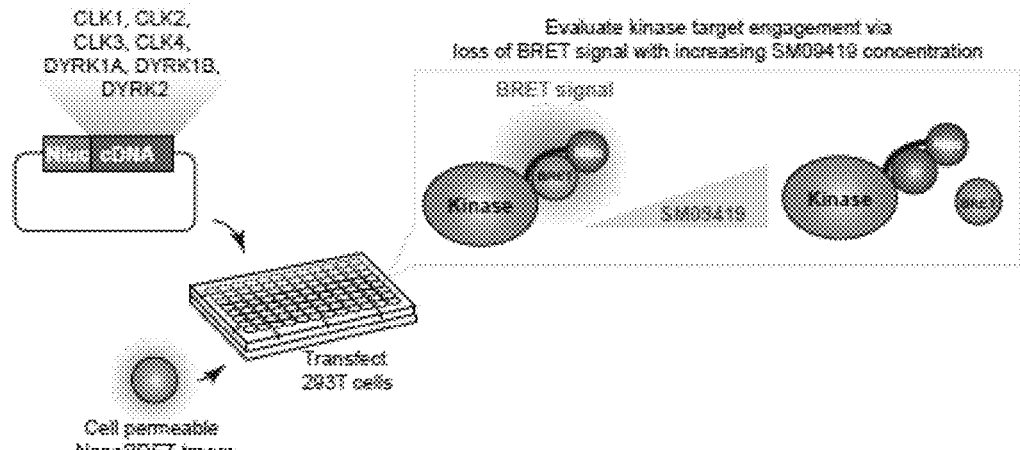
FIG. 10C
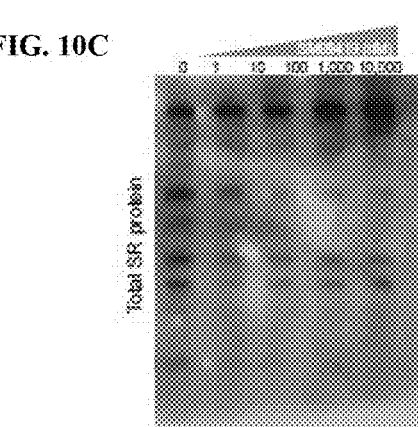

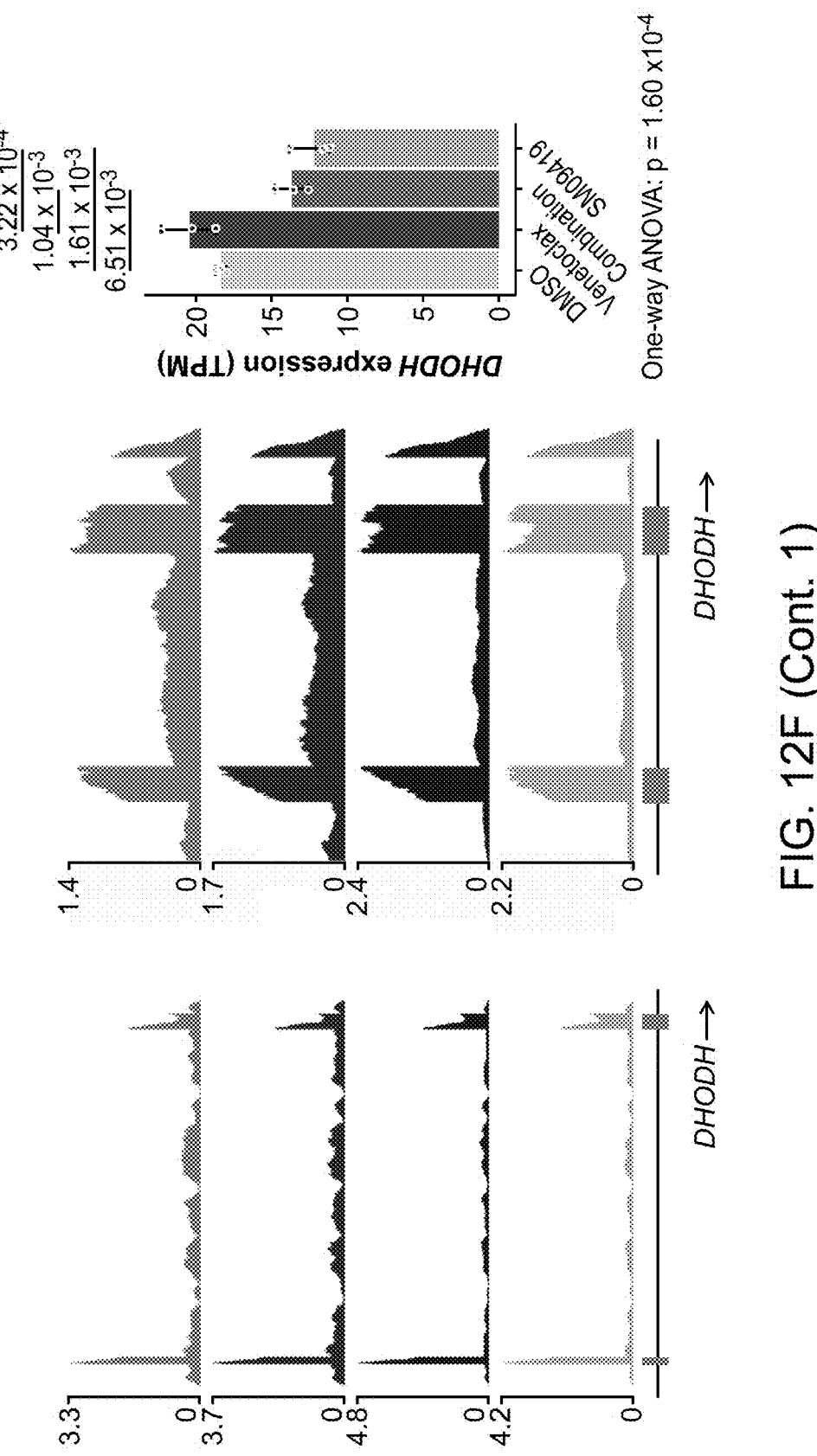
FIG. 12F (Cont. 1)

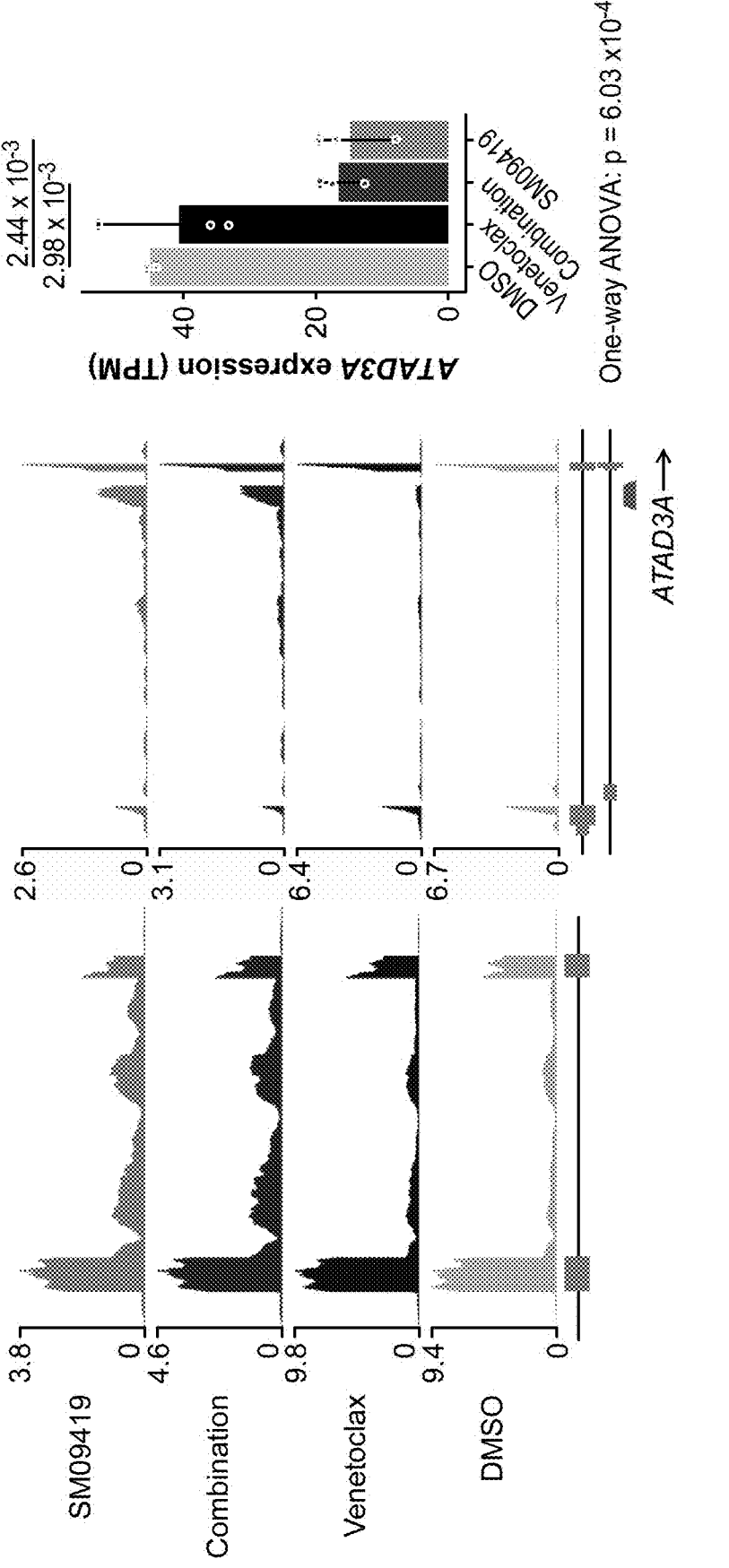
FIG. 12F (Cont. 2)

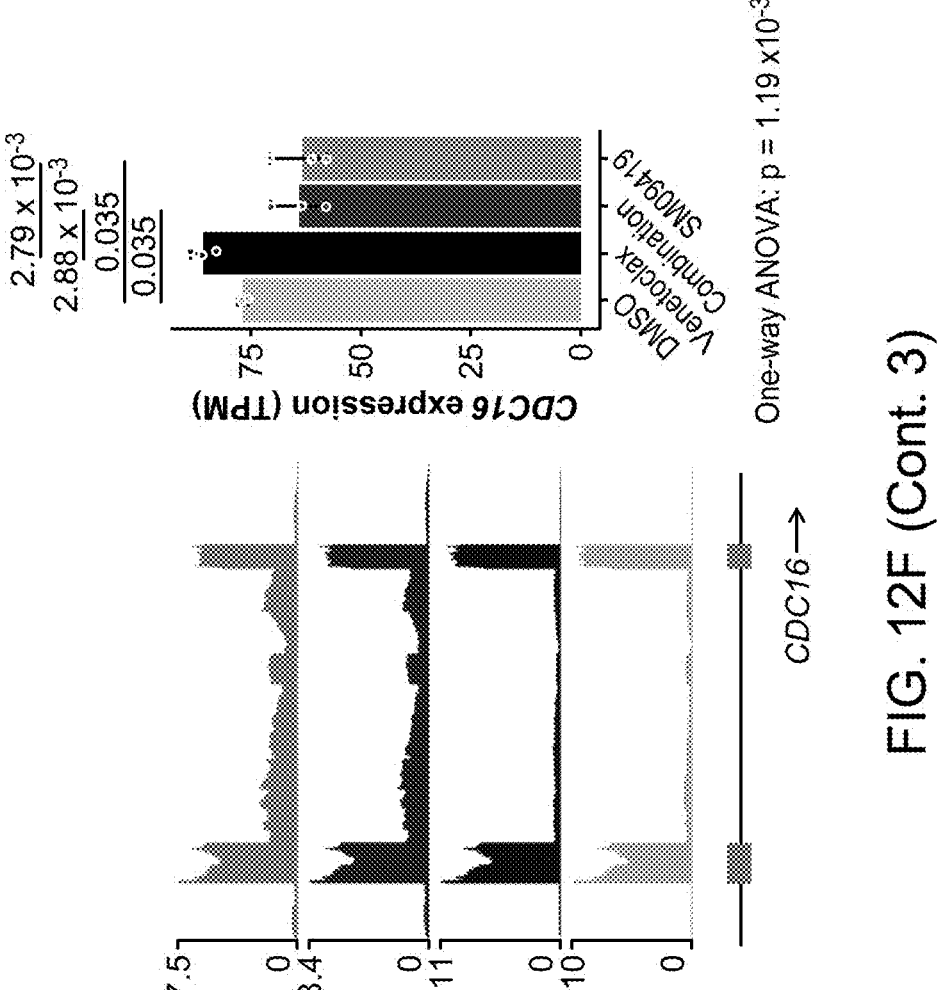
FIG. 12F (Cont. 3)

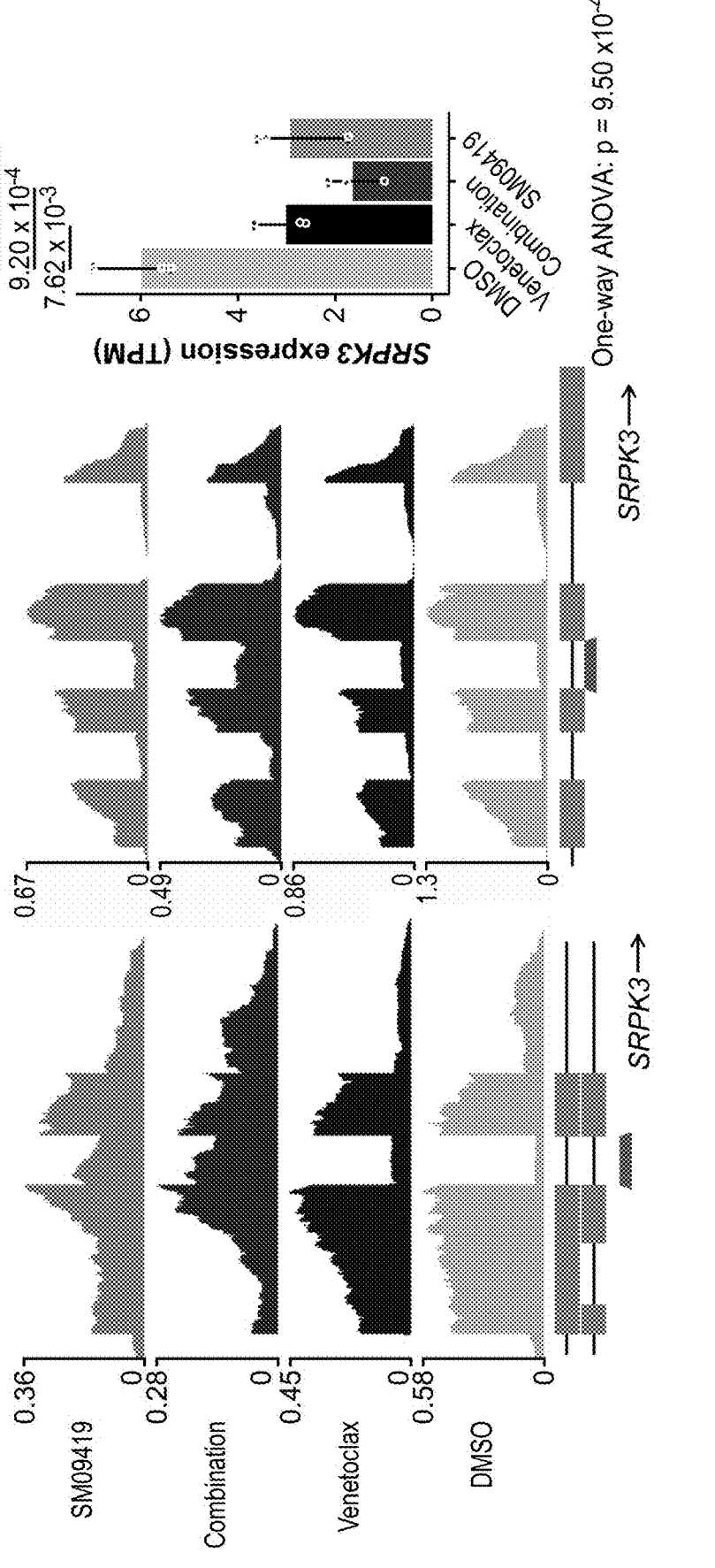
FIG. 12F (Cont. 4)

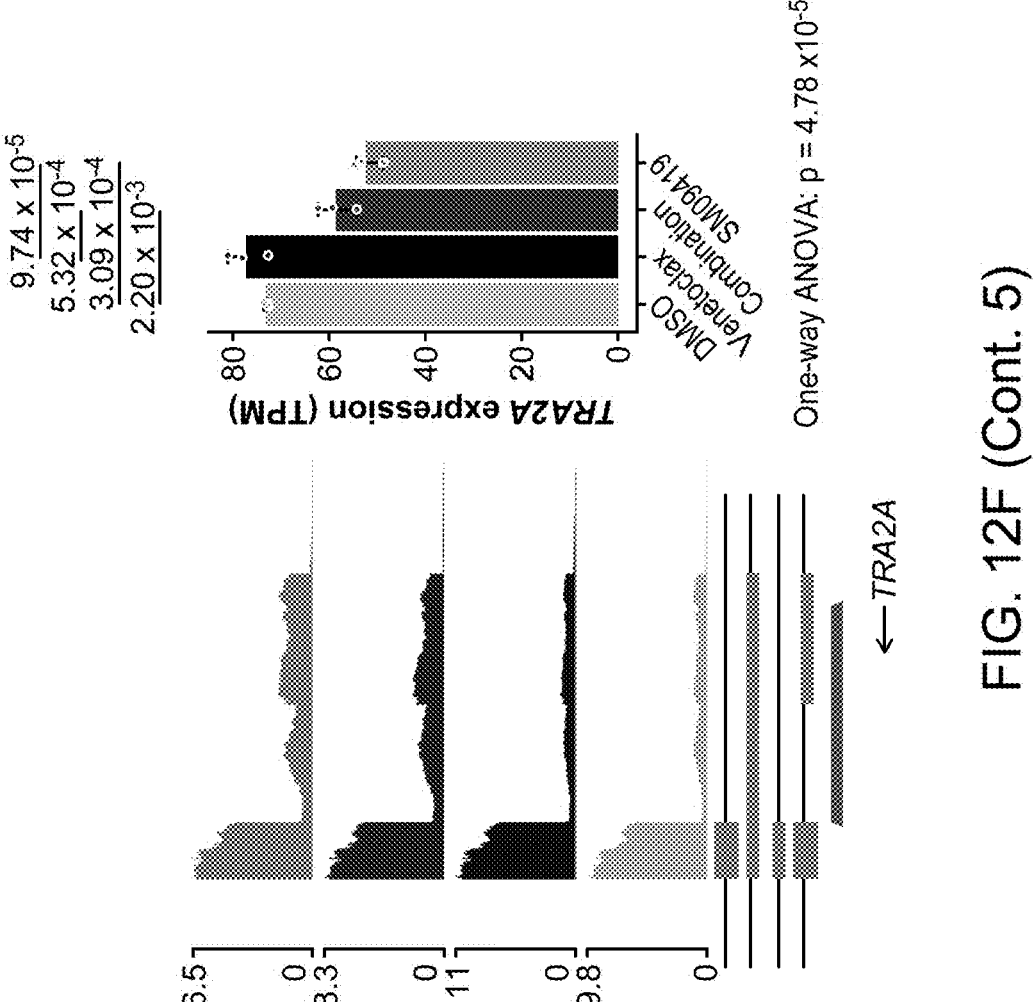
FIG. 12F (Cont. 5)

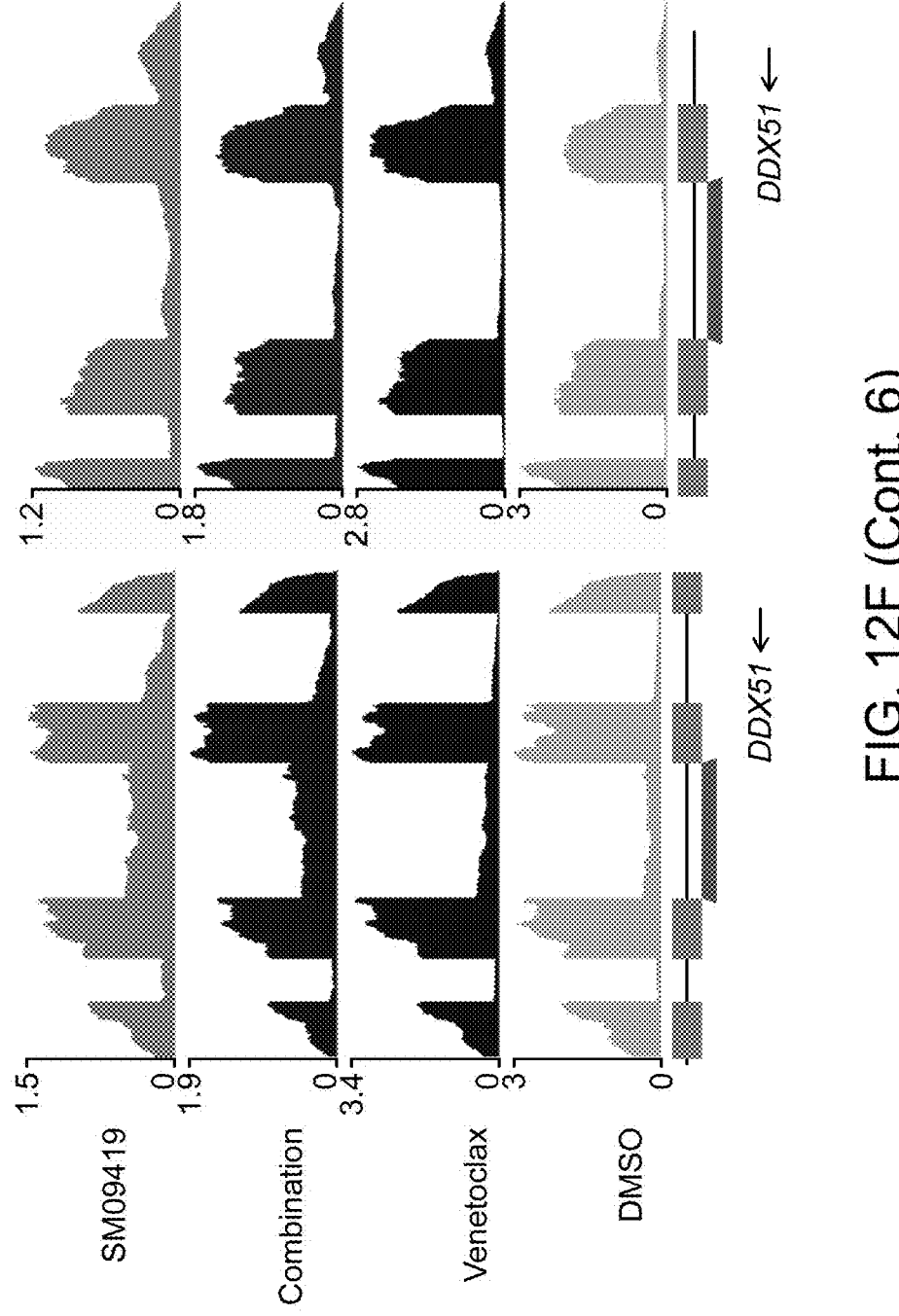
FIG. 12F (Cont. 6)

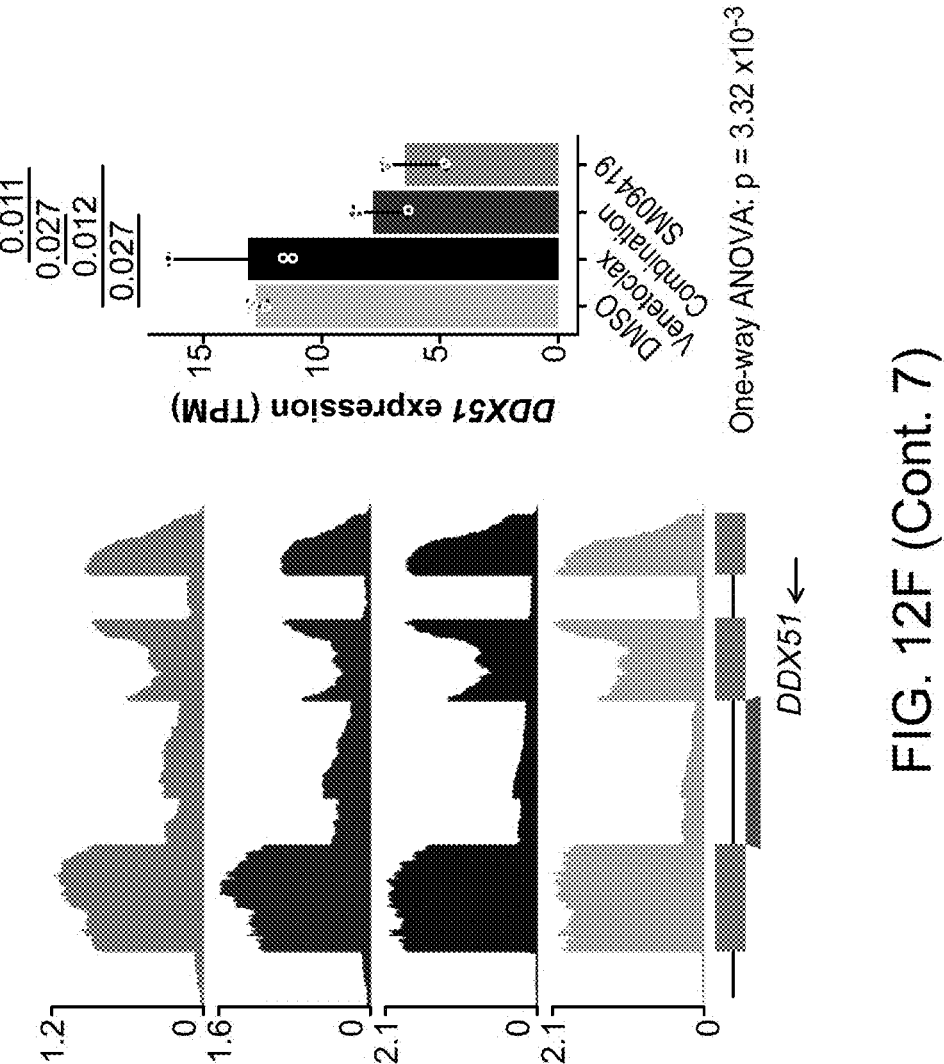
FIG. 12F (Cont. 7)

SEQUENCE LISTING

Sequence total quantity: 5
SEQ ID NO: 1              moltype = DNA   length = 3397
FEATURE                   Location/Qualifiers
source                    1..3397
                          mol_type = genomic DNA
                          organism = Homo sapiens
SEQUENCE: 1
agtaggtgga tggtggtcgg agcgccgact cccttctcgt cgtcgccatt ttgagctggt   60
gactgtggcc ggctgggagt aggcggcagt gagtttccct gggagggcag cgcgcttggc  120
gcttctcccc tcccccgat ctgcctccag tctcggactt ggttgttgcg cgctccggct  180
ccggctgagc tgggagagtt ggaggaggtg gcggcgggca gaggtgatgt ctgggagccc  240
ttccttgaca gcccgggccg agaagagtcc ctgcaggaag catcacccag gctggcagat  300
catggtagca gcagcggggg tggctgggaa gtgaaacgga gccagcggct gaggaggggc  360
cccagcagcc cccgaaggcc ctatcaggac atggagtatg aaagacgtgg tggtcgtggt  420
gacaggactg gccgctatgg agccactgac cgctcgcagg atgatggtgg ggagaaccgc  480
agccgagacc acgactaccg ggacatggac taccgttcat atcctcgcga gtatggcagc  540
caggagggca agcatgacta tgacgactca tctgaggagc agagtgcgga ggattcctac  600
gaggcctccc cgggctccga gactcagcgt aggcggcggc ggcggcacag gcacagcccc  660
accggcccgc caggcttccc ccgagacggc gactatcggg accaggacta tcggaccgag  720
caaggggagg aggaggagga ggaggaggat gaggaggacg aggagaaggc cagtaacatc  780
gtcatgctga ggatgctgcc acaggcagcc actgaggatg acatccgtgg ccagctgcag  840
tcgcacggcg tgcaagcacg ggaggttcgg ctgatgcgga acaaatcttc aggtcagagc  900
cggggcttcg ccttcgtcga gtttagtcac ttgcaggacg ctacacgatg gatggaagcc  960
aatcagcact ccctcaacat cctgggccag aaggtgtcga tgcactacag tgaccccaag 1020
cccaagatca atgaggactg gctgtgcaat aagtgtggcg tccagaactt caaacgccga 1080
gagaagtgct tcaaatgtgg cgtgcccaag tcagaggcag agcagaagct gcccctcggc 1140
acgaggctgg atcagcagac actgccactg ggtggccggg agctgagcca gggcctgctt 1200
cccctgccgc agccctacca ggcccaggga gtcctggcct cccaagccct gtcacagggc 1260
tcggagccaa gctcagagaa cgccaatgac accatcattt tgcgcaacct gaacccacac 1320
agcaccatgg attccatcct gggggccctg gcaccctacg cggtgctgtc ctcctccaac 1380
gtgcgcgtca taaaggacaa gcagacccaa ctgaaccgcg gctttgcctt catccagctc 1440
tccaccatcg tggaggcagc ccagctgctg cagatcctgc aggccctgca cccaccactc 1500
actatcgacg gcaagaccat caatgttgag tttgccaagg gttctaagag ggacatggcc 1560
tccaatgaag gcagtcgcat cagtgctgcc tctgtggcca gcactgccat tgctgcggcc 1620
cagtgggcca tctcacaggc ctcccaaggt ggggagggta cctgggccac ctccgaggag 1680
ccgccggtcg actacagcta ctaccaacag gatgagggct atggcaacag ccagggcaca 1740
gagtcttccc tctatgccca tggctacctc aagggcacca agggccctgg catcactgga 1800
accaaagggg atcccactgg agcaggtccc gaggcctccc tagagcctgg ggccgactct 1860
gtgtcgatgc aggctttctc tcgcgcccag cctggtgctg ctcctggcat ctaccaacaa 1920
tcagccgagg cgagcagtag ccaggccact gctgccaaca gccagtcgta taccatcatg 1980
tcacccgctg tgctcaaatc tgagctccag agccctaccc atcctagttc tgctctccca 2040
ccggctacca gccccactgc ccaggaatcc tacagccagt accctgttcc cgacgtctct 2100
acctaccagt acgatgagac ctccggctac tactatgacc cccagaccgg cctctactat 2160
gaccccaact cccagtatta ctacaatgct cagagccagc agtacctgta ctgggatagg 2220
gagaggcgca cctatgttcc cgccctggag cagtcggccg acggacataa ggagacaggg 2280
gcaccctcga aggagggcaa agagaagaag gagaagcaca agaccaagac agctcaacag 2340
attgccaagg acatggaacg ctgggcccgc agtctcaaca aacaaaaaga aaacttcaaa 2400
aatagcttcc agcctatcag ctccctgcga gatgacgaga ggcgggagtc agccactgca 2460
gatgctggct atgccatcct cgagaagaag ggagcactag ccgagagaca gcacaccagc 2520
atggatctcc cgaaattggc cagtgacgac cgcccaagcc ctccgcgagg actggtggca 2580
gcctacagcg gggagagtga cagtgaggag gagcaggagc gtgggggccc tgagcgggag 2640
gagaagctca ccgactggca gaagctggcc tgtctgctct gccgacgcca gttccccagc 2700
aaagaggcgc tcatccggca ccagcagctc tcagggctcc acaagcaaaa ccttgagatt 2760
caccggcgag cccacttgtc agaaaacgag ctagaagcac tagagaagaa tgacatggag 2820
caaatgaagt accgggaccg tgcagctgaa cgcagagaaa agtatggcat ccccgagccg 2880
ccagagccca gaggaggaa gtacggcggc atatccacag cctctgtaga cttcgagcag 2940
cctactcggg acgggctggg cagtgacaac attggcagtc ggatgctgca ggccatgggc 3000
tggaaagagg gcagcggcct gggccgcaag aagcaggca ttgtaacgcc tatcgaggcc 3060
caaacacggg tgcggggctc cggcctgggt gcacggggca gctcctacgg ggtcacctca 3120
accgagtcct acaaggagac actgcacaag acaatggtga cccgcttcaa cgaggcccag 3180
tgagcagctt caagagcaac ttctccacat gttgggtgtc catcctgggg cagggaagga 3240
cagagtgttg gatggctggg acggggcctt gctcttgtcg gccagcccac tccccagcca 3300
gagagggctt gaccaaatca aattgaggtg gtgacttttg ttggaaaatt gggctgggat 3360
cacgtcctgt tttgtaataa aagctgaaaa gtctgca                          3397

SEQ ID NO: 2              moltype = DNA   length = 3397
FEATURE                   Location/Qualifiers
source                    1..3397
                          mol_type = genomic DNA
                          organism = Homo sapiens
SEQUENCE: 2
agtaggtgga tggtggtcgg agcgccgact cccttctcgt cgtcgccatt ttgagctggt   60
gactgtggcc ggctgggagt aggcggcagt gagtttccct gggagggcag cgcgcttggc  120
gcttctcccc tcccccgat ctgcctccag tctcggactt ggttgttgcg cgctccggct  180
ccggctgagc tgggagagtt ggaggaggtg gcggcgggca gaggtgatgt ctgggagccc  240
ttccttgaca gcccgggccg agaagagtcc ctgcaggaag catcacccag gctggcagat  300
catggtagca gcagcggggg tggctgggaa gtgaaacgga gccagcggct gaggaggggc  360
cccagcagcc cccgaaggcc ctatcaggac atggagtatg aaagacgtgg tggtcgtggt  420

-continued

```
gacaggactg gccgctatgg agccactgac cgctcgcagg atgatggtgg ggagaaccgc    480
agccgagacc acgactaccg ggacatggac taccgttcat atcctcgcga gtatggcagc    540
caggagggca agcatgacta tgacgactca tctgaggagc agagtgcgga ggattcctac    600
gaggcctccc cgggctccga gactcagcgt aggcggcggc ggcggcacag gcacagcccc    660
accggcccgc caggcttccc ccgagacggc gactatcggg accaggacta tcggaccgag    720
caaggggagg aggaggagga ggaggaggat gaggaggacg aggagaaggc cagtaacatc    780
gtcatgctga ggatgctgcc acaggcagcc actgaggatg acatccgtgg ccagctgcag    840
tcgcacggcg tgcaagcacg ggaggttcgg ctgatgcgca caaatcttc aggtcagagc    900
cggggcttcg ccttcgtcga gtttagtcac ttgcaggacg ctacacgatg gatggaagcc    960
aatcagcact ccctcaacat cctgtgccag aaggtgtcga tgcactacag tgacccaag   1020
cccaagatca atgaggactg gctgtgcaat aagtgtggcg tccagaactt caaacgccga   1080
gagaagtgct tcaaatgtgg cgtgcccaag tcagaggcag agcagaagct gcccctcggc   1140
acgaggctgg atcagcagac actgccactg ggtggccggg agctgagcca gggcctgctt   1200
ccctgccgc agccctacca ggcccaggga gtcctggcct cccaagccct gtcacagggc   1260
tcggagccaa gctcagagaa cgccaatgac accatcattt tgcgcaacct gaacccacac   1320
agcaccatgg attccatcct gggggccctg gcacccacg cggtgctgtc ctcctccaac   1380
gtgcgcgtca taaaggacaa gcagacccaa ctgaaccgcg gctttgcctt catccagctc   1440
tccaccatcg tggaggcagc ccagctgctg cagatcctgc aggccctgca cccaccactc   1500
actatcgacg gcaagaccat caatgttgag tttgccaagg gttctaagag ggacatggcc   1560
tccaatgaag gcagtcgcat cagtgctgcc tctgtggcca gcactgccat tgctgcggcc   1620
cagtgggcca tctcacaggc ctcccaaggt ggggagggta cctgggccac ctccgaggag   1680
ccgccggtcg actacagcta ctaccaacag gatgagggct atggcaacag ccagggcaca   1740
gagtcttccc tctatgccca tggctacctc aagggcacca agggccctgg catcactgga   1800
accaaagggg atcccactgg agcaggtccc gaggcctccc tagagcctgg ggccgactct   1860
gtgtcgatgc aggcttctc tcgcgcccag cctggtgctg ctcctggcat ctaccaacaa   1920
tcagccgagg cgagcagtag ccaggcact gctgccaaca gccagtcgta taccatcatg   1980
tcacccgctg tgctcaaatc tgagctccag agccctaccc atcctagttc tgctctccca   2040
ccggctacca gccccactgc ccaggaatcc tacagccagt accctgttcc cgacgtctct   2100
acctaccagt acgatgagac ctccggctac tactatgacc cccagaccgg cctctactat   2160
gaccccaact cccagtatta ctacaatgct cagagccagc agtacctgta ctgggatgg   2220
gagaggcgga cctatgttcc cgccctggag cagtcggccg acggacataa ggagacaggg   2280
gcaccctcga aggagggcaa agagaagaag gagaagcaca agaccaagac agctcaacag   2340
attgccaagg acatggaacg ctgggcccgc agtctcaaca acaaaaaga aaacttcaa    2400
aatagcttcc agcctatcag ctccctgcga gatgacgaga ggcgggagtc agccactgca   2460
gatgctggct atgccatcct cgagaagaag ggagcactag ccgagacaca gcacaccagc   2520
atggatctcc cgaaattggc cagtgacgac cgcccaagcc ctccgcgagg actggtggca   2580
gcctacagcg gggagagtga cagtgaggag gagcaggagc gtgggggccc tgagcgggag   2640
gagaagctca ccgactggca gaagctggcc tgtctgctct gccgacgcca gttccccagc   2700
aaagaggcgc tcatccggca ccagcagctc tcagggctca acaagcaaaa ccttgagatt   2760
caccggcgag cccacttgtc agaaaacgag ctagaagcac tagagaagaa tgacatggag   2820
caaatgaagt accgggaccg tgcagctgaa cgcagagaaa agtatggcat ccccgagccg   2880
ccagagccca agaggaggaa gtacggcggc atatccacag cctctgtaga cttcgagcag   2940
cctactcggg acgggctggg cagtgacaac attggcagtc ggatgctgca ggccatggcc   3000
tggaaagagg gcagcggcct gggccgcaag aagcaggca ttgtaacgcc tatcgaggcc   3060
caaacacggg tgcggggctc cggcctgggt gcacggggca gctcctacgg ggtcacctca   3120
accgagtcct acaaggagac actgcacaag acaatggtga cccgcttcaa cgaggcccag   3180
tgagcagctt caagagcaac ttctccacat gttgggtgtc catcctgggg cagggaagga   3240
cagagtgttg gatggctggg acggggcctt gctcttgtcg gccagcccac tccccagcca   3300
gagagggctt gaccaaatca aattgaggtg gtgacttttg ttggaaaatt gggctgggat   3360
cacgtcctgt tttgtaataa aagctgaaaa gtctgca                            3397
```

SEQ ID NO: 3       moltype = DNA  length = 3166
FEATURE            Location/Qualifiers
source             1..3166
                    mol_type = genomic DNA
                    organism = Homo sapiens
SEQUENCE: 3

```
agtaggtgga tggtggtcgg agcgccgact cccttctcgt cgtcgccatt ttgagctggt     60
gactgtggcc ggctgggagt aggcggcagt gagtttccct gggagggcag cgcgcttggc    120
gcttctcccc tcccccgat ctgcctccag tctcggactt ggttgttgcg cgctccggct    180
ccggctgagc tgggagagtt ggaggaggtg gcggcgggca gaggtgatgt ctgggagccc    240
ttccttgaca gcccggcccg agaagagtcc ctgcaggaag catcacccag gctggcagat    300
catggtagca gcagcggggg tggctgggaa gtgaaacgga gccagcggct gaggaggggc    360
cccagcagcc cccgaaggcc ctatcaggac atggagtatg aaagacgtgg tggtcgtggt    420
gacaggactg gccgctatgg agccactgac cgctcgcagg atgatggtgg ggagaaccgc    480
agccgagacc acgactaccg ggacatggac taccgttcat atcctcgcga gtatggcagc    540
caggagggca agcatgacta tgacgactca tctgaggagc agagtgcgga gatccgtggc    600
cagctgcagt cgcacggcgt gcaagcacgg gaggttcggc tgatgcggaa caaatcttca    660
ggtcagagcc ggggcttcgc cttcgtcgag tttagtcact tgcaggacgc tacacgatgg    720
atggaagcca atcagcactc cctcaacatc ctgtgccaga aggtgtcgat gcactacagt    780
gacccaagc caagatcaa tgaggactgg ctgtgcaata agtgtggcgt ccagaacttc    840
aaacgccgag agaagtgctt caaatgtggc gtgcccaagt cagaggcaga gcagaagctg    900
cccctcggca cgaggctgga tcagcagaca ctgccactg gtggccggga gctgagccag    960
ggcctgctt ccctgccgca gccctaccag gcccaggga gtcctggcct cccaagcct   1020
tcacagggct cggagccaag ctcagagaac gccaatgaca ccatcatttt gcgcaacctg   1080
aacccacaca gcaccatgga ttccatcctg ggggccctgg cacccacgc ggtgctgtcc   1140
tcctccaacg tgcgcgtcat aaaggacaag cagacccaac tgaaccgcgg ctttgccttc   1200
atccagctct ccaccatcgt ggaggcagcc cagctgctga gatcctgca ggccctgcac   1260
ccaccactca ctatcgacgg caagaccatc aatgttgagt ttgccaaggg ttctaagagg   1320
```

-continued

```
gacatggcct ccaatgaagg cagtcgcatc agtgctgcct ctgtggccag cactgccatt   1380
gctgcggccc agtgggccat ctcacaggcc tcccaaggtg gggagggtac ctgggccacc   1440
tccgaggagc cgccggtcga ctacagctac taccaacagg atgagggcta tggcaacagc   1500
cagggcacag agtcttccct ctatgcccat ggctacctca agggcaccaa gggccctggc   1560
atcactggaa ccaaagggga tcccactgga gcaggtcccg aggcctcct agagcctggg   1620
gccgactctg tgtcgatgca ggctttctct cgcgcccagc ctggtgctgc tcctggcatc   1680
taccaacaat cagccgaggc gagcagtagc cagggcactg ctgccaacag ccagtcgtat   1740
accatcatgt cacccgctgt gctcaaatct gagctccaga gccctaccca tcctagttct   1800
gctctcccac cggctaccag ccccactgcc caggaatcct acagccagta ccctgttccc   1860
gacgtctcta cctaccagta cgatgagacc tccggctact actatgaccc ccagaccggc   1920
ctctactatg accccaactc ccagtattac tacaatgctc agagccagca gtacctgtac   1980
tgggatgggg agaggcggac ctatgttccc gccctggagc agtcggccga cggacataag   2040
gagacagggg caccctcgaa ggagggcaaa gagaagaagg agaagcacaa gaccaagaca   2100
gctcaacaga ttgccaagga catggaacgc tgggcccgca gtctcaacaa acaaaaagaa   2160
aacttcaaaa atagcttcca gcctatcagc tccctgcgag atgacgagag gcgggagtca   2220
gccactgcag atgctggcta tgccatcctc gagaagaagg gagcactagc cgagagacag   2280
cacaccagca tggatctccc gaaattggcc agtgacgacc gcccaagccc tccgcgagga   2340
ctggtggcag cctacagcgg ggagagtgac agtgaggagg agcaggagcg tgggggccct   2400
gagcgggagg agaagctcac cgactggcag aagctggcct gtctgctctg ccgacgccag   2460
ttccccagca aagaggcgct catccggcac cagcagctct cagggctcca caagcaaaac   2520
cttgagattc accggcgagc ccacttgtca gaaaacgagc tagaagcact agagaagaat   2580
gacatggagc aaatgaagta ccgggaccgt gcagctgaac gcagagaaaa gtatggcatc   2640
cccgagccgc cagagcccaa gaggaggaag tacggcggca tatccacagc ctctgtagac   2700
ttcgagcagc ctactcggga cgggctgggc agtgacaaca ttggcagtcg gatgctgcag   2760
gccatgggct ggaaagaggg cagcggcctg ggccgcaaga agcagggcat tgtaacgcct   2820
atcgaggccc aaacacgggt gcggggctcc ggcctggtg cacggggcag ctcctacggg   2880
gtcacctcaa ccgagtccta caaggagaca ctgcacaaga caatggtgac ccgcttcaac   2940
gaggcccagt gagcagcttc aagagcaact tctccacatg ttgggtgtcc atcctggggc   3000
agggaaggac agagtgttgg atggctggga cggggccttg ctcttgtcgg ccagcccact   3060
ccccagccag agagggcttg accaaatcaa attgaggtgg tgacttttgt tggaaaattg   3120
ggctgggatc acgtcctgtt ttgtaataaa agctgaaaag tctgca                  3166
```

```
SEQ ID NO: 4              moltype = DNA   length = 3394
FEATURE                  Location/Qualifiers
source                   1..3394
                         mol_type = genomic DNA
                         organism = Homo sapiens
SEQUENCE: 4
agtaggtgga tggtggtcgg agcgccgact cccttctcgt cgtcgccatt ttgagctggt   60
gactgtggcc ggctgggagt aggcggcagt gagtttccct gggagggcag cgcgcttggc   120
gcttctcccc tcccccgat ctgcctccag tctcggactt ggttgttgcg cgctccggct   180
ccggctgagc tgggagagtt ggaggaggtg gcggcgggca gaggtgatgt ctgggagccc   240
ttccttgaca gcccgggccg agaagagtcc ctgcaggaag catcacccag gctggcagat   300
catggtagca gcagcggggg tggctgggaa gtgaaacgga gccagcggct gaggaggggc   360
cccagcagcc cccgaaggcc ctatcaggac atggagtatg aaagacgtgg tggtcgtggt   420
gacaggactg gccgctatgg agccactgac cgctcgcagg atgatggtgg ggagaaccgc   480
agccgagacc acgactaccg ggacatggac taccgttcat atcctcgcga gtatggcagc   540
caggagggca agcatgacta tgacgactca tctgaggagc agagtgcgga ggattcctac   600
gaggcctccc cgggctccga gactcagcgt aggcggcggc ggcggcacag gcacagcccc   660
accggccgc caggcttccc ccgagacggc gactatcggg accaggacta tcggaccgag   720
caagggagga aggaggagga ggaggaggat gaggaggagg aggagaaggc cagtaacatc   780
gtcatgctga ggatgctgcc acaggcagcc actgaggatg acatccgtgg ccagctgcag   840
tcgcacggcg tgcaagcacg ggaggttcgg ctgatgcgga acaaatcttc aggtcagagc   900
cggggcttcg ccttcgtcga gtttagtcac ttgcaggacg ctacacgatg gatggaagcc   960
aatcagcact ccctcaacat cctgggccag aaggtgtcga tgcactacag tgaccccaag   1020
cccaagatca atgaggactg gctgtgcaat aagtgtgacg tccagaactt caaacgccga   1080
gagaagtgct tcaaatgtgg cgtgcccaag tcagaggcag agcagaagct gccctcggc    1140
acgaggctg atcagcagac actgccactg ggtggccggg agctgagcca gggcctgctt    1200
ccctgcccgc agccctacca ggcccaggga gtcctgacct cccaagccct gtcacagggc   1260
tcggagccaa gctcagagaa cgccaatgac accatcattt tgcgcaacct gaacccacac   1320
agcaccatgg attccatcct gggggccctg gcacctacg cggtgctgtc ctcctccaac    1380
gtgcgcgtca taaaggacaa gcagacccaa ctgaaccgcg gctttgcctt catccagctc   1440
tccaccatcg aggcagccca gctgctgcag atcctgcagg ccctgcaccc accactcact   1500
atcgacggca agaccatcaa tgttgagttt gccaaggtt ctaagaggga catggcctcc     1560
aatgaaggca gtcgcatcag tgctgcctct gtggccagca ctgccattgc tgcggcccag   1620
tgggccatct cacaggcctc ccaaggtggg agggtaccg ggccacctc gaggagccg      1680
ccggtcgact acagctacta ccaacaggat gagggctatg caacagcca gggcacagag   1740
tcttccctct atgcccatgg ctacctcaag gcaccaagg gccctggcat cactggaacc     1800
aaaggggatc ccactggagc aggtcccgag gcctccctag agctggggc cgactctgtg     1860
tcgatgcagg ctttctctcg cgcccagcct ggtgctgctc ctggcatcta ccaacaatca   1920
gccgaggcga gcagtagcca gggcactgct gccaacagcc agtcgtatac catcatgtca   1980
cccgctgtgc tcaaatctga gctccagagc cctacccatc ctagttctgc tctcccaccg   2040
gctaccagcc ccactgccca ggaatcctac agccagtacc ctgttcccga cgtctctacc   2100
taccagtacg atgagacctc cggctactac tatgacccc agaccggcct ctactatgac    2160
cccaactccc agtattacta caatgctcag agccagcagt acctgtactg ggatggggag   2220
aggcggacct atgttcccgc cctggagcag tcggccgacg gacataagga cagggca      2280
ccctcgaagg agggcaaaga gaagaaggag aagcacaaga ccaagacagc tcaacagatt   2340
gccaaggaca tggaacgctg ggcccgcagt ctcaacaaac aaaaagaaaa cttcaaaaat   2400
agcttccagc ctatcagctc cctgcgagat gacgagaggc gggagtcagc cactgcagat   2460
```

-continued

```
gctggctatg ccatcctcga gaagaaggga gcactagccg agagacagca caccagcatg   2520
gatctcccga aattggccag tgacgaccgc ccaagccctc cgcgaggact ggtggcagcc   2580
tacagcgggg agagtgacag tgaggaggag caggagcgtg ggggccctga gcgggaggag   2640
aagctcaccg actggcagaa gctggcctgt ctgctctgcc gacgccagtt ccccagcaaa   2700
gaggcgctca tccggcacca gcagctctca gggctccaca agcaaaacct tgagattcac   2760
cggcgagccc acttgtcaga aaacgagcta gaagcactag agaagaatga catggagcaa   2820
atgaagtacc gggaccgtgc agctgaacgc agagaaaagt atggcatccc cgagccgcca   2880
gagcccaaga ggaggaagta cggcggcata tccacagcct ctgtagactt cgagcagcct   2940
actcgggacg ggctgggcag tgacaacatt ggcagtcgga tgctgcaggc catgggctgg   3000
aaagagggca gcggcctggg ccgcaagaag cagggcattg taacgcctat cgaggcccaa   3060
acacgggtgc ggggctccgg cctgggtgca cggggcagct cctacggggt cacctcaacc   3120
gagtcctaca aggagacact gcacaagaca atggtgaccc gcttcaacga ggcccagtga   3180
gcagcttcaa gagcaacttc tccacatgtt gggtgtccat cctgggggcag ggaaggacag   3240
agtgttggat ggctgggacg gggccttgct cttgtcggcc agcccactcc ccagccagac   3300
agggcttgac caaatcaaat tgaggtggtg acttttgttg gaaaattggg ctgggatcac   3360
gtcctgtttt gtaataaaag ctgaaaagtc tgca                              3394
```

```
SEQ ID NO: 5              moltype = DNA   length = 3428
FEATURE                   Location/Qualifiers
source                    1..3428
                          mol_type = genomic DNA
                          organism = Homo sapiens
SEQUENCE: 5
agtaggtgga tggtggtcgg agcgccgact cccttctcgt cgtcgccatt ttgagctggt   60
gactgtggcc ggctgggagt aggcggcagt gagtttccct gggagggcag cgcgcttggc   120
gcttctcccc tccccccgat ctgcctccag tctcggcatc ggttgttgcg cgctccggct   180
ccggctgagc tgggagagtt ggaggaggtg gcggcgggca gaggtgatgt ctgggagccc   240
ttccttgaca gcccgggccg agaaggtgag cgtcgacgct ggtcgtgggg gcggagagtc   300
cctgcaggaa gcatcaccca ggctggcaga tcatggtagc agcagcgggg gtggctggga   360
agtgaaacgg agccagcggc tgaggagggg ccccagcaga ccccgaaggc cctatcagga   420
catggagtat gaaagacgtg gtggtcgtgg tgacaggact ggccgctatg gagccactga   480
ccgctcgcag gatgatggtg gggagaaccg cagccgagac cacgactacc gggacatgga   540
ctaccgttca tatcctcgcg agtatggcag ccaggagggc aagcatgact atgacgactc   600
atctgaggag cagagtgcgg aggattccta cgaggcctcc ccgggctccg agactcagcg   660
taggcggcgg cggcggcaca ggcacagccc caccggcccg ccaggcttcc cccgagacgg   720
cgactatcgg gaccaggact atcggaccga gcaagggagg gaggaggagg aggaggagga   780
tgaggaggag gaggagaagg ccagtaacat cgtcatgctg aggatgctgc cacaggcagc   840
cactgaggat gacatccgtg gccagctgca gtcgcacggc gtgcaagcac gggaggttcg   900
gctgatgcgc aacaaatctt caggtcagag ccggggcttc gccttcgtcg agtttagtca   960
cttgcaggac gctacacgat ggatggaagc caatcagcac tccctcaaca tcctgggcca   1020
gaaggtgtcg atgcactaca gtgaccccaa gcccaagatc aatgaggact ggctgtgcaa   1080
taagtgtggc gtccagaact tcaaacgccg agagaagtgc ttcaaatgtg gcgtgcccaa   1140
gtcagaggca gagcagaagc tgcccctcgg cacgaggctg gatcagcaga cactgccact   1200
gggtggccgg gagctgagcc agggcctgct tcccctgccg cagccctacc aggcccaggg   1260
agtcctggcc tcccaagccc tgtcacaggg ctcggagcca agctcagaga cgccaatga   1320
caccatcatt ttgcgcaacc tgaacccaca cagcaccatg gattccatcc tgggggccct   1380
ggcaccctac gcggtgctgt cctcctccaa cgtgcgcgtc ataaaggaca agcagaccca   1440
actgaaccgc ggctttgcct tcatccagct ctccaccatc gtggaggcag cccagctgct   1500
gcagatcctg caggccctgc acccaccact cactatcgac ggcaagacca tcaatgttga   1560
gtttgccaag ggttctaaga gggacatggc ctccaatgaa ggcagtcgca tcagtgctgc   1620
ctctgtggcc agcactgcca ttgctgcggc ccagtgggcc atctcacagg cctcccaagg   1680
tgggggagggt acctgggcca cctccgagga gccgccggtc gactacagct actaccaaca   1740
ggatgagggc tatggcaaca gccagggcac agagtcttcc ctctatgccc atggctacct   1800
caagggcacc aagggccctg gcatcactgg aaccaaaggg gatcccactg gagcaggtcc   1860
cgaggcctcc ctagagcctg gggccgactc tgtgtcgatg caggctttct ctcgcgccca   1920
gcctgtgct gctcctggca tctaccaaca atcagccgag gcgagcagta gccaggggcac   1980
tgctgccaac agccagtcgt ataccatcat gtcaccgct gtgctcaaat ctgagctcca   2040
gagccctacc catcctagtt ctgctctccc accggctacc agcccactg cccaggaatc   2100
ctacagccag taccctgttc ccgacgtgtc tacctaccag tacgatgaga cctccggcta   2160
ctactatgac ccccagaccg gcctctacta tgaccccaac tcccagtatt actacaatgc   2220
tcagagccag cagtacctgt actgggatgg ggagaggcgg acctatgttc ccgccctgga   2280
gcagtcggcc gacggacata aggagacagg ggcaccctcg aaggagggca aagagaagaa   2340
ggagaagcac aagaccaaga cagctcaaca gattgccaag gacatggaac gctgggcccg   2400
cagtctcaac aaacaaaaag aaaacttcaa aaatagcttc cagcctatca gctccctgcg   2460
agatgacgag aggcgggagt cagccactgc agatgctggc tatgccatcc tcgagaagaa   2520
gggagcgcacta gccgagagac agcaccagca tggatctc ccgaaattgg ccagtgacga   2580
ccgcccaagc cctccgcgag gactggtggc agcctacagc gggagagtga cagtacggagga   2640
ggagcaggag cgtgggggcc ctgagcggga ggagaagctc accgactggc agaagctggc   2700
ctgtctgctc tgccgacgcc agttccccag caaagaggcg ctcatccggc accagcagct   2760
ctcagggctc cacaagcaaa accttgagat tcaccggcga gcccacttgt cagaaaacga   2820
gctagaagca ctagagaaga atgacatgga gcaaatgaag taccgggacc gtgcagctga   2880
acgcagagaa aagtatggca tccccgagcc gccagagagcc aagaggagga agtacggagga   2940
catatccaca gcctctgtag acttcgagca gcctactcgg gacgggctgg gcagtgacaa   3000
cattggcagt cggatgctgc aggccatggg ctggaaagag ggcagcggcc tgggccgcaa   3060
gaagcagggc attgtaacgc ctatcgaggc ccaaacacgg gtgcggggct ccggcctggg   3120
tgcacggggc agctcctacg gggtcacctc aaccgagtcc tacaaggaga cactgcacaa   3180
gacaatggtg acccgcttca cgaggcccca gtgagcagct tcaagagcaa cttctccaca   3240
```

-continued

```
tgttgggtgt ccatcctggg gcagggaagg acagagtgtt ggatggctgg gacggggcct   3300
tgctcttgtc ggccagccca ctccccagcc agagagggct tgaccaaatc aaattgaggt   3360
ggtgactttt gttggaaaat tgggctggga tcacgtcctg ttttgtaata aaagctgaaa   3420
agtctgca                                                             3428
```

COMBINATION THERAPY WITH CLK/DYRK INHIBITORS AND BCL2 INHIBITORS TO TREAT LEUKEMIA

CROSS-REFERENCE TO RELATED APPLICATIONS

This application is a continuation application of International Application No. PCT/US2023/085214, filed Dec. 20, 2023, which claims the benefit of and priority to U.S. Provisional Patent Application No. 63/589,873, filed Oct. 12, 2023, the contents of both of which are incorporated herein by reference in their entirety.

SEQUENCE LISTING

The instant application contains a Sequence Listing which has been submitted electronically in .xml format and is hereby incorporated by reference in its entirety. Said .xml copy, created on Feb. 28, 2024, is named 115872-2644_SL.xml and is 22,161 bytes in size.

TECHNICAL FIELD

The present disclosure relates to methods for treating leukemia (e.g., AML) using a CLK/DYRK inhibitor and a B-cell lymphoma 2 (BCL2) inhibitor (e.g., venetoclax). Kits for use in practicing the methods are also provided.

BACKGROUND

The following description of the background of the present technology is provided simply as an aid in understanding the present technology and is not admitted to describe or constitute prior art to the present technology.

Therapy resistance is a major challenge in the treatment of cancer. Acute myeloid leukemia (AML) is an aggressive hematologic malignancy marked by a dismal prognosis[1]. For decades, the standard therapy for newly diagnosed AML has been intensive cytotoxic chemotherapy. Recently, several targeted therapies have been approved for AML, including inhibitors of IDH1/2, FLT3, and BCL2[2]. Despite the introduction of these agents, most patients ultimately relapse and acquire resistance to long-term, continuous drug exposure[3,4]. Genetic mutations, such as in TP53, have been shown to contribute to poor prognosis in patients treated with chemotherapy or the BCL2 inhibitor venetoclax[5-7]. More recently, acquired BAX mutations have been shown to confer resistance to venetoclax in a subset of AML patients[8]. However, in the majority of cases, genetic lesions are not known to be the main underlying mechanism of AML relapse[9,10], possibly implicating non-genetic mechanisms that allow persistent survival of leukemia cells upon exposure to drug therapy[11]. For instance, upregulation of anti-apoptotic proteins[12,13] and dysregulated mitochondrial metabolism[14-16] can alter responsiveness to venetoclax. Such findings have demonstrated that epigenetic plasticity and transcriptional variability can act as critical evolutionary drivers of clonal fitness and drug resistance in leukemia[17,18]. In AML, the combination of venetoclax with hypomethylating agents is now widely used and has significantly improved the response and survival rates of patients[21,22]. However, despite the success of venetoclax and hypomethylating agent combination therapy, this regimen is not curative. Furthermore, the majority of patients are unable to undergo curative allogeneic stem cell transplantation and ultimately become resistant to therapy[22].

As such, identifying and targeting drug resistance mechanisms in AML with combinatorial treatment regimens is of critical importance.

SUMMARY OF THE PRESENT TECHNOLOGY

In one aspect, the present disclosure provides a method for preventing or treating leukemia in a subject in need thereof comprising administering to the subject an effective amount of a CLK/DYRK inhibitor and an effective amount of a BCL2 inhibitor. In some embodiments, the CLK/DYRK inhibitor is selected from the group consisting of SM09419, SM08502 (Cirtuvivint), CA-4948 (Emavusertib), CTX-712, AnnH75, EGCG, EHT-1610, Harmine, INDY, Leucettine L41, Lorecivivint, GNF4877, MU1210, and TCMDC-135051. In another aspect, the present disclosure provides a method for preventing or treating leukemia in a subject in need thereof comprising administering to the subject an effective amount of a RBM10-specific inhibitory nucleic acid and an effective amount of a BCL2 inhibitor, wherein the RBM10-specific inhibitory nucleic acid is a siRNA, a shRNA, an antisense oligonucleotide, or a sgRNA.

Additionally or alternatively, in some embodiments, the BCL2 inhibitor is selected from among venetoclax (ABT-199), navitoclax (ABT-263), obatoclax (GX15-070), oblimersen sodium (G3139), Palcitoclax (APG-1252), and AT-101 (R-(—)-gossypol acetic acid).

Additionally or alternatively, in some embodiments of the methods disclosed herein, the subject is resistant to BCL2 inhibitor monotherapy or combination therapy with a BCL2 inhibitor and a pyrimidine analog. Examples of pyrimidine analogs include, but are not limited to, 5-azacytidine, cytarabine, 5-fluorouracil, floxuridine, capecitabine, decitabine, or gemcitabine. The resistance to BCL2 inhibitor therapy may be acquired or intrinsic. In some embodiments, the subject harbors acquired mutations in BAX, PMAIP, or TP53. In certain embodiments, the subject is human. The subject may be a child or an adult.

In any and all embodiments of the methods disclosed herein, the leukemia is chronic lymphocytic leukemia (CLL) or acute myeloma leukemia (AML). Additionally or alternatively, in some embodiments, the leukemia comprises an MLL-translocation (MLL-t), an MLL-rearrangement (MLL-r), or an MLL-partial tandem duplication (MLL-PTD). Additionally or alternatively, in some embodiments, the leukemia comprises mutations in one or more of p53, FLT3, RUNX1, PTPN11, SF3B1, STAG2, DNMT3A or IDH2.

Additionally or alternatively, in some embodiments of the methods disclosed herein, the CLK/DYRK inhibitor and the BCL2 inhibitor are administered sequentially, simultaneously, or separately. In some embodiments, the CLK/DYRK inhibitor or the BCL2 inhibitor is administered orally, intravenously, intramuscularly, intraperitoneally, or subcutaneously.

In another aspect, the present disclosure provides a method for selecting a leukemia patient for treatment with a BCL2 inhibitor comprising (a) detecting the presence of at least one mutation in RBM10 in a biological sample obtained from the leukemia patient and (b) administering to the leukemia patient an effective amount of a BCL2 inhibitor. Additionally or alternatively, in some embodiments, the at least one mutation in RBM10 is a frameshift mutation, a missense mutation, a deletion, an insertion, a nonsense mutation, an inversion, or a translocation. The at least one mutation in RBM10 may be detected using any nucleic acid detection assay known in the art such as next-generation sequencing, PCR, real-time quantitative PCR (qPCR), digital PCR (dPCR), Southern blotting, Reverse transcriptase-PCR (RT-PCR), Northern blotting, microarray, dot or slot blots, in situ hybridization, or fluorescent in situ hybridization (FISH).

The present disclosure also provides kits for the prevention and/or treatment of leukemia (e.g., AML), comprising one or more CLK/DYRK inhibitors and/or BCL2 inhibitors disclosed herein and instructions for using the same.

BRIEF DESCRIPTION OF THE DRAWINGS

FIG. 1A: Schematic of genome-wide CRISPR screens in MOLM-13 AML cells treated with a panel of clinically approved AML drugs. FIG. 1B: Manhattan plot depicting top 10 genes that sensitizes or confer resistance in individual CRISPR drug screens. Boxed dots represent RNA processing genes. CRISPR score represents the $\log_2$ (fold-change) values of sgRNAs normalized to DMSO. FIG. 1C: Gene ontology (GO) enrichment analysis of top sensitizers in the venetoclax screen. FIG. 1D: Clustered heatmap of results of the RNA-binding protein-focused CRISPR drug screens in MOLM-13 AML cells treated with drugs. CRISPR score represents $\log_2$ fold change of sgRNAs normalized to DMSO. FIG. 1E: Histogram of CRISPR scores for all sgRNAs in the venetoclax screen in FIG. 1D. Values represent the $\log_2$ (fold-change) values of sgRNAs normalized to DMSO. The blue lines represent individual sgRNAs targeting the indicated genes among the top splicing factor candidates. FIG. 1F: Polar plots of top synergistic splicing factors identified in FIG. 1D treated with various AML drugs. The height of the wedge corresponds to the sgRNA fold change normalized to DMSO. FIG. 1G: Competition-based assay in MOLM-13 cells 10 days post-transduction with top 2 sgRNAs targeting each splicing factor or non-targeting sgRosa control (n=3 per condition, mean+SEM) treated with 50 nM venetoclax. Statistical analysis was performed using unpaired Student's t test by Prism Graph-Pad (*p<0.05, p<0.01, *p<0.001, n.s., not significant). See also FIGS. 7A-7D.

FIGS. 2A-2K. RBM10 loss enhances BCL2 inhibition in AML cells but is dispensable for normal hematopoiesis. FIG. 2A: Western blot of CRISPR-mediated knockout of RBM10 in MOLM-13 cells. FIG. 2B: Dose-response curves of sgRBM10 or sgRosa treated with indicated venetoclax concentrations on the x-axis and cell viability on the y-axis at 48 hours. IC50 values were calculated from technical triplicates per experiment, error bars represent SEM. FIG. 2C: Competition proliferation assays of sgRBM10 or non-targeting sgRosa in human AML cell line expressing Cas9 and treated with 50 nM of venetoclax or DMSO (n=3 biological replicates per time point and condition, mean+SEM). FIG. 2D: Bioluminescent imaging of mice transplanted with MOLM-13 cells transduced with sgRBM10 or sgRosa and treated daily with venetoclax (100 mg/kg) or vehicle control. Representative images of 4 mice per condition is shown. Images were taken 4 days post-treatment. FIG. 2E: Flow cytometry analysis of GFP-positive sgRNA-expressing indicated by y-axis MOLM-13 cells in peripheral blood at day 6 post-treatment. Statistical analysis was performed using One-way ANOVA with post-hoc testing as indicated (number of mice used in each group is indicated in F, mean+SEM). FIG. 2F: Kaplan-Meier survival curves of mice transplanted with MOLM-13 cells transduced with sgRBM10 or sgRosa and treated daily with venetoclax (100 mg/kg) or vehicle. The p values were determined using a log-rank Mantel-Cox test (p<0.01, *p<0.001, n.s., not significant). FIG. 2G: Schematic depiction of the targeting strategy to generate Rbm10 cKO mice. The Rbm10 allele was deleted by targeting exon 3 that resulted in a frameshift following excision. Two LoxP sites flanking exon 3 and an Frt-flanked neomycin selection cassette were inserted in the downstream intron. FIG. 2H: Western blot of Rbm10 in bone marrow mononuclear cells from Mx1-cre Rbm10fl/y (Rbm10 cKO) or Mx1-cre control 7 days after polyinosinic-polycytidylic acid (pIpC) treatment. FIG. 2I: Total number of colony-forming units (CFU) from bone marrow cells of Mx1-cre Rbm10fl/y (Rbm10 cKO) or Mx1-cre control mice following 7 days of culture (n=6, mean+SEM). The p values were determined by unpaired student t test. n.s., not significant. FIG. 2J: Percentage of CD45.2$^+$ cells in peripheral blood over the course of 4 months competitive transplantation (n=6 for Mx1-cre control and n=7 mice for Rbm10 cKO, mean+SEM). FIG. 2K: Percentage of CD45.2$^+$ of hematopoietic stem and progenitor cells in the bone marrow (left) and mature immune cells in the peripheral blood (right) (n=6 for Mx1-cre control and n=7 mice for Rbm10 cKO, mean+SEM). See also FIGS. 8A-8K.

FIGS. 3A-3L. Impact of RBM10 on RNA binding, RNA splicing, and response to venetoclax. FIG. 3A: Competition-based assay of RBM10 KO in MOLM-13 cells and transduced with RBM10 cDNA wild-type (WT) or individual mutant (lacking RNA-binding domains) RBM10 cDNA and treated with venetoclax (50 nM) or DMSO at 48 hours (n=3, mean+SEM). The p-values were determined by One-way ANOVA with post-hoc testing. FIG. 3B: Metaintron plots of average number indicated by y-axis of RBM10 peaks mapped to intronic regions flanking exons in MOLM-13 cells (n=4 eCLIP replicates). This plot is exon-centered (500-600 bp) on the x-axis. Enhanced crosslinking and immunoprecipitation (eCLIP) was performed in 4 replicates. FIG. 3C: Percentage of treatment-responsive (RBM10 KO, venetoclax, or RBM10 KO and venetoclax) differentially spliced event types: cassette exons (SE), alternative 5' ss exon (A5E), alternative 3' ss exon (A3E), mutually exclusive exons (MXE), retained intron (RI), constitutive intron (CI), and tandem 3' UTR (TUTR) from RNA-seq (n=3 per condition). FIG. 3D: Scatter plot of cassette exons (SE) promoted (red circles) or repressed (blue circles) in MOLM-13 cells transduced with sgRosa (y-axis) or sgRBM10 (x-axis) treated with DMSO or venetoclax RNA-seq (n=3 per condition). p denotes Spearman's rank correlation coefficient. FIG. 3E: RBM10 splicing map generated by integrating RBM10 KO splicing changes from RNA-seq and RBM10 eCLIP binding sites. FIG. 3F: RNA-seq and eCLIP (bottom) coverage plots of XIAP Δexon1 in MOLM-13 cells with RBM10 KO or non-targeting sgRNAs treated with DMSO or venetoclax. Yellow shadow depicts exon exclusion event in RBM10KO venetoclax-treated MOLM-13 cells overlapped with functional protein domains of XIAP. FIG. 3G: Western blotting of XIAP after 50 nM venetoclax treatment of MOLM-13 cells with sgRosa or sgRBM10 for 48 hrs. FIG. 3H: Western blotting of XIAP protein levels after ectopic overexpression of XIAP full-length (FL) or XIAP Δexon1. FIG. 3I: Competition-based assay of XIAP full-length (FL) or XIAP Δexon1 linked to GFP reporter after 24 hrs of venetoclax treatment (n=3, mean+SEM). Y-axis denotes GFP positive cells. FIG. 3J: Annexin V staining of XIAP full-length (FL) or XIAP Δexon1 after 24 hrs of venetoclax treatment (n=3, mean+SEM). Y-axis denotes Annexin V positive cells. Statistical analysis was performed using unpaired Student's t test by Prism Graph- Pad (*p<0.05, **p<0.01, n.s., not significant). FIG. 3K: Volcano plot of differentially expressed genes (DEGs) upon RBM10KO venetoclax-treated MOLM-13 cells compared to DMSO RNA-seq (n=3 per condition). FIG. 3L: Competition-based assay measuring Cherry-expressing sgRBM10 or sgRosa cells transduced with overexpression (OE) of BCL2A1 cDNA or empty vector GFP-positive cells in MOLM-13 cells treated with 50 nM venetoclax for 48 hours (n=3, mean+SEM). Y-axis denotes mCherry positive cells. See also FIGS. 9A-9I and data not shown.

FIG. 4A: Structure of SM09419 selectivity. FIG. 4B: Kinase dendrogram of SM09419. Kinases with IC50 values of 0.01 to 0.1 μM are indicated by small red circle, whereas larger red circles represent more potent IC50 values with 0.001 to 0.0 μM. FIG. 4C: NanoBRET target engagement assay of CLK1-4, DYRK1A/B, and DYRK2 upon 24 hrs of SM09419 treatment. FIG. 4D: Inhibition of CLK kinases (CLK2 and CLK3) and CDK1 kinase (n=3). IC50 values were determined from dose response curves. Y-axis denotes the percent inhibition for CLK2, CLK3, and CDK1 (n=3, mean+SEM). FIG. 4E: Western blot of phosphorylated SR proteins treated with increasing concentration of SM09419 for 48 hrs in MOLM-13 cells. FIGS. 4F-4G: 2D synergy plots using Zero interaction potency (ZIP) model (left) and dose-response curves (right) of SM09419 and venetoclax combination at various concentration treated for 48 hrs in (FIG. 4F) MOLM-13 (n=3, mean+SEM) and (FIG. 4G) KG-1 cells (n=3, mean+SEM). The presence of synergy was determined using the SynergyFinder computational package and the ZIP synergy index in which red signifies synergism and blue is antagonism. A positive synergy score is the percent more cell death than expected. IC50 values were calculated from technical triplicates per experiment. FIGS. 4H-4I: Annexin V staining (left) and quantification (right) of (FIG. 4H) MOLM-13 parental and (FIG. 4I) venetoclax-resistant cell lines treated with SM09419, venetoclax, or the combination at 48 hrs post-treatment (n=3, mean+SEM). Y-axis denotes percent of Annexin V positive cells. Statistical analysis was performed using unpaired Student's t test by Prism GraphPad (****p<0.0001). See also FIGS. 10A-10E, 11A-11H.

FIG. 5A: Total number of splicing changes observed after SM09419 (100 nM), venetoclax (10 nM), or combination of SM09419 (100 nM) and venetoclax (10 nM) treatment for 48 hours RNA-seq (n=3 per condition). Cassette exons (SE), alternative 5' ss exon (A5E), alternative 3' ss exon (A3E), mutually exclusive exons (MXE), retained intron (RI), constitutive intron (CI), and tandem 3' UTR (TUTR). FIG. 5B: Spatial distribution of pyrimidines-rich (YYYY) and purine-rich (RRRR) motifs comparing sequence enrichment of excluded exons (n=674) against included exons (n=370) in SM0419-treated (100 nM) MOLM-13 cells. FIG. 5C: Scatter plot of NMD-inducing retained intron (RI) events (red circles) in MOLM-13 cells treated with venetoclax (left), SM09419 (middle) or the combination of venetoclax and SM09419 (right) RNA-seq in triplicates for each condition. FIG. 5D: Percentage of NMD-inducing events indicated on the y-axis in RBM10 KO venetoclax (compared to non-targeting sgRosa) and SM09419, or SM09419+venetoclax (compared to DMSO) RNA-seq in triplicates for each condition (mean+SEM). FIG. 5E: Venn diagram of NMD-inducing events in RBM10 KO venetoclax (compared to non-targeting sgRosa) and SM09419, or SM09419+venetoclax (compared to DMSO). FIG. 5F: RNA-seq coverage plot (left) and mean PSI of XIAP cassette exon inclusion isoform (n=3 per condition, mean+SEM). FIG. 5G: RNA-seq coverage plots of the splicing factors SRSF5, U2AF2, RBM17, and RBM5 in MOLM-13 cells. Yellow regions represent retained intron events in each of the genes. FIG. 5H: Western blotting of XIAP, U2AF2, RBM5, FLT3, MCL-1, and actin in MOLM-13 parental or venetoclax-resistant (VR1) cells treated with varying concentration of SM09419 for 24 hrs. FIG. 5I: Normalized sgRNA counts of top splicing factors from RNA-binding protein CRISPR screen that synergized with venetoclax treatment in MOLM-13 cells. FIG. 5J: RNA-seq coverage plots (left) and gene expression (right) plots for FLT3 mRNA (n=3 per condition, mean+SEM). p-values were determined by One-way ANOVA with post-hoc testing as indicated. See also FIGS. 12A-12F and data not shown.

FIGS. 6A-6I. SM09419 circumvents therapeutic resistance to venetoclax. FIG. 6A: Dose-response curves of human AML cell lines treated with various concentrations of venetoclax (top) or SM09419 (bottom). IC50 values were calculated from technical triplicates per experiment, error bars represent SEM. FIG. 6B: Dose-response curves of venetoclax-resistant MOLM-13 cells treated with different concentrations of venetoclax (top) and SM09419 (bottom) as indicated by x-axis (n=3, mean+SEM). Cell viability is denoted on the y-axis. FIG. 6C: Schematic of patient-derived xenograft (PDXs) generation and treated daily with SM09419 (25 mg/kg, QD, PO) or vehicle. FIG. 6D: Diagnosis, treatment regimen and genetic characteristics of AML patient-derived xenograft samples. FIGS. 6E-6F: Percentage of human CD45+ (hCD45+) cells in (FIG. 6E) bone marrow and (FIG. 6F) peripheral blood of PDXs following 3-weeks of SM09419 treatment. FIG. 6G: Representative flow-cytometry plots of hCD45+ and mouse CD45+ (mCD45+) in bone marrow from PDXs treated daily with 25 mg/kg SM09419 after 3-weeks. FIGS. 6H-6I: Synergy scores (Loewe and HSA) (left) and 2D synergy plots (right) from ex vivo cultured (FIG. 6H) patient #1 and (FIG. 6I) patient #2 samples treated with venetoclax, SM09419 or the combination after 48 hours.

FIG. 7A: Distribution of CRISPR scores of sgRNAs targeting RNA processing genes (left) and variance comparisons (against venetoclax; right) from the genome-wide drug screens. The variance ratios and 95% confidence intervals were estimated via an F-test denoted on y-axis. FIGS. 7B-7D: Competition-based assay in MOLM-13 cells 10 days post-transduction with top 2 sgRNAs targeting each splicing factor or non-targeting sgRosa control (n=3, mean+SEM) treated with (FIG. 7B) 50 nM cytarabine, (FIG. 7C) 400 nM etoposide, or (FIG. 7D) 25 nM midostaurin. Statistical analysis was performed using unpaired Student's t-test by Prism GraphPad (*p<0.05, **p<0.01, n.s., not significant).

FIGS. 8A-8K. RBM10 ablation sensitizes AML cells to death from venetoclax but RBM10 is not required for normal hematopoiesis. FIG. 8A: Competition-based assay in MOLM-13 cells transduced with sgRBM10 treated with the indicated drugs (same dose used in CRISPR screens and indicated in the Methods section). Values are normalized to DMSO control. FIG. 8B: Box-and-whisker plot of RBM10 dependency score (CERES) as indicated on the y-axis across cancer types from DepMap database. Higher negative values are indicative that gene is essential. For the Box-and-whisker plot, the minimum to maximum showing all points, 25th-75th percentiles and median (horizontal line). FIGS. 8C-8D: Competition proliferation assay of sgRBM10 or non-targeting sgRosa in (FIG. 8C) NKM-1 and (FIG. 8D)

TP53-mutated cell lines (U937 and THP-1) treated with venetoclax or DMSO (n=3 for each condition, error bars represent SEM). FIG. 8E: Quantification of bioluminescent images from mice transplanted with RBM10 KO or sgRosa MOLM-13 cells at day 4 post-venetoclax (100 mg/kg) daily treatment (n=3, mean+SEM). FIG. 8F: CRISPResso indel analysis of RBM10 sgRNAs in MOLM-13 cells at the indicated timepoints. FIG. 8G: Genotyping of embryonic stem cell clones containing floxed Rbm10 allele using three distinct genotyping primers. FIG. 8H: Southern blot confirmation of floxed ES cell clones using the Southern probe labeled as "PB3/4." FIG. 8I: Validation of Rbm10 floxed alleles and excision of exon 3 of Rbm10 using genomic PCR. FIGS. 8J-8K: Peripheral blood counts (FIG. 8J) and (FIG. 8K) total cell numbers of tissues from primary non-competitive transplantation of Rbm10 cKO (n=4) and Mx1-cre control (n=4) after 1 month of pIpC treatment. Grey represents normal levels of blood counts. Statistical analysis was performed using an unpaired Student's t-test and error bars represent SEM.

FIG. 9A: Immunoblotting of endogenous RBM10 (left) and RNA visualization (right) of immunoprecipitation in MOLM-13 cells. FIG. 9B: Genomic distribution of RBM10 eClip binding sites in MOLM-13 cells. FIG. 9C: UpSet plot of overlapping splicing events in RBM10 KO and sgRosa treated with DMSO or venetoclax. FIG. 9D: Scatter plots of constitutive introns [in MOLM-13 cells transduced with sgRosa (x-axis) or sgRBM10 (y-axis)] in DMSO (left) or venetoclax treatment (right). FIG. 9E: Percent spliced in (PSI) values of the cassette exon (exon 1) inclusion isoform of XIAP Δexon1 (n=3, mean+SEM). FIGS. 9F-9G: Annexin V staining of (FIG. 9F) ectopic overexpression of XIAP full-length or XIAP Δexon1 treated with DMSO or venetoclax for 24 hours and (FIG. 9G) upon RBM10 KO compared to non-targeting sgRosa. FIG. 9H: RT-qPCR of BCL2A1 mRNA expression in MV4-11 human AML cells with two independent RBM10 sgRNAs and treated with 50 nM venetoclax for 48 hrs (n=3, mean+SEM). Statistical analysis was performed using unpaired Student's t-test by Prism GraphPad (*p<0.05). FIG. 9I: Correlation of BCL2A1 expression and venetoclax resistance (AUC) from BeatAML AML patients.

FIGS. 10A-10E. SM09419 is a highly specific CLK/DYRK inhibitor and synergizes with venetoclax. FIG. 10A: DepMap co-dependency CRISPR screen analysis of DYRK1A. FIG. 10B: NanoBRET target engagement assay of CLK1-4, DYRK1A/B, and DYRK2 after treatment with varying concentrations of SM09419. FIG. 10C: Western blot of total SR protein levels in MOLM-13 cells. FIG. 10D: Four synergy scores (ZIP, Loewe, HSA, and Bliss) (left) and 2D synergy plots (right) of MOLM-13 parental or venetoclax-resistant cells treated with venetoclax, SM09419, or the combination after 48 hours (Values were calculated from technical triplicates per experiment). FIG. 10E: Same as in FIG. 10D except treated with 5-azacytidine, cytarabine, midostaurin, or the combination of each.

FIGS. 11A-11B: (FIG. 11A) Analysis of normal C57BL/6 mice body weight and (FIG. 11B) complete blood counts (CBCs) at the indicated timepoints after daily treatment of SM09419 (25 mg/kg) (n=7) or vehicle (n=6). Yellow area represents the normal ranges for blood counts. (error bars represent mean+SEM). FIG. 11C: Total number of colony-forming units (CFUs) using methylcellulose assays with normal C57BL/6 treated with SM09419 daily for 3-weeks (n=3, mean+SEM). Colonies were assessed at day 7 after plating. FIG. 11D: Total cell numbers of tissues from normal C57BL/6 mice treated daily with SM09419 (25 mg/kg) (n=7) or vehicle (n=6) for 3 weeks (error bars represent SEM). FIG. 11E: Flow cytometry analysis of T-cells from spleen and peripheral blood after 3 weeks of SM09419 (n=7) or vehicle (n=6) daily treatment (error bars represent SEM). FIG. 11F: Flow cytometric analysis of hematopoietic stem and progenitor cells (HSPCs) in bone marrow from mice treated daily with SM09419 (n=7) or vehicle (n=6) daily treatment (error bars represent SEM) for 3 weeks. FIG. 11G: Assessment of kidney function (creatinine test) and liver function (AST, ALT, Alkaline phosphate, total Bilirubin) after treatment with daily SM09419 (n=7) or vehicle (n=6) daily treatment (error bars represent SEM) for 3 weeks. FIG. 11H: Hematoxylin and eosin (H&E) staining of liver after treatment with daily SM09419 for 3 weeks (bar: 500 μM). Statistical analysis was performed using unpaired Student's t-test by Prism GraphPad (*p<0.05, n.s., not significant).

FIG. 12A: Venn diagram of differentially genes expressed in RBM10 KO treated with venetoclax (compared to sgRosa) and SM09419 monotherapy or venetoclax-combined (compared to DMSO) from RNA-seq in MOLM-13 cells. FIG. 12B: Gene expression for MYC and MYB mRNA from MOLM-13 RNA-seq (n=3, mean+SEM). FIG. 12C: Mean PSI values of three replicates of each group treated with venetoclax or combination of SM09419 and venetoclax (n=3, mean+SEM). FIG. 12D: Dose-response curves of KG-1a parental and venetoclax-resistant cell lines treated with venetoclax or SM09419 (normalized to DMSO) after 96 hours (n=3, mean+SEM). FIG. 12E: Western blotting of XIAP, FLT3, MCL-1, and Actin in KG-1a parental or venetoclax-resistant cells after 24 hours of treatment. FIG. 12F: Mean PSI values and gene expression of SMYD2, DHODH, ATAD3A, CDC16, SRPK3, TRA2A, and DDX51 of each group treated with venetoclax or combination of SM09419 and venetoclax. p-values were determined by One-way ANOVA with post-hoc testing as indicated (n=3, mean+SEM).

DETAILED DESCRIPTION

Figure 1A:
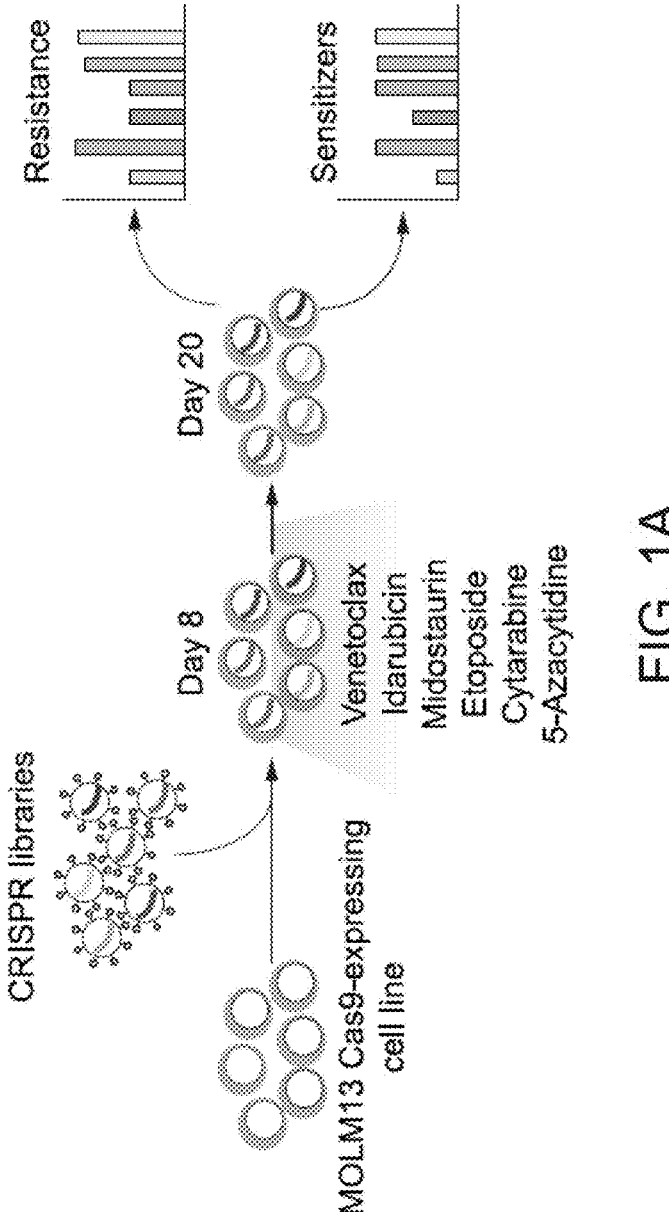
FIGS. 1A-1G. Mapping genomic determinants of AML drug response and synthetic lethal relationship between RNA splicing factors and venetoclax sensitivity.

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

Disclosed herein are unbiased genetic screens to map drug/gene interactions for a variety of clinically approved therapies used in the treatment of leukemia (e.g., AML). This effort highlighted a unique genetic relationship between response to venetoclax and the function of specific RNA splicing factors. While there is a well-established role for RNA splicing in the regulation of apoptosis 23, clinically viable means to manipulate splicing to enhance cell death in cancer have been limited to date. As genetic proof of concept, a number of splicing factors whose loss promotes cell death in the setting of venetoclax and are dispensable for normal hematopoiesis were identified, suggesting a therapeutic index for augmenting venetoclax response by modulating RNA splicing. Disclosed herein are compounds to modulate RNA splicing and enhance venetoclax response via inhibition of the splicing kinase families known as CLKs (CDC-like kinases) and DYRKs (dual-specificity tyrosine-regulated kinases).

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including but not limited to, orally, intranasally, intrathecally, parenterally (intravenously, intramuscularly, intraperitoneally, or subcutaneously), rectally, intrathecally, intraocularly, intradermally, transmucosally, iontophoretically, or topically. Administration includes self-administration and the administration by another.

The terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5.'" Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be an RNA sequence complementary to the DNA sequence or its complement sequence, and can also be a cDNA.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

"Detecting" as used herein refers to determining the presence of a mutation or alteration in a nucleic acid of interest in a sample. Detection does not require the method to provide 100% sensitivity. Analysis of nucleic acid markers can be performed using techniques known in the art including, but not limited to, sequence analysis, and electrophoretic analysis. Non-limiting examples of sequence analysis include Maxam-Gilbert sequencing, Sanger sequencing, capillary array DNA sequencing, thermal cycle sequencing (Scars et al., *Biotechniques,* 13:626-633 (1992)), solid-phase sequencing (Zimmerman et al., *Methods Mol. Cell Biol,* 3:39-42 (1992)), sequencing with mass spectrometry such as matrix-assisted laser desorption/ionization time-of-flight mass spectrometry (MALDI-TOF/MS; Fu et al., *Nat. Biotechnol,* 16:381-384 (1998)), and sequencing by hybridization. Chee et al., *Science,* 274:610-614 (1996); Drmanac et al., *Science,* 260:1649-1652 (1993); Drmanac et al., *Nat. Biotechnol,* 16:54-58 (1998). Non-limiting examples of electrophoretic analysis include slab gel electrophoresis such as agarose or polyacrylamide gel electrophoresis, capillary electrophoresis, and denaturing gradient gel electrophoresis. Additionally, next generation sequencing methods can be performed using commercially available kits and instruments from companies such as the Life Technologies/Ion Torrent PGM or Proton, the Illumina HiSEQ or MiSEQ, and the Roche/454 next generation sequencing system.

"Detectable label" as used herein refers to a molecule or a compound or a group of molecules or a group of compounds used to identify a nucleic acid or protein of interest. In some embodiments, the detectable label may be detected directly. In other embodiments, the detectable label may be a part of a binding pair, which can then be subsequently detected. Signals from the detectable label may be detected by various means and will depend on the nature of the detectable label. Detectable labels may be isotopes, fluorescent moieties, colored substances, and the like. Examples of means to detect detectable labels include but are not limited to spectroscopic, photochemical, biochemical, immuno-chemical, electromagnetic, radiochemical, or chemical means, such as fluorescence, chemifluorescence, or chemi-luminescence, or any other appropriate means.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associ-ated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in com-bination with one or more additional therapeutic com-pounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifi-cations of the translation product, if required for proper expression and function.

As used herein, the term "gene" means a segment of DNA that contains all the information for the regulated biosyn-thesis of an RNA product, including promoters, exons, introns, and other untranslated regions that control expres-sion.

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropri-ately stringent conditions to form a duplex or heteroduplex through formation of hydrogen bonds between complemen-tary base pairs. Hybridizations are typically and preferably conducted with probe-length nucleic acid molecules, pref-erably 15-100 nucleotides in length, more preferably 18-50 nucleotides in length. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point ($T_m$) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and param-eters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current*

*Protocols in Molecular Biology*, John Wiley & Sons, Secau-cus, N.J. In some embodiments, specific hybridization occurs under stringent hybridization conditions. An oligo-nucleotide or polynucleotide (e.g., a probe or a primer) that is specific for a target nucleic acid will "hybridize" to the target nucleic acid under suitable conditions.

"Next-generation sequencing or NGS" as used herein, refers to any sequencing method that determines the nucleo-tide sequence of either individual nucleic acid molecules (e.g., in single molecule sequencing) or clonally expanded proxies for individual nucleic acid molecules in a high throughput parallel fashion (e.g., greater than 103, 104, 105 or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. *Nature Biotechnology Reviews* 11:31-46 (2010).

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligo-nucleotide. The most common oligonucleotides have a back-bone of sugar phosphate units. A distinction may be made between oligodeoxyribonucleotides that do not have a hydroxyl group at the 2' position and oligoribonucleotides that have a hydroxyl group at the 2' position. Oligonucle-otides may also include derivatives, in which the hydrogen of the hydroxyl group is replaced with organic groups, e.g., an allyl group. Oligonucleotides of the method which func-tion as primers or probes are generally at least about 10-15 nucleotides long and more preferably at least about 15 to 25 nucleotides long, although shorter or longer oligonucle-otides may be used in the method. The exact size will depend on many factors, which in turn depend on the ultimate function or use of the oligonucleotide. The oligonucleotide may be generated in any manner, including, for example, chemical synthesis, DNA replication, restriction endonu-clease digestion of plasmids or phage DNA, reverse tran-scription, PCR, or a combination thereof. The oligonucle-otide may be modified e.g., by addition of a methyl group, a biotin or digoxigenin moiety, a fluorescent tag or by using radioactive nucleotides.

As used herein, the term "pharmaceutically-acceptable carrier" is intended to include any and all solvents, disper-sion media, coatings, antibacterial and antifungal com-pounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences (20$^{th}$ edition, ed. A. Gennaro, 2000, Lippincott, Williams & Wilkins, Philadelphia, Pa.).

As used herein, the terms "polypeptide," "peptide," and "protein" are used interchangeably herein to mean a polymer comprising two or more amino acids joined to each other by peptide bonds or modified peptide bonds, i.e., peptide isos-teres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "primer" refers to an oligonucleotide, which is capable of acting as a point of initiation of nucleic acid sequence synthesis when placed under conditions in which synthesis of a primer extension product which is complementary to a target nucleic acid strand is induced, i.e., in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. The term primer as used herein includes all forms of primers that may be synthesized including peptide nucleic acid primers, locked nucleic acid primers, phosphorothioate modified primers, labeled primers, and the like. The term "forward primer" as used herein means a primer that anneals to the anti-sense strand of dsDNA. A "reverse primer" anneals to the sense-strand of dsDNA.

As used herein, "primer pair" refers to a forward and reverse primer pair (i.e., a left and right primer pair) that can be used together to amplify a given region of a nucleic acid of interest.

"Probe" as used herein refers to nucleic acid that interacts with a target nucleic acid via hybridization. A probe may be fully complementary to a target nucleic acid sequence or partially complementary. The level of complementarity will depend on many factors based, in general, on the function of the probe. A probe or probes can be used, for example to detect the presence or absence of a mutation in a nucleic acid sequence by virtue of the sequence characteristics of the target. Probes can be labeled or unlabeled, or modified in any of a number of ways well known in the art. A probe may specifically hybridize to a target nucleic acid. Probes may be DNA, RNA or a RNA/DNA hybrid. Probes may be oligo-nucleotides, artificial chromosomes, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may comprise modified nucleobases, modified sugar moieties, and modified inter-nucleotide linkages. A probe may be used to detect the presence or absence of a target nucleic acid. Probes are typically at least about 10, 15, 20, 25, 30, 35, 40, 50, 60, 75, 100 nucleotides or more in length.

As used herein, "prevention," "prevent," or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample. As used herein, prevention includes preventing or delaying the initiation of symptoms of a disease or condition described herein and/or preventing a recurrence of one or more signs or symptoms of a disease or condition described herein.

As used herein, a "sample" or "biological sample" refers to a body fluid or a tissue sample isolated from a subject. In some cases, a biological sample may consist of or comprise whole blood, platelets, red blood cells, white blood cells, plasma, sera, urine, feces, epidermal sample, vaginal sample, skin sample, cheek swab, sperm, amniotic fluid, cultured cells, bone marrow sample, tumor biopsies, aspirate and/or chorionic villi, cultured cells, endothelial cells, synovial fluid, lymphatic fluid, ascites fluid, interstitial or extracellular fluid and the like. The term "sample" may also encompass the fluid in spaces between cells, including gingival crevicular fluid, bone marrow, cerebrospinal fluid (CSF), saliva, mucus, sputum, semen, sweat, urine, or any other bodily fluids. Samples can be obtained from a subject by any means including, but not limited to, venipuncture, excretion, ejaculation, massage, biopsy, needle aspirate, lavage, scraping, surgical incision, or intervention or other means known in the art. A blood sample can be whole blood or any fraction thereof, including blood cells (red blood cells, white blood cells or leukocytes, and platelets), serum and plasma.

The term "sensitivity," as used herein in reference to the methods of the present technology, is a measure of the ability of a method to detect a preselected sequence variant in a heterogeneous population of sequences. A method has a sensitivity of S % for variants of F % if, given a sample in which the preselected sequence variant is present as at least F % of the sequences in the sample, the method can detect the preselected sequence at a preselected confidence of C %, S % of the time. By way of example, a method has a sensitivity of 90% for variants of 5% if, given a sample in which the preselected variant sequence is present as at least 5% of the sequences in the sample, the method can detect the preselected sequence at a preselected confidence of 99%, 9 out of 10 times (F=5%; C=99%; S=90%).

As used herein, the term "separate" therapeutic use refers to an administration of at least two active ingredients at the same time or at substantially the same time by different routes.

As used herein, the term "sequential" therapeutic use refers to administration of at least two active ingredients at different times. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

The term "specific" as used herein in reference to an oligonucleotide primer means that the nucleotide sequence of the primer has at least 12 bases of sequence identity with a portion of the nucleic acid to be amplified when the oligonucleotide and the nucleic acid are aligned. An oligonucleotide primer that is specific for a nucleic acid is one that, under the stringent hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

"Specificity," as used herein, is a measure of the ability of a method to distinguish a truly occurring preselected sequence variant from sequencing artifacts or other closely related sequences. It is the ability to avoid false positive detections. False positive detections can arise from errors introduced into the sequence of interest during sample preparation, sequencing error, or inadvertent sequencing of closely related sequences like pseudo-genes or members of a gene family. A method has a specificity of X % if, when applied to a sample set of $N_{Total}$ sequences, in which $X_{True}$ sequences are truly variant and $X_{Not\ true}$ are not truly variant, the method selects at least X % of the not truly variant as not variant. E.g., a method has a specificity of 90% if, when applied to a sample set of 1,000 sequences, in which 500 sequences are truly variant and 500 are not truly variant, the method selects 90% of the 500 not truly variant sequences as not variant. Exemplary specificities include 90, 95, 98, and 99%.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

As used herein, the terms "subject", "patient", or "individual" can be an individual organism, a vertebrate, a mammal, or a human. In some embodiments, the subject, patient or individual is a human.

As used herein, a "synergistic therapeutic effect" refers to a greater-than-additive therapeutic effect which is produced by a combination of at least two agents, and which exceeds that which would otherwise result from the individual administration of the agents. For example, lower doses of one or more agents may be used in treating a disease or disorder, resulting in increased therapeutic efficacy and decreased side-effects. As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Nucleic Acid Amplification and/or Detection

Polynucleotides associated with responsiveness to intra-operative opioid analgesics can be detected by the use of nucleic acid amplification techniques that are well known in the art. The starting material may be genomic DNA, cDNA, RNA or mRNA. Nucleic acid amplification can be linear or exponential. Specific variants or mutations may be detected by the use of amplification methods with the aid of oligo-nucleotide primers or probes designed to interact with or hybridize to a particular target sequence in a specific manner, thus amplifying only the target variant.

Non-limiting examples of nucleic acid amplification techniques include polymerase chain reaction (PCR), real-time quantitative PCR (qPCR), digital PCR (dPCR), reverse transcriptase polymerase chain reaction (RT-PCR), nested PCR, ligase chain reaction (see Abravaya, K. et al., *Nucleic Acids Res.* (1995), 23:675-682), branched DNA signal amplification (see Urdea, M. S. et al., *AIDS* (1993), 7(suppl 2):S11-S14), amplifiable RNA reporters, Q-beta replication, transcription-based amplification, boomerang DNA amplification, strand displacement activation, cycling probe technology, isothermal nucleic acid sequence based amplification (NASBA) (see Kievits, T. et al., *J Virological Methods* (1991), 35:273-286), Invader Technology, next-generation sequencing technology or other sequence replication assays or signal amplification assays.

Primers: Oligonucleotide primers for use in amplification methods can be designed according to general guidance well known in the art as described herein, as well as with specific requirements as described herein for each step of the particular methods described. In some embodiments, oligonucleotide primers for cDNA synthesis and PCR are 10 to 100 nucleotides in length, preferably between about 15 and about 60 nucleotides in length, more preferably 25 and about 50 nucleotides in length, and most preferably between about 25 and about 40 nucleotides in length.

$T_m$ of a polynucleotide affects its hybridization to another polynucleotide (e.g., the annealing of an oligonucleotide primer to a template polynucleotide). In certain embodiments of the disclosed methods, the oligonucleotide primer used in various steps selectively hybridizes to a target template or polynucleotides derived from the target template (i.e., first and second strand cDNAs and amplified products). Typically, selective hybridization occurs when two polynucleotide sequences are substantially complementary (at least about 65% complementary over a stretch of at least 14 to 25 nucleotides, preferably at least about 75%, more preferably at least about 90% complementary). See Kanehisa, M., *Polynucleotides Res.* (1984), 12:203, incorporated herein by reference. As a result, it is expected that a certain degree of mismatch at the priming site is tolerated. Such mismatch may be small, such as a mono-, di- or tri-nucleotide. In certain embodiments, 100% complementarity exists.

Probes: Probes are capable of hybridizing to at least a portion of the nucleic acid of interest or a reference nucleic acid (i.e., wild-type sequence). Probes may be an oligonucleotide, artificial chromosome, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may be used for detecting and/or capturing/purifying a nucleic acid of interest.

Typically, probes can be about 10 nucleotides, about 20 nucleotides, about 25 nucleotides, about 30 nucleotides, about 35 nucleotides, about 40 nucleotides, about 50 nucleotides, about 60 nucleotides, about 75 nucleotides, or about 100 nucleotides long. However, longer probes are possible. Longer probes can be about 200 nucleotides, about 300 nucleotides, about 400 nucleotides, about 500 nucleotides, about 750 nucleotides, about 1,000 nucleotides, about 1,500 nucleotides, about 2,000 nucleotides, about 2,500 nucleotides, about 3,000 nucleotides, about 3,500 nucleotides, about 4,000 nucleotides, about 5,000 nucleotides, about 7,500 nucleotides, or about 10,000 nucleotides long.

Probes may also include a detectable label or a plurality of detectable labels. The detectable label associated with the probe can generate a detectable signal directly. Additionally, the detectable label associated with the probe can be detected indirectly using a reagent, wherein the reagent includes a detectable label, and binds to the label associated with the probe.

In some embodiments, detectably labeled probes can be used in hybridization assays including, but not limited to Northern blots, Southern blots, microarray, dot or slot blots, and in situ hybridization assays such as fluorescent in situ hybridization (FISH) to detect a target nucleic acid sequence within a biological sample. Certain embodiments may employ hybridization methods for measuring expression of a polynucleotide gene product, such as mRNA. Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2nd Ed. Cold Spring Harbor, N.Y., 1989); Berger and Kimmel *Methods in Enzymology*, Vol. 152, Guide to Molecular Cloning Techniques (Academic Press, Inc., San Diego, Calif, 1987); Young and Davis, *PNAS.* 80: 1194 (1983).

Detectably labeled probes can also be used to monitor the amplification of a target nucleic acid sequence. In some embodiments, detectably labeled probes present in an amplification reaction are suitable for monitoring the amount of amplicon(s) produced as a function of time. Examples of such probes include, but are not limited to, the 5'-exonuclease assay (TAQMAN® probes described herein (see also U.S. Pat. No. 5,538,848) various stem-loop molecular beacons (see for example, U.S. Pat. Nos. 6,103,476 and 5,925, 517 and Tyagi and Kramer, 1996, *Nature Biotechnology* 14:303-308), stemless or linear beacons (see, e.g., WO 99/21881), PNA Molecular Beacons™ (see, e.g., U.S. Pat. Nos. 6,355,421 and 6,593,091), linear PNA beacons (see, for example, Kubista et al., 2001, *SPIE* 4264:53-58), non-FRET probes (see, for example, U.S. Pat. No. 6,150,097), Sunrise®/Amplifluor™ probes (U.S. Pat. No. 6,548,250), stemloop and duplex Scorpion probes (Solinas et al., 2001, *Nucleic Acids Research* 29: E96 and U.S. Pat. No. 6,589, 743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, *Methods* 25:463-471; Whitcombe et al., 1999, *Nature Biotechnology.* 17:804-807; Isacsson et al., 2000, *Molecular Cell Probes.* 14:321-328; Svanvik et al., 2000, Anal Biochem. 281:26-35; Wolffs et al., 2001, *Biotechniques* 766:769-771; Tsourkas et al., 2002, *Nucleic Acids Research.* 30:4208-4215; Riccelli et al., 2002, *Nucleic Acids Research* 30:4088-4093; Zhang et al., 2002 *Shanghai.* 34:329-332; Maxwell et al., 2002, *J. Am. Chem. Soc.* 124:9606-9612; Broude et al., 2002, *Trends Biotechnol.* 20:249-56; Huang et al., 2002, *Chem. Res. Toxicol.* 15:118-126; and Yu et al., 2001, *J. Am. Chem. Soc* 14:11155-11161.

In some embodiments, the detectable label is a fluorophore. Suitable fluorescent moieties include but are not limited to the following fluorophores working individually or in combination: 4-acetamido-4'-isothiocyanatostilbene-2, 2'disulfonic acid; acridine and derivatives: acridine, acridine isothiocyanate; Alexa Fluors: Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes); 5-(2-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Black Hole Quencher™ (BHQ™) dyes (biosearch Technologies); BODIPY dyes: BODIPY® R-6G, BOPIPY® 530/550, BODIPY® FL; Brilliant Yellow; coumarin and derivatives: coumarin, 7-amino-4-methylcoumarin (AMC, Coumarin 120), 7-amino-4-trifluoromethylcouluarin (Coumarin 151); Cy2®, Cy3®, Cy3.5®, Cy5®, Cy5.5®; cyanosine; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); Eclipse™ (Epoch Biosciences Inc.); eosin and derivatives: eosin, eosin isothiocyanate; erythrosin and derivatives: erythrosin B, erythrosin isothiocyanate; ethidium; fluorescein and derivatives: 5-carboxyfluorescein (FAM), 5-(4,6-dichlorotriazin-2-yl)amino fluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescem (TET); fluorescamine; IR144; IR1446; lanthamide phosphors; Malachite Green isothiocyanate; 4-methylumbelliferone; ortho cresolphthalein; nitrotyrosine; pararosaniline; Phenol Red; B-phycocrythrin, R-phycoerythrin; allophycocyanin; o-phthaldialdehyde; Oregon Green®; propidium iodide; pyrene and derivatives: pyrene, pyrene butyrate, succinimidyl 1-pyrene butyrate; QSY® 7; QSY® 9; QSY® 21; QSY® 35 (Molecular Probes); Reactive Red 4 (Cibacron® Brilliant Red 3B-A); rhodamine and derivatives: 6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, riboflavin, rosolic acid, sulforhodamine B, sulforhodamine 101, sulfonyl chloride derivative of sulforhodamine 101 (Texas Red); terbium chelate derivatives; N,N,N',N'-tetramethyl-6-carboxyrhodamine (TAMRA); tetramethyl rhodamine; tetramethyl rhodamine isothiocyanate (TRITC); and VIC®. Detector probes can also comprise sulfonate derivatives of fluorescenin dyes with S03 instead of the carboxylate group, phosphoramidite forms of fluorescein, phosphoramidite forms of CY 5 (commercially available for example from Amersham).

Detectably labeled probes can also include quenchers, including without limitation black hole quenchers (Biosearch), Iowa Black (IDT), QSY quencher (Molecular Probes), and Dabsyl and Dabcel sulfonate/carboxylate Quenchers (Epoch).

Detectably labeled probes can also include two probes, wherein for example a fluorophore is on one probe, and a quencher is on the other probe, wherein hybridization of the two probes together on a target quenches the signal, or wherein hybridization on the target alters the signal signature via a change in fluorescence.

In some embodiments, interchelating labels such as ethidium bromide, SYBR® Green I (Molecular Probes), and PicoGreen® (Molecular Probes) are used, thereby allowing visualization in real-time, or at the end point, of an amplification product in the absence of a detector probe. In some embodiments, real-time visualization may involve the use of both an intercalating detector probe and a sequence-based detector probe. In some embodiments, the detector probe is at least partially quenched when not hybridized to a complementary sequence in the amplification reaction, and is at least partially unquenched when hybridized to a complementary sequence in the amplification reaction.

In some embodiments, the amount of probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator.

Primers or probes may be designed to selectively hybridize to any portion of a nucleic acid sequence encoding a RBM10 polypeptide.

Exemplary nucleic acid sequences of the human RBM10 is provided below:

```
NM_005676.5 Homo sapiens RNA binding motif protein 10 (RBM10), transcript
variant 1, mRNA
                                                             (SEQ ID NO: 1)
AGTAGGTGGATGGTGGTCGGAGCGCCGACTCCCTTCTCGTCGTCGCCATTTTGAGCTGGTGACTGTGGCC

GGCTGGGAGTAGGCGGCAGTGAGTTTCCCTGGGAGGGCAGCGCGCTTGGCGCTTCTCCCCTCCCCCCGAT

CTGCCTCCAGTCTCGGACTTGGTTGTTGCGCGCTCCGGCTCCGGCTGAGCTGGGAGAGTTGGAGGAGGTG

GCGGCGGGCAGAGGTGATGTCTGGGAGCCCTTCCTTGACAGCCCGGGCCGAGAAGAGTCCCTGCAGGAAG

CATCACCCAGGCTGGCAGATCATGGTAGCAGCAGCGGGGGTGGCTGGGAAGTGAAACGGAGCCAGCGGCT

GAGGAGGGGCCCCAGCAGCCCCCGAAGGCCCTATCAGGACATGGAGTATGAAAGACGTGGTGGTCGTGGT

GACAGGACTGGCCGCTATGGAGCCACTGACCGCTCGCAGGATGATGGTGGGGAGAACCGCAGCCGAGACC

ACGACTACCGGGACATGGACTACCGTTCATATCCTCGCGAGTATGGCAGCCAGGAGGGCAAGCATGACTA

TGACGACTCATCTGAGGAGCAGAGTGCGGAGGATTCCTACGAGGCCTCCCCGGGCTCCGAGACTCAGCGT

AGGCGGCGGCGGCGGCACAGGCACAGCCCCACCGGCCCGCCAGGCTTCCCCCGAGACGGCGACTATCGGG

ACCAGGACTATCGGACCGAGCAAGGGGAGGAGGAGGAGGAGGAGGAGGATGAGGAGGAGGAGGAGAAGGC

CAGTAACATCGTCATGCTGAGGATGCTGCCACAGGCAGCCACTGAGGATGACATCCGTGGCCAGCTGCAG

TCGCACGGCGTGCAAGCACGGGAGGTTCGGCTGATGCGGAACAAATCTTCAGGTCAGAGCCGGGGCTTCG

CCTTCGTCGAGTTTAGTCACTTGCAGGACGCTACACGATGGATGGAAGCCAATCAGCACTCCCTCAACAT

CCTGGGCCAGAAGGTGTCGATGCACTACAGTGACCCCAAGCCCAAGATCAATGAGGACTGGCTGTGCAAT

AAGTGTGGCGTCCAGAACTTCAAACGCCGAGAGAAGTGCTTCAAATGTGGCGTGCCCAAGTCAGAGGCAG

AGCAGAAGCTGCCCCTCGGCACGAGGCTGGATCAGCAGACACTGCCACTGGGTGGCCGGGAGCTGAGCCA

GGGCCTGCTTCCCCTGCCGCAGCCCTACCAGGCCCAGGGAGTCCTGGCCTCCCAAGCCCTGTCACAGGGC

TCGGAGCCAAGCTCAGAGAACGCCAATGACACCATCATTTTGCGCAACCTGAACCCACACAGCACCATGG

ATTCCATCCTGGGGGCCCTGGCACCCTACGCGGTGCTGTCCTCCTCCAACGTGCGCGTCATAAAGGACAA

GCAGACCCAACTGAACCGCGGCTTTGCCTTCATCCAGCTCTCCACCATCGTGGAGGCAGCCCAGCTGCTG

CAGATCCTGCAGGCCCTGCACCCACCACTCACTATCGACGGCAAGACCATCAATGTTGAGTTTGCCAAGG

GTTCTAAGAGGGACATGGCCTCCAATGAAGGCAGTCGCATCAGTGCTGCCTCTGTGGCCAGCACTGCCAT

TGCTGCGGCCCAGTGGGCCATCTCACAGGCCTCCCAAGGTGGGGAGGGTACCTGGGCCACCTCCGAGGAG

CCGCCGGTCGACTACAGCTACTACCAACAGGATGAGGGCTATGGCAACAGCCAGGGCACAGAGTCTTCCC

TCTATGCCCATGGCTACCTCAAGGGCACCAAGGGCCCTGGCATCACTGGAACCAAAGGGGATCCCACTGG

AGCAGGTCCCGAGGCCTCCCTAGAGCCTGGGGCCGACTCTGTGTCGATGCAGGCTTTCTCTCGCGCCCAG

CCTGGTGCTGCTCCTGGCATCTACCAACAATCAGCCGAGGCGAGCAGTAGCCAGGGCACTGCTGCCAACA

GCCAGTCGTATACCATCATGTCACCCGCTGTGCTCAAATCTGAGCTCCAGAGCCCTACCCATCCTAGTTC

TGCTCTCCCACCGGCTACCAGCCCCACTGCCCAGGAATCCTACAGCCAGTACCCTGTTCCCGACGTCTCT

ACCTACCAGTACGATGAGACCTCCGGCTACTACTATGACCCCCAGACCGGCCTCTACTATGACCCCAACT

CCCAGTATTACTACAATGCTCAGAGCCAGCAGTACCTGTACTGGGATGGGGAGAGGCGGACCTATGTTCC
```

-continued

CGCCCTGGAGCAGTCGGCCGACGGACATAAGGAGACAGGGGCACCCTCGAAGGAGGGCAAAGAGAAGAAG

GAGAAGCACAAGACCAAGACAGCTCAACAGATTGCCAAGGACATGGAACGCTGGGCCCGCAGTCTCAACA

AACAAAAAGAAAACTTCAAAAATAGCTTCCAGCCTATCAGCTCCCTGCGAGATGACGAGAGGCGGGAGTC

AGCCACTGCAGATGCTGGCTATGCCATCCTCGAGAAGAAGGGAGCACTAGCCGAGAGACAGCACACCAGC

ATGGATCTCCCGAAATTGGCCAGTGACGACCGCCCAAGCCCTCCGCGAGGACTGGTGGCAGCCTACAGCG

GGGAGAGTGACAGTGAGGAGGAGCAGGAGCGTGGGGGCCCTGAGCGGGAGGAGAAGCTCACCGACTGGCA

GAAGCTGGCCTGTCTGCTCTGCCGACGCCAGTTCCCCAGCAAAGAGGCGCTCATCCGGCACCAGCAGCTC

TCAGGGCTCCACAAGCAAAACCTTGAGATTCACCGGCGAGCCCACTTGTCAGAAAACGAGCTAGAAGCAC

TAGAGAAGAATGACATGGAGCAAATGAAGTACCGGGACCGTGCAGCTGAACGCAGAGAAAAGTATGGCAT

CCCCGAGCCGCCAGAGCCCAAGAGGAGGAAGTACGGCGGCATATCCACAGCCTCTGTAGACTTCGAGCAG

CCTACTCGGGACGGGCTGGGCAGTGACAACATTGGCAGTCGGATGCTGCAGGCCATGGGCTGGAAAGAGG

GCAGCGGCCTGGGCCGCAAGAAGCAGGGCATTGTAACGCCTATCGAGGCCCAAACACGGGTGCGGGGCTC

CGGCCTGGGTGCACGGGGCAGCTCCTACGGGGTCACCTCAACCGAGTCCTACAAGGAGACACTGCACAAG

ACAATGGTGACCCGCTTCAACGAGGCCCAGTGAGCAGCTTCAAGAGCAACTTCTCCACATGTTGGGTGTC

CATCCTGGGGCAGGGAAGGACAGAGTGTTGGATGGCTGGGACGGGGCCTTGCTCTTGTCGGCCAGCCCAC

TCCCCAGCCAGAGAGGGCTTGACCAAATCAAATTGAGGTGGTGACTTTTGTTGGAAAATTGGGCTGGGAT

CACGTCCTGTTTTGTAATAAAAGCTGAAAGTCTGCA

NM_005676.5 *Homo sapiens* RNA binding motif protein 10 (RBM10),
transcript variant 1, mRNA (SEQ ID NO: 2)

AGTAGGTGGATGGTGGTCGGAGCGCCGACTCCCTTCTCGTCGTCGCCATTTTGAGCTGGTGACTGTGGCC

GGCTGGGAGTAGGCGGCAGTGAGTTTCCCTGGGAGGGCAGCGCGCTTGGCGCTTCTCCCCTCCCCCCGAT

CTGCCTCCAGTCTCGGACTTGGTTGTTGCGCGCTCCGGCTCCGGCTGAGCTGGGAGAGTTGGAGGAGGTG

GCGGCGGGCAGAGGTGATGTCTGGGAGCCCTTCCTTGACAGCCCGGGCCGAGAAGAGTCCCTGCAGGAAG

CATCACCCAGGCTGGCAGATCATGGTAGCAGCAGCGGGGGTGGCTGGGAAGTGAAACGGAGCCAGCGGCT

GAGGAGGGGCCCCAGCAGCCCCCGAAGGCCCTATCAGGACATGGAGTATGAAAGACGTGGTGGTCGTGGT

GACAGGACTGGCCGCTATGGAGCCACTGACCGCTCGCAGGATGATGGTGGGGAGAACCGCAGCCGAGACC

ACGACTACCGGGACATGGACTACCGTTCATATCCTCGCGAGTATGGCAGCCAGGAGGGCAAGCATGACTA

TGACGACTCATCTGAGGAGCAGAGTGCGGAGGATTCCTACGAGGCCTCCCCGGGCTCCGAGACTCAGCGT

AGGCGGCGGCGGCGGCACAGGCACAGCCCCACCGGCCGCCAGGCTTCCCCCGAGACGGCGACTATCGGG

ACCAGGACTATCGGACCGAGCAAGGGGAGGAGGAGGAGGAGGAGGAGGATGAGGAGGAGGAGGAGAAGGC

CAGTAACATCGTCATGCTGAGGATGCTGCCACAGGCAGCCACTGAGGATGACATCCGTGGCCAGCTGCAG

TCGCACGGCGTGCAAGCACGGGAGGTTCGGCTGATGCGGAACAAATCTTCAGGTCAGAGCCGGGGCTTCG

CCTTCGTCGAGTTTAGTCACTTGCAGGACGCTACACGATGGATGGAAGCCAATCAGCACTCCCTCAACAT

CCTGGGCCAGAAGGTGTCGATGCACTACAGTGACCCCAAGCCCAAGATCAATGAGGACTGGCTGTGCAAT

AAGTGTGGCGTCCAGAACTTCAAACGCCGAGAGAAGTGCTTCAAATGTGGCGTGCCCAAGTCAGAGGCAG

AGCAGAAGCTGCCCCTCGGCACGAGGCTGGATCAGCAGACACTGCCACTGGGTGGCCGGGAGCTGAGCCA

GGGCCTGCTTCCCCTGCCGCAGCCCTACCAGGCCCAGGGAGTCCTGGCCTCCCAAGCCCTGTCACAGGGC

TCGGAGCCAAGCTCAGAGAACGCCAATGACACCATCATTTTGCGCAACCTGAACCCACACAGCACCATGG

ATTCCATCCTGGGGGCCCTGGCACCCTACGCGGTGCTGTCCTCCTCCAACGTGCGCGTCATAAAGGACAA

GCAGACCCAACTGAACCGCGGCTTTGCCTTCATCCAGCTCTCCACCATCGTGGAGGCAGCCCAGCTGCTG

CAGATCCTGCAGGCCCTGCACCCACCACTCACTATCGACGGCAAGACCATCAATGTTGAGTTTGCCAAGG

-continued

GTTCTAAGAGGGACATGGCCTCCAATGAAGGCAGTCGCATCAGTGCTGCCTCTGTGGCCAGCACTGCCAT

TGCTGCGGCCCAGTGGGCCATCTCACAGGCCTCCCAAGGTGGGGAGGGTACCTGGGCCACCTCCGAGGAG

CCGCCGGTCGACTACAGCTACTACCAACAGGATGAGGGCTATGGCAACAGCCAGGGCACAGAGTCTTCCC

TCTATGCCCATGGCTACCTCAAGGGCACCAAGGGCCCTGGCATCACTGGAACCAAAGGGGATCCCACTGG

AGCAGGTCCCGAGGCCTCCCTAGAGCCTGGGGCCGACTCTGTGTCGATGCAGGCTTTCTCTCGCGCCCAG

CCTGGTGCTGCTCCTGGCATCTACCAACAATCAGCCGAGGCGAGCAGTAGCCAGGGCACTGCTGCCAACA

GCCAGTCGTATACCATCATGTCACCCGCTGTGCTCAAATCTGAGCTCCAGAGCCCTACCCATCCTAGTTC

TGCTCTCCCACCGGCTACCAGCCCCACTGCCCAGGAATCCTACAGCCAGTACCCTGTTCCCGACGTCTCT

ACCTACCAGTACGATGAGACCTCCGGCTACTACTATGACCCCCAGACCGGCCTCTACTATGACCCCAACT

CCCAGTATTACTACAATGCTCAGAGCCAGCAGTACCTGTACTGGGATGGGGAGAGGCGGACCTATGTTCC

CGCCCTGGAGCAGTCGGCCGACGGACATAAGGAGACAGGGGCACCCTCGAAGGAGGGCAAAGAGAAGAAG

GAGAAGCACAAGACCAAGCAGCTCAACAGATTGCCAAGGACATGGAACGCTGGGCCCGCAGTCTCAACA

AACAAAAAGAAAACTTCAAAAATAGCTTCCAGCCTATCAGCTCCCTGCGAGATGACGAGAGGCGGGAGTC

AGCCACTGCAGATGCTGGCTATGCCATCCTCGAGAAGAAGGGAGCACTAGCCGAGAGACAGCACACCAGC

ATGGATCTCCCGAAATTGGCCAGTGACGACCGCCCAAGCCCTCCGCGAGGACTGGTGGCAGCCTACAGCG

GGGAGAGTGACAGTGAGGAGGAGCAGGAGCGTGGGGGCCCTGAGCGGGAGGAGAAGCTCACCGACTGGCA

GAAGCTGGCCTGTCTGCTCTGCCGACGCCAGTTCCCCAGCAAAGAGGCGCTCATCCGGCACCAGCAGCTC

TCAGGGCTCCACAAGCAAAACCTTGAGATTCACCGGCGAGCCCACTTGTCAGAAAACGAGCTAGAAGCAC

TAGAGAAGAATGACATGGAGCAAATGAAGTACCGGGACCGTGCAGCTGAACGCAGAGAAAAGTATGGCAT

CCCCGAGCCGCCAGAGCCCAAGAGGAGGAAGTACGGCGGCATATCCACAGCCTCTGTAGACTTCGAGCAG

CCTACTCGGGACGGGCTGGGCAGTGACAACATTGGCAGTCGGATGCTGCAGGCCATGGGCTGGAAAGAGG

GCAGCGGCCTGGGCCGCAAGAAGCAGGGCATTGTAACGCCTATCGAGGCCCAAACACGGGTGCGGGGCTC

CGGCCTGGGTGCACGGGGCAGCTCCTACGGGGTCACCTCAACCGAGTCCTACAAGGAGACACTGCACAAG

ACAATGGTGACCCGCTTCAACGAGGCCCAGTGAGCAGCTTCAAGAGCAACTTCTCCACATGTTGGGTGTC

CATCCTGGGGCAGGGAAGGACAGAGTGTTGGATGGCTGGGACGGGGCCTTGCTCTTGTCGGCCAGCCCAC

TCCCCAGCCAGAGAGGGCTTGACCAAATCAAATTGAGGTGGTGACTTTTGTTGGAAAATTGGGCTGGGAT

CACGTCCTGTTTTGTAATAAAAGCTGAAAGTCTGCA

NM_001204466.2 *Homo sapiens* RNA binding motif protein 10 (RBM10),
transcript variant 3, mRNA (SEQ ID NO: 3)
AGTAGGTGGATGGTGGTCGGAGCGCCGACTCCCTTCTCGTCGTCGCCATTTTGAGCTGGTGACTGTGGCC

GGCTGGGAGTAGGCGGCAGTGAGTTTCCCTGGGAGGGCAGCGCGCTTGGCGCTTCTCCCCTCCCCCCGAT

CTGCCTCCAGTCTCGGACTTGGTTGTTGCGCGCTCCGGCTCCGGCTGAGCTGGGAGAGTTGGAGGAGGTG

GCGGCGGGCAGAGGTGATGTCTGGGAGCCCCTTCCTTGACAGCCCGGGCCGAGAAGAGTCCCTGCAGGAAG

CATCACCCAGGCTGGCAGATCATGGTAGCAGCAGCGGGGGTGGCTGGGAAGTGAAACGGAGCCAGCGGCT

GAGGAGGGGCCCCAGCAGCCCCCGAAGGCCCTATCAGGACATGGAGTATGAAAGACGTGGTGGTCGTGGT

GACAGGACTGGCCGCTATGGAGCCACTGACCGCTCGCAGGATGATGGTGGGGAGAACCGCAGCCGAGACC

ACGACTACCGGGACATGGACTACCGTTCATATCCTCGCGAGTATGGCAGCCAGGAGGGCAAGCATGACTA

TGACGACTCATCTGAGGAGCAGAGTGCGGAGATCCGTGGCCAGCTGCAGTCGCACGGCGTGCAAGCACGG

GAGGTTCGGCTGATGCGGAACAAATCTTCAGGTCAGAGCCGGGGCTTCGCCTTCGTCGAGTTTAGTCACT

TGCAGGACGCTACACGATGGATGGAAGCCAATCAGCACTCCCTCAACATCCTGGGCCAGAAGGTGTCGAT

GCACTACAGTGACCCCAAGCCCAAGATCAATGAGGACTGGCTGTGCAATAAGTGTGGCGTCCAGAACTTC

-continued

```
AAACGCCGAGAGAAGTGCTTCAAATGTGGCGTGCCCAAGTCAGAGGCAGAGCAGAAGCTGCCCCTCGGCA

CGAGGCTGGATCAGCAGACACTGCCACTGGGTGGCCGGGAGCTGAGCCAGGGCCTGCTTCCCCTGCCGCA

GCCCTACCAGGCCCAGGGAGTCCTGGCCTCCCAAGCCCTGTCACAGGGCTCGGAGCCAAGCTCAGAGAAC

GCCAATGACACCATCATTTTGCGCAACCTGAACCCACACAGCACCATGGATTCCATCCTGGGGGCCCTGG

CACCCTACGCGGTGCTGTCCTCCTCCAACGTGCGCGTCATAAAGGACAAGCAGACCCAACTGAACCGCGG

CTTTGCCTTCATCCAGCTCTCCACCATCGTGGAGGCAGCCCAGCTGCTGCAGATCCTGCAGGCCCTGCAC

CCACCACTCACTATCGACGGCAAGACCATCAATGTTGAGTTTGCCAAGGGTTCTAAGAGGGACATGGCCT

CCAATGAAGGCAGTCGCATCAGTGCTGCCTCTGTGGCCAGCACTGCCATTGCTGCGGCCCAGTGGGCCAT

CTCACAGGCCTCCCAAGGTGGGGAGGGTACCTGGGCCACCTCCGAGGAGCCGCCGGTCGACTACAGCTAC

TACCAACAGGATGAGGGCTATGGCAACAGCCAGGGCACAGAGTCTTCCCTCTATGCCCATGGCTACCTCA

AGGGCACCAAGGGCCCTGGCATCACTGGAACCAAAGGGGATCCCACTGGAGCAGGTCCCGAGGCCTCCCT

AGAGCCTGGGGCCGACTCTGTGTCGATGCAGGCTTTCTCTCGCGCCCAGCCTGGTGCTGCTCCTGGCATC

TACCAACAATCAGCCGAGGCGAGCAGTAGCCAGGGCACTGCTGCCAACAGCCAGTCGTATACCATCATGT

CACCCGCTGTGCTCAAATCTGAGCTCCAGAGCCCTACCCATCCTAGTTCTGCTCTCCCACCGGCTACCAG

CCCCACTGCCCAGGAATCCTACAGCCAGTACCCTGTTCCCGACGTCTCTACCTACCAGTACGATGAGACC

TCCGGCTACTACTATGACCCCCAGACCGGCCTCTACTATGACCCCAACTCCCAGTATTACTACAATGCTC

AGAGCCAGCAGTACCTGTACTGGGATGGGGAGAGGCGGACCTATGTTCCCGCCCTGGAGCAGTCGGCCGA

CGGACATAAGGAGACAGGGGCACCCTCGAAGGAGGGCAAAGAGAAGAAGGAGAAGCACAAGACCAAGACA

GCTCAACAGATTGCCAAGGACATGGAACGCTGGGCCCGCAGTCTCAACAAACAAAAAGAAAACTTCAAAA

ATAGCTTCCAGCCTATCAGCTCCCTGCGAGATGACGAGAGGCGGGAGTCAGCCACTGCAGATGCTGGCTA

TGCCATCCTCGAGAAGAAGGGAGCACTAGCCGAGAGACAGCACACCAGCATGGATCTCCCGAAATTGGCC

AGTGACGACCGCCCAAGCCCTCCGCGAGGACTGGTGGCAGCCTACAGCGGGGAGAGTGACAGTGAGGAGG

AGCAGGAGCGTGGGGGCCCTGAGCGGGAGGAGAAGCTCACCGACTGGCAGAAGCTGGCCTGTCTGCTCTG

CCGACGCCAGTTCCCCAGCAAAGAGGCGCTCATCCGGCACCAGCAGCTCTCAGGGCTCCACAAGCAAAAC

CTTGAGATTCACCGGCGAGCCCACTTGTCAGAAAACGAGCTAGAAGCACTAGAGAAGAATGACATGGAGC

AAAATGAAGTACCGGGACCGTGCAGCTGAACGCAGAGAAAAGTATGGCATCCCCGAGCCGCCAGAGCCCAA

GAGGAGGAAGTACGGCGGCATATCCACAGCCTCTGTAGACTTCGAGCAGCCTACTCGGGACGGGCTGGGC

AGTGACAACATTGGCAGTCGGATGCTGCAGGCCATGGGCTGGAAAGAGGGCAGCGGCCTGGGCCGCAAGA

AGCAGGGCATTGTAACGCCTATCGAGGCCCAAACACGGGTGCGGGGCTCCGGCCTGGGTGCACGGGGCAG

CTCCTACGGGGTCACCTCAACCGAGTCCTACAAGGAGACACTGCACAAGACAATGGTGACCCGCTTCAAC

GAGGCCCAGTGAGCAGCTTCAAGAGCAACTTCTCCACATGTTGGGTGTCCATCCTGGGGCAGGGAAGGAC

AGAGTGTTGGATGGCTGGGACGGGGCCTTGCTCTTGTCGGCCAGCCCACTCCCCAGCCAGAGAGGGCTTG

ACCAAATCAAATTGAGGTGGTGACTTTTGTTGGAAAATTGGGCTGGATCACGTCCTGTTTTGTAATAAA

AGCTGAAAAGTCTGCA
```

NM_001204467.2 *Homo sapiens* RNA binding motif protein 10 (RBM10),
transcript variant 4, mRNA (SEQ ID NO: 4)

```
AGTAGGTGGATGGTGGTCGGAGCGCCGACTCCCTTCTCGTCGTCGCCATTTTGAGCTGGTGACTGTGGCC

GGCTGGGAGTAGGCGGCAGTGAGTTTCCCTGGGAGGGCAGCGCGCTTGGCGCTTCTCCCCTCCCCCCGAT

CTGCCTCCAGTCTCGGACTTGGTTGTTGCGCGCTCCGGCTCCGGCTGAGCTGGGAGAGTTGGAGGAGGTG

GCGGCGGGCAGAGGTGATGTCTGGGAGCCCTTCCTTGACAGCCCGGGCCGAGAAGAGTCCCTGCAGGAAG

CATCACCCAGGCTGGCAGATCATGGTAGCAGCAGCGGGGGTGGCTGGGAAGTGAAACGGAGCCAGCGGCT
```

-continued

GAGGAGGGGCCCCAGCAGCCCCCGAAGGCCCTATCAGGACATGGAGTATGAAAGACGTGGTGGTCGTGGT

GACAGGACTGGCCGCTATGGAGCCACTGACCGCTCGCAGGATGATGGTGGGGAGAACCGCAGCCGAGACC

ACGACTACCGGGACATGGACTACCGTTCATATCCTCGCGAGTATGGCAGCCAGGAGGGCAAGCATGACTA

TGACGACTCATCTGAGGAGCAGAGTGCGGAGGATTCCTACGAGGCCTCCCCGGGCTCCGAGACTCAGCGT

AGGCGGCGGCGGCGGCACAGGCACAGCCCCACCGGCCCGCCAGGCTTCCCCCGAGACGGCGACTATCGGG

ACCAGGACTATCGGACCGAGCAAGGGGAGGAGGAGGAGGAGGAGGAGGATGAGGAGGAGGAGGAGAAGGC

CAGTAACATCGTCATGCTGAGGATGCTGCCACAGGCAGCCACTGAGGATGACATCCGTGGCCAGCTGCAG

TCGCACGGCGTGCAAGCACGGGAGGTTCGGCTGATGCGGAACAAATCTTCAGGTCAGAGCCGGGGCTTCG

CCTTCGTCGAGTTTAGTCACTTGCAGGACGCTACACGATGGATGGAAGCCAATCAGCACTCCCTCAACAT

CCTGGGCCAGAAGGTGTCGATGCACTACAGTGACCCCAAGCCCAAGATCAATGAGGACTGGCTGTGCAAT

AAGTGTGGCGTCCAGAACTTCAAACGCCGAGAGAAGTGCTTCAAATGTGGCGTGCCCAAGTCAGAGGCAG

AGCAGAAGCTGCCCCTCGGCACGAGGCTGGATCAGCAGACACTGCCACTGGGTGGCCGGGAGCTGAGCCA

GGGCCTGCTTCCCCTGCCGCAGCCCTACCAGGCCCAGGGAGTCCTGGCCTCCCAAGCCCTGTCACAGGGC

TCGGAGCCAAGCTCAGAGAACGCCAATGACACCATCATTTTGCGCAACCTGAACCCACACAGCACCATGG

ATTCCATCCTGGGGGCCCTGGCACCCTACGCGGTGCTGTCCTCCTCCAACGTGCGCGTCATAAAGGACAA

GCAGACCCAACTGAACCGCGGCTTTGCCTTCATCCAGCTCTCCACCATCGAGGCAGCCCAGCTGCTGCAG

ATCCTGCAGGCCCTGCACCCACCACTCACTATCGACGGCAAGACCATCAATGTTGAGTTTGCCAAGGGTT

CTAAGAGGGACATGGCCTCCAATGAAGGCAGTCGCATCAGTGCTGCCTCTGTGGCCAGCACTGCCATTGC

TGCGGCCCAGTGGGCCATCTCACAGGCCTCCCAAGGTGGGGAGGGTACCTGGGCCACCTCCGAGGAGCCG

CCGGTCGACTACAGCTACTACCAACAGGATGAGGGCTATGGCAACAGCCAGGGCACAGAGTCTTCCCTCT

ATGCCCATGGCTACCTCAAGGGCACCAAGGGCCCTGGCATCACTGGAACCAAAGGGGATCCCACTGGAGC

AGGTCCCGAGGCCTCCCTAGAGCCTGGGGCCGACTCTGTGTCGATGCAGGCTTTCTCTCGCGCCCAGCCT

GGTGCTGCTCCTGGCATCTACCAACAATCAGCCGAGGCGAGCAGTAGCCAGGGCACTGCTGCCAACAGCC

AGTCGTATACCATCATGTCACCCGCTGTGCTCAAATCTGAGCTCCAGAGCCCTACCCATCCTAGTTCTGC

TCTCCCACCGGCTACCAGCCCCACTGCCCAGGAATCCTACAGCCAGTACCCTGTTCCCGACGTCTCTACC

TACCAGTACGATGAGACCTCCGGCTACTACTATGACCCCCAGACCGGCCTCTACTATGACCCCAACTCCC

AGTATTACTACAATGCTCAGAGCCAGCAGTACCTGTACTGGGATGGGGAGAGGCGGACCTATGTTCCCGC

CCTGGAGCAGTCGGCCGACGGACATAAGGAGACAGGGGCACCCTCGAAGGAGGGCAAAGAGAAGAAGGAG

AAGCACAAGACCAAGACAGCTCAACAGATTGCCAAGGACATGGAACGCTGGGCCCGCAGTCTCAACAAAC

AAAAAGAAAACTTCAAAAATAGCTTCCAGCCTATCAGCTCCCTGCGAGATGACGAGAGGCGGGAGTCAGC

CACTGCAGATGCTGGCTATGCCATCCTCGAGAAGAAGGGAGCACTAGCCGAGAGACAGCACACCAGCATG

GATCTCCCGAAATTGGCCAGTGACGACCGCCCAAGCCCTCCGCGAGGACTGGTGGCAGCCTACAGCGGGG

AGAGTGACAGTGAGGAGGAGCAGGAGCGTGGGGGCCCTGAGCGGGAGGAGAAGCTCACCGACTGGCAGAA

GCTGGCCTGTCTGCTCTGCCGACGCCAGTTCCCCAGCAAAGAGGCGCTCATCCGGCACCAGCAGCTCTCA

GGGCTCCACAAGCAAAACCTTGAGATTCACCGGCGAGCCCACTTGTCAGAAAACGAGCTAGAAGCACTAG

AGAAGAATGACATGGAGCAAATGAAGTACCGGGACCGTGCAGCTGAACGCAGAGAAAAGTATGGCATCCC

CGAGCCGCCAGAGCCCAAGAGGAGGAAGTACGGCGGCATATCCACAGCCTCTGTAGACTTCGAGCAGCCT

ACTCGGGACGGGCTGGGCAGTGACAACATTGGCAGTCGGATGCTGCAGGCCATGGGCTGGAAAGAGGGCA

GCGGCCTGGGCCGCAAGAAGCAGGGCATTGTAACGCCTATCGAGGCCCAAACACGGGTGCGGGGCTCCGG

CCTGGGTGCACGGGGCAGCTCCTACGGGGTCACCTCAACCGAGTCCTACAAGGAGACACTGCACAAGACA

-continued

```
ATGGTGACCCGCTTCAACGAGGCCCAGTGAGCAGCTTCAAGAGCAACTTCTCCACATGTTGGGTGTCCAT

CCTGGGGCAGGGAAGGACAGAGTGTTGGATGGCTGGGACGGGGCCTTGCTCTTGTCGGCCAGCCCACTCC

CCAGCCAGAGAGGGCTTGACCAAATCAAATTGAGGTGGTGACTTTTGTTGGAAAATTGGGCTGGGATCAC

GTCCTGTTTTGTAATAAAAGCTGAAAAGTCTGCA
```

NM_001204468.2 *Homo sapiens* RNA binding motif protein 10 (RBM10),
transcript variant 5, mRNA
(SEQ ID NO: 5)
```
AGTAGGTGGATGGTGGTCGGAGCGCCGACTCCCTTCTCGTCGTCGCCATTTTGAGCTGGTGACTGTGGCC

GGCTGGGAGTAGGCGGCAGTGAGTTTCCCTGGGAGGGCAGCGCGCTTGGCGCTTCTCCCCTCCCCCCGAT

CTGCCTCCAGTCTCGGACTTGGTTGTTGCGCGCTCCGGCTCCGGCTGAGCTGGGAGAGTTGGAGGAGGTG

GCGGCGGGCAGAGGTGATGTCTGGGAGCCCTTCCTTGACAGCCCGGGCCGAGAAGGTGAGCGTCGACGCT

GGTCGTGGGGGCGGAGAGTCCCTGCAGGAAGCATCACCCAGGCTGGCAGATCATGGTAGCAGCAGCGGGG

GTGGCTGGGAAGTGAAACGGAGCCAGCGGCTGAGGAGGGGCCCCAGCAGCCCCGAAGGCCCTATCAGGA

CATGGAGTATGAAAGACGTGGTGGTCGTGGTGACAGGACTGGCCGCTATGGAGCCACTGACCGCTCGCAG

GATGATGGTGGGGAGAACCGCAGCCGAGACCACGACTACCGGGACATGGACTACCGTTCATATCCTCGCG

AGTATGGCAGCCAGGAGGGCAAGCATGACTATGACGACTCATCTGAGGAGCAGAGTGCGGAGGATTCCTA

CGAGGCCTCCCCGGGCTCCGAGACTCAGCGTAGGCGGCGGCGGCGGCACAGGCACAGCCCCACCGGCCCG

CCAGGCTTCCCCCGAGACGGCGACTATCGGGACCAGGACTATCGGACCGAGCAAGGGGAGGAGGAGGAGG

AGGAGGAGGATGAGGAGGAGGAGGAGAAGGCCAGTAACATCGTCATGCTGAGGATGCTGCCACAGGCAGC

CACTGAGGATGACATCCGTGGCCAGCTGCAGTCGCACGGCGTGCAAGCACGGGAGGTTCGGCTGATGCGG

AACAAATCTTCAGGTCAGAGCCGGGGCTTCGCCTTCGTCGAGTTTAGTCACTTGCAGGACGCTACACGAT

GGATGGAAGCCAATCAGCACTCCCTCAACATCCTGGGCCAGAAGGTGTCGATGCACTACAGTGACCCCAA

GCCCAAGATCAATGAGGACTGGCTGTGCAATAAGTGTGGCGTCCAGAACTTCAAACGCCGAGAGAAGTGC

TTCAAATGTGGCGTGCCCAAGTCAGAGGCAGAGCAGAAGCTGCCCCTCGGCACGAGGCTGGATCAGCAGA

CACTGCCACTGGGTGGCCGGGAGCTGAGCCAGGGCCTGCTTCCCCTGCCGCAGCCCTACCAGGCCCAGGG

AGTCCTGGCCTCCCAAGCCCTGTCACAGGGCTCGGAGCCAAGCTCAGAGAACGCCAATGACACCATCATT

TTGCGCAACCTGAACCCACACAGCACCATGGATTCCATCCTGGGGGCCCTGGCACCCTACGCGGTGCTGT

CCTCCTCCAACGTGCGCGTCATAAAGGACAAGCAGACCCAACTGAACCGCGGCTTTGCCTTCATCCAGCT

CTCCACCATCGTGGAGGCAGCCCAGCTGCTGCAGATCCTGCAGGCCCTGCACCCACCACTCACTATCGAC

GGCAAGACCATCAATGTTGAGTTTGCCAAGGGGTTCTAAGAGGGACATGGCCTCCAATGAAGGCAGTCGCA

TCAGTGCTGCCTCTGTGGCCAGCACTGCCATTGCTGCGGCCCAGTGGGCCATCTCACAGGCCTCCCAAGG

TGGGGAGGGTACCTGGGCCACCTCCGAGGAGCCGCCGGTCGACTACAGCTACTACCAACAGGATGAGGGC

TATGGCAACAGCCAGGGCACAGAGTCTTCCCTCTATGCCCATGGCTACCTCAAGGGCACCAAGGGCCCTG

GCATCACTGGAACCAAAGGGGATCCCACTGGAGCAGGTCCCGAGGCCTCCCTAGAGCCTGGGGCCGACTC

TGTGTCGATGCAGGCTTTCTCTCGCGCCCAGCCTGGTGCTGCTCCTGGCATCTACCAACAATCAGCCGAG

GCGAGCAGTAGCCAGGGCACTGCTGCCAACAGCCAGTCGTATACCATCATGTCACCCGCTGTGCTCAAAT

CTGAGCTCCAGAGCCCTACCCATCCTAGTTCTGCTCTCCCACCGGCTACCAGCCCCACTGCCCAGGAATC

CTACAGCCAGTACCCTGTTCCCGACGTCTCTACCTACCAGTACGATGAGACCTCCGGCTACTACTATGAC

CCCCAGACCGGCCTCTACTATGACCCCAACTCCCAGTATTACTACAATGCTCAGAGCCAGCAGTACCTGT

ACTGGGATGGGGAGAGGCGGACCTATGTTCCCGCCCTGGAGCAGTCGGCCGACGGACATAAGGAGACAGG

GGCACCCTCGAAGGAGGGCAAAGAGAAGAAGGAGAAGCACAAGACCAAGACAGCTCAACAGATTGCCAAG

GACATGGAACGCTGGGCCCGCAGTCTCAACAAACAAAAAGAAAACTTCAAAAATAGCTTCCAGCCTATCA
```

```
-continued
GCTCCCTGCGAGATGACGAGAGGCGGGAGTCAGCCACTGCAGATGCTGGCTATGCCATCCTCGAGAAGAA

GGGAGCACTAGCCGAGAGACAGCACACCAGCATGGATCTCCCGAAATTGGCCAGTGACGACCGCCCAAGC

CCTCCGCGAGGACTGGTGGCAGCCTACAGCGGGGAGAGTGACAGTGAGGAGGAGCAGGAGCGTGGGGGCC

CTGAGCGGGAGGAGAAGCTCACCGACTGGCAGAAGCTGGCCTGTCTGCTCTGCCGACGCCAGTTCCCCAG

CAAAGAGGCGCTCATCCGGCACCAGCAGCTCTCAGGGCTCCACAAGCAAAACCTTGAGATTCACCGGCGA

GCCCACTTGTCAGAAAACGAGCTAGAAGCACTAGAGAAGAATGACATGGAGCAAATGAAGTACCGGGACC

GTGCAGCTGAACGCAGAGAAAAGTATGGCATCCCCGAGCCGCCAGAGCCCAAGAGGAGGAAGTACGGCGG

CATATCCACAGCCTCTGTAGACTTCGAGCAGCCTACTCGGGACGGGCTGGGCAGTGACAACATTGGCAGT

CGGATGCTGCAGGCCATGGGCTGGAAAGAGGGCAGCGGCCTGGGCCGCAAGAAGCAGGGCATTGTAACGC

CTATCGAGGCCCAAACACGGGTGCGGGGCTCCGGCCTGGGTGCACGGGGCAGCTCCTACGGGGTCACCTC

AACCGAGTCCTACAAGGAGACACTGCACAAGACAATGGTGACCCGCTTCAACGAGGCCCAGTGAGCAGCT

TCAAGAGCAACTTCTCCACATGTTGGGTGTCCATCCTGGGGCAGGGAAGGACAGAGTGTTGGATGGCTGG

GACGGGGCCTTGCTCTTGTCGGCCAGCCCACTCCCCAGCCAGAGAGGGCTTGACCAAATCAAATTGAGGT

GGTGACTTTTGTTGGAAAATTGGGCTGGGATCACGTCCTGTTTTGTAATAAAAGCTGAAAGTCTGCA
```

Primers or probes can be designed so that they hybridize under stringent conditions to mutant nucleotide sequences of RBM10, but not to the respective wild-type nucleotide sequences. Primers or probes can also be prepared that are complementary and specific for the wild-type nucleotide sequence of RBM10, but not to any one of the corresponding mutant nucleotide sequences. In some embodiments, the mutant nucleotide sequences of RBM10 may be a frameshift mutation, a missense mutation, a deletion, an insertion, a nonsense mutation, an inversion, or a translocation, that results in the loss of expression and/or activity of RBM10 (i.e., loss of function mutations).

In some embodiments, detection can occur through any of a variety of mobility dependent analytical techniques based on the differential rates of migration between different nucleic acid sequences. Exemplary mobility-dependent analysis techniques include electrophoresis, chromatography, mass spectroscopy, sedimentation, gradient centrifugation, field-flow fractionation, multi-stage extraction techniques, and the like. In some embodiments, mobility probes can be hybridized to amplification products, and the identity of the target nucleic acid sequence determined via a mobility dependent analysis technique of the eluted mobility probes, as described in Published PCT Applications WO04/46344 and WO01/92579. In some embodiments, detection can be achieved by various microarrays and related software such as the Applied Biosystems Array System with the Applied Biosystems 1700 Chemiluminescent Microarray Analyzer and other commercially available array systems available from Affymetrix, Agilent, Illumina, and Amersham Biosciences, among others (see also Gerry et al., *J. Mol. Biol.* 292:251-62, 1999; De Bellis et al., *Minerva Biotec* 14:247-52, 2002; and Stears et al., *Nat. Med.* 9:14045, including supplements, 2003).

It is also understood that detection can comprise reporter groups that are incorporated into the reaction products, either as part of labeled primers or due to the incorporation of labeled dNTPs during an amplification, or attached to reaction products, for example but not limited to, via hybridization tag complements comprising reporter groups or via linker arms that are integral or attached to reaction products.

In some embodiments, unlabeled reaction products may be detected using mass spectrometry.

CLK/DYRK Inhibitors

Dual-specificity tyrosine phosphorylation-regulated kinases (DYRK1A, 1B, 2-4) and cdc2-like kinases (CLK1-4) belong to the CMGC group of serine/threonine kinases. These protein kinases are involved in multiple cellular functions, including intracellular signaling, mRNA splicing, chromatin transcription, DNA damage repair, cell survival, cell cycle control, differentiation, homocysteine/methionine/folate regulation, body temperature regulation, endocytosis, neuronal development, synaptic plasticity, etc. DYRKs and CLKs are also involved in several solid cancers (glioblastoma, breast, and pancreatic cancers) and leukemias (acute lymphoblastic leukemia, acute megakaryoblastic leukemia).

Examples of CLK/DYRK inhibitors include, but are not limited to, SM09419, SM08502 (Cirtuvivint), CA-4948 (Emavusertib), CTX-712, AnnH75, EGCG, EHT-1610, Harmine, INDY, Leucettine L41, Lorecivivint, GNF4877, MU1210, and TCMDC-135051. See Lindberg et al., *Int J Mol Sci.* 22(11): 6047 (2021).

BCL2 Inhibitors

The BCL2 family consists of numerous pro- and anti-apoptotic proteins. The anti-apoptotic proteins include BCL2, BCLXL, MCL, BCLW, and BFL1. These proteins contain 4 BCL2 homology (BH) domains and a transmembrane domain that allows them to insert into the endoplasmic reticulum or mitochondrial membrane. Their expression varies from cell type to cell type, and one cell type can express multiple proteins. Cancer cells often upregulate expression of one or more anti-apoptotic proteins in order to survive.

Many Bcl-2 protein family inhibitors have been developed over the past years, including venetoclax (ABT-199), navitoclax (ABT-263), obatoclax (GX15-070), oblimersen sodium (G3139), Palcitoclax (APG-1252), AT-101 (R-(—)-gossypol acetic acid), etc., and are mostly used in leukemia, lymphomas, and other hematological malignancies.

Formulations Including BCL2 Inhibitors and/or
CLK/DYRK Inhibitors of the Present Technology The pharmaceutical compositions of the present technology can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired. In certain embodiments, the compositions disclosed herein are formulated for administration to a mammal, such as a human.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, cyclodextrins, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Compositions formulated for parenteral administration may be injected by bolus injection or by timed push, or may be administered by continuous infusion.

In order to prolong the effect of a compound of the present disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition that they release the active ingredient(s) only, or in a certain part of the intestinal tract, optionally, in a delayed manner. Examples of embedding compositions that can be used include polymeric substances and waxes.

The active compounds can also be in micro-encapsulated form with one or more excipients as noted above. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or in a certain part of the intestinal tract, optionally, in a delayed manner. Examples of embedding compositions that can be used include polymeric substances and waxes.

Methods of Treatment of the Present Technology

In one aspect, the present disclosure provides a method for selecting a leukemia patient for treatment with a BCL2 inhibitor comprising (a) detecting the presence of at least one mutation in RBM10 in a biological sample obtained from the leukemia patient and (b) administering to the leukemia patient an effective amount of a BCL2 inhibitor. Additionally or alternatively, in some embodiments, the at least one mutation in RBM10 is a frameshift mutation, a missense mutation, a deletion, an insertion, a nonsense mutation, an inversion, or a translocation. The at least one mutation in RBM10 may be detected using any nucleic acid detection assay known in the art such as next-generation sequencing, PCR, real-time quantitative PCR (qPCR), digital PCR (dPCR), Southern blotting, Reverse transcriptase-PCR (RT-PCR), Northern blotting, microarray, dot or slot blots, in situ hybridization, or fluorescent in situ hybridization (FISH).

In one aspect, the present disclosure provides a method for preventing or treating leukemia in a subject in need thereof comprising administering to the subject an effective amount of a CLK/DYRK inhibitor and an effective amount of a BCL2 inhibitor. In some embodiments, the CLK/DYRK inhibitor is selected from the group consisting of SM09419, SM08502 (Cirtuvivint), CA-4948 (Emavusertib), CTX-712, AnnH75, EGCG, EHT-1610, Harmine, INDY, Leucettine L41, Lorecivivint, GNF4877, MU1210, and TCMDC-135051. In another aspect, the present disclosure provides a method for preventing or treating leukemia in a subject in need thereof comprising administering to the subject an effective amount of a RBM10-specific inhibitory nucleic acid and an effective amount of a BCL2 inhibitor, wherein the RBM10-specific inhibitory nucleic acid is a siRNA, a shRNA, an antisense oligonucleotide, or a sgRNA.

Additionally or alternatively, in some embodiments of the methods disclosed herein, the BCL2 inhibitor is selected from among venetoclax (ABT-199), navitoclax (ABT-263), obatoclax (GX15-070), oblimersen sodium (G3139), Palcitoclax (APG-1252), and AT-101 (R-(—)-gossypol acetic acid).

Additionally or alternatively, in some embodiments of the methods disclosed herein, the subject is resistant to BCL2 inhibitor monotherapy or combination therapy with a BCL2 inhibitor and a pyrimidine analog. Examples of pyrimidine analogs include, but are not limited to, 5-azacytidine, cytarabine, 5-fluorouracil, floxuridine, capecitabine, decitabine, or gemcitabine. The resistance to BCL2 inhibitor therapy may be acquired or intrinsic. In some embodiments, the subject harbors acquired mutations in BAX, PMAIP, or TP53. In certain embodiments, the subject is human.

In any and all embodiments of the methods disclosed herein, the leukemia is chronic lymphocytic leukemia (CLL) or acute myeloma leukemia (AML). Additionally or alternatively, in some embodiments, the leukemia comprises an MLL-translocation (MLL-t), an MLL-rearrangement (MLL-r), or an MLL-partial tandem duplication (MLL-PTD). Additionally or alternatively, in some embodiments, the leukemia comprises mutations in one or more of p53, FLT3, RUNX1, PTPN11, SF3B1, STAG2, DNMT3A or IDH2.

In some embodiments, administration of the CLK/DYRK inhibitor and BCL2 inhibitor will ameliorate or prevent one or more symptoms of leukemia including, but are not limited to, leukemic cell proliferation, enlarged lymph nodes, fatigue, weakness, pale skin, recurring or frequent infections, fever, bleeding, hepatomegaly, splenomegaly, lymphadenopathy, excess bruising, shortness of breath, chest pain, dizziness, headaches, blurred vision, aches in bones and joints, loss of appetite and weight loss, sores or wounds that don't heal, and swollen gums, lymph nodes, liver, or spleen. In any of the preceding embodiments of the methods disclosed herein, the subject is a child or an adult.

Additionally or alternatively, in some embodiments of the combination therapy methods disclosed herein, the time to response and/or duration of response is improved relative to that observed with CLK/DYRK inhibitor monotherapy or BCL2 inhibitor monotherapy.

Additionally or alternatively, in some embodiments of the methods disclosed herein, the CLK/DYRK inhibitor and the BCL2 inhibitor are administered sequentially, simultaneously, or separately. The CLK/DYRK inhibitor and/or the BCL2 inhibitor may be administered orally, parenterally, by inhalation spray, intranasally, buccally, or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intravenously, or subcutaneously. Formulations including CLK/DYRK inhibitor and/or BCL2 inhibitor disclosed herein may be designed to be short-acting, fast-releasing, or long-acting. In other embodiments, compounds can be administered in a local rather than systemic means, such as administration (e.g., by injection) at a tumor site.

Additionally or alternatively, in some embodiments of the methods disclosed herein, the CLK/DYRK inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), simultaneously with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a BCL2 inhibitor to a patient with leukemia.

In some embodiments, the CLK/DYRK inhibitor and BCL2 inhibitor are administered to a patient, for example, a mammal, such as a human, in a sequence and within a time interval such that the inhibitor that is administered first acts together with the inhibitor that is administered second to provide greater benefit than if each inhibitor were administered alone. For example, the CLK/DYRK inhibitor and BCL2 inhibitor can be administered at the same time or sequentially in any order at different points in time; however, if not administered at the same time, the CLK/DYRK inhibitor and BCL2 inhibitor are administered sufficiently close in time so as to provide the desired therapeutic or prophylactic effect of the combination of the at least two inhibitors. In one embodiment, the CLK/DYRK inhibitor and BCL2 inhibitor exert their effects at times which overlap. In some embodiments, the CLK/DYRK inhibitor and BCL2 inhibitor are each administered as separate dosage forms, in any appropriate form and by any suitable route. In other embodiments, the CLK/DYRK inhibitor and BCL2 inhibitor are administered simultaneously in a single dosage form.

It will be appreciated that the frequency with which any of these therapeutic agents can be administered can be once or more than once over a period of about 2 days, about 3 days, about 4 days, about 5 days, about 6 days, about 7 days, about 8 days, about 9 days, about 10 days, about 11 days, about 12 days, about 13 days, about 14 days, about 20 days, about 28 days, about a week, about 2 weeks, about 3 weeks, about 4 weeks, about a month, about every 2 months, about every 3 months, about every 4 months, about every 5 months, about every 6 months, about every 7 months, about every 8 months, about every 9 months, about every 10 months, about every 11 months, about every year, about every 2 years, about every 3 years, about every 4 years, or about every 5 years.

For example, the CLK/DYRK inhibitor, or BCL2 inhibitor may be administered daily, weekly, biweekly, or monthly for a particular period of time. The CLK/DYRK inhibitor, or BCL2 inhibitor may be dosed daily over a 14 day time period, or twice daily over a seven day time period. The CLK/DYRK inhibitor, or BCL2 inhibitor may be administered daily for 7 days.

Alternatively, the CLK/DYRK inhibitor, or BCL2 inhibitor may be administered daily, weekly, biweekly, or monthly for a particular period of time followed by a particular period of non-treatment. In some embodiments, the CLK/DYRK inhibitor, or BCL2 inhibitor can be administered daily for 14 days followed by seven days of non-treatment, and repeated for two more cycles of daily administration for 14 days followed by seven days of non-treatment. In some embodiments, the CLK/DYRK inhibitor, or BCL2 inhibitor can be administered twice daily for seven days followed by 14 days of non-treatment, which may be repeated for one or two more cycles of twice daily administration for seven days followed by 14 days of non-treatment.

In some embodiments, the CLK/DYRK inhibitor, or BCL2 inhibitor is administered daily over a period of 14 days. In another embodiment, the CLK/DYRK inhibitor, or the BCL2 inhibitor is administered daily over a period of 12 days, or 11 days, or 10 days, or nine days, or eight days. In another embodiment, the CLK/DYRK inhibitor, or BCL2 inhibitor is administered daily over a period of seven days. In another embodiment, the CLK/DYRK inhibitor, or BCL2 inhibitor is administered daily over a period of six days, or five days, or four days, or three days.

In some embodiments, individual doses of the CLK/DYRK inhibitor and the BCL2 inhibitor are administered within a time interval such that the two inhibitors can work together (e.g., within 1 hour, 2 hours, 4 hours, 6 hours, 12 hours, 24 hours, 48 hours, 72 hours, 96 hours, 5 days, 6 days, 1 week, or 2 weeks). In some embodiments, the treatment period during which the therapeutic agents are administered is then followed by a non-treatment period of a particular time duration, during which the therapeutic agents are not administered to the patient. This non-treatment period can then be followed by a series of subsequent treatment and non-treatment periods of the same or different frequencies for the same or different lengths of time. In some embodiments, the treatment and non-treatment periods are alternated. It will be understood that the period of treatment in cycling therapy may continue until the patient has achieved a complete response or a partial response, at which point the treatment may be stopped. Alternatively, the period of treatment in cycling therapy may continue until the patient has achieved a complete response or a partial response, at which point the period of treatment may continue for a particular number of cycles. In some embodiments, the length of the period of treatment may be a particular number of cycles, regardless of patient response. In some other embodiments, the length of the period of treatment may continue until the patient relapses.

In some embodiments, the CLK/DYRK inhibitor and the BCL2 inhibitor are cyclically administered to a patient. Cycling therapy involves the administration of a first agent (e.g., a first prophylactic or therapeutic agent) for a period of time, followed by the administration of a second agent and/or third agent (e.g., a second and/or third prophylactic or therapeutic agent) for a period of time and repeating this sequential administration. Cycling therapy can reduce the development of resistance to one or more of the therapies, avoid or reduce the side effects of one of the therapies, and/or improve the efficacy of the treatment.

In some embodiments, the CLK/DYRK inhibitor is administered for a particular length of time prior to administration of the BCL2 inhibitor. For example, in a 21-day cycle, the CLK/DYRK inhibitor may be administered on days 1 to 5, days 1 to 7, days 1 to 10, or days 1 to 14, and the BCL2 inhibitor may be administered on days 6 to 21, days 8 to 21, days 11 to 21, or days 15 to 21. In other embodiments, the BCL2 inhibitor is administered for a particular length of time prior to administration of CLK/DYRK inhibitor. For example, in a 21-day cycle, the BCL2 inhibitor may be administered on days 1 to 5, days 1 to 7, days 1 to 10, or days 1 to 14, and the CLK/DYRK inhibitor may be administered on days 6 to 21, days 8 to 21, days 11 to 21, or days 15 to 21.

In one embodiment, the administration is on a 21-day dose schedule in which a once daily dose of CLK/DYRK inhibitor is administered beginning on day eight for seven days, followed by seven days of non-treatment, in combination with twice-daily administration of the BCL2 inhibitor for seven days followed by 14 days of non-treatment (e.g., the CLK/DYRK inhibitor is administered on days 8-14 and the BCL2 inhibitor is administered on days 1-7 of the 21-day schedule). In another embodiment, the administration is on a 21-day dose schedule in which a once daily dose of BCL2 inhibitor is administered beginning on day eight for seven days, followed by seven days of non-treatment, in combination with twice-daily administration of CLK/DYRK inhibitor for seven days followed by 14 days of non-treatment (e.g., the BCL2 inhibitor is administered on days 8-14 and CLK/DYRK inhibitor is administered on days 1-7 of the 21-day schedule).

In some embodiments, the CLK/DYRK inhibitor in combination with a BCL2 inhibitor are each administered at a dose and schedule typically used for that agent during monotherapy. In other embodiments, the CLK/DYRK inhibitor and BCL2 inhibitor are administered concomitantly, one or both of the agents can advantageously be administered at a lower dose than typically administered when the agent is used during monotherapy, such that the dose falls below the threshold that an adverse side effect is elicited.

The therapeutically effective amounts or suitable dosages of CLK/DYRK inhibitor, and the BCL2 inhibitor in combination depends upon a number of factors, including the nature of the severity of the condition to be treated, the particular inhibitor, the route of administration and the age, weight, general health, and response of the individual patient. In certain embodiments, the suitable dose level is one that achieves a therapeutic response as measured by tumor regression or other standard measures of disease progression, progression free survival, or overall survival. In other embodiments, the suitable dose level is one that achieves this therapeutic response and also minimizes any side effects associated with the administration of the therapeutic agent.

Suitable daily dosages of BCL2 inhibitors can generally range, in single or divided or multiple doses, from about 10% to about 120% of the maximum tolerated dose as a single agent. In certain embodiments, the suitable dosages of BCL2 inhibitors are from about 20% to about 100% of the maximum tolerated dose as a single agent. In other embodiments, the suitable dosages of BCL2 inhibitors are from about 25% to about 90% of the maximum tolerated dose as a single agent. In some embodiments, the suitable dosages of BCL2 inhibitors are from about 30% to about 80% of the maximum tolerated dose as a single agent. In other embodiments, the suitable dosages of BCL2 inhibitors are from about 40% to about 75% of the maximum tolerated dose as a single agent. In some embodiments, the suitable dosages of BCL2 inhibitors are from about 45% to about 60% of the maximum tolerated dose as a single agent. In other embodiments, suitable dosages of BCL2 inhibitors are about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, or about 120% of the maximum tolerated dose as a single agent.

Suitable daily dosages of CLK/DYRK inhibitors can generally range, in single or divided or multiple doses, from about 10% to about 120% of the maximum tolerated dose as a single agent. In certain embodiments, the suitable dosages of CLK/DYRK inhibitors are from about 20% to about 100% of the maximum tolerated dose as a single agent. In other embodiments, the suitable dosages of CLK/DYRK inhibitors are from about 25% to about 90% of the maximum tolerated dose as a single agent. In some embodiments, the suitable dosages of CLK/DYRK inhibitors are from about 30% to about 80% of the maximum tolerated dose as a single agent. In other embodiments, the suitable dosages of CLK/DYRK inhibitors are from about 40% to about 75% of the maximum tolerated dose as a single agent. In some embodiments, the suitable dosages of CLK/DYRK inhibitors are from about 45% to about 60% of the maximum tolerated dose as a single agent. In other embodiments, suitable dosages of CLK/DYRK inhibitors are about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, or about 120% of the maximum tolerated dose as a single agent.

For therapeutic and/or prophylactic applications, a composition comprising a CLK/DYRK inhibitor or BCL2 inhibitor disclosed herein, is administered to the subject. In some embodiments, the CLK/DYRK inhibitor or BCL2 inhibitor is administered one, two, three, four, or five times per day. In some embodiments, the CLK/DYRK inhibitor or BCL2 inhibitor is administered more than five times per day. Additionally or alternatively, in some embodiments, the CLK/DYRK inhibitor or BCL2 inhibitor is administered every day, every other day, every third day, every fourth day, every fifth day, or every sixth day. In some embodiments, the CLK/DYRK inhibitor or BCL2 inhibitor is administered weekly, bi-weekly, tri-weekly, or monthly. In some embodiments, the CLK/DYRK inhibitor or BCL2 inhibitor is administered for a period of one, two, three, four, or five weeks. In some embodiments, the CLK/DYRK inhibitor or BCL2 inhibitor is administered for six weeks or more. In some embodiments, the CLK/DYRK inhibitor or BCL2 inhibitor is administered for twelve weeks or more. In some embodiments, the CLK/DYRK inhibitor or BCL2 inhibitor is administered for a period of less than one year. In some embodiments, the CLK/DYRK inhibitor or BCL2 inhibitor is administered for a period of more than one year. In some embodiments, the CLK/DYRK inhibitor or BCL2 inhibitor is administered throughout the subject's life.

In some embodiments of the methods of the present technology, the CLK/DYRK inhibitor or BCL2 inhibitor is administered daily for 1 week or more. In some embodiments of the methods of the present technology, the CLK/

DYRK inhibitor or BCL2 inhibitor is administered daily for 2 weeks or more. In some embodiments of the methods of the present technology, the CLK/DYRK inhibitor or BCL2 inhibitor is administered daily for 3 weeks or more. In some embodiments of the methods of the present technology, the CLK/DYRK inhibitor or BCL2 inhibitor is administered daily for 4 weeks or more. In some embodiments of the methods of the present technology, the CLK/DYRK inhibitor or BCL2 inhibitor is administered daily for 6 weeks or more. In some embodiments of the methods of the present technology, the CLK/DYRK inhibitor or BCL2 inhibitor is administered daily for 12 weeks or more. In some embodiments, the CLK/DYRK inhibitor or BCL2 inhibitor is administered daily throughout the subject's life.

Determination of the Biological Effect of CLK/DYRK Inhibitors or BCL2 Inhibitors In various embodiments, suitable in vitro or in vivo assays are performed to determine the effect of a specific CLK/DYRK inhibitor or BCL2 inhibitor and whether its administration is indicated for treatment. In various embodiments, in vitro assays can be performed with representative animal models, to determine if a given CLK/DYRK inhibitor or BCL2 inhibitor exerts the desired effect on reducing or eliminating signs and/or symptoms of leukemia (e.g., AML). In some embodiments, the leukemia comprises an MLL-translocation (MLL-t), an MLL-rearrangement (MLL-r), or an MLL-partial tandem duplication (MLL-PTD). Additionally or alternatively, in some embodiments, the leukemia comprises mutations in one or more of p53, FLT3, RUNX1, PTPN11, SF3B1, STAG2, DNMT3A or IDH2.

Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects. In some embodiments, in vitro or in vivo testing is directed to the biological function of one or more CLK/DYRK inhibitors or BCL2 inhibitors. In some embodiments, in vitro or in vivo testing is directed to the biological function of BCL2 protein, CLK/DYRK protein and/or p53 protein.

Animal models of leukemia (e.g., AML) may be generated using techniques known in the art (sec, e.g, Examples described herein). Such models may be used to demonstrate the biological effect of CLK/DYRK inhibitors or BCL2 inhibitors in the prevention and treatment of conditions arising from disruption of a particular gene (e.g., p53, MLL), and for determining what comprises a therapeutically effective amount of the one or more CLK/DYRK inhibitors or BCL2 inhibitors disclosed herein in a given context.

Modes of Administration and Effective Dosages

Any method known to those in the art for contacting a cell, organ or tissue with one or more CLK/DYRK inhibitors and/or BCL2 inhibitors disclosed herein may be employed. Suitable methods include in vitro, ex vivo, or in vivo methods. In vivo methods typically include the administration of one or more CLK/DYRK inhibitors and/or BCL2 inhibitors to a mammal, suitably a human. When used in vivo for therapy, the one or more CLK/DYRK inhibitors and/or BCL2 inhibitors described herein are administered to the subject in effective amounts (i.e., amounts that have desired therapeutic effect). The dose and dosage regimen will depend upon the degree of the disease state of the subject, the characteristics of the particular CLK/DYRK inhibitor or BCL2 inhibitor used, e.g., its therapeutic index, and the subject's history.

The effective amount may be determined during preclinical trials and clinical trials by methods familiar to physicians and clinicians. An effective amount of one or more CLK/DYRK inhibitors and/or BCL2 inhibitors useful in the methods may be administered to a mammal in need thereof by any of a number of well-known methods for administering pharmaceutical compounds. The CLK/DYRK inhibitor and/or BCL2 inhibitor may be administered systemically or locally.

The one or more CLK/DYRK inhibitors and/or BCL2 inhibitors described herein can be incorporated into pharmaceutical compositions for administration, singly or in combination, to a subject for the treatment or prevention of leukemia (e.g., AML). In some embodiments, the leukemia comprises an MLL-translocation (MLL-t), an MLL-rearrangement (MLL-r), or an MLL-partial tandem duplication (MLL-PTD). Additionally or alternatively, in some embodiments, the leukemia comprises mutations in one or more of p53, FLT3, RUNX1, PTPN11, SF3B1, STAG2, DNMT3A or IDH2. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The pharmaceutical compositions having one or more CLK/DYRK inhibitors and/or BCL2 inhibitors disclosed herein can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic agent can be formulated in a carrier system. The carrier can be a colloidal system. The colloidal system can be a liposome, a phospholipid bilayer vehicle. In one embodiment, the therapeutic agent is encapsulated in a liposome while maintaining the agent's structural integrity. One skilled in the art would appreciate that there are a variety of methods to prepare liposomes. (See Lichtenberg, et al., *Methods Biochem. Anal.,* 33:337-462 (1988); Anselem, et al., *Liposome Technology,* CRC Press (1993)). Liposomal formulations can delay clearance and increase cellular uptake (See Reddy, *Ann. Pharmacother.,* 34 (7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic agent can be embedded in the polymer matrix, while maintaining the agent's structural integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.,* 34(7-8):915-923 (2000)). A polymer formulation for human growth hormone (hGH) has been used in clinical trials. (See Kozarich and Rich, *Chemical Biology,* 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods,* 4(3): 201-9 (1994); and Gregoriadis, "Engineering Liposomes for Drug Delivery: Progress and Problems," *Trends Biotechnol.,* 13(12) 527-37 (1995). Mizguchi, et al., *Cancer Lett.,* 100: 63-69 (1996), describes the use of fusogenic liposomes to deliver a protein to cells both in vivo and in vitro.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the one or more CLK/DYRK inhibitors and/or BCL2 inhibitors disclosed herein sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example, dosages can be 1 mg/kg body weight or 10 mg/kg body weight every day, every two days or every three days or within the range of 1-10 mg/kg every week, every two weeks or every three weeks. In one embodiment, a single dosage of the therapeutic compound ranges from 0.001-10,000 micrograms per kg body weight. In one embodiment, one or more CLK/DYRK inhibitor or BCL2 inhibitor concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In some embodiments, a therapeutically effective amount of one or more CLK/DYRK inhibitors or BCL2 inhibitors may be defined as a concentration of inhibitor at the target tissue of 10-32 to 106 molar, e.g., approximately 10-7 molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

Kits

The present disclosure also provides kits for the prevention and/or treatment of leukemia (e.g., AML), comprising one or more CLK/DYRK inhibitors and/or BCL2 inhibitors disclosed herein. Optionally, the above described components of the kits of the present technology are packed in suitable containers and labeled for the prevention and/or treatment of leukemia (e.g., AML). In some embodiments, the leukemia comprises an MLL-translocation (MLL-t), an MLL-rearrangement (MLL-r), or an MLL-partial tandem duplication (MLL-PTD). Additionally or alternatively, in some embodiments, the leukemia comprises mutations in one or more of p53, FLT3, RUNX1, PTPN11, SF3B1, STAG2, DNMT3A or IDH2.

The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic products, that contain information about, for example, the indications, usage, dosage, manufacture, administration, contraindications and/or warnings concerning the use of such therapeutic products.

The kit can also comprise, e.g., a buffering agent, a preservative or a stabilizing agent. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit. In certain embodiments, the use of the reagents can be according to the methods of the present technology.

EXAMPLES

The present technology is further illustrated by the following Examples, which should not be construed as limiting in any way.

Example 1: Materials and Methods

Cell Lines and Cell Culture

All human leukemia cell lines were cultured in recommended media, typically RPMI medium with 20% FBS and 1% penicillin/streptomycin. TF-1 human AML cell line was cultured in RPMI 20% FBS, 1% penicillin/streptomycin and 2 ng/ml GM-CSF. HEK293T cells were grown in DMEM medium with 10% FBS and 1% penicillin streptomycin. Cell lines transduced with retroviral Cas9 blasticidin (Addgene plasmid no. 59262) were selected with blasticidin (Fisher) 48 hours after transduction. All transfections were performed in HEK293T cells using Polyethylenimine (PEI) reagent at 4:2:3 ratios of plasmid:pVSVG:pPax2 in OPTI-MEM solution. Viral supernatant was collected 48 hrs and 72 hrs post-transfection. Spin infections were performed at room temperature at 1,800 RPM for 30 mins with polybrene reagent (1:2000 dilution) (Fisher Scientific). All cell lines were authenticated in-house by Integrated Genomics Operation (IGO) core based on fragment and STR analysis.

Animals 8-10 weeks-old female and male C57BL/6 and Mx1-Cre mice were purchased from Jackson Laboratory. 8 weeks-old NOD scid gamma and NSG-S female mice were obtained from Jackson Laboratory. Mice were bred and maintained in individual ventilated cages and fed with autoclaved food and water at Memorial Sloan Kettering Animal Facility. All animal procedures were completed in accordance with the Guidelines for the Care and Use of Laboratory Animals and were approved by the Institutional Animal Care and Use Committees at MSKCC. All mouse experiments were performed in accordance with a protocol approved by the MSKCC Institutional Animal Care and Use Committees (13-04-003).

Human Patient Samples

Studies were approved by the Institutional Review Boards of Memorial Sloan Kettering Cancer Center and conducted in accordance with the Declaration of Helsinki protocol. Primary human de-identified AML samples derived from whole peripheral blood or BM mononuclear cells were utilized. Mutational genotyping of each sample was performed by the MSKCC IMPACT assay as described previously[80,81]. Cord blood was acquired from NY Blood Bank. Informed consent was obtained from all subjects to obtain the patient specimens used in the studies described. Patient 1 is a 62 year old male and patient 2 is a 85 year old male. Specimens were obtained as part of the Memorial Sloan-Kettering Cancer Center Institutional Review Board approved clinical protocol #16-171 to which all subjects consented.

CRISPR Screen 250 million MOLM13 Cas9-expressing cells were transduced with the Brunello sgRNA library 82 at a low multiplicity of infection (~0.3) to obtain at least 500 cells per sgRNA (500×). Spin infections were performed at room temperature at 1,500 RCF for 90 mins with polybrene reagent (1:2000 dilution) (Fisher Scientific). On Day 4 post-transduction, GFP percentage was assessed to determine infection efficiency and sgRNA coverage (~300-500×). Remaining 300-500× cells were placed back into culture after each passage until 20 days post-transduction. At day 8 post-transduction, pooled sgRNA cells were treated with either DMSO (1%), cytarabine (50 nM), 5-azacytidine (3 µM), etoposide (400 nM), idarubicin (5 nM), midostaurin (25 nM) or venetoclax (25 nM). Genomic DNA (gDNA) extraction using NucleoSpin Blood XL, Maxi kit for DNA from blood (Takara) according to manufacturer's protocol. For pooled CRISPR screen analysis, sgRNAs were normalized using the formula (sgRNA read count/total read count)× CPM+1. Subsequently, normalized reads were then used to calculate $\log_2$ fold change (normalized read count drug treatment/normalized read count DMSO). CRISPR library amplifications were performed according to published study 82. Competition assays were performed using MOLM-13 cells transduced with sgRNA or cDNA constructs and mixed with parental cells at fixed ratios followed by 4 days of treatment with either vehicle (DMSO) or venetoclax, and GFP percentages were analyzed using BD LSR Fortessa FlowCytometer. The RNA processing factor (genes in the "RNA processing" gene ontology term, GO: 0006396) sgRNA $\log_2$ fold change distributions in cytarabine, 5-azacytidine, etoposide, idarubicin, and midostaurin were compared to venetoclax. Specifically, a two-sided F-test for equality of variances was used to assess if the drug: venetoclax ratios significantly deviated from 1. Variance ratios and the 95% confidence intervals were estimated using the stats R package.

CRISPR Indel Analysis

To quantify the spectrum of indel mutations with RBM10 sgRNAs, MOLM-13 cells were transduced with sgRBM10 or sgRosa (non-targeting), followed by cell sorting of GFP+/sgRNA+ populations at day 4 and day 28 post-infection. Cells were then harvested for gDNA and PCR amplicon (~200 bp) was designed to flank the sgRNA recognition sequence. 200 ng of gDNA was amplified using 2× Phusion Master Mix. Sequencing libraries were prepared from amplicons with an average size of 200 bp. The reported concentration was 3-7 ng/µL, and 50 µL were used as input for the KAPA Hyper Library Preparation Kit (Kapa Biosystems KK8504) according to the manufacturer's instructions with 8 cycles of PCR. Barcoded libraries were pooled in equal volumes and run on MiSeq in a PE150 run, using the MiSeq Reagent Micro Kit v2 (300 Cycles) (Illumina). The average number of read pairs per sample was 203,000.

Indel analysis was performed using CRISPResso (http://crispresso.pinellolab.partners.org/)

RNA-Sequencing Library Preparation and Sequencing

For cell line RNA sequencing (RNA-seq), RNA was extracted from MOLM13 cells using the Qiagen RNeasy extraction kit, according to the manufacturer's instructions. A minimum of 500 ng of high-quality RNA (as determined by Agilent Bioanalyzer) per replicate was used as input for library preparation. Poly(A)-selected, strand-specific (dUTP method) Illumina libraries were prepared by the Integrated Genomics Operation (IGO) at Memorial Sloan Kettering with a modified TruSeq protocol and sequenced on the Illumina HiSeq 2000 to obtain ~50-60M 2×101 bp paired-end reads per sample.

eCLIP Library Preparation eCLIP studies were performed in duplicates by Eclipse Bioinnovations Inc (San Diego, www.eclipsebio.com) according to the published single-end enhanced CLIP protocol with the following modifications. For Rbm10 immunoprecipitation, 10% of IP samples and 1% of input samples were run on NuPAGE 4-12% Bis-Tris protein gels, transferred to PVDF membrane, probed with 1:1,000 of RBM10 antibody and 1:10,000 TrueBlot Anti Rabbit IgG (HRP) and imaged with C300 Imager for 1 minute on normal settings using Azure Radiance ECL. Only the region from ~100 kDa to 180 kDa (protein size to 80 kDa above) was isolated during eCLIP. For RNA visualization, 10% of IP samples were run on NuPAGE 4-12% Bis-Tris protein gels, transferred to nitrocellulose membrane, visualized using the Chemiluminescent Nucleic Acid Detection Kit (cat. no. 89880) from Thermo Fisher Scientific and imaged with C300 Imager for 30 seconds on normal settings. For eCLIP preparation, 10 million MOLM-13 cells were UV crosslinked at 400 mJoules/cm2 with 254 nm radiation, and snap frozen. Cells were then lysed and treated with RNase I to fragment RNA as previously described. RBM10 antibody (A301-006A, Bethyl) was then pre-coupled to Protein G Dynabeads (Thermo Fisher), added to lysate, and incubated overnight at 4 deg C. Prior to immunoprecipitation, 2% of the sample was taken as the paired input sample, with the remainder magnetically separated and washed with lysis buffer only (as the standard high-salt eCLIP wash buffer gave poor immunoprecipitation yield). eCLIP was performed by excising the area from ~100 kDa to ~180 kDa. RNA adapter ligation, IP-western, reverse transcription, DNA adapter ligation, and PCR amplification were performed as previously described.

Whole-Exome Sequencing and Targeted Capture Sequencing

For MSKCC-IMPACT, after PicoGreen quantification and quality control by Agilent BioAnalyzer, 100 ng of DNA were used to prepare libraries using the KAPA Hyper Prep Kit (Kapa Biosystems KK8504) with 8 cycles of PCR. 80-190 ng of each barcoded library were captured by hybridization in pools of 6-14 samples using the IMPACT (Integrated Mutation Profiling of Actionable Cancer Targets) assay 80 (Nimblegen SeqCap), designed to capture all protein-coding exons and select introns of 505 commonly implicated oncogenes, tumor suppressor genes, and members of pathways deemed actionable by targeted therapies.

Captured pools were sequenced on a NovaSeq 6000 in a PE100 run using the NovaSeq 6000 S4 Reagent Kit (200 Cycles) (Illumina) producing an average of 540× coverage per sample. For exome capture and sequencing, after PicoGreen quantification and quality control by Agilent BioAnalyzer, 100 ng of DNA were used to prepare libraries using the KAPA Hyper Prep Kit (Kapa Biosystems KK8504) with 8 cycles of PCR. After sample barcoding, 500 ng of library were captured by hybridization using the xGen Exome Research Panel v2.0 (IDT) according to the manufacturer's protocol. PCR amplification of the post-capture libraries was carried out for 12 cycles. Samples were run on a NovaSeq 6000 in a PE100 run, using the NovaSeq 6000 S4 Reagent Kit (200 Cycles) (Illumina). Samples were covered to an average of 251×.

Western Blotting

MOLM-13 Cas9-expressing cells were transduced with sgRNAs and harvested for protein on day 6 post-transduction. For SM09419, MOLM-13 cells were treated with varying concentrations of SM09419, and protein was harvested 48 hours post-treatment. Lysate protein concentration was measured with the BCA reagent and 10-30 mcg was loaded per lane onto 4-12% NuPAGE™ Bis-Tris protein gels. After transfer, PVDF membranes were probed with anti-RBM10 (Bethyl Laboratories), anti-Phosphoepitope SR proteins Antibody (clone 1H4, Millipore Sigma), total SR protein (Santa Cruz), anti-XIAP (Cell signaling), anti-MCL-1 (Cell signaling), anti-RBM5 (Abcam), anti-FLT3 clone 8F2 (Cell signaling), anti-U2AF2/U2AF65 (Abcam) and anti-BCL-2 (Abcam) at 1:1,000 and visualized by standard methods.

Colony-Forming Assays

Total bone marrow from Mx1-Cre WT and Mx1-Cre Rbm10$^{fl/y}$ mice were harvested and seeded at a density of 20,000 cells per replicate into cytokine-supplemented methylcellulose medium (MethoCult M3434, Stemcell Technologies). For SM09419 experiments, total bone marrow from C57BL/6 treated with 25 mg/kg SM09419 for 3 weeks were harvested and seeded as described above. Colonies propagated in culture were scored at day 7.

Annexin V Assay

Apoptotic analysis was determined using APC Annexin V (BD Bioscience) and performed according to manufacturer's specifications and co-stained with 4',6-Diamidino-2-Phenylindole, Dihydrochloride (DAPI) for DNA content. Cells were analyzed by flow cytometry and FlowJo software.

Generation of Rbm10 Conditional Knockout Mice

The Rbm10 allele was deleted by targeting exon 4. Two LoxP sites flanking exon 3 and a Frt flanked neomycin selection cassette were inserted in the downstream intron. Ten micrograms of the targeting vector were linearized and then transfected by electroporation of HF4 (129/SvEv× C57B1/6) (FLP Hybrid) embryonic stem cells. After selection with G418 antibiotic, surviving clones were expanded for PCR analysis to identify recombinant ES clones. The Neo cassette in targeting vector has been removed during ES clone expansion. Screening primer A1 was designed downstream of the short homology arm (SA) outside the 3' region used to generate the targeting construct. Clones 182, 184, 211, 212, and 284 were expanded and reconfirmed for SA integration. A PCR was performed on clones 182, 184, 211, 212, and 284 to detect presence of the distal LoxP site using the LOX1 and SDL2 primers. This reaction amplifies a wild-type product 472 bp in size. The presence of a second PCR product 48 bp greater than the wild-type product indicates a positive LoxP PCR. Confirmation of distal LoxP retention was performed by PCR using the LOX1 and FRTN2C primers. This reaction produces a product 1.05 kb in size. Sequencing was performed on purified PCR DNA to confirm presence of the distal LoxP cassette using the SDL2 primer. Secondary confirmation of positive clones identified by PCR was performed by Southern Blotting analysis. DNA was digested with Apa I, and electrophoretically separated on a 0.8% agarose gel. After transfer to a nylon membrane, the digested DNA was hybridized with a probe targeted against the 5' external region. DNA from HF4 mouse ES cells was used as a wild-type control. Positive clones were further confirmed by Southern Blotting analysis using an internal probe. DNA was digested with BamH I, and electrophoretically separated on a 0.8% agarose gel. After transfer to a nylon membrane, the digested DNA was hybridized with a probe targeted against the 3' internal region. DNA from HF4 mouse ES cells was used as a wild-type control. Primer set NDEL1 and NDEL2 was used to screen mice for the deletion of the Neo cassette. The PCR product for the wild-type is 322 bp. After Neo deletion, one set of LoxP-FRT sites remains (147 bp). A second band with a size of 469 bp indicates Neo deletion. A PCR was performed to detect presence of the distal LoxP site using the LOX1 and SDL2 primers. This reaction amplifies a wild-type product 473 bp in size. The presence of a second PCR product 48 bp greater than the wild-type product indicates a positive LoxP PCR. Tail DNA samples from positive mice were amplified with primers NEOGT and A1. NEOGT is located inside the Neo cassette and A1 is located downstream of the short homology arm, outside the region used to create the targeting construct. NEOGT/A1 amplifies a fragment of 2.32 kb in length.

Bone Marrow (BM) Transplantation

Freshly dissected femora and tibiae were isolated from Mx1-cre WT and Mx1-cre Rbm10$^{fl/y}$, CD45.2$^+$ mice. BM was flushed with a 3-cc insulin syringe into PBS supplemented with 3% fetal bovine serum. The BM was spun at 0.5 g by centrifugation and RBCs were lysed in ammonium chloride-potassium bicarbonate lysis buffer for 5 min. After centrifugation, cells were resuspended in PBS plus 3% FBS, passed through a cell strainer, and counted. Finally, 0.5 million total BM cells of Mx1-cre WT and Mx1-cre Rbm10$^{fl/y}$ CD45.2$^+$ mice were mixed with 0.5 million WT CD45.1$^+$ support BM and transplanted via tail vein injection into lethally irradiated (two times 450 cGy) CD45.1$^+$ recipient mice. Chimerism was measured by FACS from the peripheral blood 4 weeks after transplant. Chimerism was followed via FACS in the peripheral blood every 4 weeks (week 0, 4, 6, 8,12, and 16 after polyI:polyC injection). For noncompetitive transplantation experiments, 1 million total BM cells of Mx1-cre WT and Mx1-cre Rbm10$^{fl/y}$ CD45.2$^+$ mice were injected into lethally irradiated (two times 450 cGy) CD45.1$^+$ recipient mice.

Drug Treatment IC$_{50}$ Measurements

Cell lines were plated in 96 well plates and exposed to the indicated compounds at various concentration ranges with a minimum of three technical replicates per concentration per cell line. Cell viability was measured with the CellTiter Glo reagent (Promega) as per manufacturer's instructions. Absolute viability values were converted to percentage viability versus DMSO control treatment, and then non-linear fit of log (inhibitor) versus response (three parameters) was performed in GraphPad Prism v7.0 to obtain an $IC_{50}$ values. Two-dimensional heatmaps of Synergy Scores from Bliss synergy models were generated based on Demidenko et al., 2019[83].

QPCR Measurement of BCL2A1 Gene Expression

RNA was extracted from the indicated cell lines and reverse transcribed into cDNA using the Verso cDNA synthesis Kit (ThermoFisher Scientific). Measurement of BCL2A1 gene expression was performed using primers amplifying BCL2A1 CDS region and designed by primer3 (https://bioinfo.ut.ee/primer3-0.4.0/) with ACTB as the housekeeping gene. Relative expression levels across cell lines were calculated using the Delta-delta Ct method as per standard procedures.

cDNA Overexpression

BCL2A1, RBM10 wild-type and RBM10 domain mutants as well as XIAP full-length and Dexon 1 were codon optimized and synthesized as gene blocks by Integrated DNA Technologies (IDT) and was sublconed cloned into lentiviral Puro-IRES-GFP construct using NEBuilder Hifi DNA assembly. MOLM-13 RBM10-KO cells were transduced with either BCL2A1, RBM10 wild-type, or RBM10 mutant constructs and treated with venetoclax.

Animal Experiments

For in vivo Cas9 experiments, MOLM-13 Cas9-expressing cells were transduced with sgRosa (negative control) or sgRBM10 constructs. At day 2 post-transduction, sgRNA positive cells (GFP+) were sorted by FACS. 100,000 leukemia-sgRNA expressing cells were intravenously injected into each sub-lethal irradiated (5.5 Gy) 8 weeks-old NOD scid gamma mice mice. For venetoclax trials, a 100 mg/ml venetoclax (Sigma Aldrich) stock was diluted in a carrier containing 10% ethanol, 30% polyethyleneglycol-400 (Sigma), and 60% phosal 50 propylene glycol (Lipoid) to obtain a final concentration of 100 mg/kg. Upon disease onset as measured by bioluminescent imaging, oral gavage was performed once daily with either 100 mg/kg venetoclax or vehicle (1% DMSO). All whole-body bioluminescent imaging was performed by intraperitoneally injection of Luciferin (Goldbio) at a 50 mg/kg concentration and imaging was performed after 5 mins using an IVIS imager. Bioluminescent signals (radiance) were quantified using Living Image software with standard regions of interests (ROI) rectangles.

Kinase Assays $IC_{50}$ values for CLK2, CLK3, DYRK1A and CDK1 were determined by transferring test compounds to 1536-well plates (Echo 550, LabCyte) and by optimizing and performing Z'-LYTE™ kinase assays per the manufacturer's instructions (Thermo Fisher). In addition, a full kinome screen (464 kinases) with 1 μM SM09419 was performed by Thermo Fisher Select Screen service. The $IC_{50}$ for each kinase demonstrating >80% inhibition was then determined. Kinase tree dendrogram was generated using Coral[84].

NanoBRET Target Engagement Assay

Cellular target engagement assays were performed using NanoBRET in 293T cells expressing CLK1, CLK2, CLK3, CLK4, DYRK1A, DYRK1B, and DYRK2 in-frame with a nanoluciferase (NanoLuc) tag. A cell permeable NanoBRET fluorescent tracer was then added to the cells which reversibly binds the target-NanoLuc Fusion protein in live cells to result in a BRET signal. SM09419 or vehicle were then added to each cell over a dose range and the degree of drug-target protein binding was assessed via loss of Nano-BRET signal. An $IC_{50}$ value indicating SM09419-protein binding was then identified via 10-point dose response curves.

Patient-Derived Xenograft Experiments

Frozen human peripheral blood mononuclear cells (PBMCs) from two individual PDX models were rapidly thawed and transferred into 50 ml conical tubes. 20 mL pre-warmed RPMI 1640 (Corning) was added dropwise to tubes. After centrifuging at 300× g at 4 degrees Celsius, cell pellet was resuspended in PBS (Corning). 4 million cells were intrafemorally injected per mouse. Blood was collected by retro-orbital bleeding using heparinized microhematocrit capillary tubes (Thermo Fisher Scientific) and a flow cytometry panel consisting of mCD45/hCD45/hCD3/hCD11b/hB220 were used to discriminate human from mouse cells and human myeloid vs T-cell engraftment. Upon disease onset as measured by hCD45-positive cells by flow cytometry, oral gavage was performed once daily with either 25 mg/kg SM09419 or vehicle (5% polyvinylpyrrolidone).

Quantification and Statistical Analysis

Genome-Wide Differential Gene Expression Analysis

FASTQ files were first trimmed using Trim_galore (v0.6.4) to remove sequencing adapters and low quality (Q<15) reads. Trimmed sequencing reads were aligned to the human Hg19 reference genome (GENCODE, GRCh37.p13) using STAR (v2.7.5)[85]. SAM files were subsequently converted to BAM files, sorted, and indexed using samtools (v1.9). BAM files were used to generate bigwig files using bamCoverage (part of the Deeptools package; v3.3.1). Read counting across genomic features was performed using featureCounts (part of the subread package; v1.5.0)[86].

Gene Expression Estimation and Alternative Splicing Analysis

Annotations from UCSC knownGene[87], Ensembl 71[88], and MISO v2.0[89] were combined to create a genome annotation for the human UCSC hg19 (GRCh37) assembly. All reads were mapped to the transcriptome via RSEM v1.2.4[90], using the Bowtie alignment option "-v 2"[91]. RSEM produces gene-level estimates of expression in units of transcripts per million (TPM). All gene expression estimates were normalized via the trimmed mean of M values (TMM) method[92]. Reads which failed to align were mapped to the genome with TopHat v2.0.8b[93], as well to an expanded annotation created by computing all possible combinations of annotated 5' and 3' splice sites per gene. Isoform expression was quantified with MISO v2.0[89], using the combined RSEM and TopHat alignments as input. The two-sided t-test was used to test differential isoform expression between sample groups. Differentially spliced events were defined as those with at least 20 isoform-identifying reads in each sample, a minimum absolute difference of 10% in isoform expression, and a p-value<0.05. All analyses were conducted within the R Programming environment with tools from Bioconductor[94]. The visualizations were created using the dplyr, ggplot2, and UpSetR[95] packages.

Purine/Pyrimidine Motif Enrichment Analysis

Differentially spliced cassette exon events following SM09419 treatment were identified. The enrichment of purines/pyrimidines in excluded, relative to included, cassette exons was measured within exonic regions and immediately adjacent intronic sequences. The 95% confidence interval was estimated with bootstrapping (1000 resampling iterations). The motif enrichment analysis was conducted within the R Programming environment with GenomicRanges from Bioconductor[94].

eCLIP Data Analysis

The eCLIP data was processed similarly as described previously[37] and is outlined shortly in the following. First, adapter sequences were trimmed from both reads of all read-pairs using cutadapt version 1.14. Then, all remaining reads longer than 16 bases were aligned against the human reference genome sequence hg19/GRCh37 using STAR version 2.5.0c. Only uniquely mapped reads were kept. Read-pair duplicates by position were removed using picard tools version 2.6.0. To identify binding sites, a custom script was run to identify clusters of overlapping reads that had a read-depth of at least 10 reads. Then, significant enrichments were calculated for all such identified clusters by comparing IP-samples versus input-samples using edgeR. More specifically, bamutils count version 0.5.7 was run to counted stranded reads within all identified clusters for all samples. Using this output, differential coverage between IP-vs-input for each cluster was calculated with edgeR after normalizing for total sequencing depth per replicate (resulting in counts per million/CPM per cluster). Final binding sites were called by applying log FC>2 and FDR<0.05 thresholds between IP-vs-input. Identification of RBM10 binding positions in events alternatively spliced following RBM10 KO relied on the htseq-clip suite (https://htseq-clip.readthedocs.io), and the DEWSeq 9% and GenomicRanges Bioconductor packages[97]. In brief, the GRCh38.v40 GENCODE annotation was processed into 50 nucleotide (nt) genomic sliding windows, with step size of 20 nt, using htseq-clip. From the STAR-aligned eCLIP BAM files, htseq-clip was used to identify crosslink positions and count their abundance in each window. The htseq-clip counts matrix was used as input to DEWSeq for normalization and identification of IP-vs-input significantly enriched windows (adjusted p-value<0.05, log FC>2) in protein-coding regions. The p-values were FDR-adjusted via Independent Hypothesis Weighting[98] and overlapping significantly enriched windows were combined. The positions of enriched windows in alternatively spliced regions identified from RNA-seq analyses were determined using the GenomicRanges package.

Gene Ontology Analysis

Gene set enrichment was performed using the fgsea R package (1.4.0) using the KEGG, GO and MsigDB specific signatures according to the manual.

Statistical Analysis

Kaplan-Meier survival curve p-values were performed using Log rank Mantel-COX test. For statistical comparison, unpaired Student's t test was performed. Statistical analyses were performed using Prism 7 software (GraphPad). Data with statistical significance are as indicated, *p<0.05, p<0.01, *p<0.001. Kaplan-Meier survival curves were compared using the Wilcoxon Rank-Sum test via GraphPad Prism.

Example 2: Mapping Genomic Determinants of AML Drug Response

To explore drug-gene interactions that underpin response to AML therapies, a genome-wide Clustered Regularly Interspaced Short Palindromic Repeats (CRISPR) screen containing 77,441 single guide RNA (sgRNA) targeting 19,115 genes[24] was performed. This library was transduced into the human AML cell line, MOLM-13 (an MLL-AF9 translocated cell line bearing a concomitant FLT3[ITD] mutation) and after 8 days post-transduction, cells were treated with a broad range of clinically approved AML drugs (venetoclax, 5-azacytidine, cytarabine, etoposide, midostaurin, and idarubicin) (FIG. 1A). Changes in sgRNA abundance were assessed at day 20 post-transduction by measuring the average fold change (drug/DMSO) of all sgRNAs targeting a given gene and top scoring candidates were classified as genes that sensitize (negative CRISPR score) or confer resistance (positive CRISPR score) to individual drugs (data not shown).

Figure 1B:
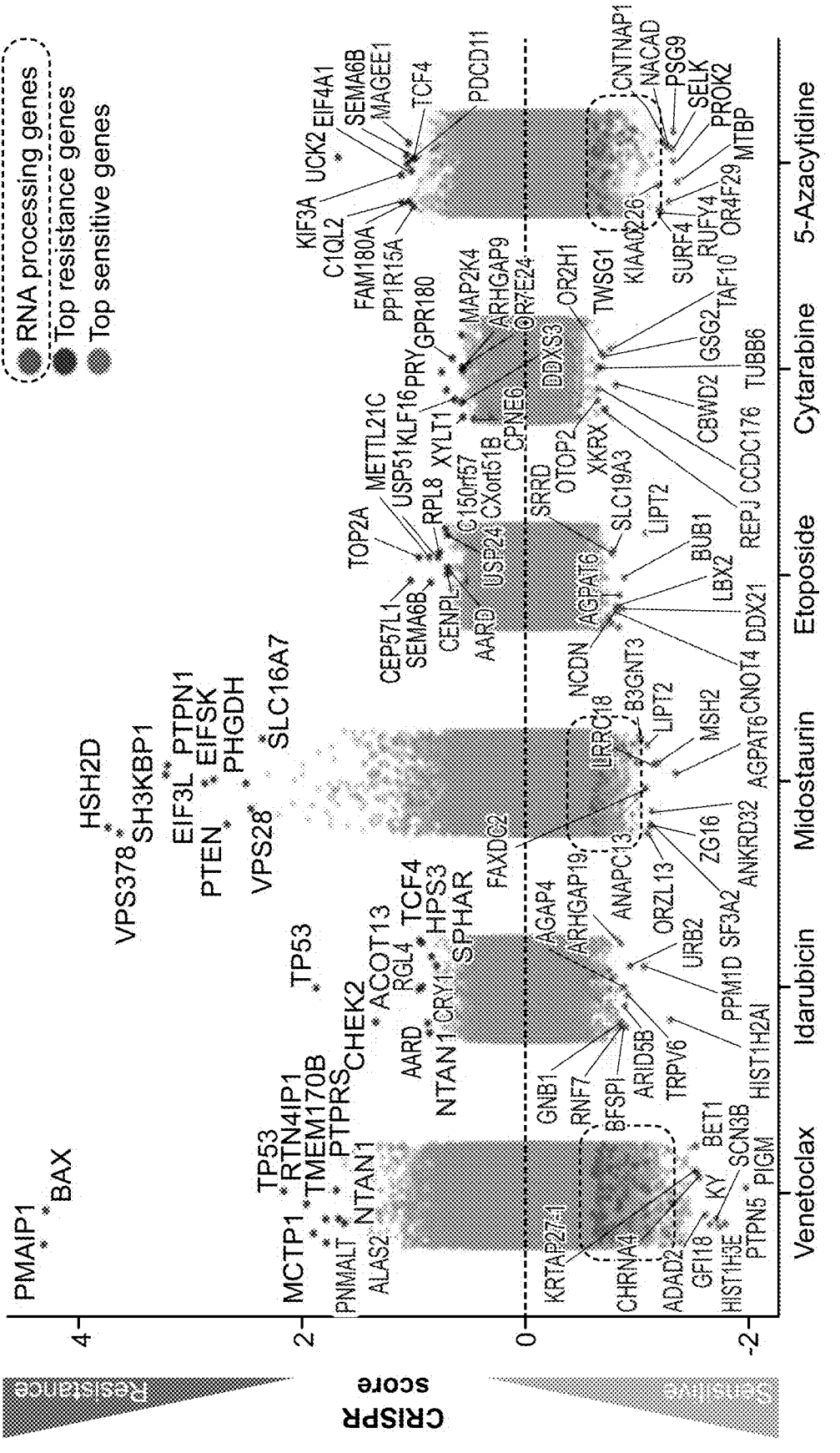

Previously characterized genes shown to mediate resistance to these compounds were identified, including sgRNAs targeting the pro-apoptotic factors, BAX and PMAIP (also known as NOXA), as well as TP53 to confer venetoclax resistance[5] (FIG. 1B). Inactivation of TOP2A, a target of etoposide, promoted survival of AML cells against etoposide exposure. Of note, sgRNAs targeting the uridine-cytidine kinase UCK2 scored as the top positive hit in the 5-azacytidine screen and UCK has been previously implicated to confer resistance to hypomethylating agent[25,26].

Figure 1C:
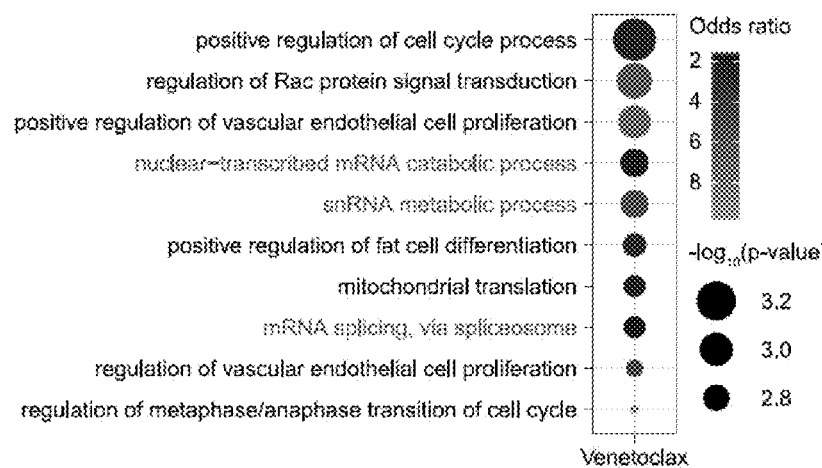
Figure 7A:
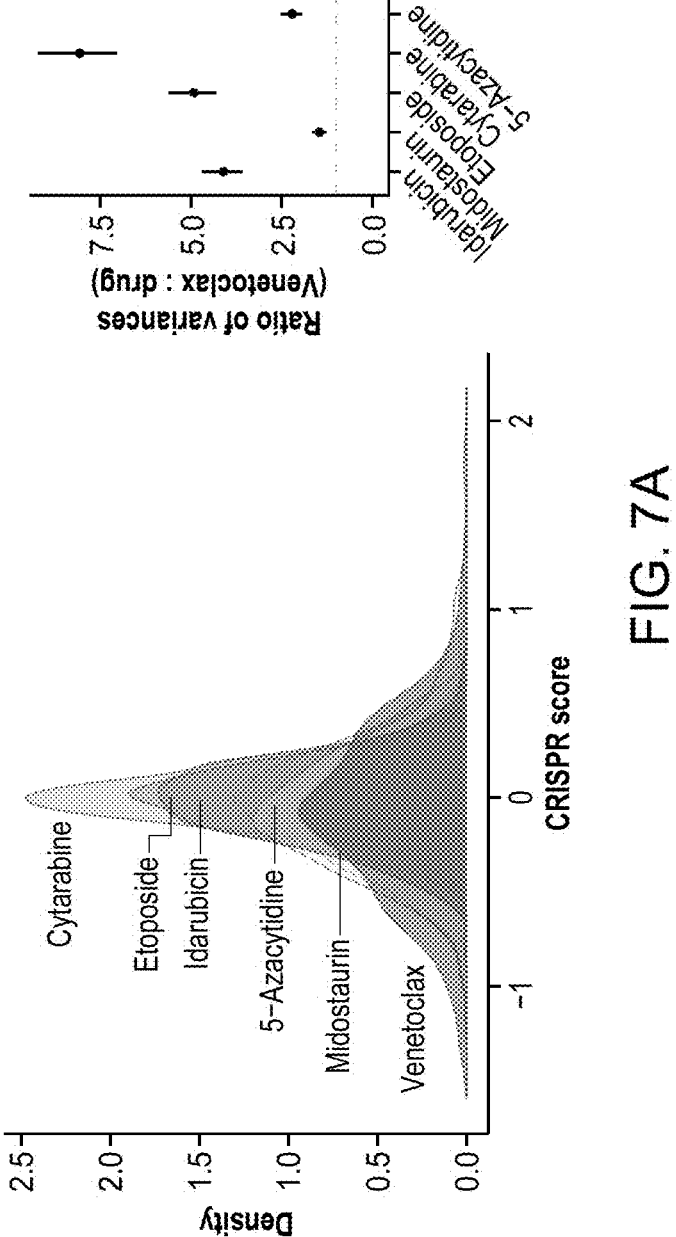
FIGS. 7A-7D. Targeting RNA splicing factors sensitizes AML cells to venetoclax.
Figure 7B:
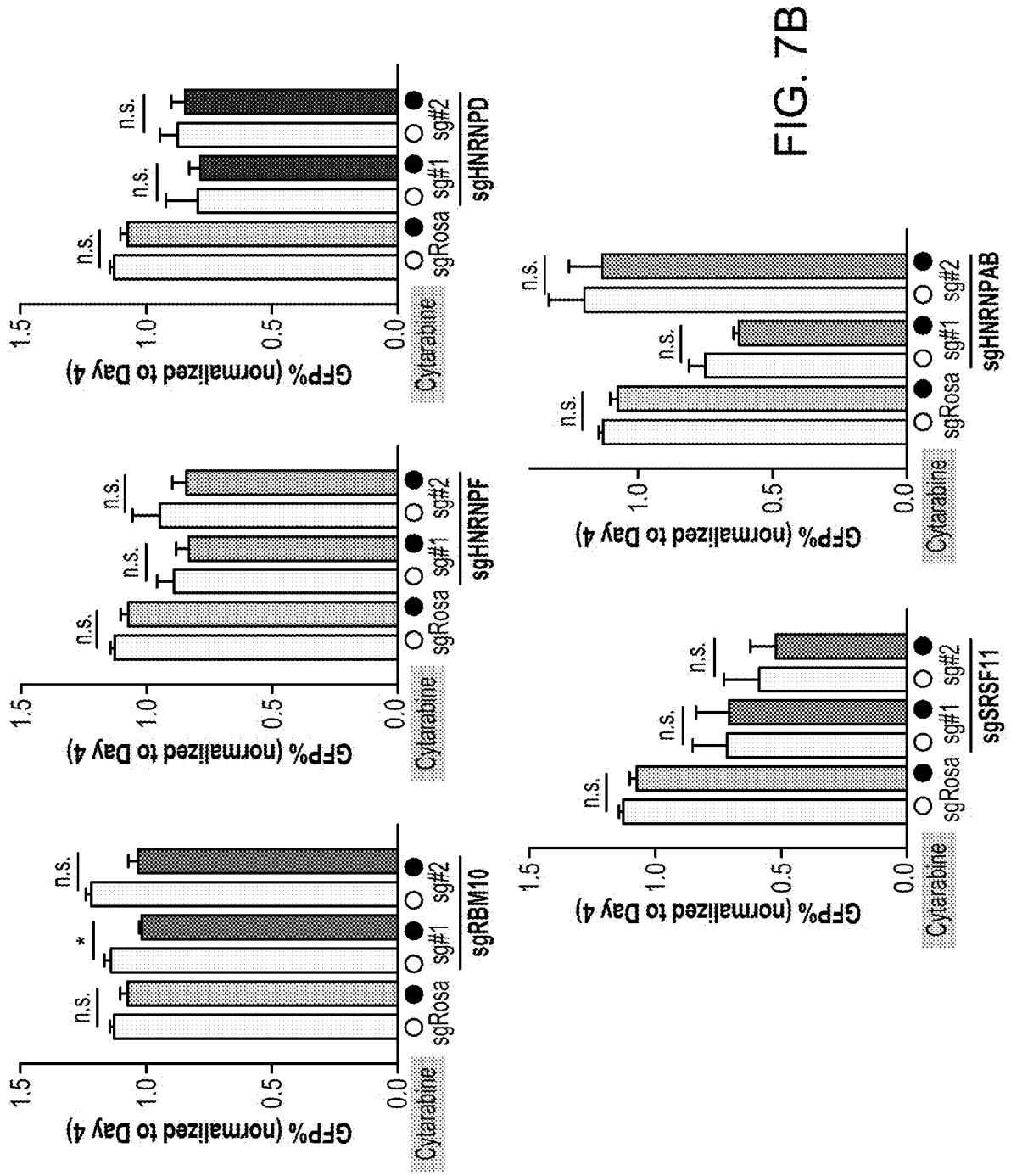
Figure 7C:
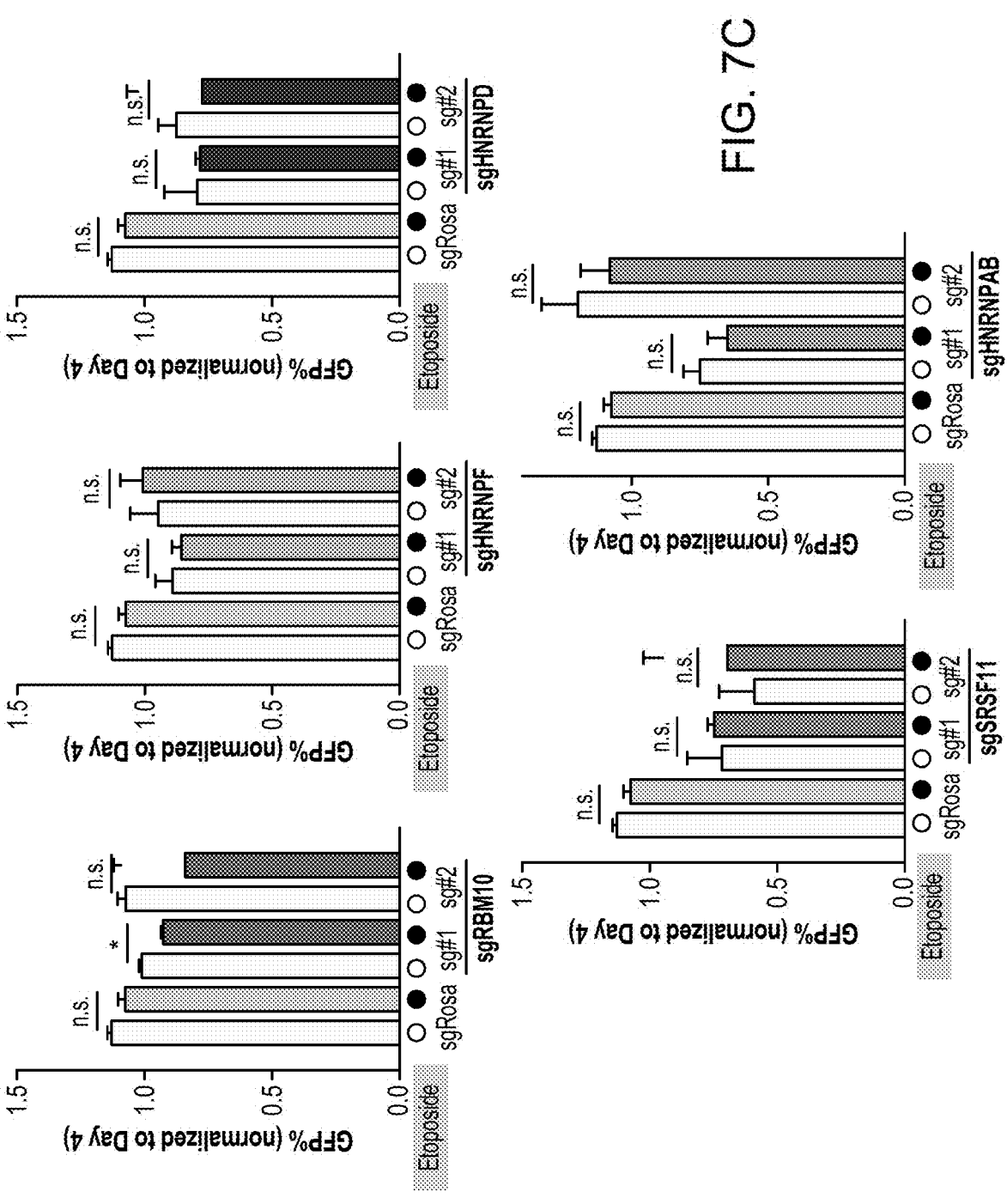
Figure 7D:
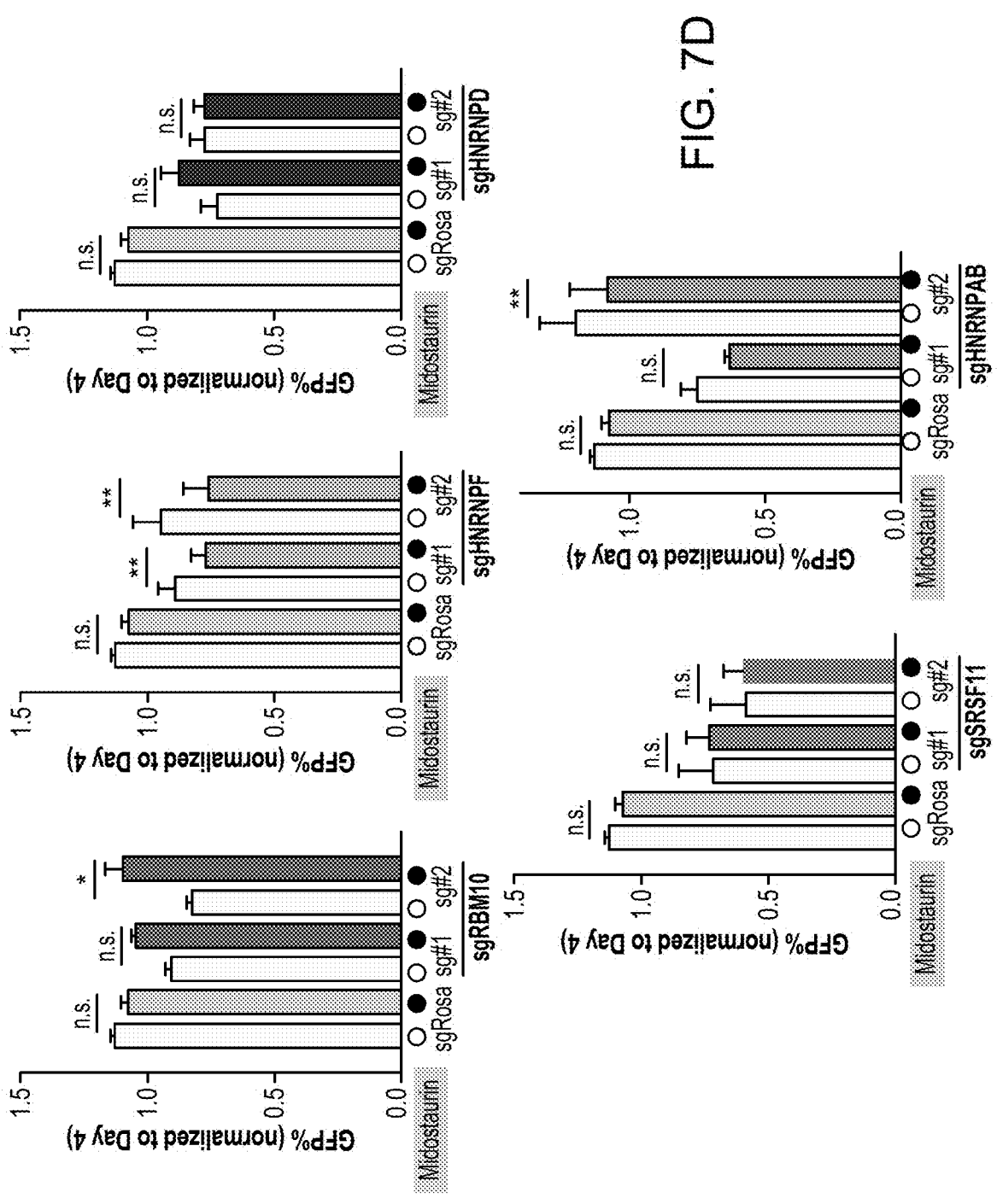

To identify combinatorial strategies that enhance existing AML therapies, genes whose sgRNAs were significantly depleted upon drug exposure were explored. Gene Ontology (GO) enrichment analysis was performed on the top scoring negative hits from each CRISPR screen and uncovered significant terms associated with RNA splicing and regulation of mRNAs, linked to venetoclax sensitization (FIG. 1C). Consistently, a significantly wider distribution (higher variance) of CRISPR scores for sgRNAs targeting RNA processing genes was observed in the setting of venetoclax treatment compared to other drugs (FIG. 7A). These data suggest a unique relationship between perturbation of RNA processing and response to venetoclax compared to other commonly used AML therapies. Previous reports have indicated the importance of leukemia cells exploiting alternative splicing and post-transcriptional mechanisms to promote tumor growth and therapy resistance[27-31]. Moreover, clinical observations in AML patients have also demonstrated correlations between spliceosome mutations and alterations in response to venetoclax[6,32].

Figure 1D:
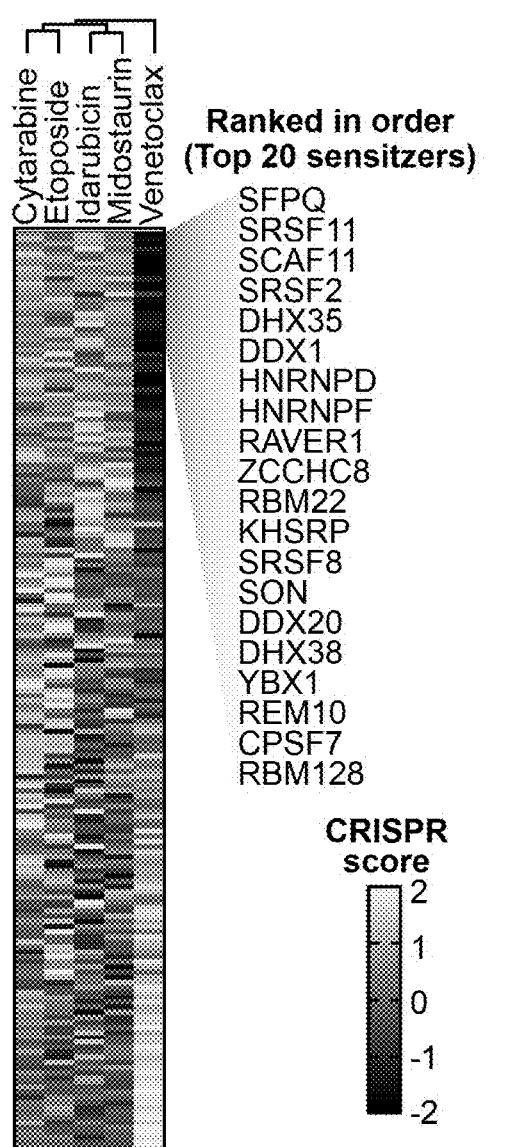
Figure 1E:
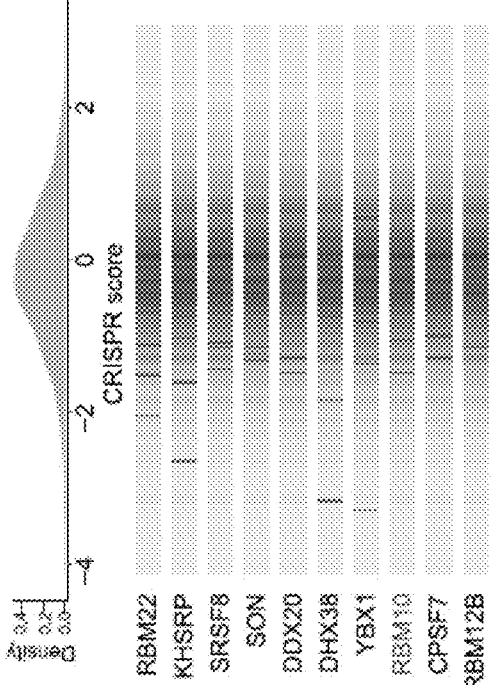
Figure 1E:
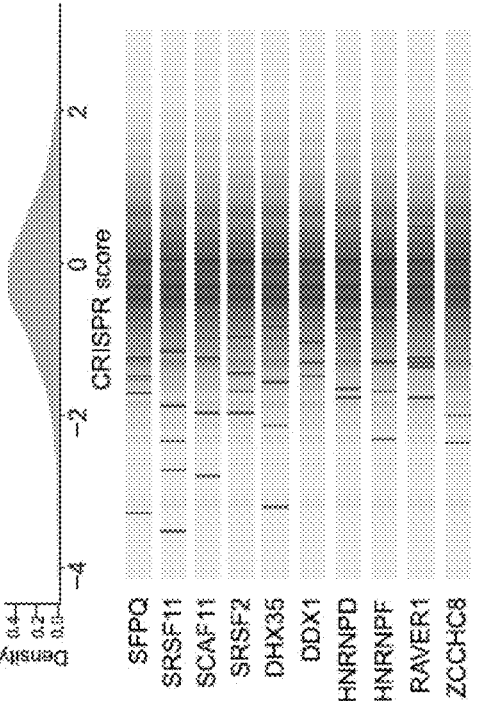
Figures 1F, 1G:
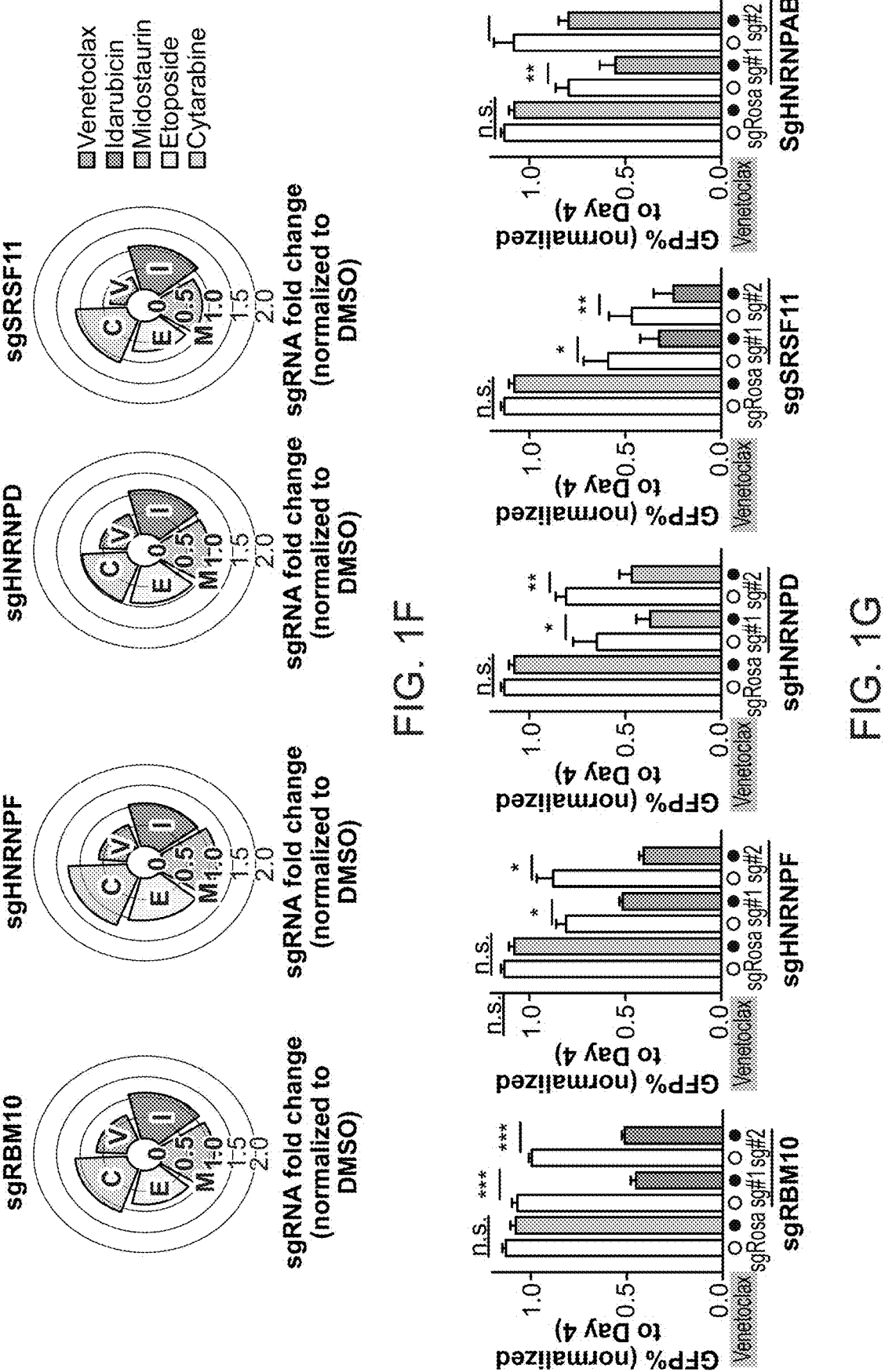

To further investigate the functional impact of RNA splicing factors in modulating drug response, a previously developed CRISPR library targeting functional domains of 492 RNA-binding proteins (RBPs) consisting of 2,855 sgRNAs[27] was applied to enhance CRISPR-Cas9 negative selection by targeting functional protein domains[33] (FIG. 1D). Consistent with initial findings from the genome-wide screen, loss-of-function of several RNA splicing factors that enhanced sensitivity or resistance to venetoclax treatment were identified (FIGS. 1E-1F). The top scoring sensitizers such as RBM10, SRSF11, SRSF8, HNRNPD, HNRNPAB, and HNRNPF were further validated—inactivation of these sensitizers led to preferential sensitivity in AML cells treated with venetoclax, which was not seen with other tested therapeutics (FIG. 1G and FIGS. 7B-7D).

Example 3: Loss of RBM10 Sensitizes Leukemia Cells to Venetoclax

Figures 8A, 8B:
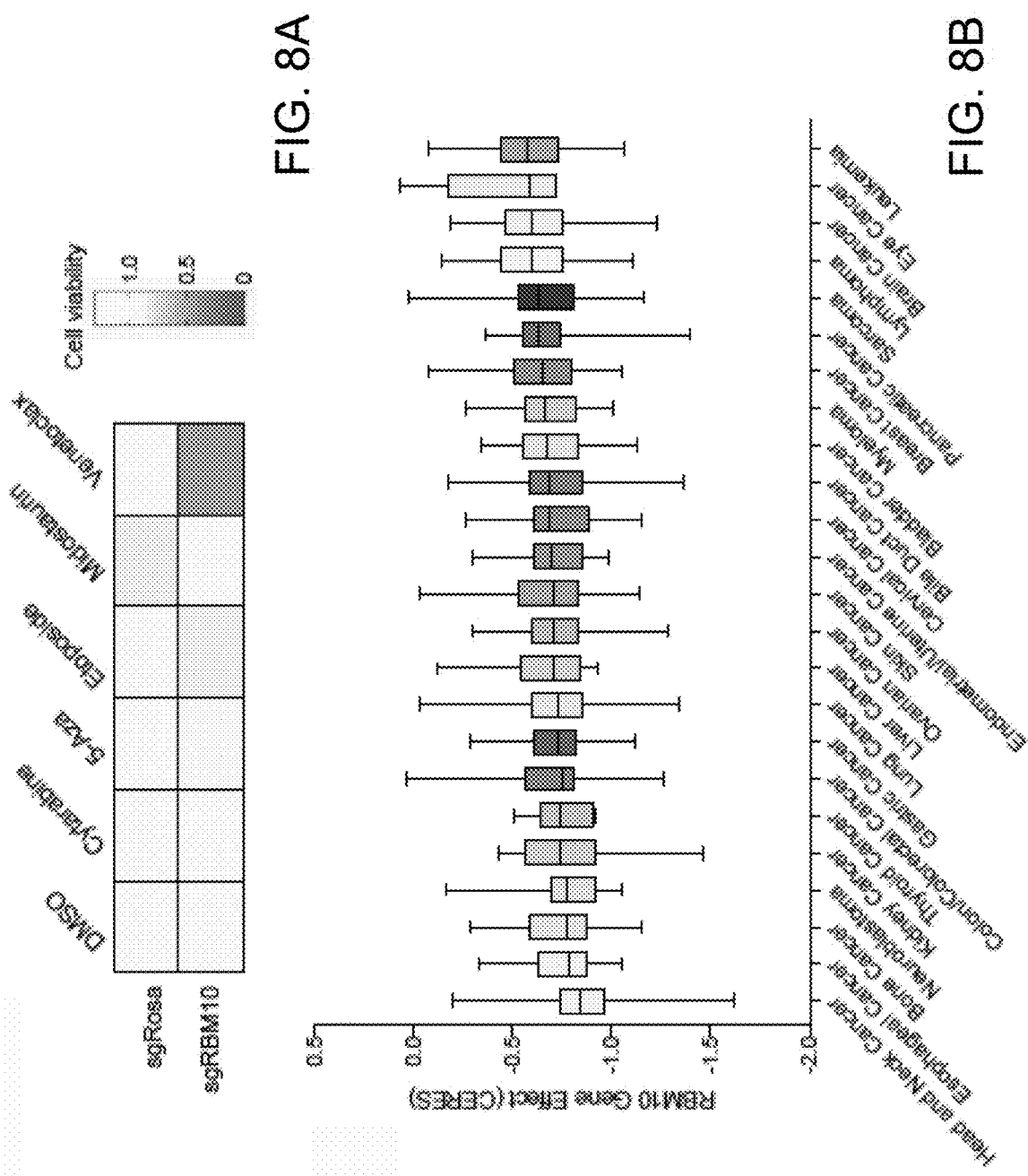
Figures 8C, 8D:
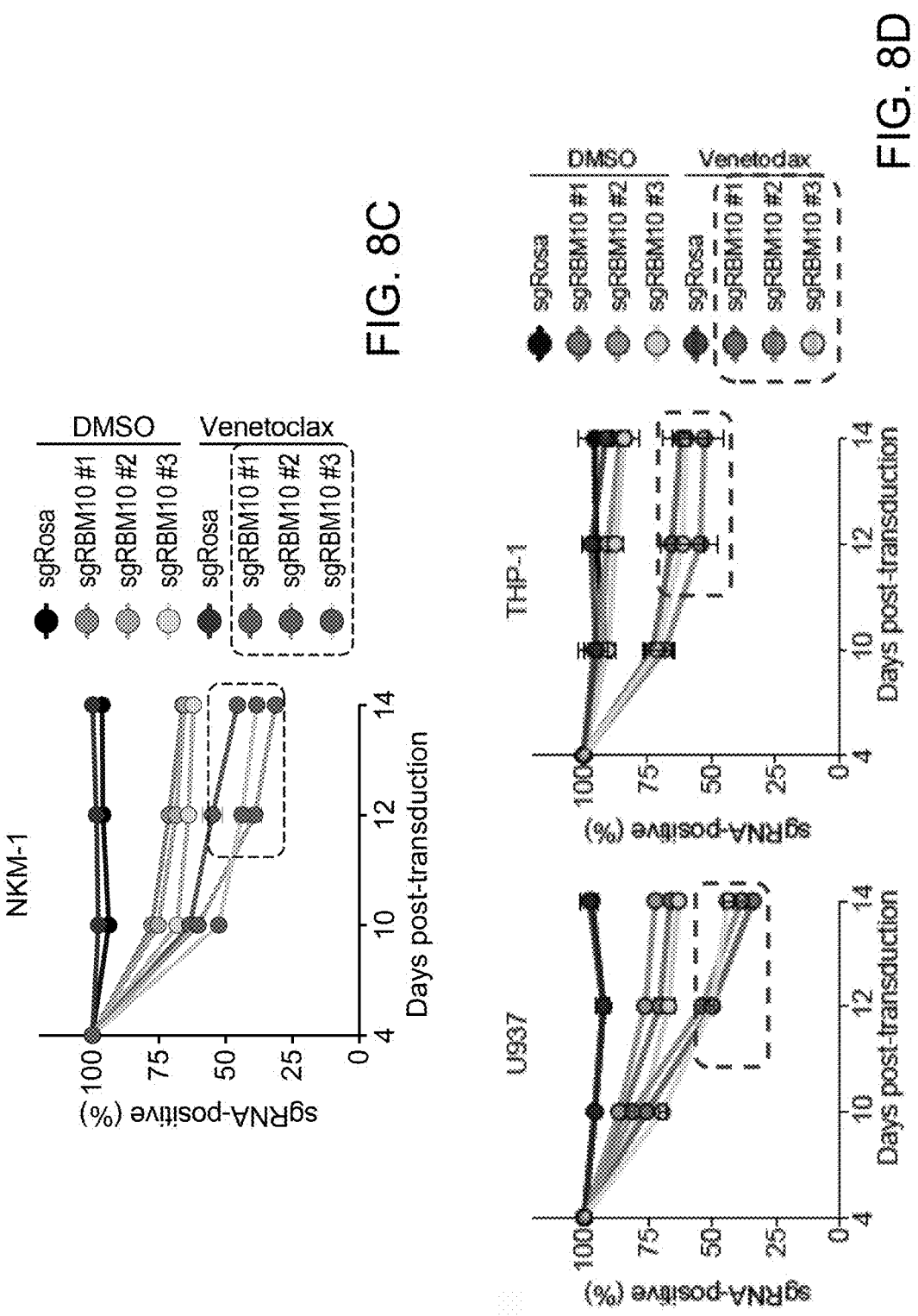

Among the top gene candidates whose loss sensitized cells to venetoclax was RBM10, whose loss-of-function exclusively enhanced venetoclax efficacy in AML amongst other drugs screened (FIGS. 1F-1G and FIG. 8A). Exploration of publicly available genome-wide CRISPR screens performed in a broad range of human cancer cell lines revealed that RBM10 loss is least essential in leukemia cell lines compared other cancer subtypes (FIG. 8B). However, in the presence of venetoclax, RBM10 deletion strikingly conferred preferential lethality and anti-leukemic effects in human AML cell lines, across a variety of molecular subtypes (FIGS. 2A-2C and FIG. 8C). Of note, RBM10 deletion even augmented BCL2 inhibition in TP53-mutated AML cell lines (THP-1, and U937)[34], which have been previously described as venetoclax resistant[5,6] (FIG. 8D).

Figures 2A, 2B, 2C:
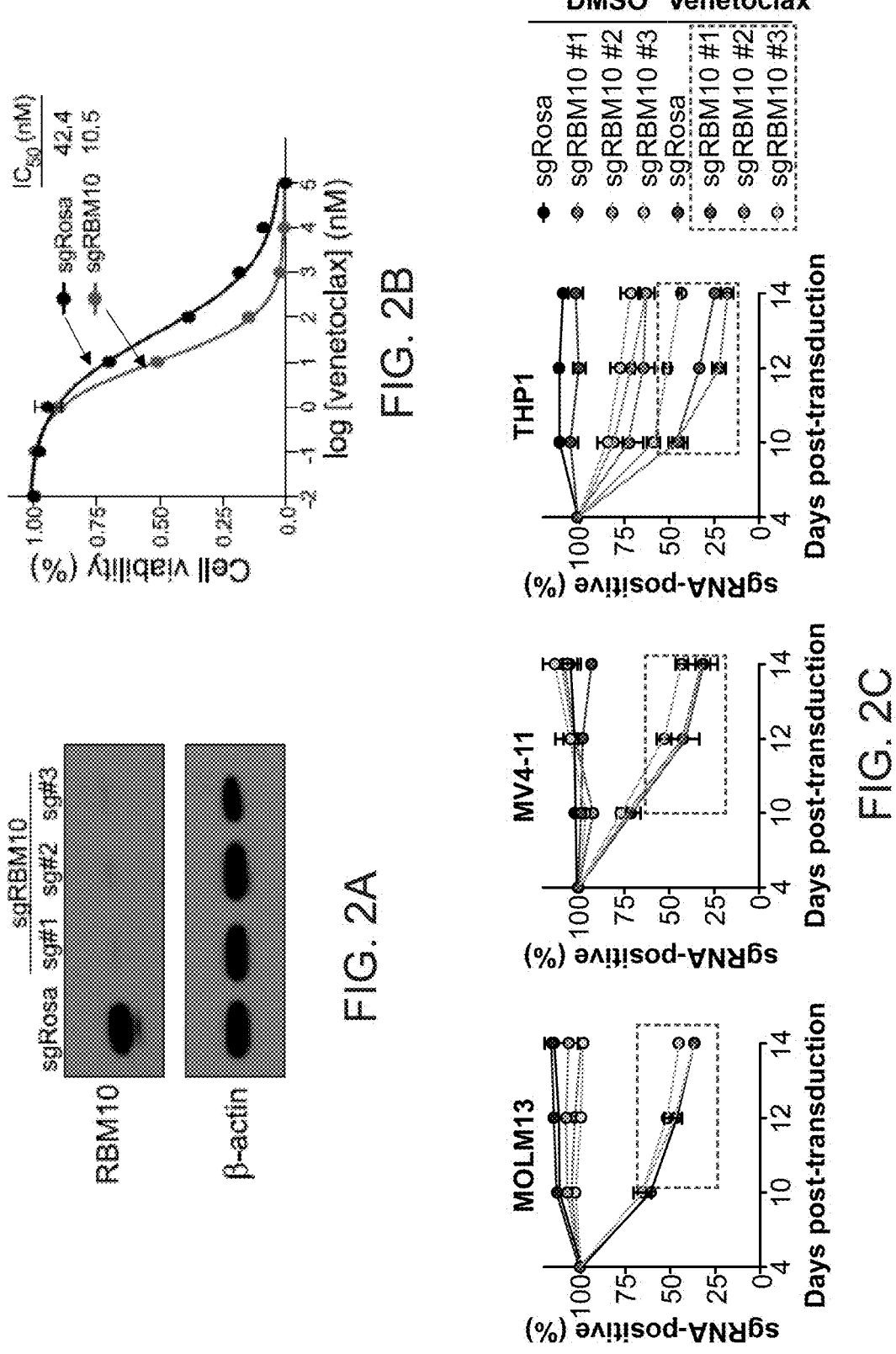
Figure 2D:
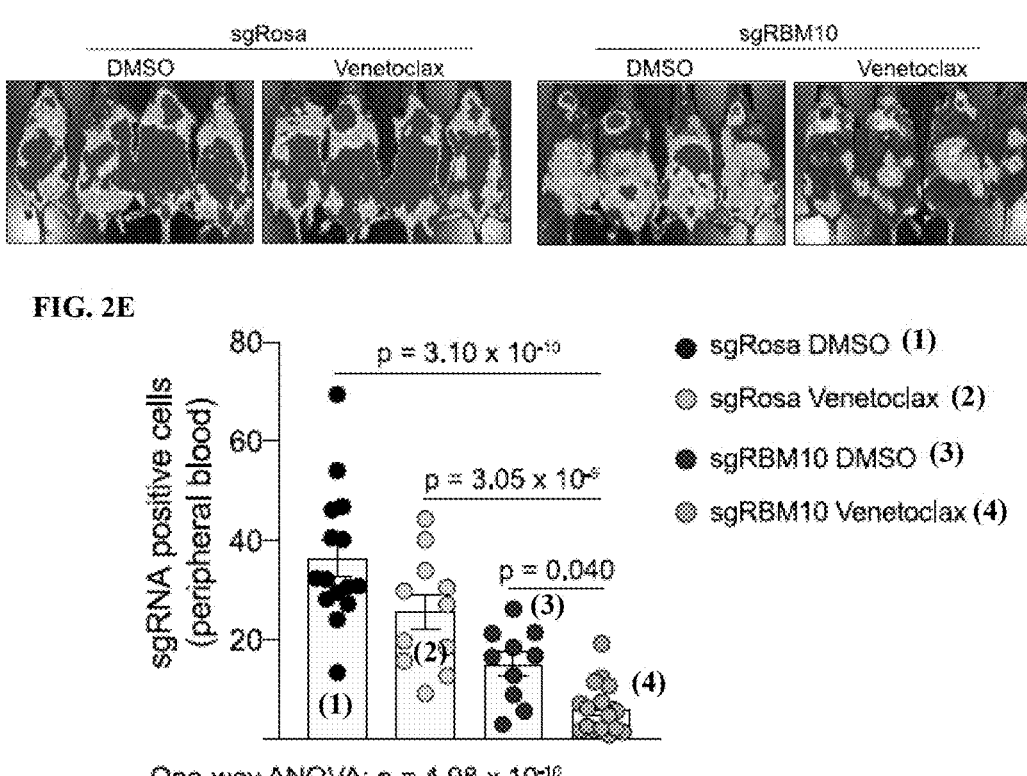
Figure 2E:
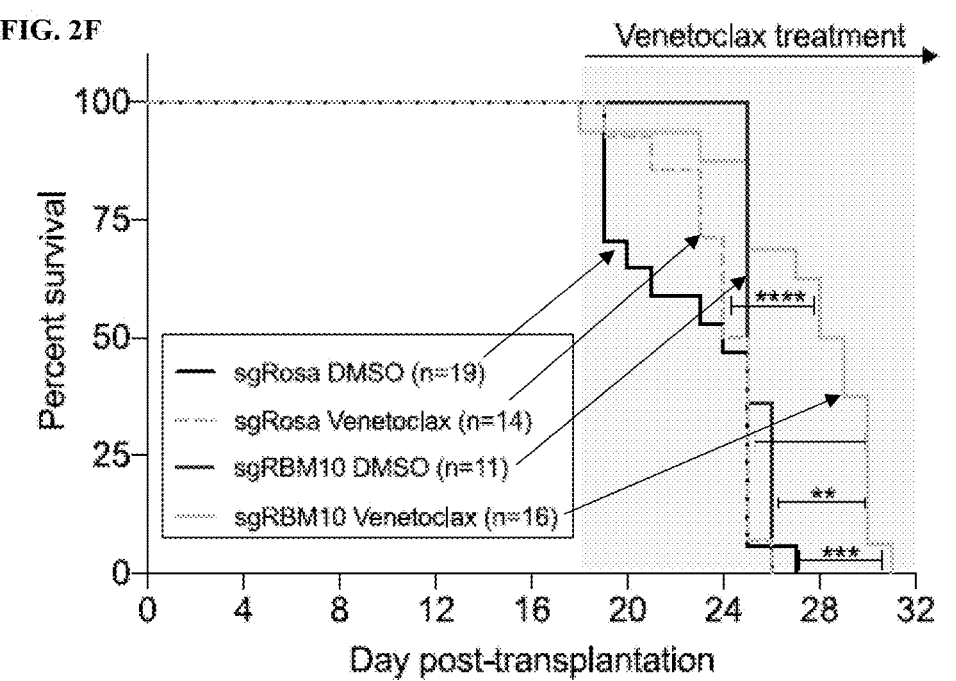
Figure 2J:
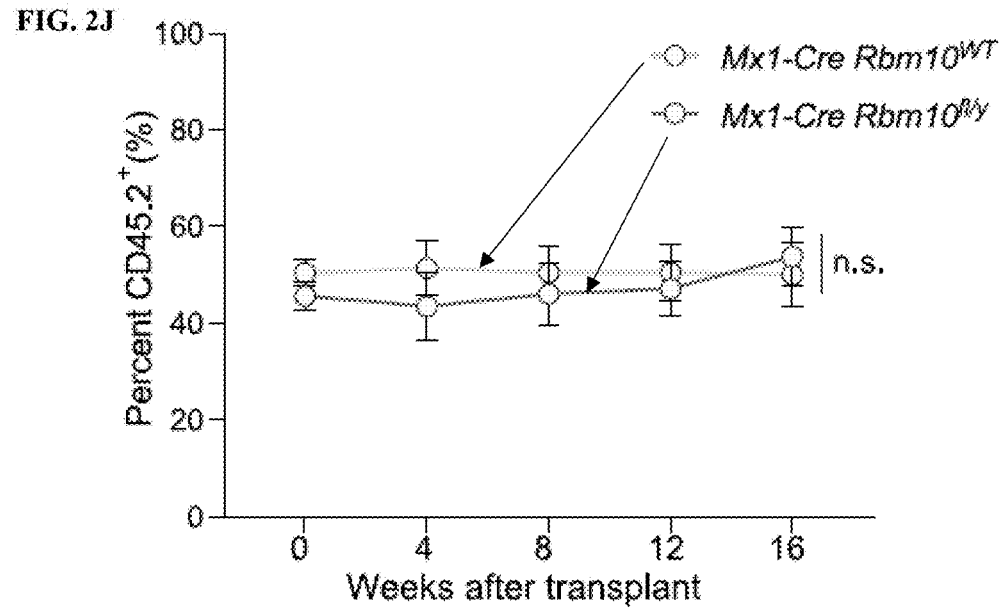
Figure 2K:
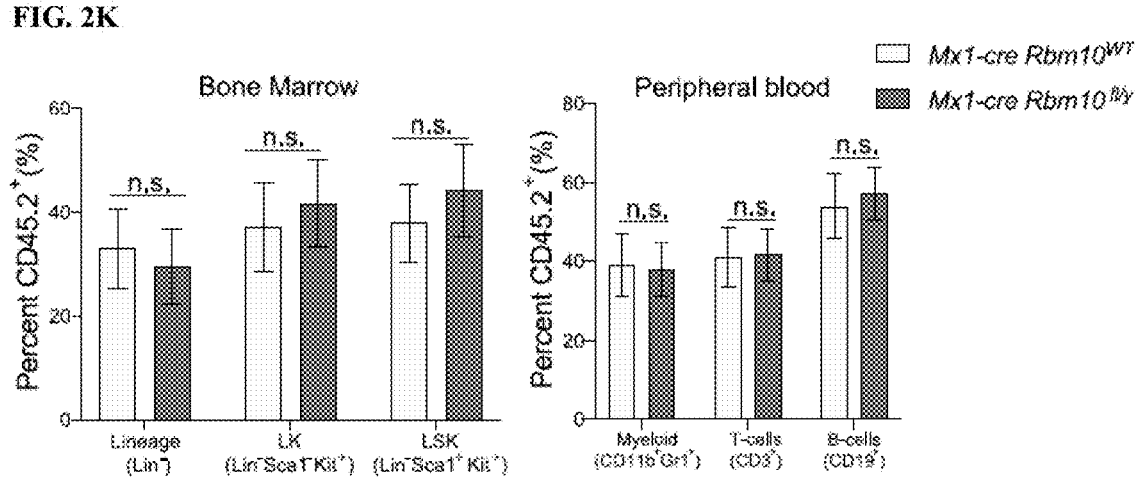
Figure 8E:
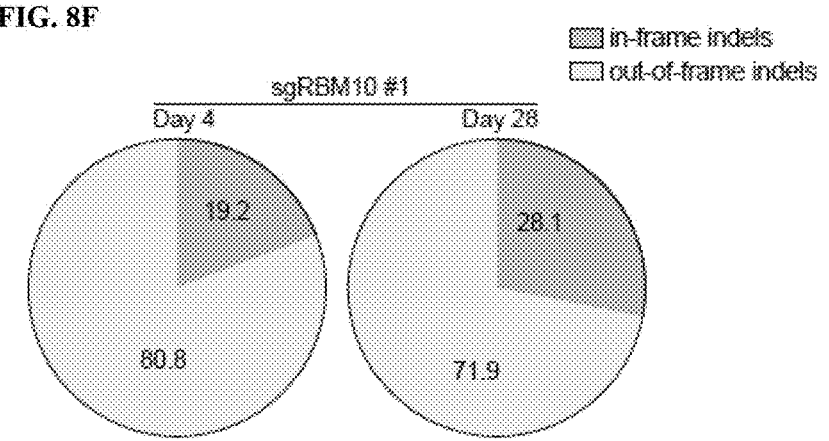
Figure 8F:
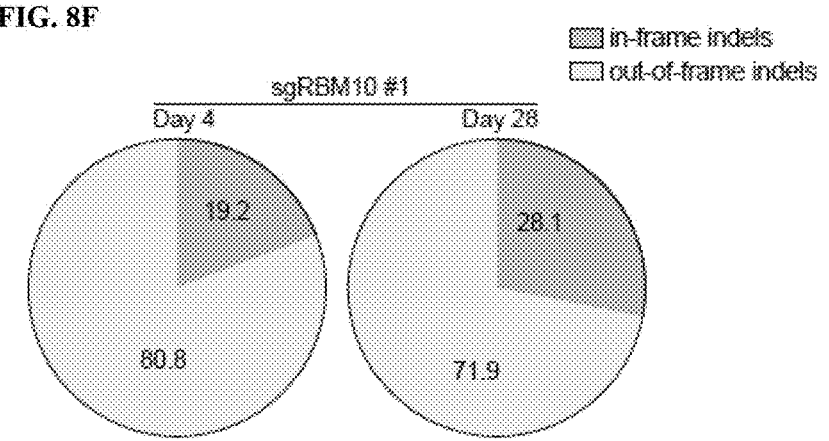
Figures 8J, 8K:
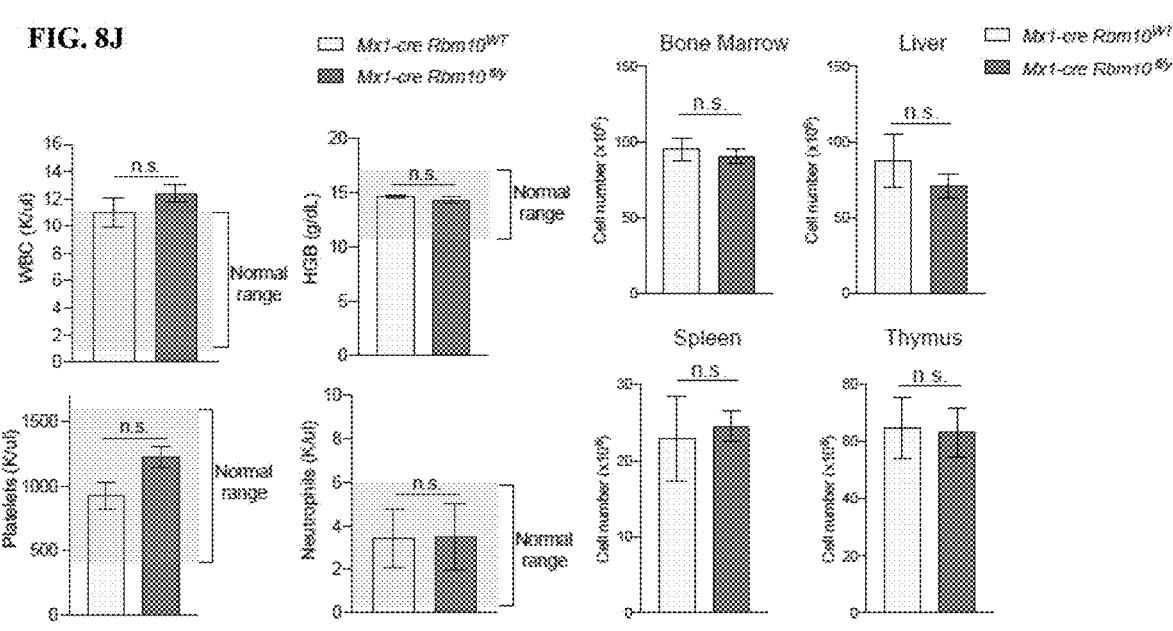

The impact of RBM10 deletion on the response of human AML cells to venetoclax in vivo was assessed. To achieve this, MOLM-13 cells stably expressing firefly luciferase and anti-RBM10 sgRNAs or the non-targeting control (sgRosa) were transplanted into (NOD)/severe combined immunodeficiency (SCID) IL2Rgamma$^{null}$ (NSG) mice. Upon disease onset, mice were treated with venetoclax (100 mg/kg/day) or vehicle control (FIG. 2D). Consistent with in vitro findings, RBM10 deletion reduced leukemia burden and extended survival in the setting of venetoclax treatment (FIGS. 2E-2F and FIG. 8E). Indel analysis of prolonged RBM10 sgRNA editing by next-generation sequencing showed an outgrowth of cells containing in-frame RBM10 mutations, implicating that mice succumb to an outgrowth of sgRNA-expressing cells that retain RBM10 functionality (FIG. 8F). Overall, these findings provide genetic evidence that loss of RBM10 has a synthetic lethal relationship with BCL2 inhibition in AML.

Many RNA splicing factors are known to be pan-essential for cell survival[35]. To evaluate the therapeutic potential of RBM10 modulation as a therapeutic candidate for venetoclax-based therapies, an Rbm10 conditional knockout (cKO) mouse was generated by inserting loxP sites flanking exon 3 of Rbm10 (Rbm10$^{fl/fl}$; FIG. 2G) and crossing with interferon-induced Mx1-driven Cre recombinase mice. Following intraperitoneal polyinosinic; polycytidylic acid (pIpC) injections, Rbm10 cKO mice were confirmed to excise exon 3 of Rbm10 leading to an early frameshift and loss of Rbm10 protein in bone marrow cells (FIG. 2H and FIGS. 8G-8I). Stem cell functionality was next assessed using in vitro colony-replating assays which demonstrated that Rbm10 deletion in hematopoietic precursors did not impair colony formation (FIG. 2I). In parallel, bone marrow-derived cells from CD45.2$^+$ Rbm10 floxed mice were transplanted in a competitive manner along with competitor Rbm10 wild-type CD45.1$^+$ cells and treated with pIpC after stable reconstitution of hematopoiesis. There was no significant effect of Rbm10 deletion on absolute numbers or frequency of peripheral blood and bone marrow cells (FIGS. 2J-2K and FIGS. 8J-8K). These data demonstrate that Rbm10 is dispensable for normal hematopoiesis.

Example 4: Dual Inhibition of RBM10 and BCL2 Promotes XIAP Mis-Splicing

Figure 3A:
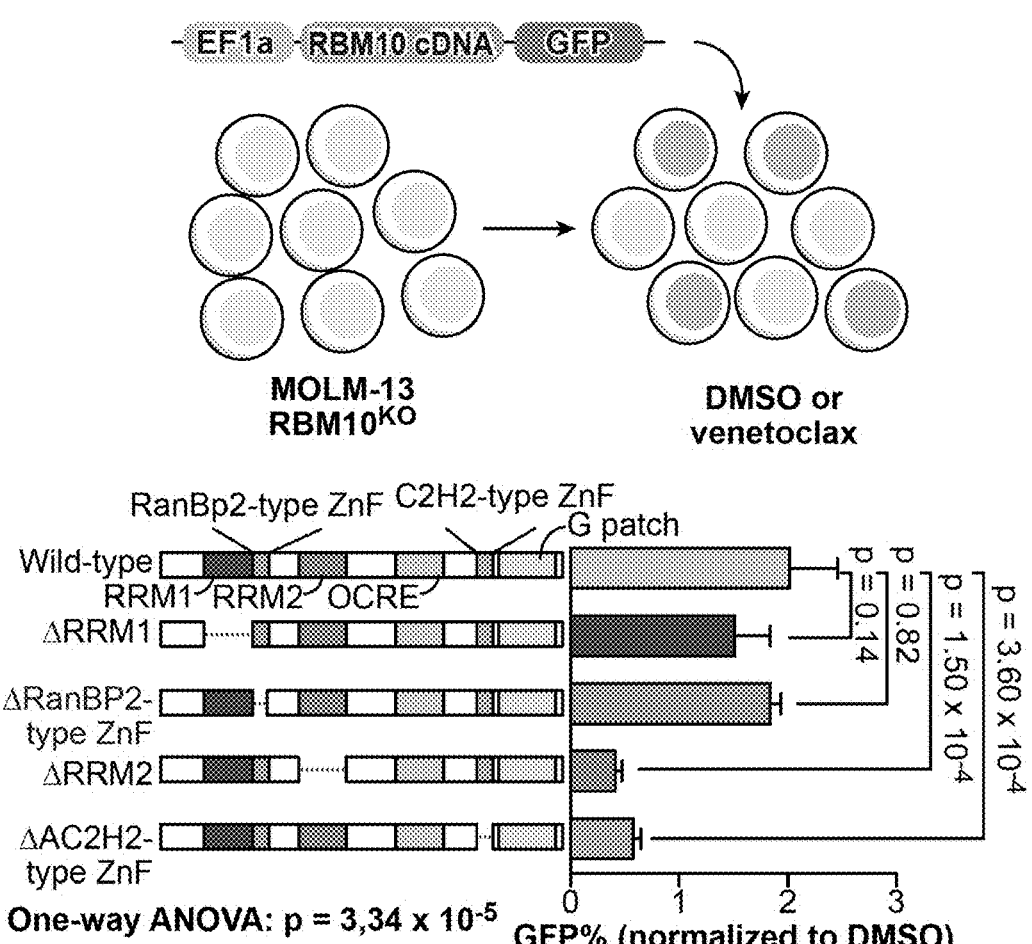

The mechanistic basis for the relationship between RBM10 loss and enhanced response to venetoclax was assessed. The effects of RBM10 knockout (KO) on venetoclax response were rescued by expressing an RBM10 cDNA impervious to anti-RBM10 sgRNAs (due to mismatches between cDNA sequence and the RBM10 sgRNAs; FIG. 3A). However, expression of RBM10 lacking its second RNA recognition motif 2 (RRM2) or C2H2-type zinc finger (C2H2 ZnF)[36] failed to rescue response to venetoclax (FIG. 3A).

Figure 3B:
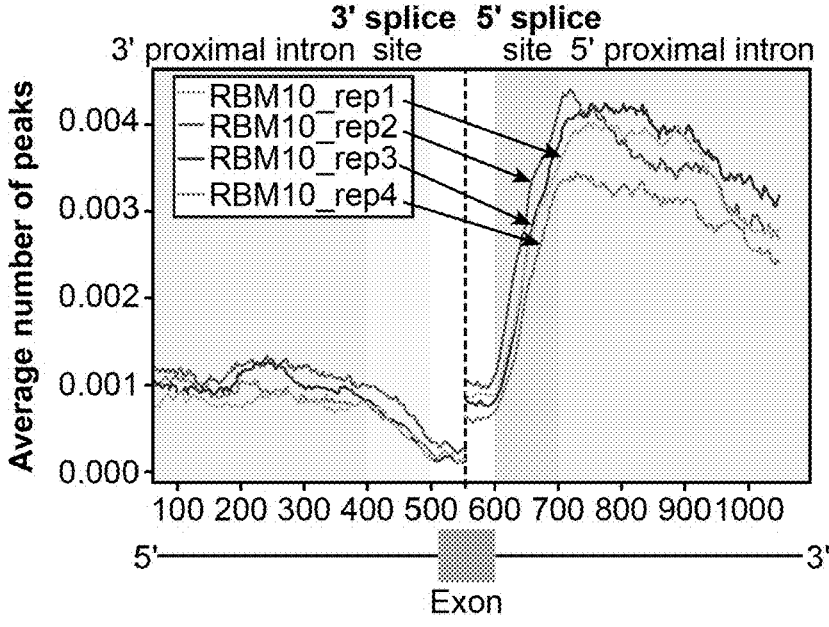
Figure 9A:
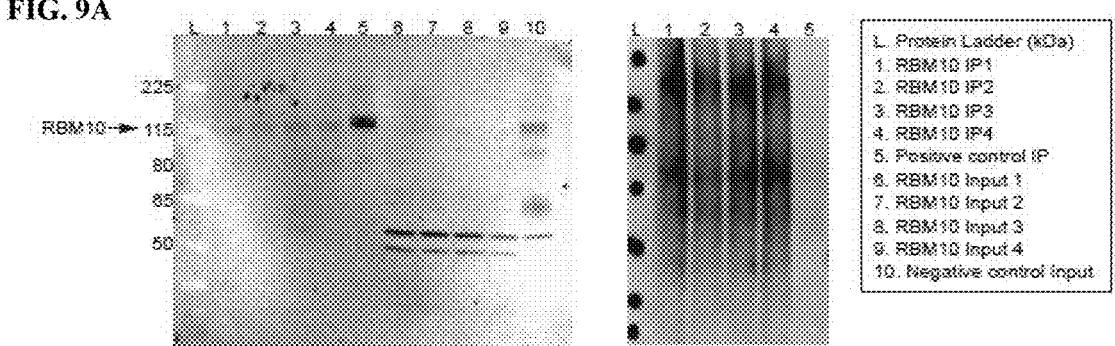
FIGS. 9A-9I. Characterization of RBM10 on RNA splicing and binding in AML cells.
Figure 9B:
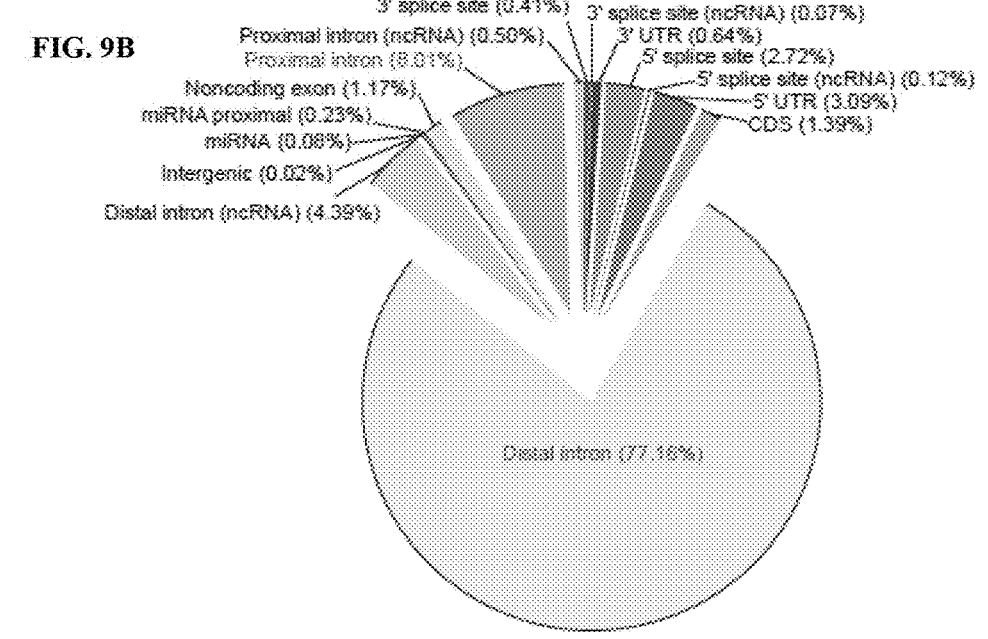

The above data indicate the importance of RBM10's RNA binding domains on venetoclax response. The direct impact of RBM10-RNA interactions on pre-mRNA binding and splicing was assessed, which have not been explored in hematopoietic cells previously. Anti-RBM10 enhanced UV cross-linking immunoprecipitation (eCLIP)[37] was performed in MOLM-13 AML cells (FIG. 9A). This approach identified approximately 29,000 significant sequence clusters bound by RBM10, which corresponded to ~5,000 annotated transcripts (data not shown). Approximately 90% of RBM10 binding sites mapped to intronic sites, with a preferential occupancy of distal (further than 500 nucleotides (nt) from the splice site region) (77.1%) and proximal (within 500 nt of splice site region) intronic (8%) sequences near 5' and 3' splice sites throughout the transcriptome (FIG. 3B and FIG. 9B).

Figure 3C:
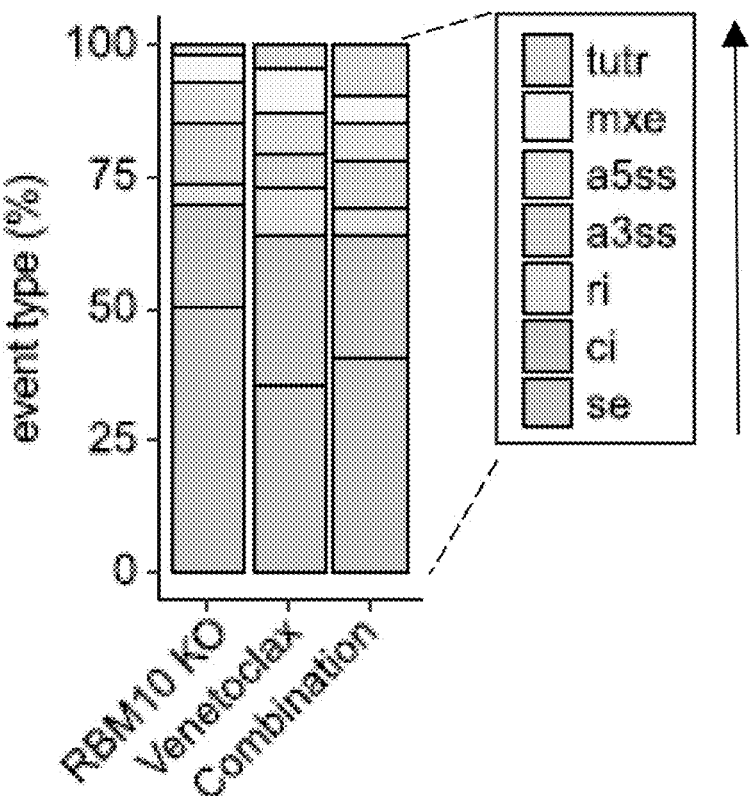
Figure 3D:
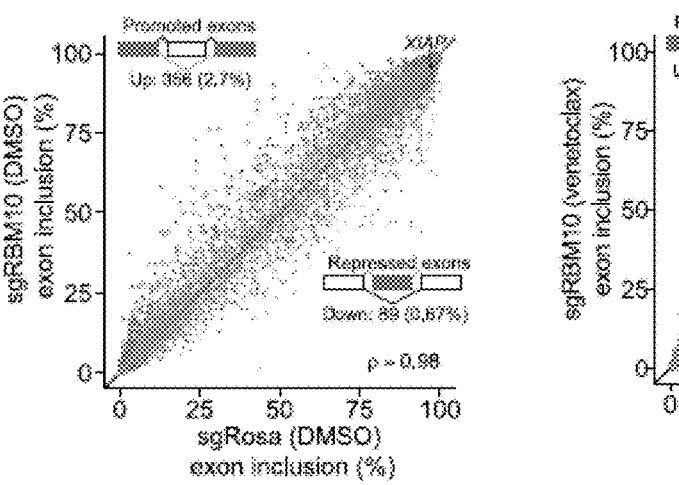
Figure 3D:
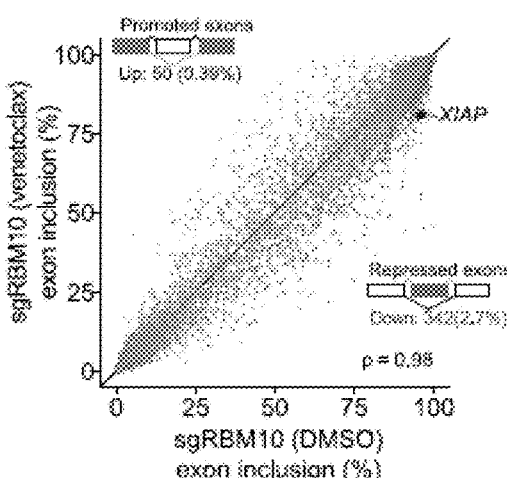
Figure 9C:
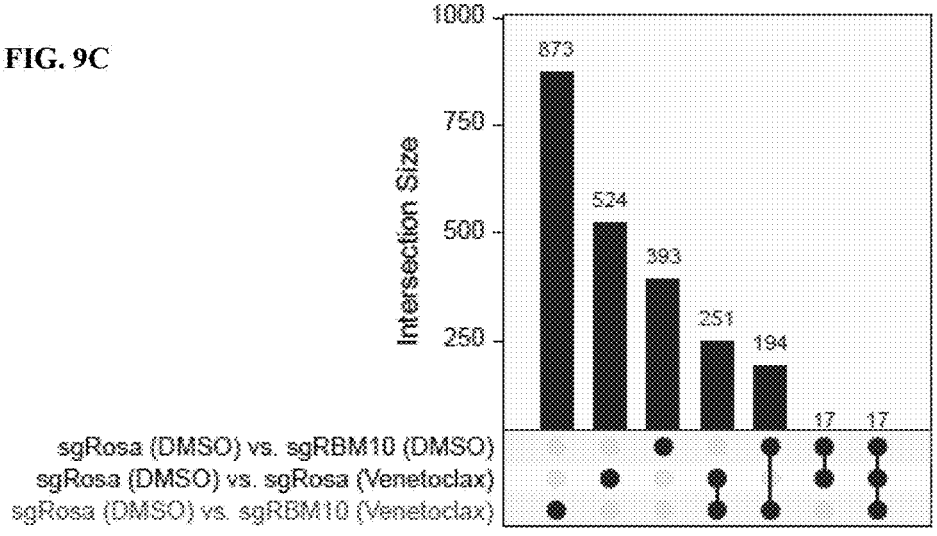
Figure 9D:
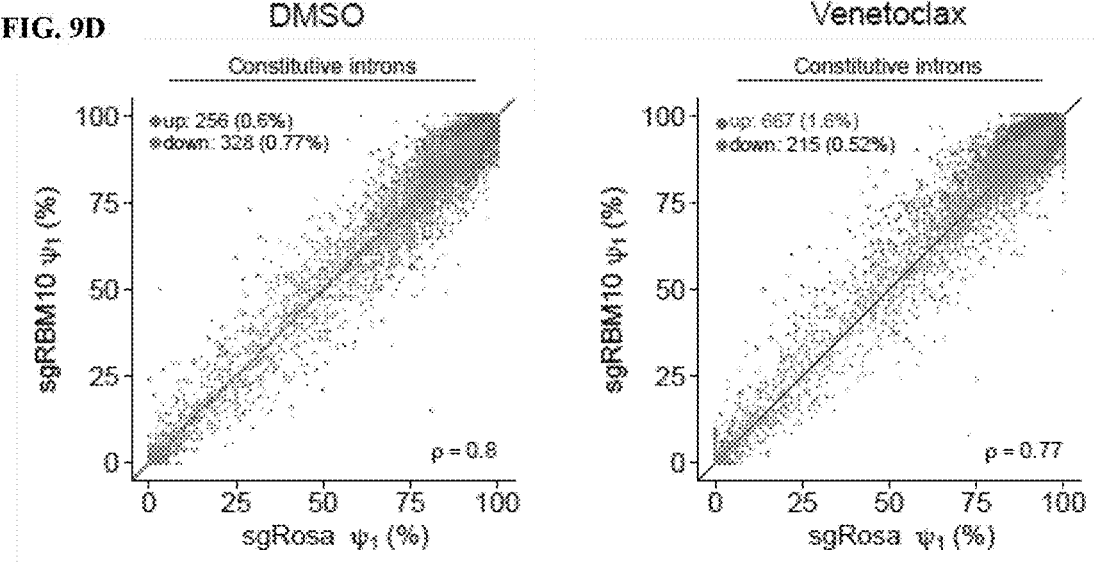

Next, the transcriptional and splicing changes in RBM10-deleted AML cells treated with venetoclax or DMSO compared to non-targeting sgRosa, were evaluated by RNA sequencing (RNA-seq) (data not shown). Isoform usage frequencies across seven main types of alternative splicing events [skipped (or retained) cassette exons (SE), alternative 5' splice sites (A5SS), alternative 3' splice sites (A3SS), mutually exclusive exons (MXE), tandem 3' UTRs (TUTR), and retained (RI) and constitutive introns (CI)] was measured to quantify splicing changes across treatments (FIGS. 9C-9D). RBM10 KO primarily led to changes in cassette exon splicing (FIG. 3C), suggesting that RBM10 most commonly regulates exon usage in AML cells. In comparison, RBM10 deletion in the presence of venetoclax amplified the degree of aberrant splicing involving constitutive introns and cassette exons. Most notably, an increase in exon exclusion events in the combination treatment versus RBM10 deletion alone was observed (n=342) (FIG. 3D).

Figure 3E:
Figure 3E:
Figure 3F:
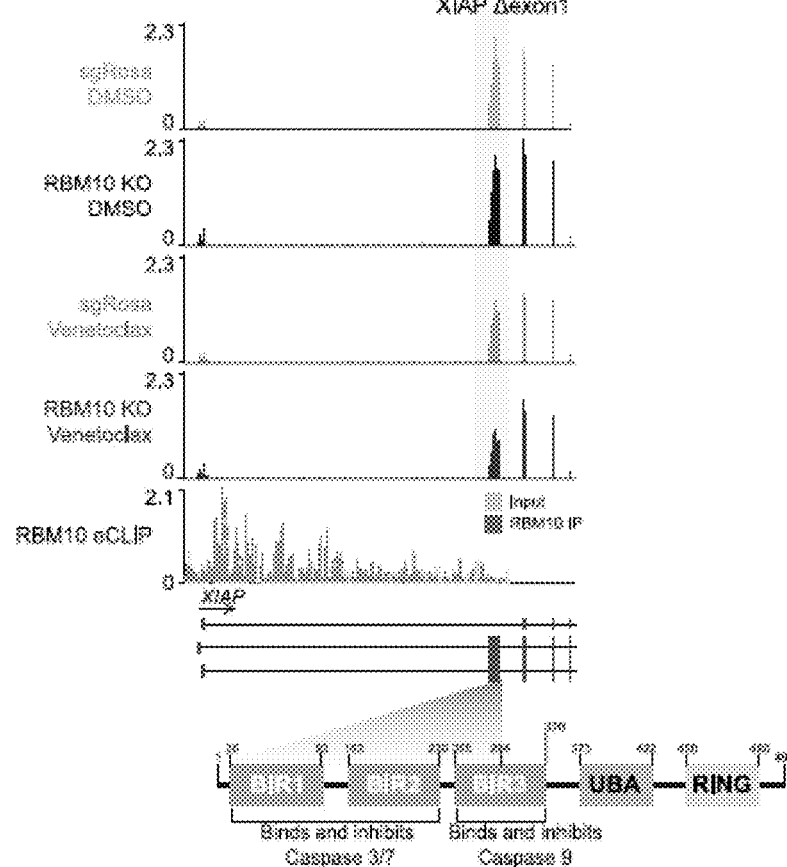
Figure 9E:
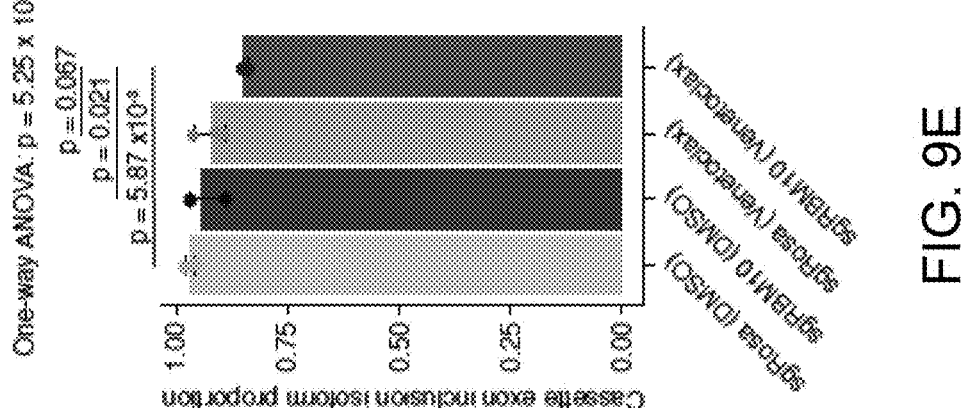
Figure 9F:
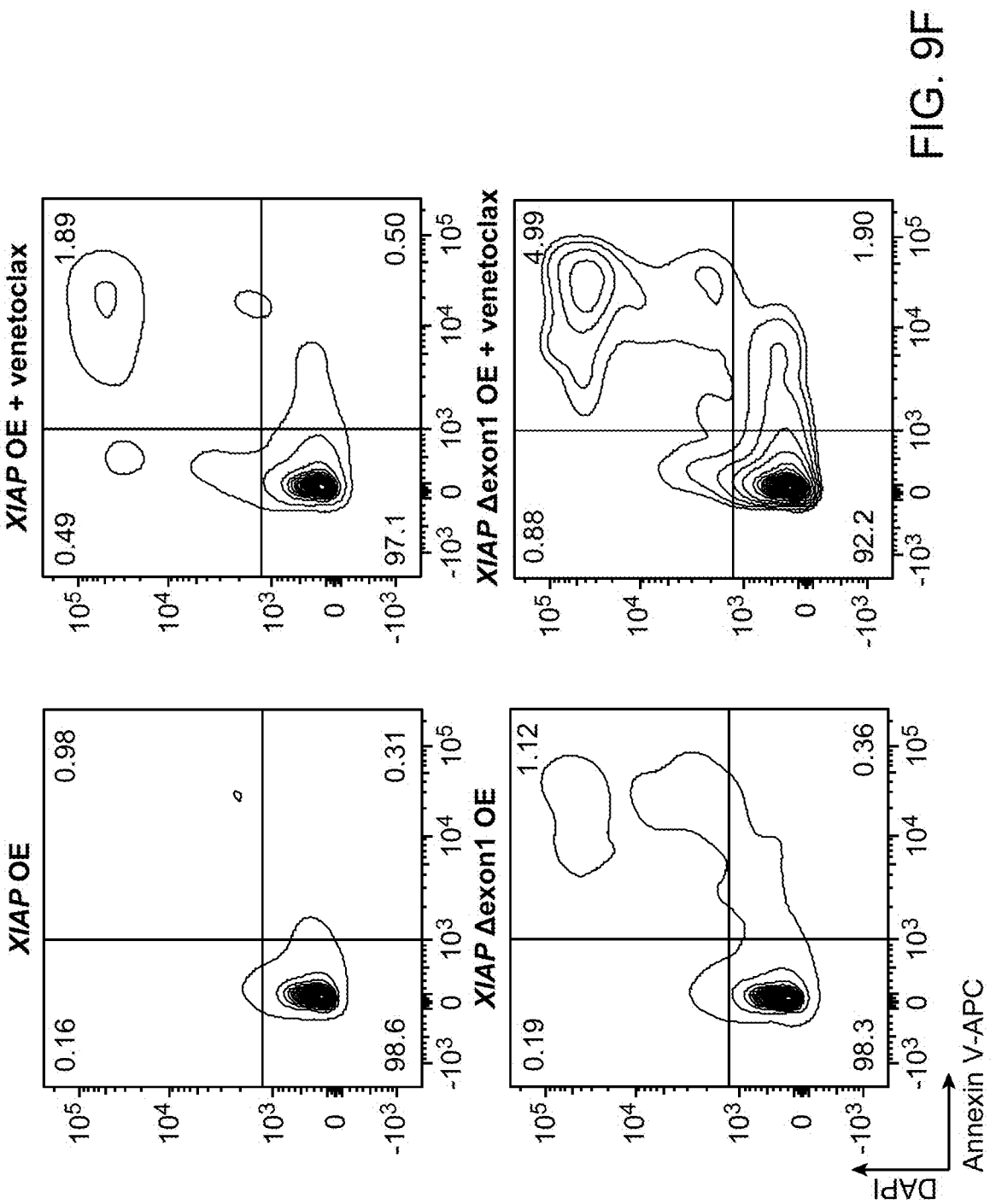
Figure 9G:
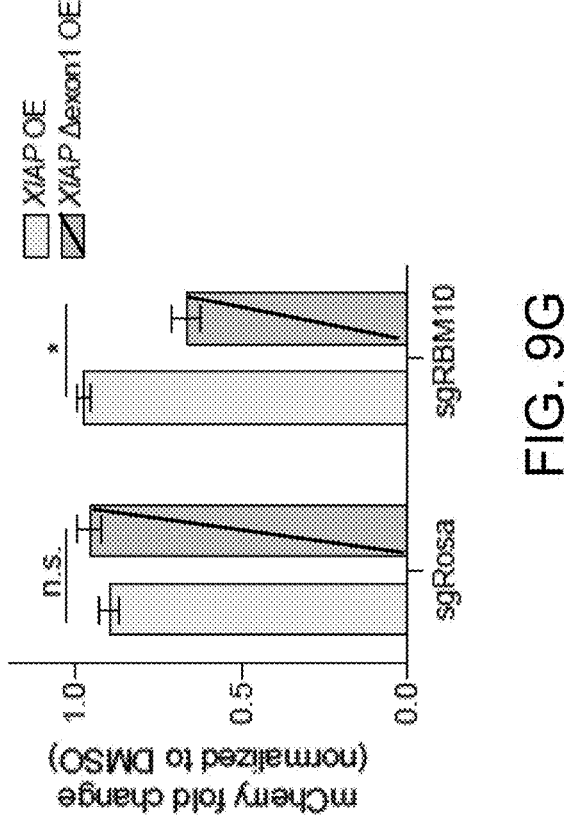

The link between RBM10 binding and differential splicing observed in combined RBM10 KO and venetoclax was further investigated. These analyses revealed RBM10 binding signal in the 5' region of the upstream intron of repressed cassette exons following combination treatment, suggestive of a role of RBM10 binding in this region in promoting exon exclusion (FIG. 3E). Interestingly, the inhibitor of apoptosis protein (IAP) family member, XIAP, displayed increased exclusion of the first coding exon in venetoclax-treated RBM10 KO AML cells, which also had significant RBM10 binding at this region (FIG. 3F and FIG. 9E). XIAP, also known as BIRC4, binds and sequesters pro-apoptotic caspases through direct protein-protein interactions with its BIR domains to prevent caspase homodimerization thereby inactivating apoptosis[38-41]. Without wishing to be bound by theory, it is believed that activation of apoptosis is a consequence of skipping the first coding exon of XIAP. The resulting mRNA lacks XIAP's canonical start codon as well as the sequence encoding the majority of its BIR1-3 domains, strongly suggesting that this splicing change results in loss of functional XIAP production (FIG. 3G). The mis-spliced isoform of XIAP event induced by RBM10 KO and venetoclax treatment (XIAP Dexon 1) was also functionally evaluated by ectopically expressing full-length XIAP (FL) or XIAP Dexon 1 linked to a GFP reporter in MOLM-13 cells (FIG. 3H). Consistent with the function of IAP proteins, XIAP FL overexpression allowed survival of AML cells after venetoclax treatment, whereas XIAP Dexon 1 resulted in increased apoptosis (FIGS. 3I-3J and FIG. 9F). Overall, these results demonstrate that XIAP Dexon 1 cannot rescue cell death induced by venetoclax treatment and RBM10 deletion (FIG. 9G). Importantly, prior work has demonstrated that inhibition of XIAP synergized with venetoclax[42], highlighting the importance of XIAP levels in BCL2 inhibitor sensitivity.

Figure 3L:
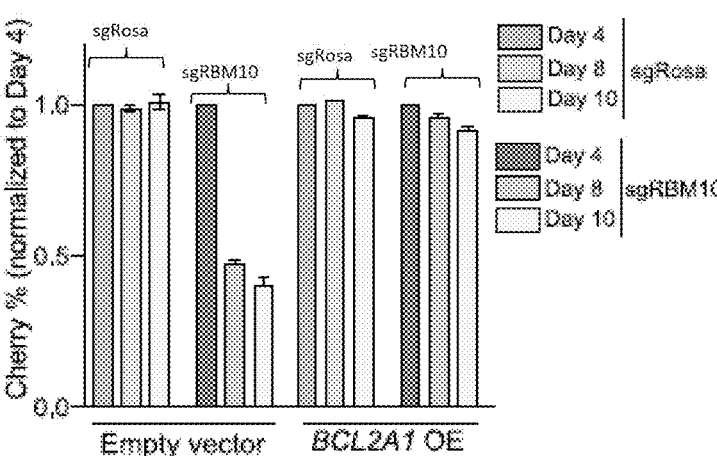
Figure 9H:
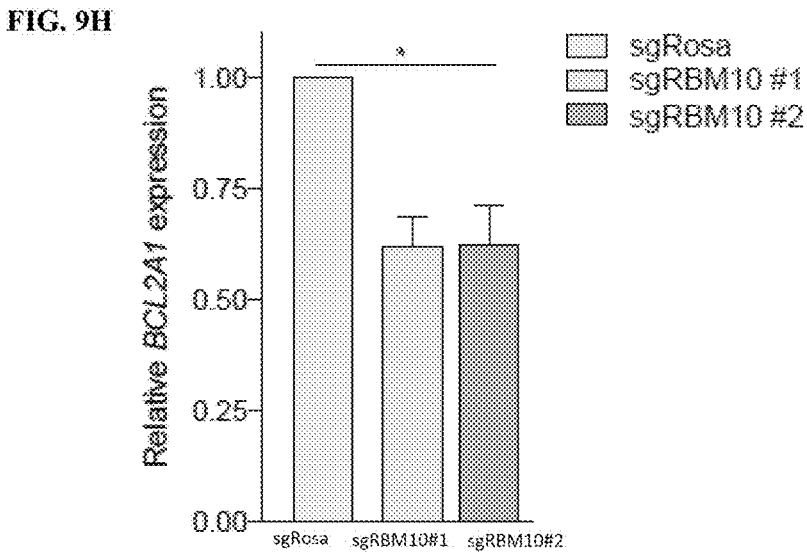
Figure 9I:
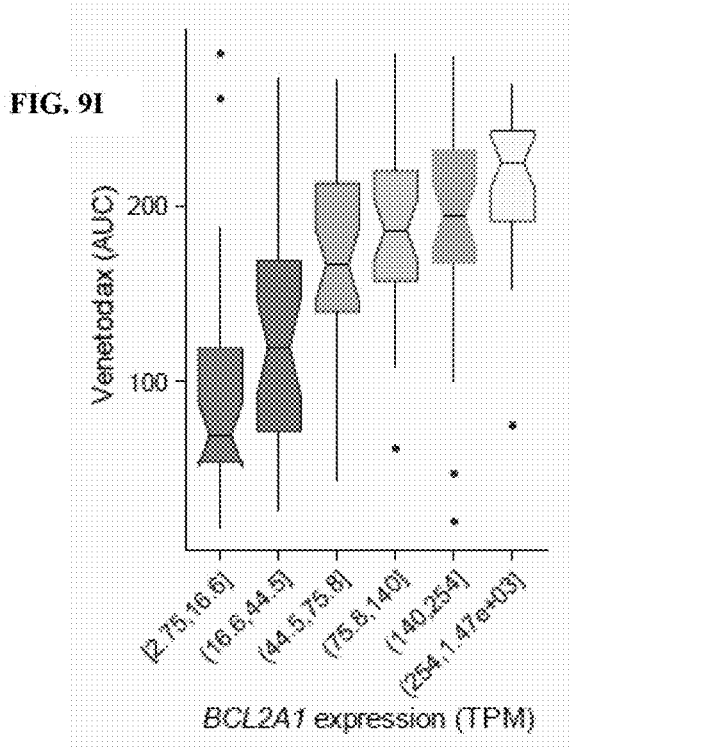

Gene expression analysis of venetoclax-treated RBM10 KO AML cells revealed downregulated expression of BCL2A1, which encodes an anti-apoptotic factor whose expression is correlated with venetoclax resistance in AML patients[6,43] (FIG. 3K and FIGS. 9H-9I). Consistent with these data, overexpression of BCL2A1 cDNA was able to fully rescue the anti-leukemic effects seen with the combined loss of RBM10 and BCL2 inhibition (FIG. 3L). Moreover, significant RBM10 eCLIP peaks or splicing alteration of BCL2A1 mRNA was not observed, which suggests that upstream factors may regulate BCL2A1 transcript. Overall, these data provide mechanistic evidence that the combined loss of RBM10 and BCL2 leads to altered splicing and expression of mRNAs encoding key apoptotic genes.

Example 5: Pharmacologic Inhibition of Splicing Kinases Synergizes With Venetoclax Utilizing CRISPR screens to identify pharmacologically intervenable splicing factors to augment venetoclax response, inactivation of several serine/arginine (SR)-rich proteins (SRSF2, SRSF3, SRSF8, and SRSF11) was found to sensitize AML cells to venetoclax (FIG. 1D and data not shown). The family of SR splicing factors are essential for alternative pre-mRNA splicing and their activity is tightly regulated by post-translational modifications placed by serine/threonine kinases[44-46]. For example, CLKs phosphorylate Arginine-Serine (RS) domains in SR proteins and regulate pre-mRNA splicing[45,47]. Moreover, DYRK1A has been reported to regulate alternative splicing via phosphorylation of SF3B1[48-50]. In addition, analysis of publicly available genome-wide CRISPR screens from DepMap[51] revealed BCL2 as one of the top co-dependencies with DYRK1A loss (FIG. 10A).

Figures 4A, 4B, 4C:
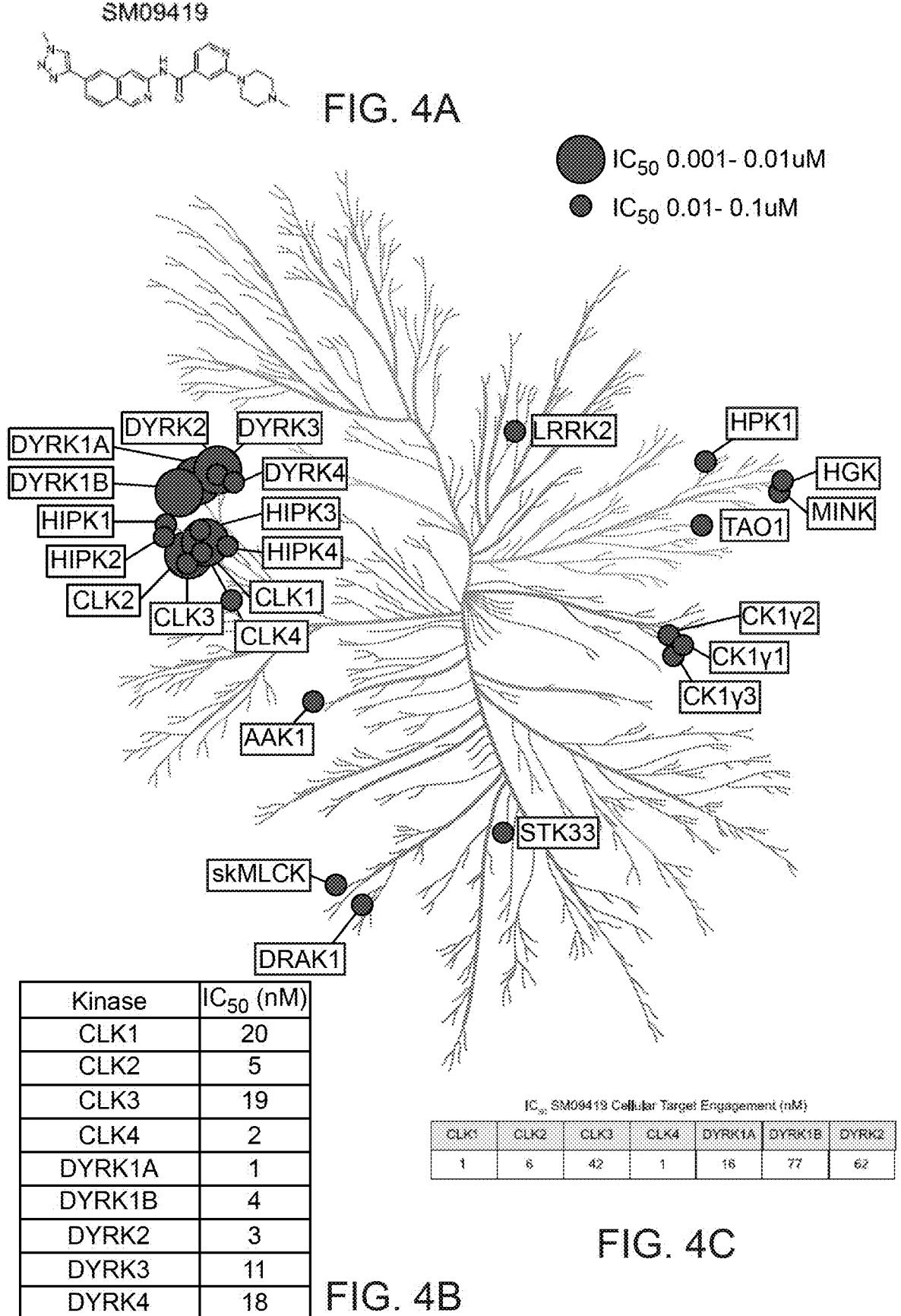
FIGS. 4A-4I. Pharmacologic inhibition of splicing-dependent kinases synergizes with venetoclax.
Figure 4D:
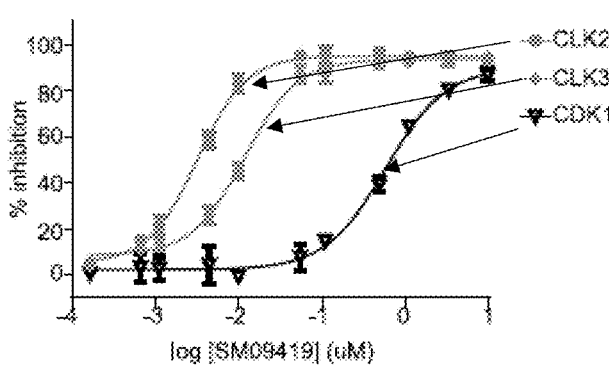
Figure 4E:
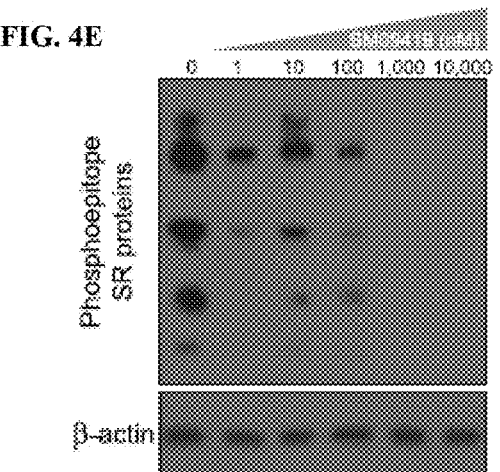
Figure 4F:
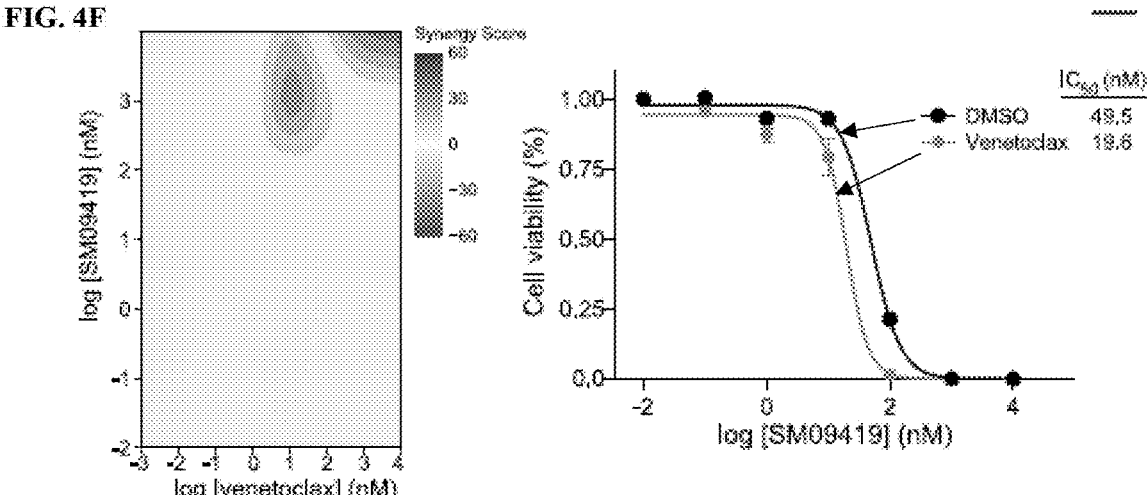
Figure 4G:
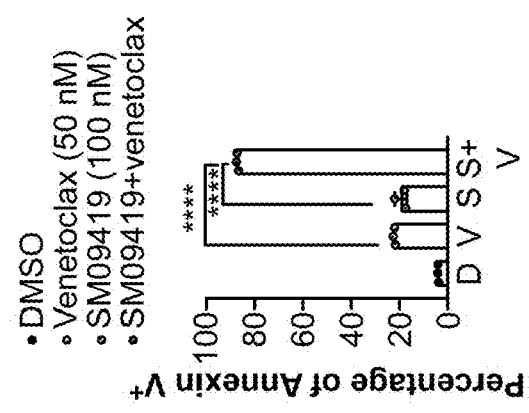
Figure 4H:
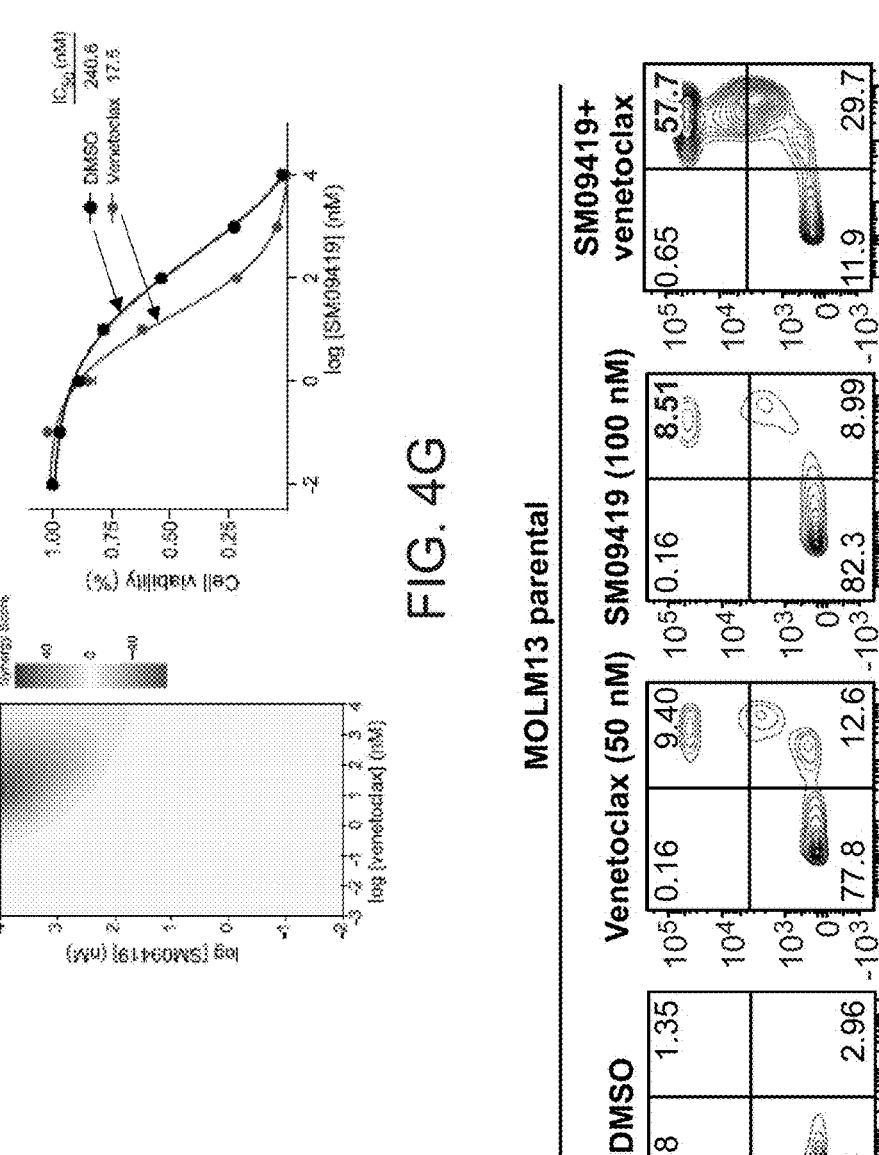
Figure 10D:
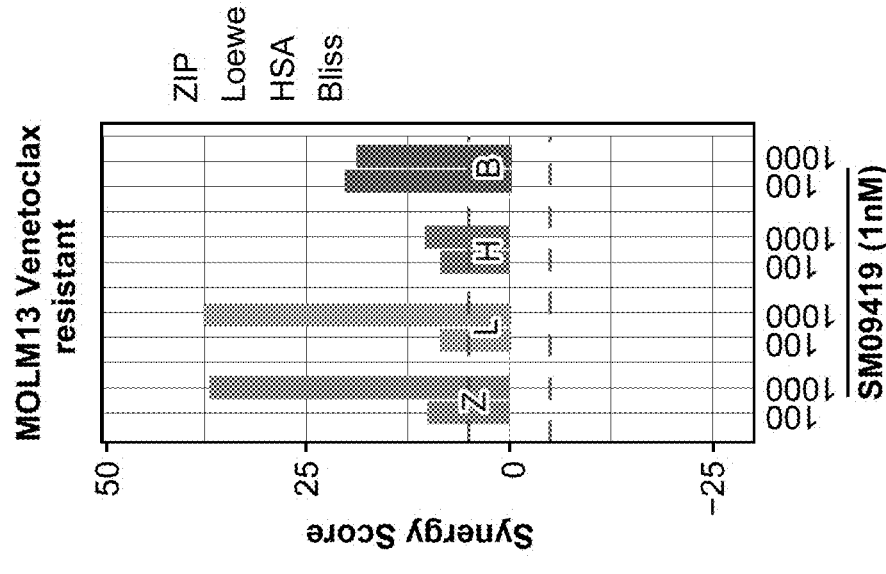
Figure 10D:
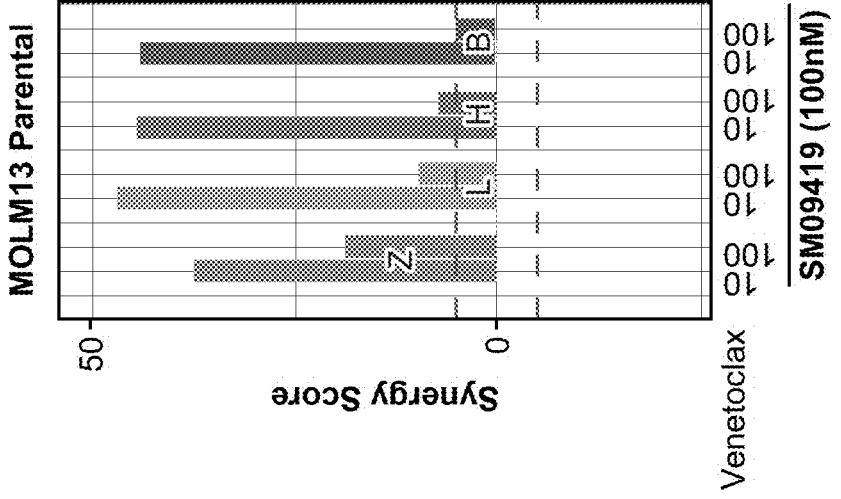
Figure 10D:
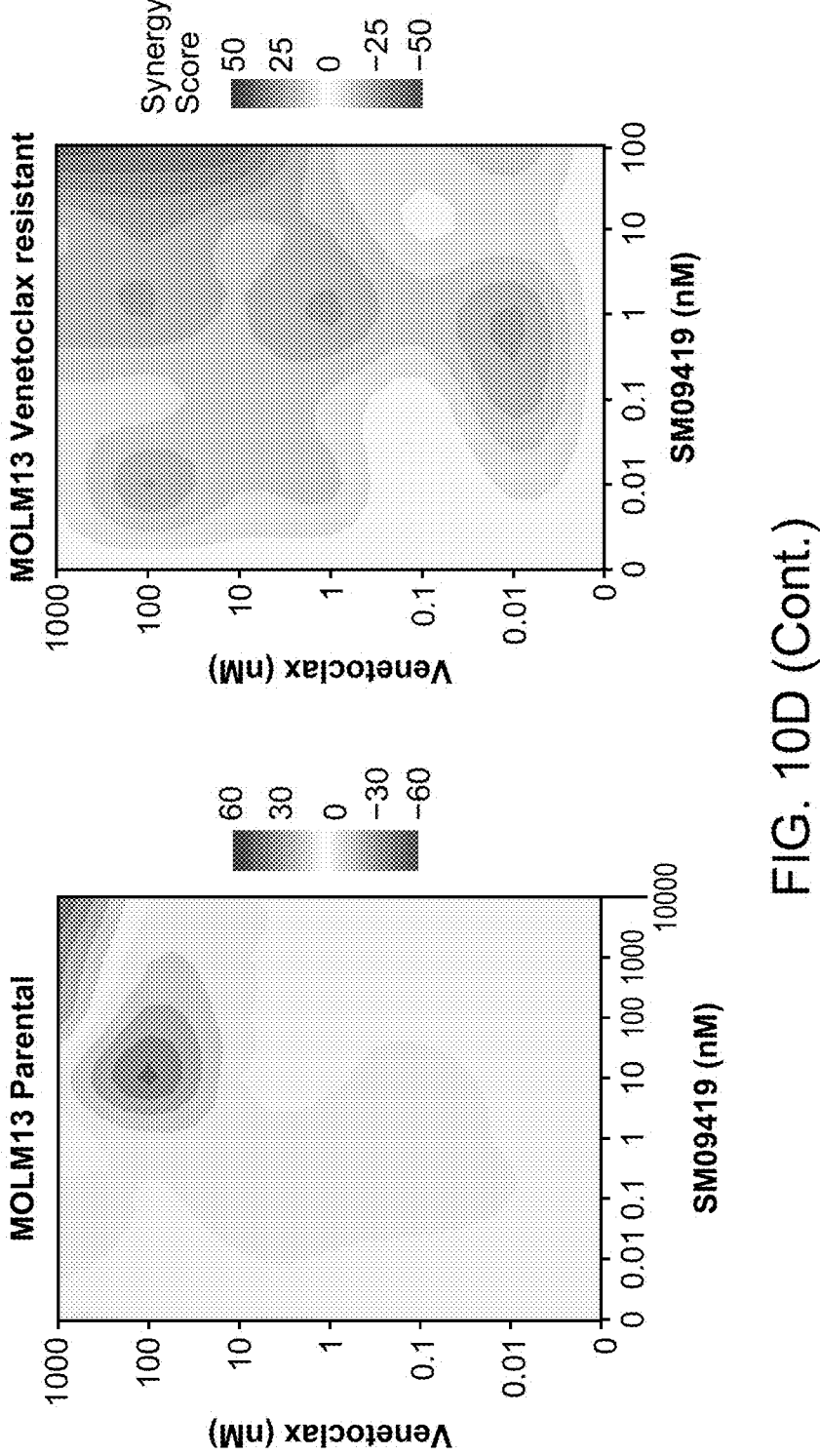
Figure 10E:
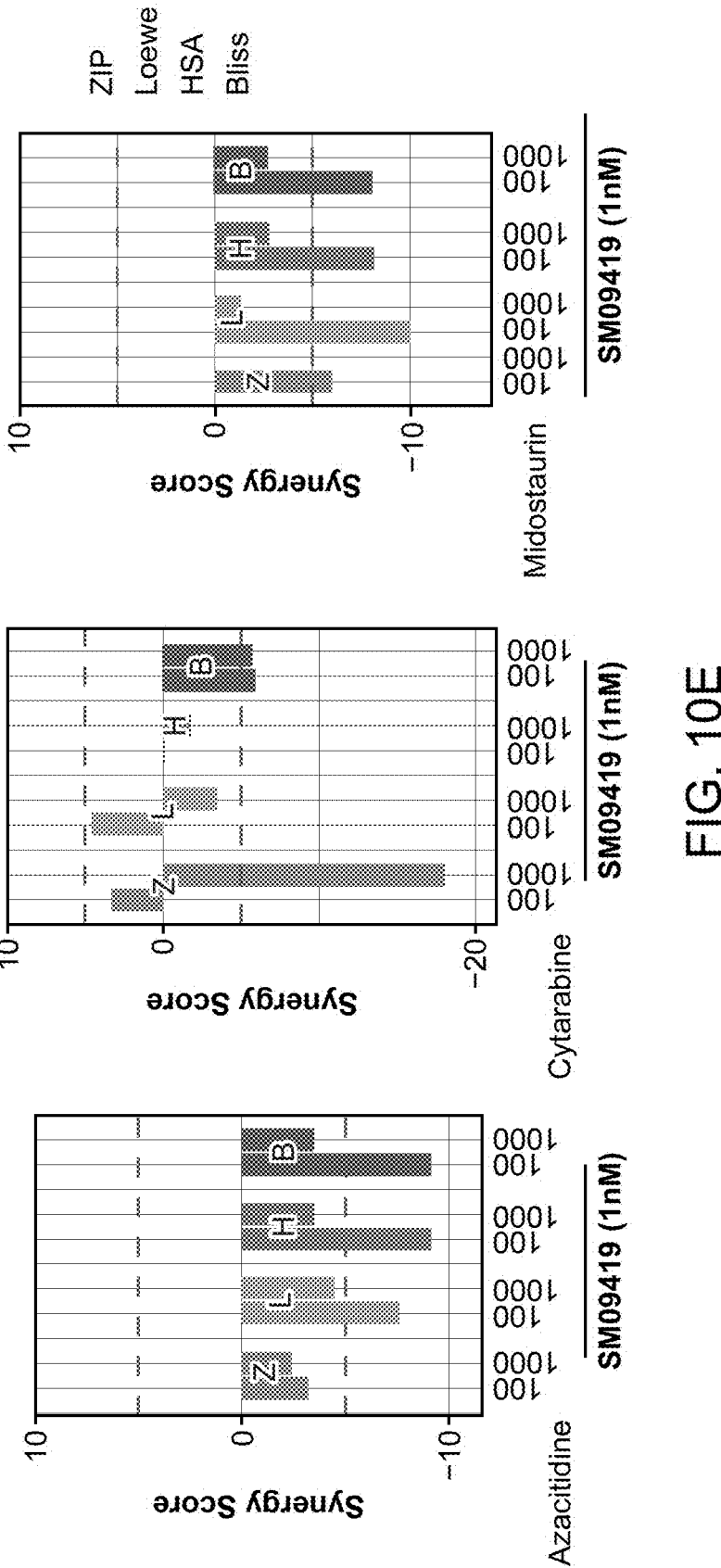
Figure 10E:
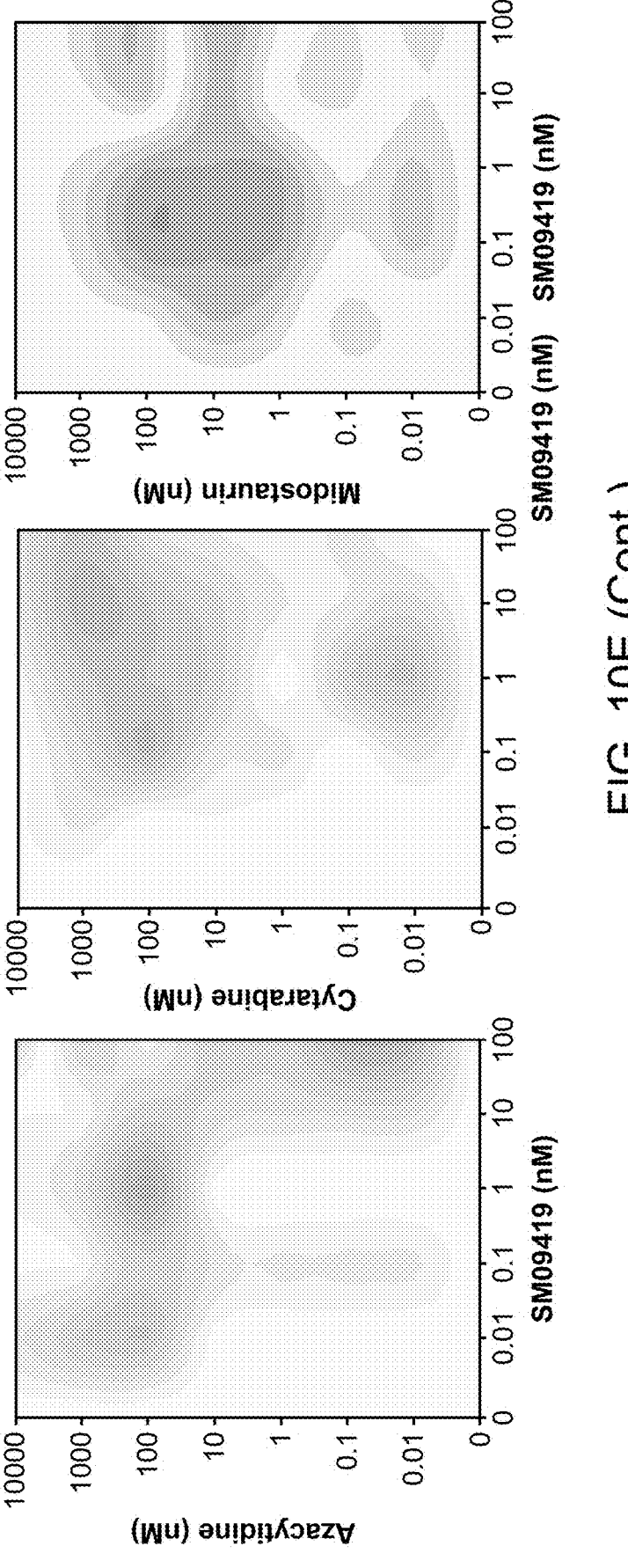
Figure 11A:
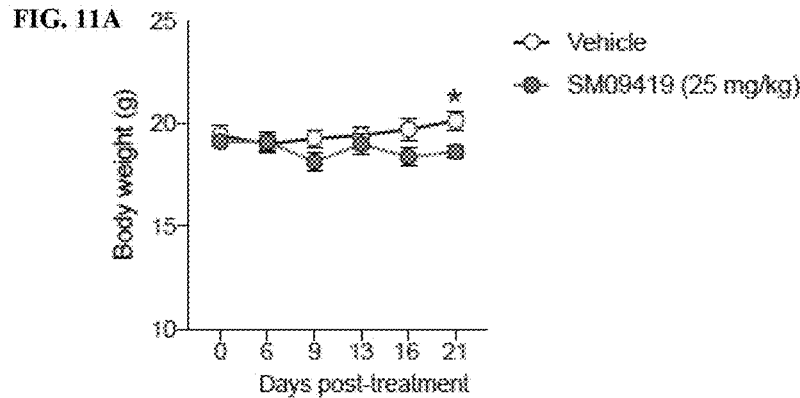
FIGS. 11A-11H. SM09419 is well-tolerable and does not alter normal hematopoiesis.
Figure 11B:
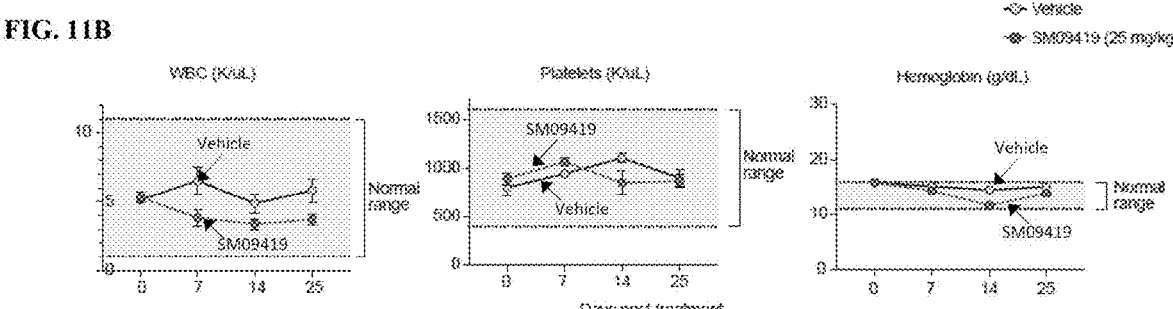
Figure 11C:
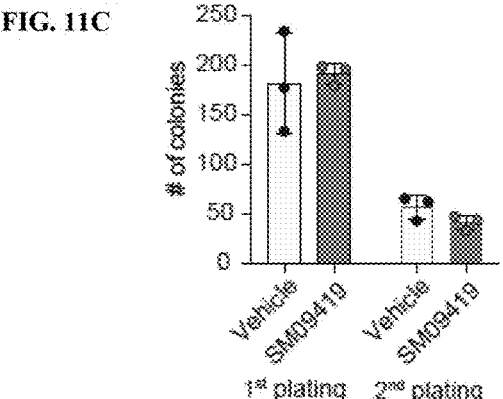
Figures 11D, 11E, 11F:
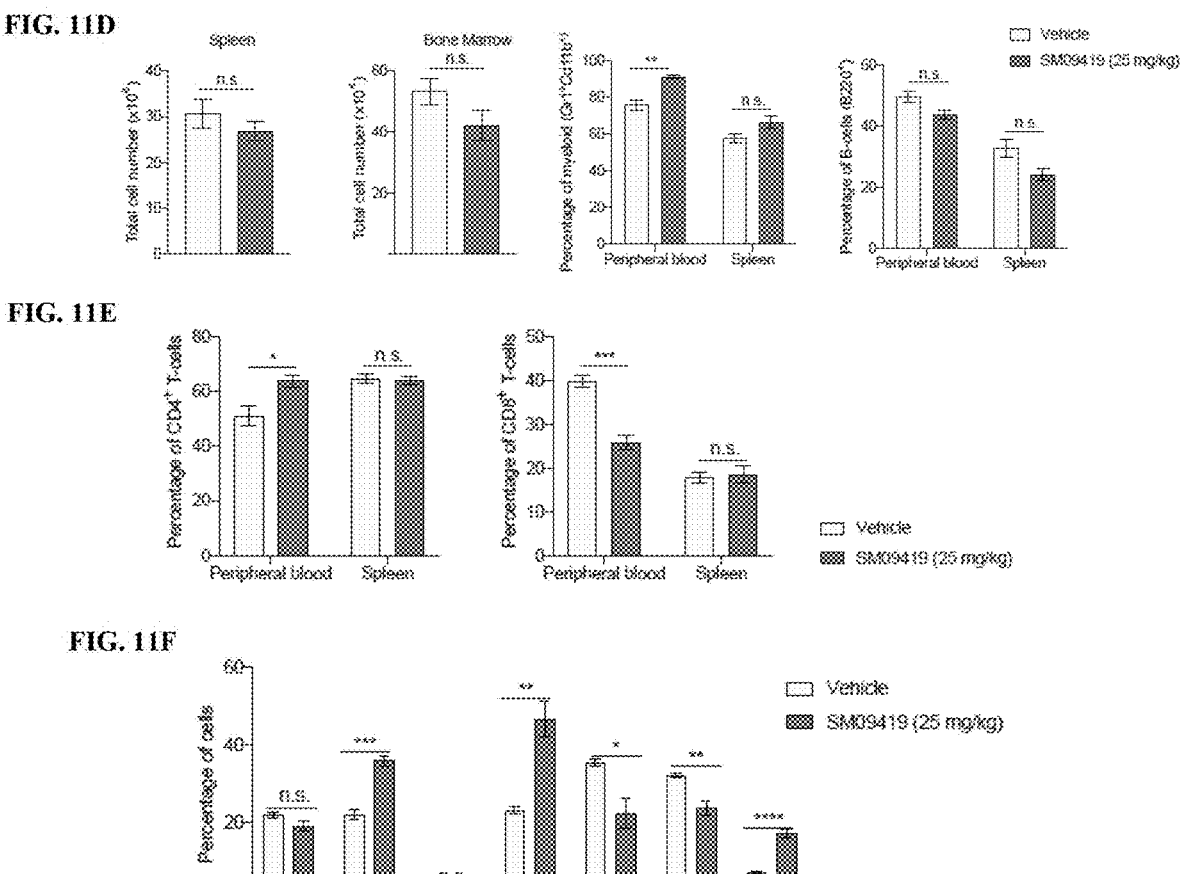
Figures 11G, 11H:
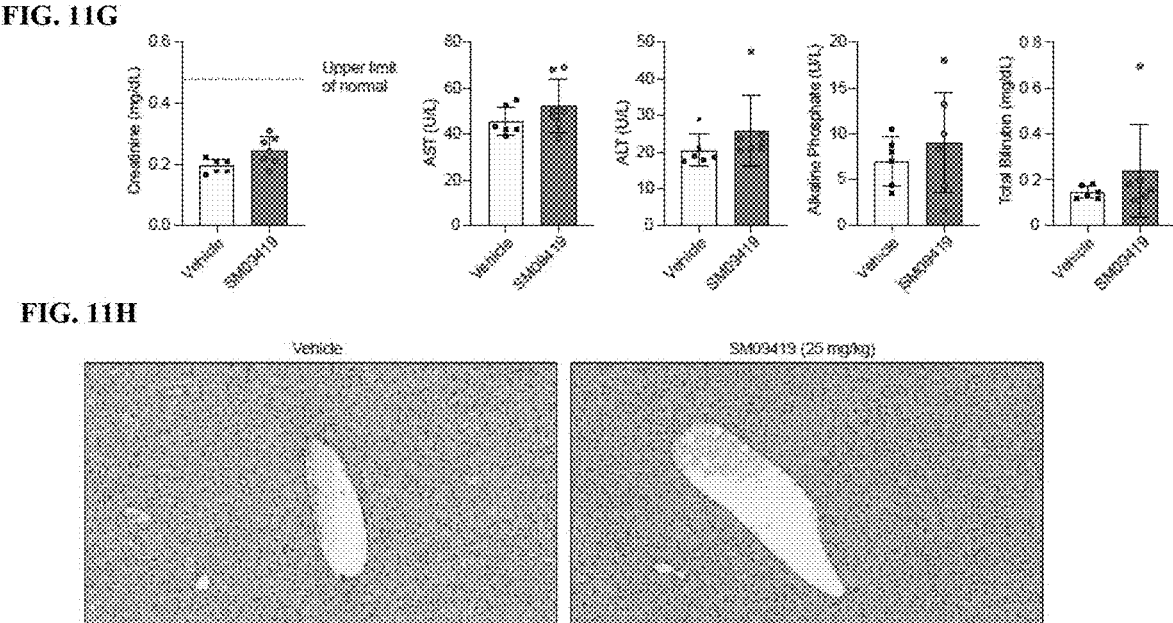

These findings support the rationale to inhibit splicing-dependent kinases as a combinatorial strategy with venetoclax treatment. To pursue therapeutic inhibition of splicing-dependent kinases, SM09419, a pan-CLK pan-DYRK inhibitor was developed via rational design and iterative medicinal chemistry to achieve drug-like and favorable pharmacokinetic profiles (FIGS. 4A-4D). The selectivity of SM09419 to target CLK kinases CLK1-4 as well as DYRK1A-B and DYRK2 was confirmed using in cell NanoBRET target engagement assays (FIG. 4C and FIG. 10B). Accordingly, SM09419 treatment resulted in dose-dependent reduction of CLK activity and SR protein phosphorylation in AML cells (FIG. 4E and FIG. 10C). Next, the combinatorial effects of SM09419 with a panel of drugs (venetoclax, 5-azacytidine, cytarabine, and midostaurin) were assessed in human AML cell lines. A synergistic effect was exclusively observed when combining SM09419 and venetoclax in MOLM-13 parental and venetoclax-resistant cells, but not with other drugs (FIGS. 4F-4I and FIGS. 10D-10E). Despite robust anti-leukemic effects of SM09419 in vitro, SM09419 (25 mg/kg) treatment in wild-type C57BL/6 mice was well tolerated in vivo with no signs of hematologic toxicities (based on serial blood counts, in vitro hematopoietic progenitor cell assays, and detailed analysis of hematopoietic cell composition in blood and bone marrow) or liver or kidney dysfunction, thus providing a rationale for pharmacologic inhibition of CLK/DYRK in combination with venetoclax in AML (FIGS. 11A-11H).

Figure 5A:
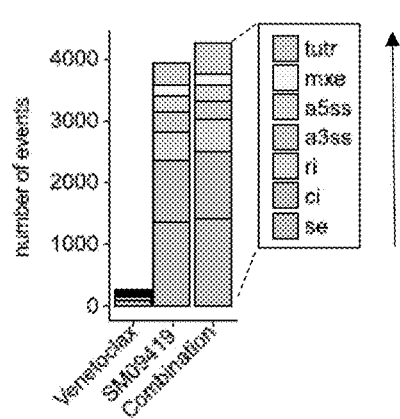
FIGS. 5A-5J. SM09419 promotes mis-splicing of key oncogenic pathways in AML.
Figure 5B:
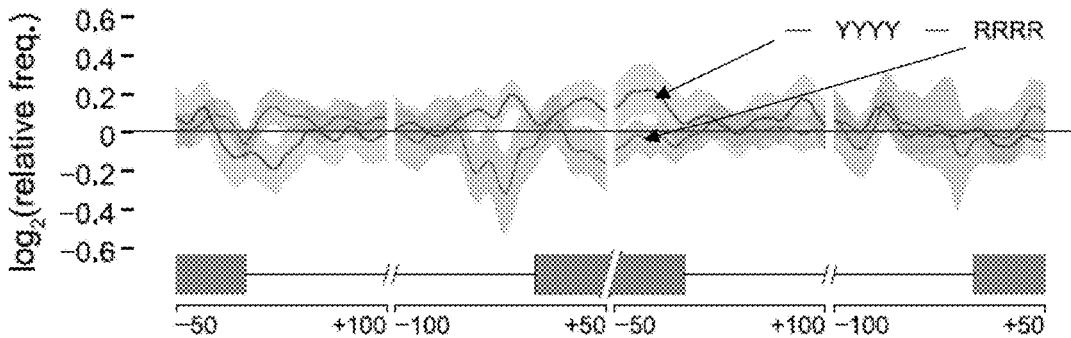
Figure 5C:
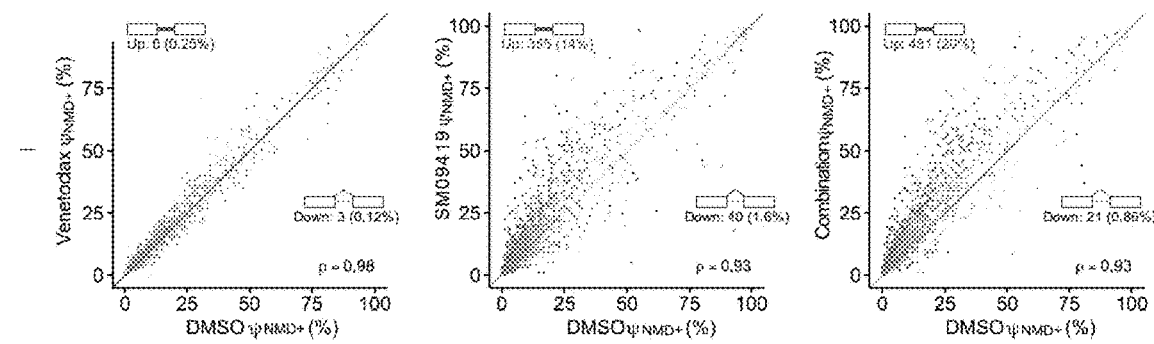

To understand the mechanistic basis for the synergy of SM09419 and venetoclax combination, RNA-seq was performed on MOLM-13 human AML cells treated with SM09419 alone or in combination with venetoclax (data not shown). Splicing analyses showed that SM09419 alone, or in combination with venetoclax, mainly resulted in changes in the processing of constitutive/retained introns and cassette exons (FIG. 5A). CLK/DYRK inhibition affects cassette exon recognition in a sequence-specific manner, as evidenced by the enrichment of pyrimidines in exons preferentially excluded upon SM09419 treatment (FIG. 5B). While venetoclax monotherapy had no significant effects on RNA splicing, treatment with SM09419 or the combination resulted in striking reductions in RNA splicing efficiency as manifested by cassette exon skipping and intron retention (FIG. 5A, FIG. 5C, and data not shown). Of note, these splicing shifts resulted in substantial increases in levels of mRNAs that contain premature termination codons and are therefore predicted substrates for degradation by nonsense-mediated decay (NMD).

Figure 5D:
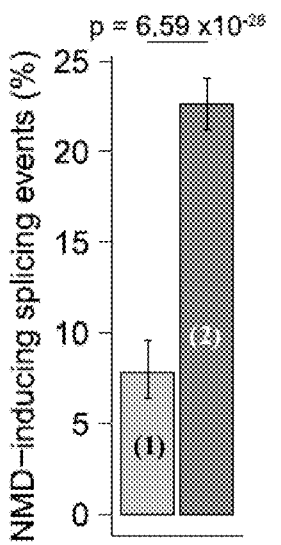
Figure 5D:
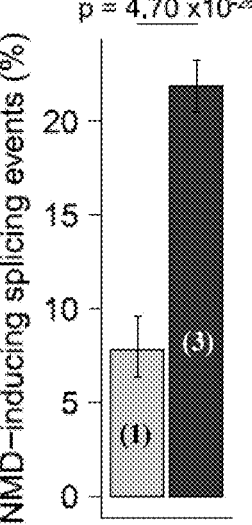
Figure 5E:
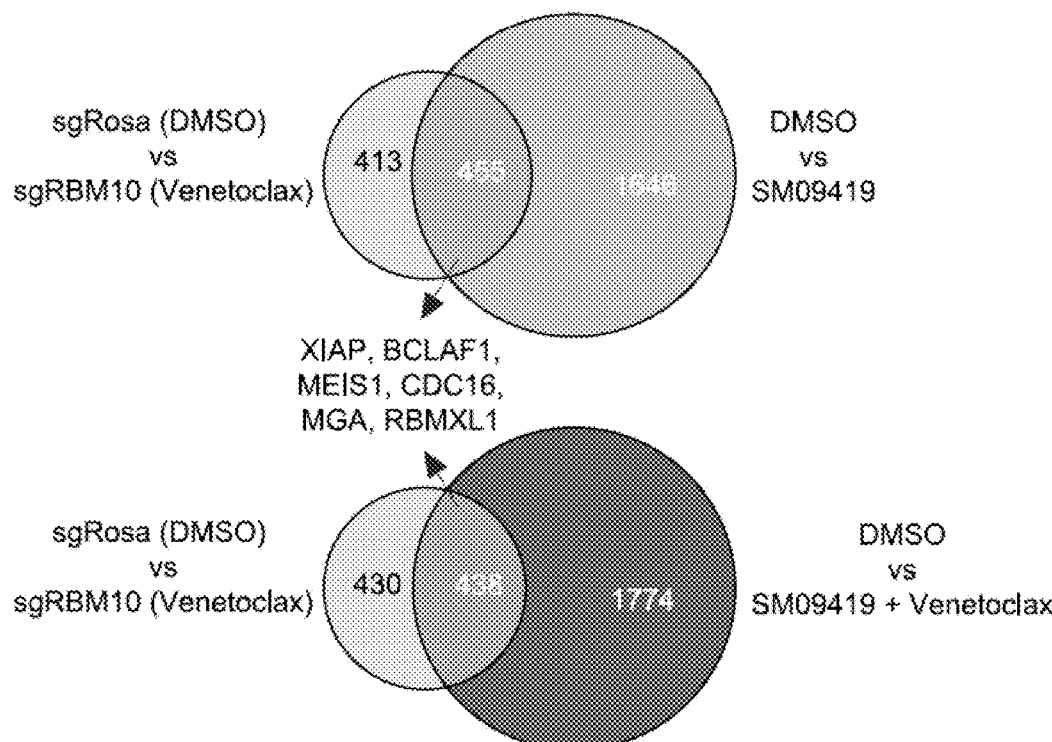
Figures 5F, 5G, 5H:
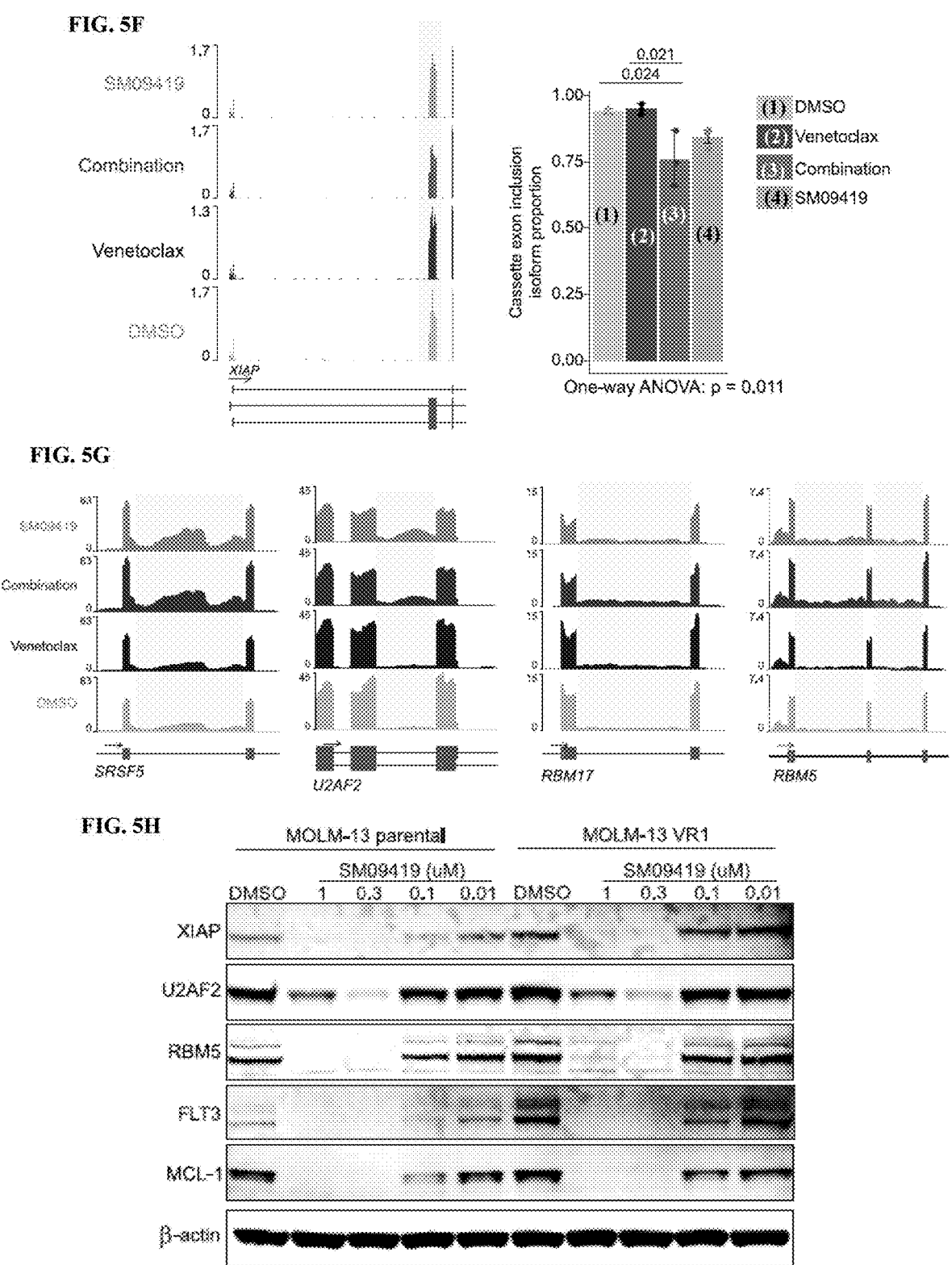
Figure 12A:
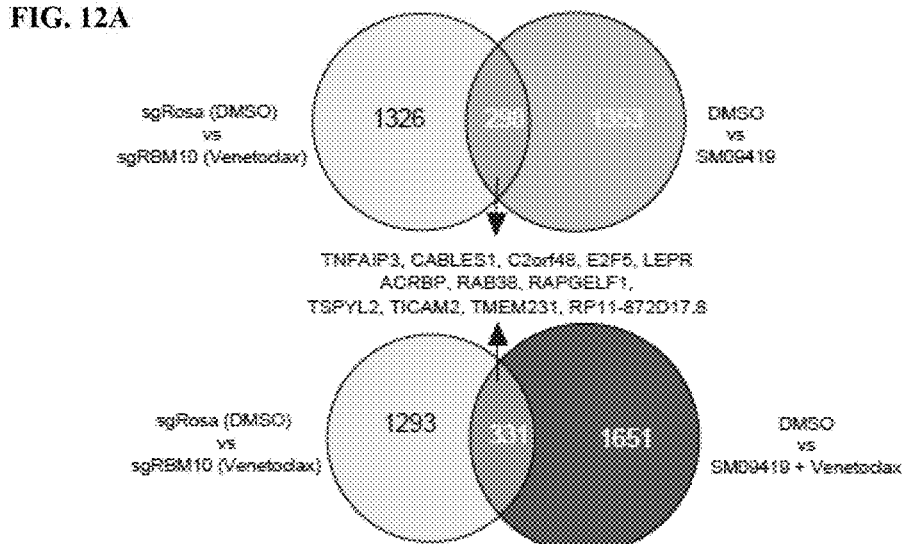
FIGS. 12A-12F. SM09419-responsive transcriptome and splicing changes in AML.
Figure 12B:
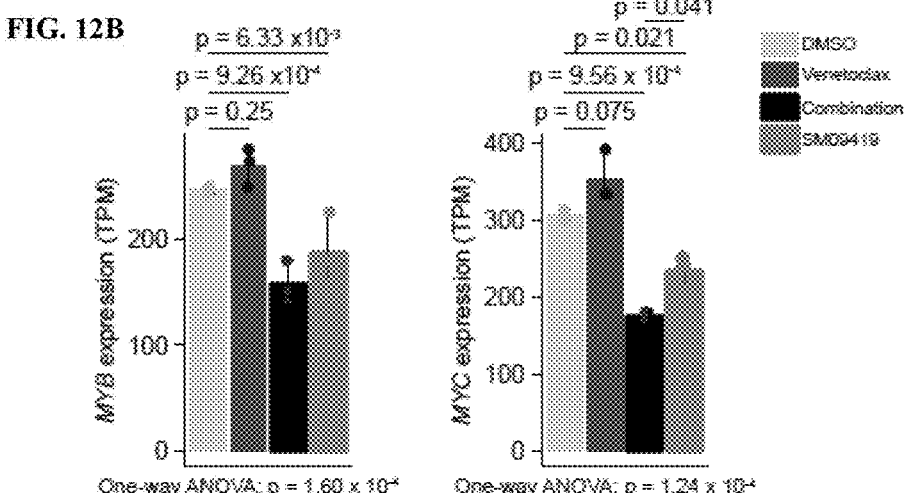
Figure 12C:
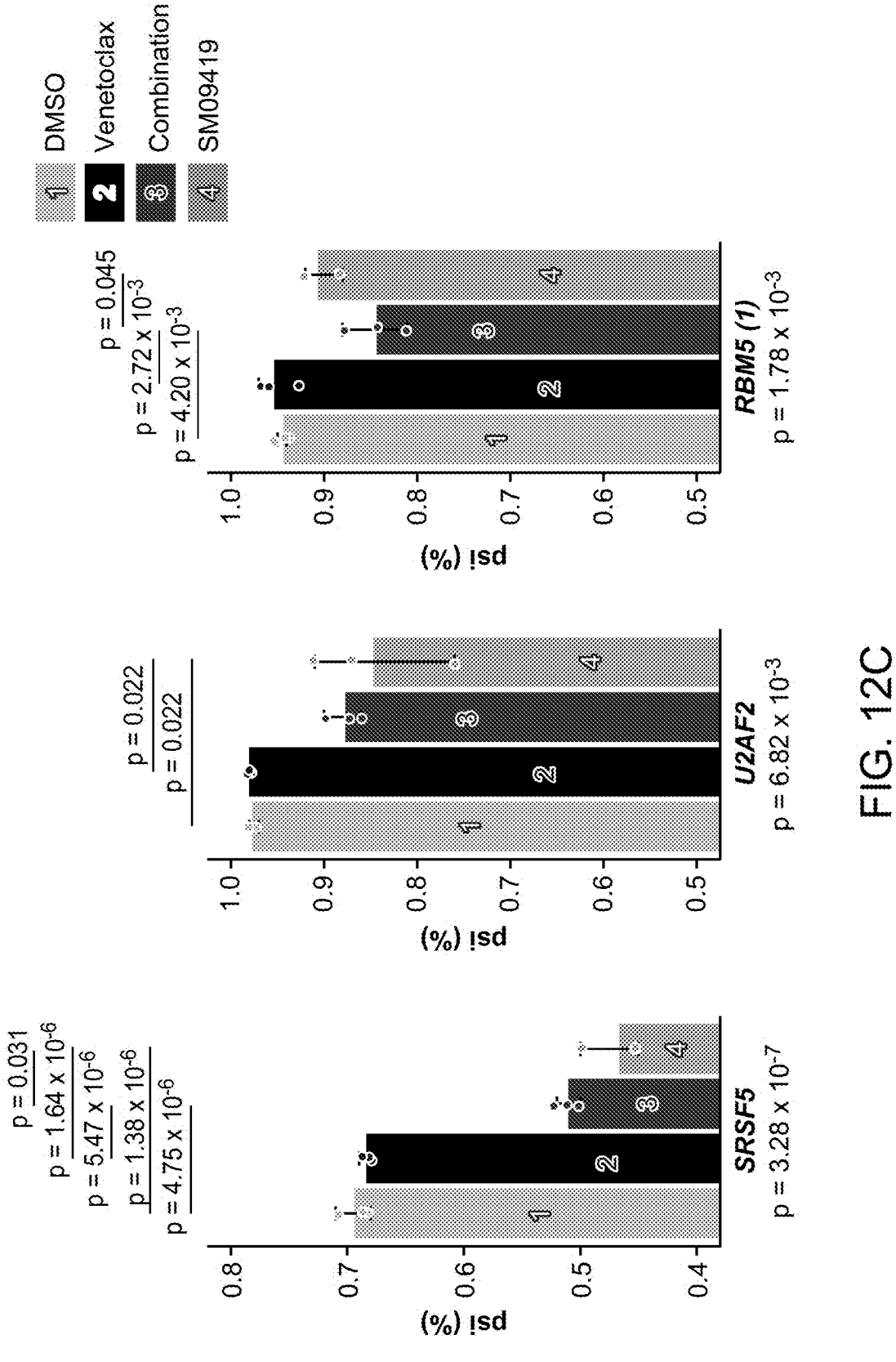
Figure 12C:
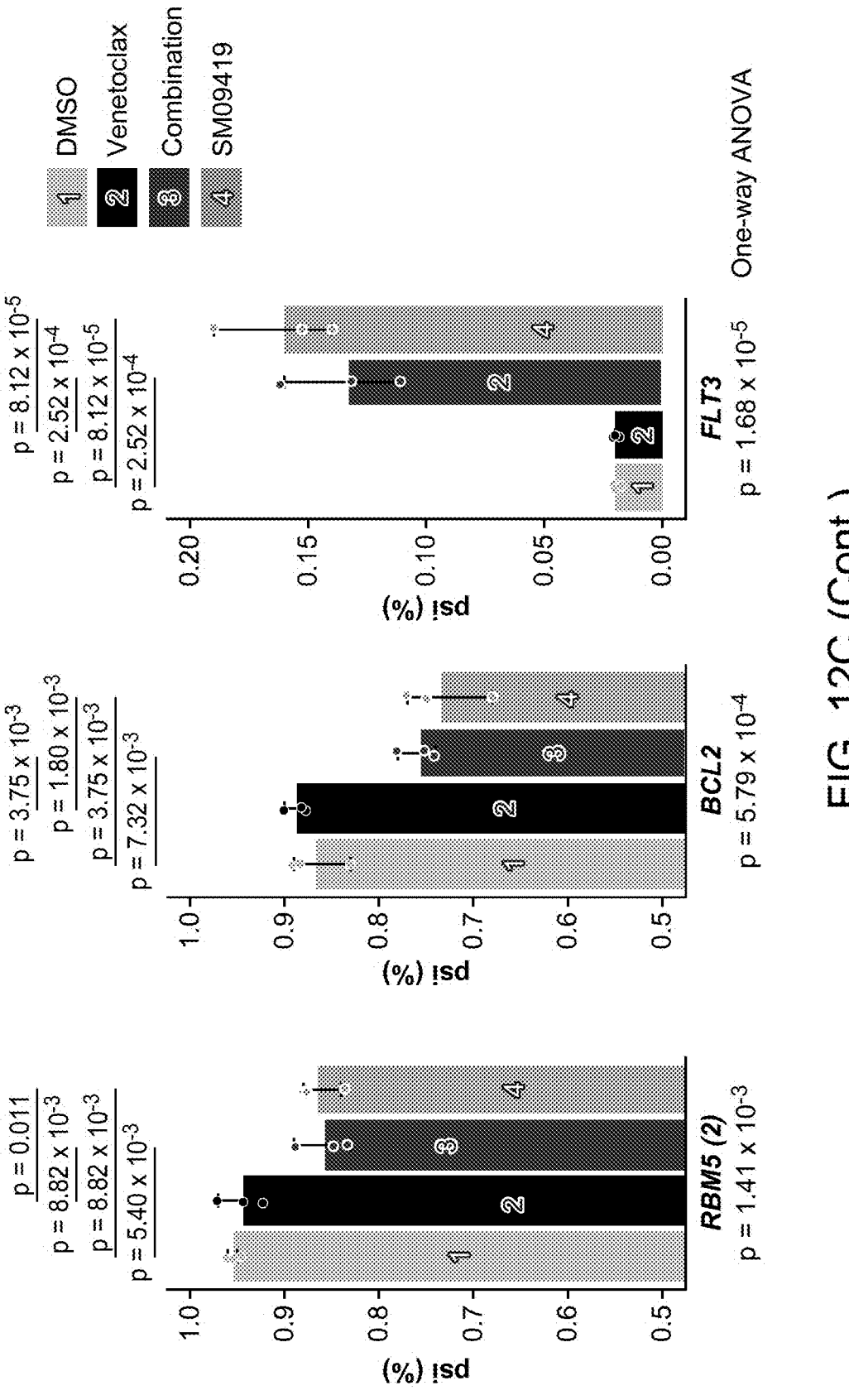

In order to understand how the effects of SM09419 relates to deletion of RBM10, a systematic comparison of the splicing changes and gene expression across both conditions was performed in the same MOLM-13 cells. Both RBM10 deletion and SM09419 treatment cause splicing changes which promote nonsense-mediated decay (NMD)-inducing transcripts. However, the magnitude of NMD-inducing splicing events is greater with SM09419 treatment (a result consistent with the fact that RBM10 deletion in the absence of any drug treatment is well-tolerated in MOLM-13 cells) (FIG. 5D). Nonetheless, a number of mRNA isoforms were shared across RBM10 deletion versus SM09419 treatment in the absence and presence of concomitant venetoclax treatment. Interestingly, one concordant effect was the same mis-splicing event in XIAP seen with RBM10 deletion (FIGS. 5E-5F). Finally, both RBM10 deletion and SM09419 treatment prominently downregulate TNFAIP3 (also known as A20) (FIG. 12A). TNFAIP3 is a well described regulator of NF-kB signaling 52 and its inhibition may explain the BCL2A1 down-regulation in RBM10 KO cells exposed to venetoclax. Transcriptomic analysis of SM09419-treated AML cells also demonstrated downregulation of MYB and MYC mRNA levels, which are essential oncogenic factors in AML (FIG. 12B)[53,54]

Figure 5I:
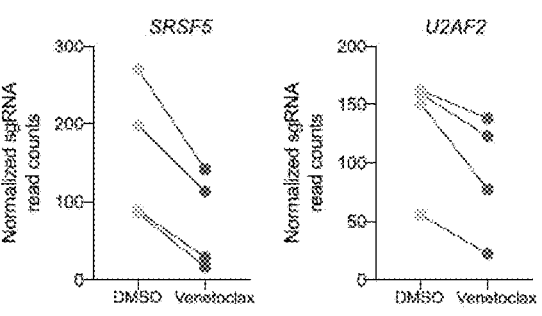
Figure 5I:
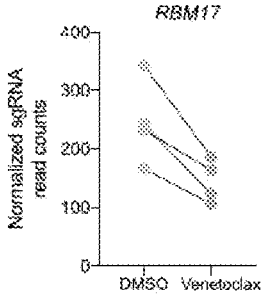
Figure 5I:
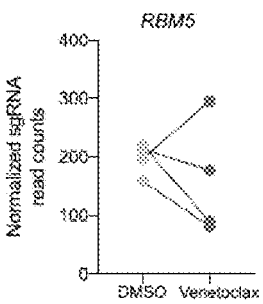
Figure 5J:
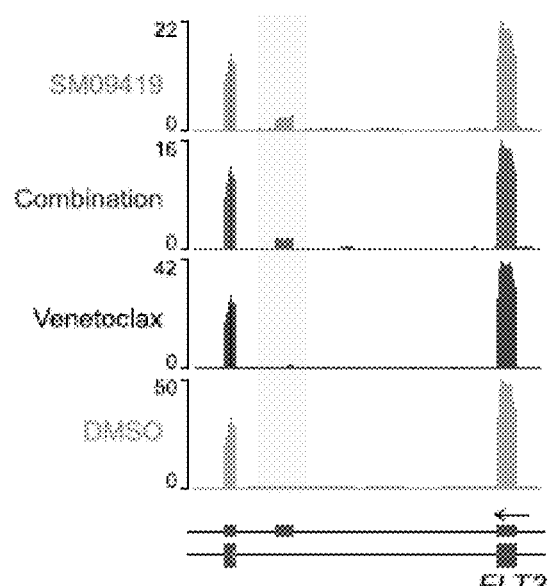
Figure 5J:
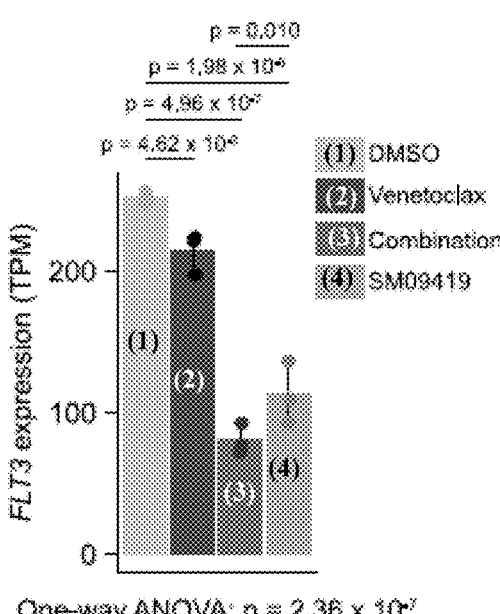
Figure 12D:
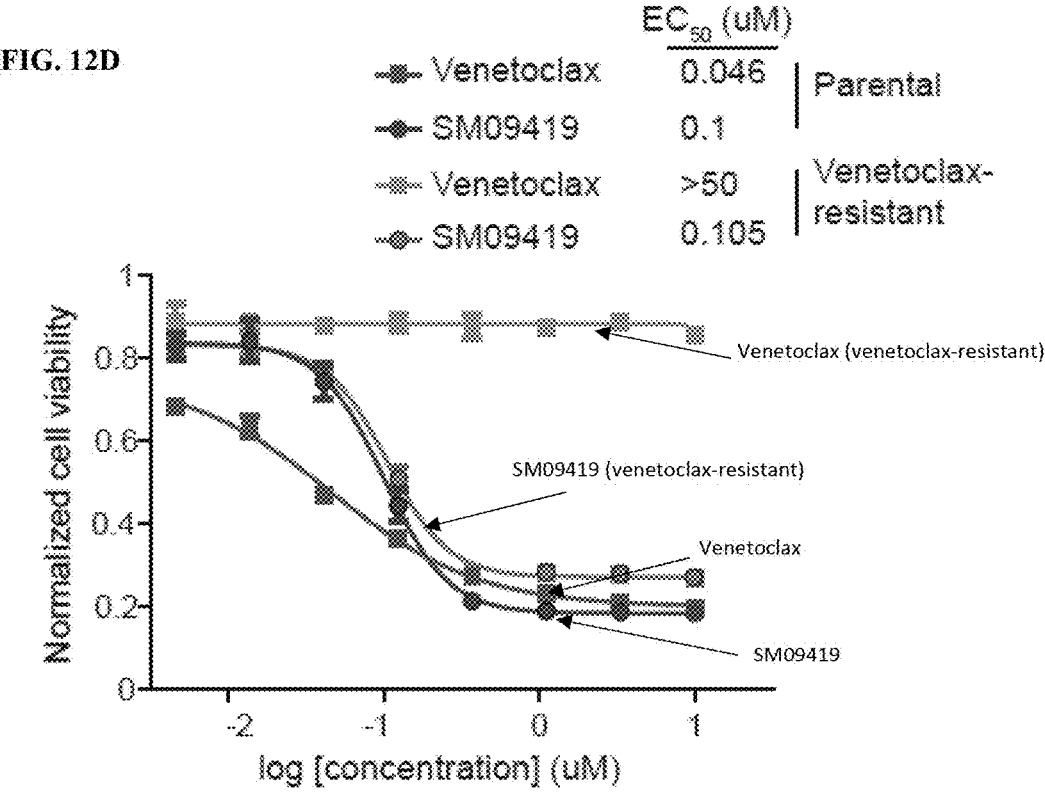
Figure 12E:
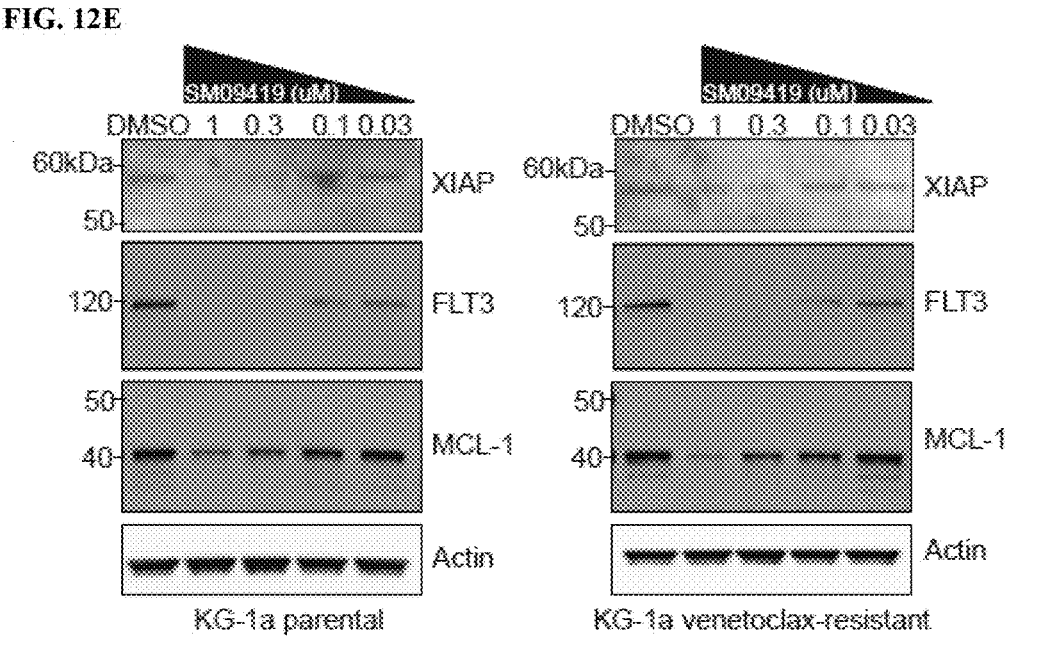

Example 6: SM09419 Induces Splicing Alterations of Key Survival Genes in AML Further characterization of SM09419-associated splicing changes revealed increased intron retention within the transcripts of a number of RNA splicing factors (SRSF5, U2AF2, RBM17, and RBM5) which also led to decreased protein expression in two independent human AML cell lines (FIGS. 5G-5H and FIGS. 12C-12E). Interestingly, several of these same splicing factors were also identified by CRISPR screens as genes whose inactivation enhanced venetoclax efficacy and therefore explains the synergistic effects when combining SM09419 and venetoclax (FIG. 5E and FIG. 5I). Furthermore, SM09419-treated AML cells led to downregulation of several key apoptotic proteins, such as MCL-1, which have been shown to be upregulated in hematologic neoplasms and confers resistance to BCL2 inhibitors[12] (FIG. 5H and FIG. 12E). Finally, SM09419 treatment promoted inclusion of an exon with an in-frame stop codon (a "poison exon," whose inclusion renders the transcript NMD-sensitive) in the receptor tyrosine kinase FLT3 (FIG. 5J). As such, there was reduced FLT3 mRNA and protein expression in SM09419 treated cells (which is especially pertinent given the known dependence of this FLT3 mutant AML cell line on FLT3 expression) (FIG. 5H and FIG. 12E). Importantly, the above results on the impact of SM09419 treatment on XIAP, FLT3, and MCL-1 levels were confirmed in an additional AML cell line. Both venetoclax resistant and sensitive KG-1a cells were similarly susceptible to SM09419 treatment and experienced comparable dose-dependent reductions in XIAP, FLT3, and MCL-1 (FIGS. 12D-12E).

Figure 12F:
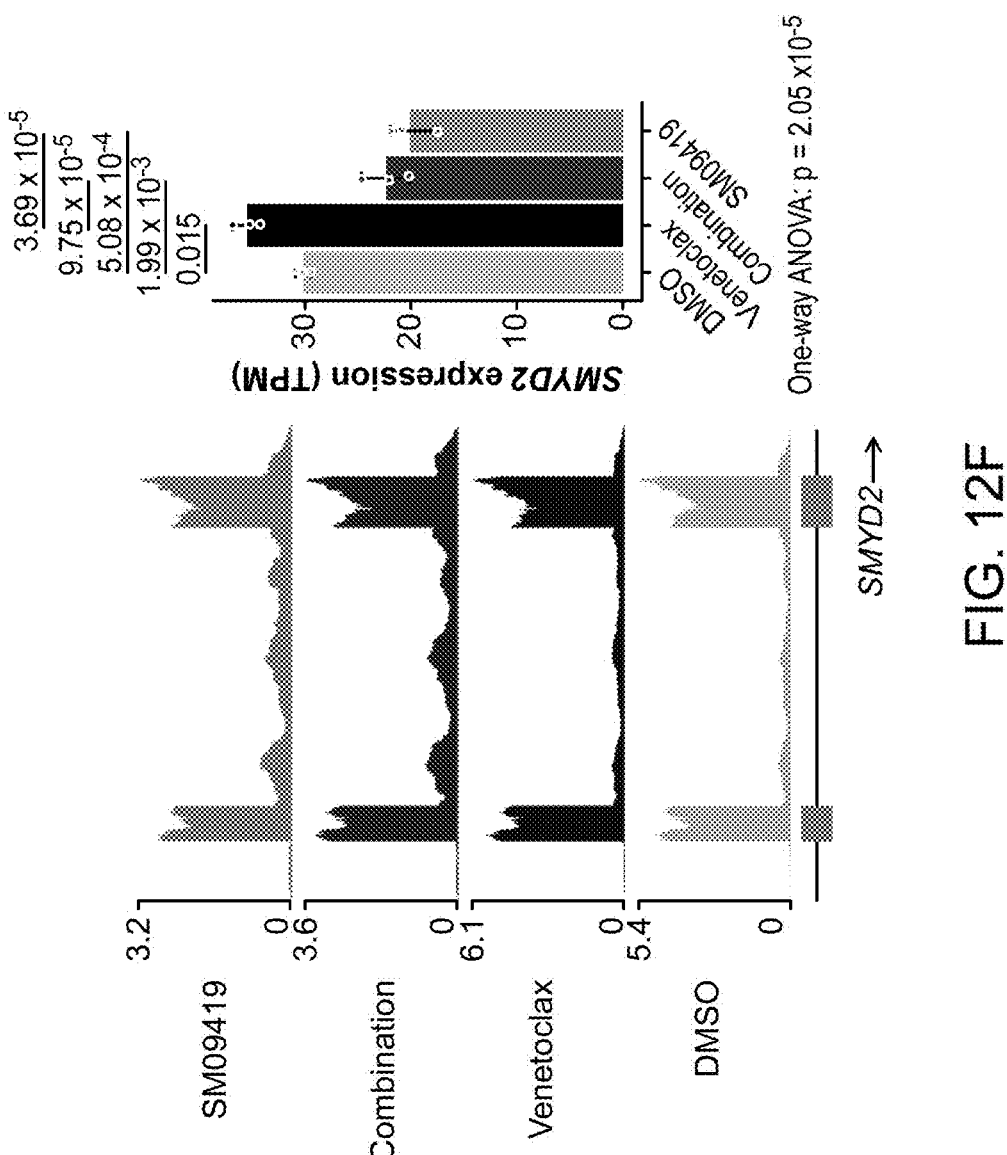

Additional predicted NMD-inducing splicing events upon SM09419 treatment with commensurate reduction in mRNA expression in SMYD2 (a lysine methyltransferase recognized as a therapeutic target in AML[53], DHODH (a metabolic enzyme and recent AML therapeutic target)[55], ATAD3A (a metabolic enzyme whose expression has been included in leukemia stem cell signatures)[56], the MYC target gene CDC16[57], and the additional RNA processing genes SRPK3, TRA2A, and DDX51 (FIG. 12F). Overall, these data identify that SM09419 downregulates expression of key RNA splicing factors as well as important apoptotic factors and FLT3 via impaired splicing to enhance response to venetoclax in AML while having minimal impact on normal hematopoiesis.

Example 7: SM09419 Overcomes Venetoclax-Based Therapy Resistance

Figure 4I:
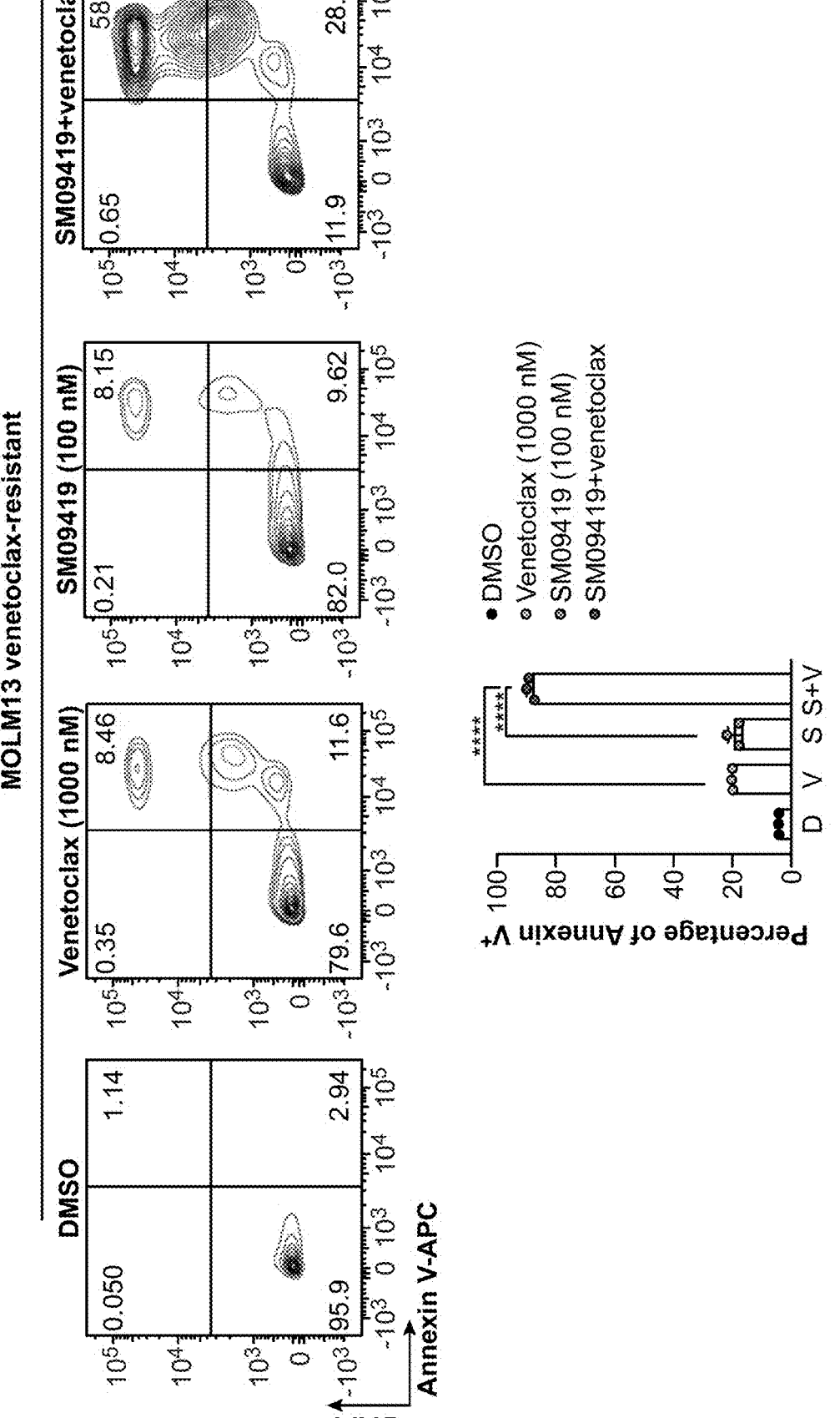
Figure 6A:
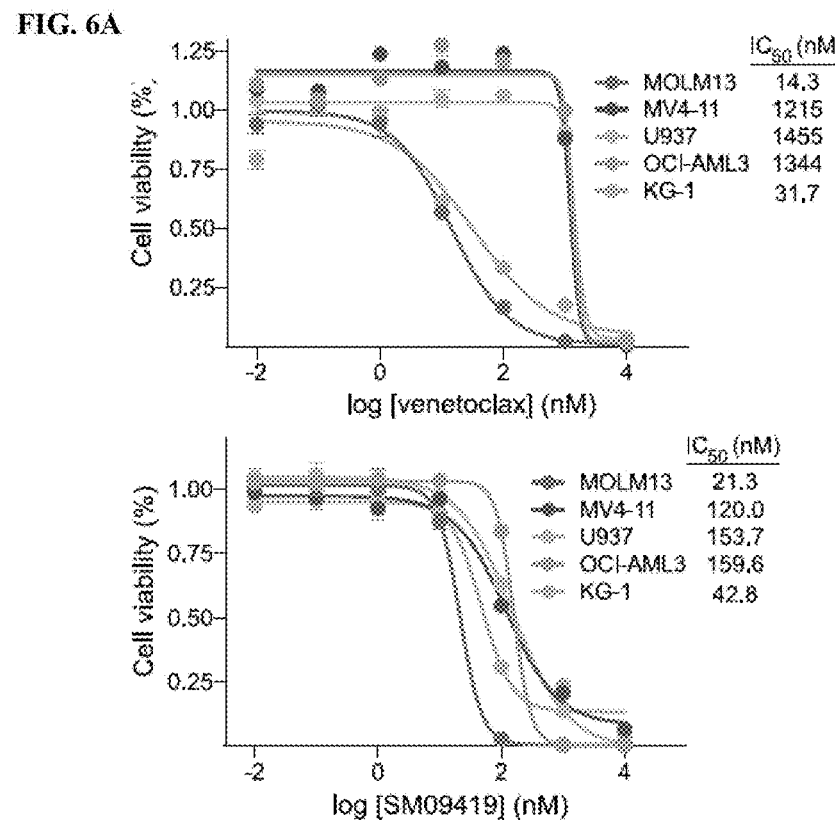
Figure 6B:
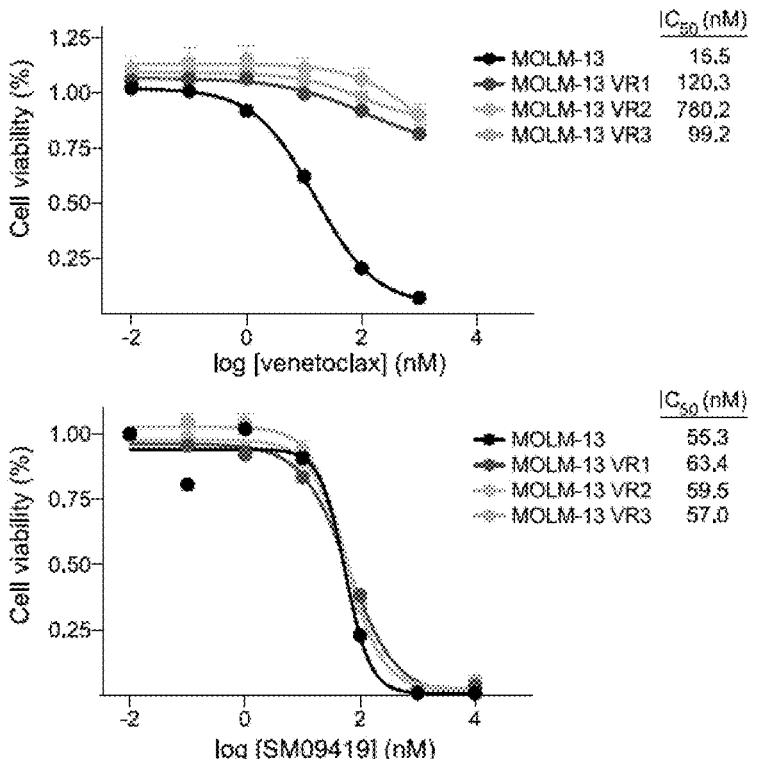
Figure 6E:
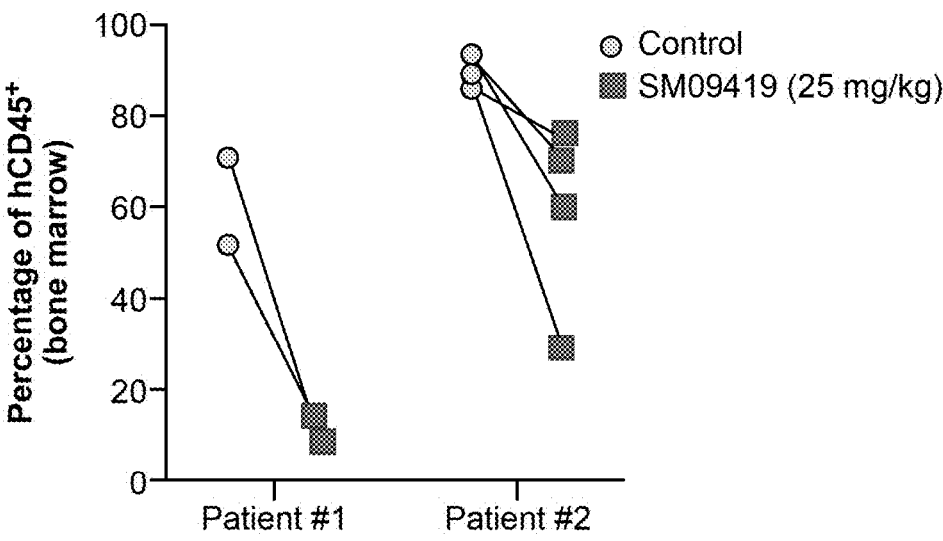
Figure 6F:
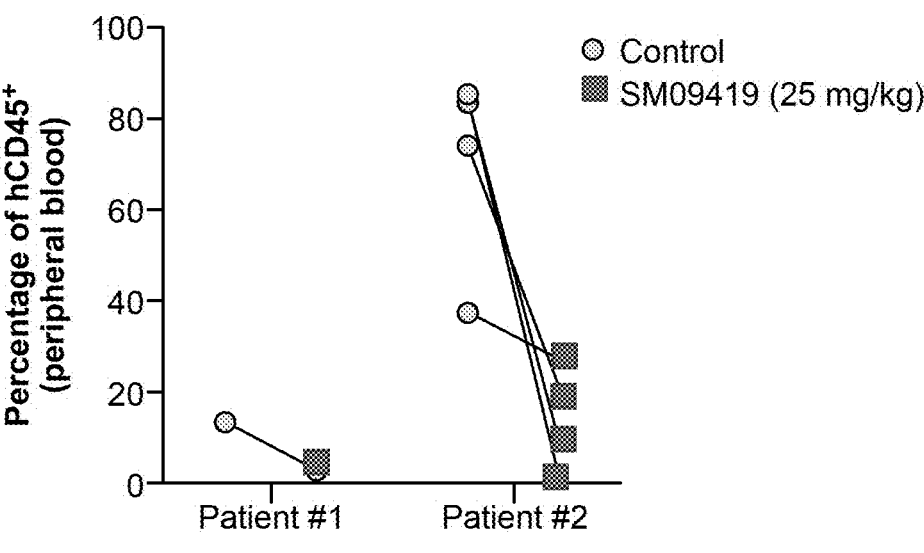
Figure 6G:
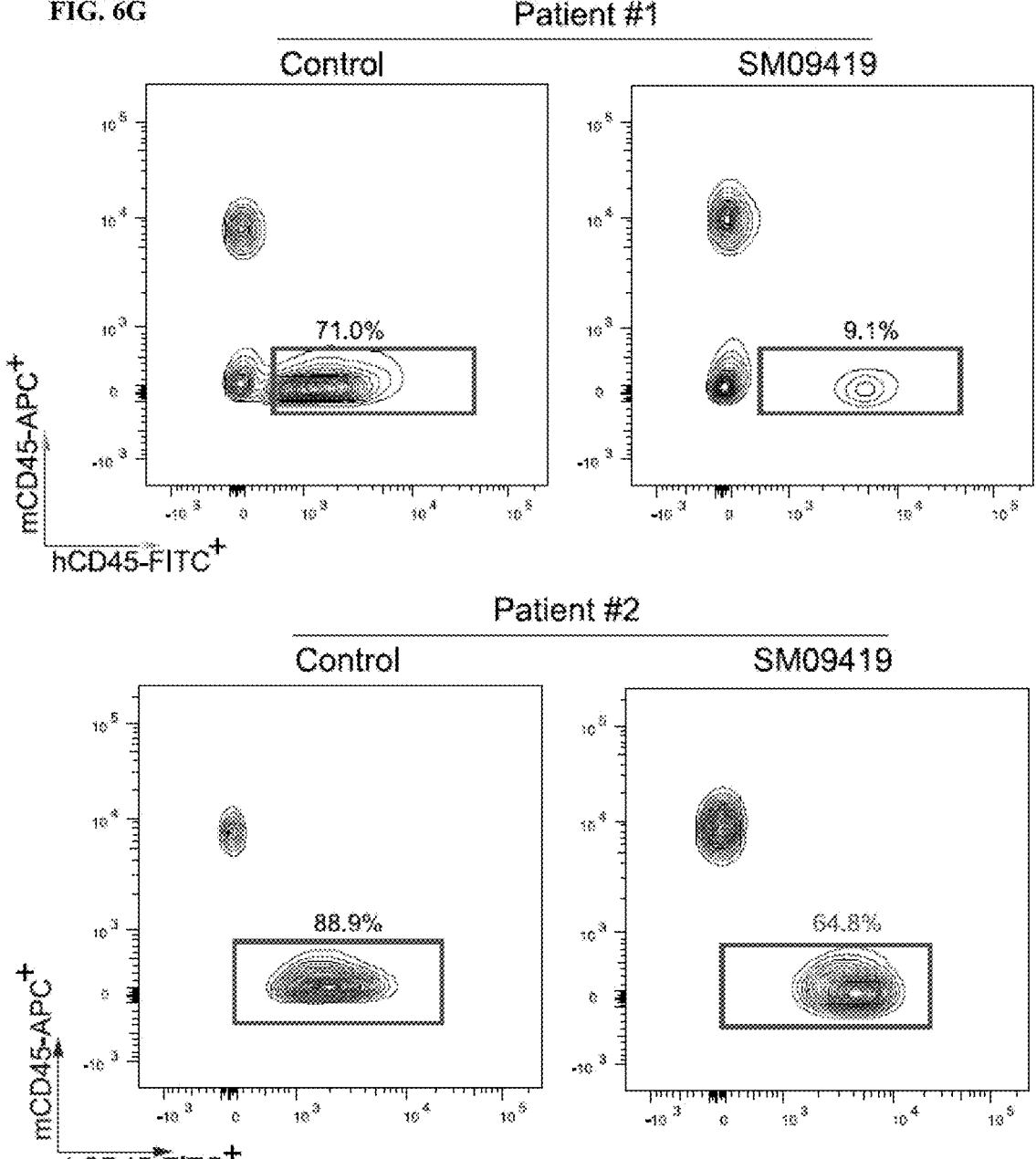
Figure 6H:
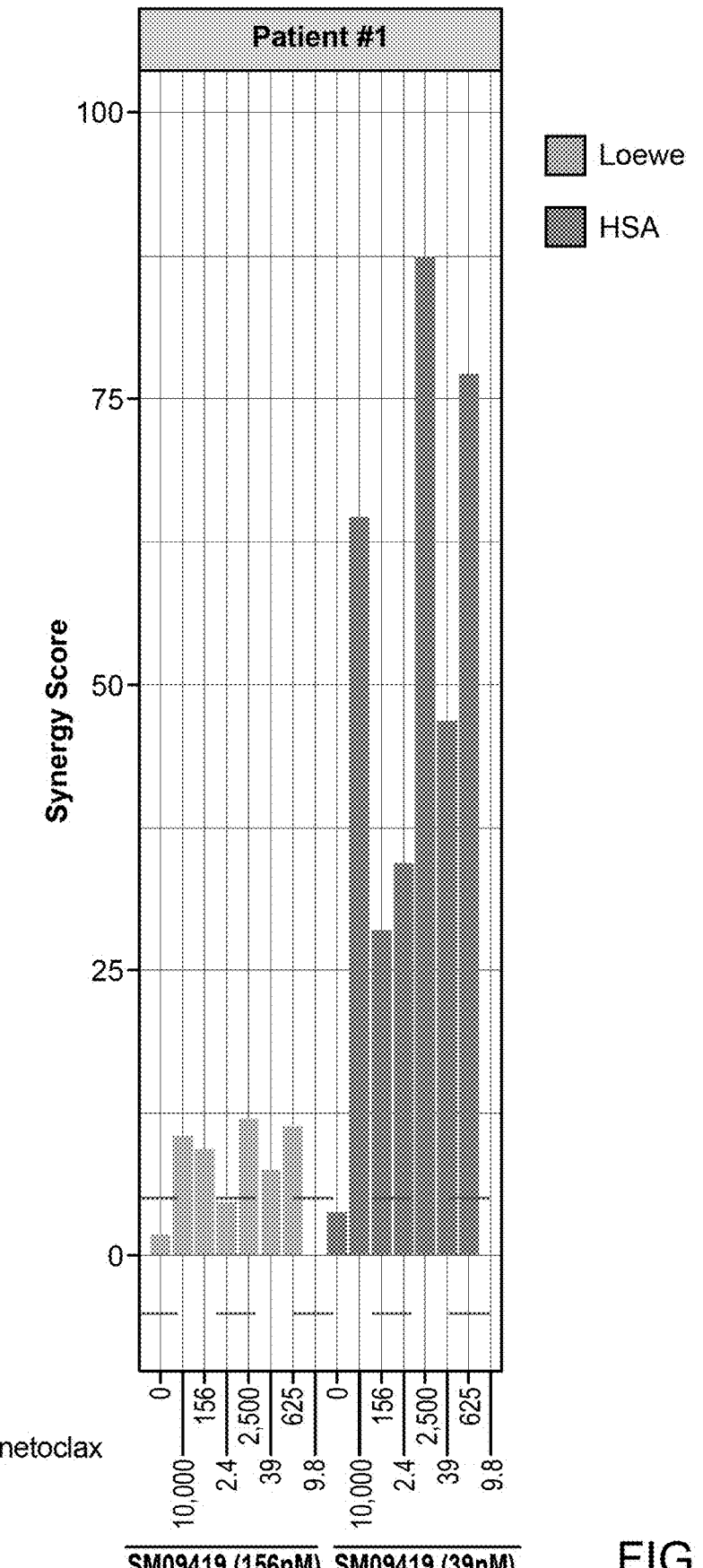
Figure 6H:
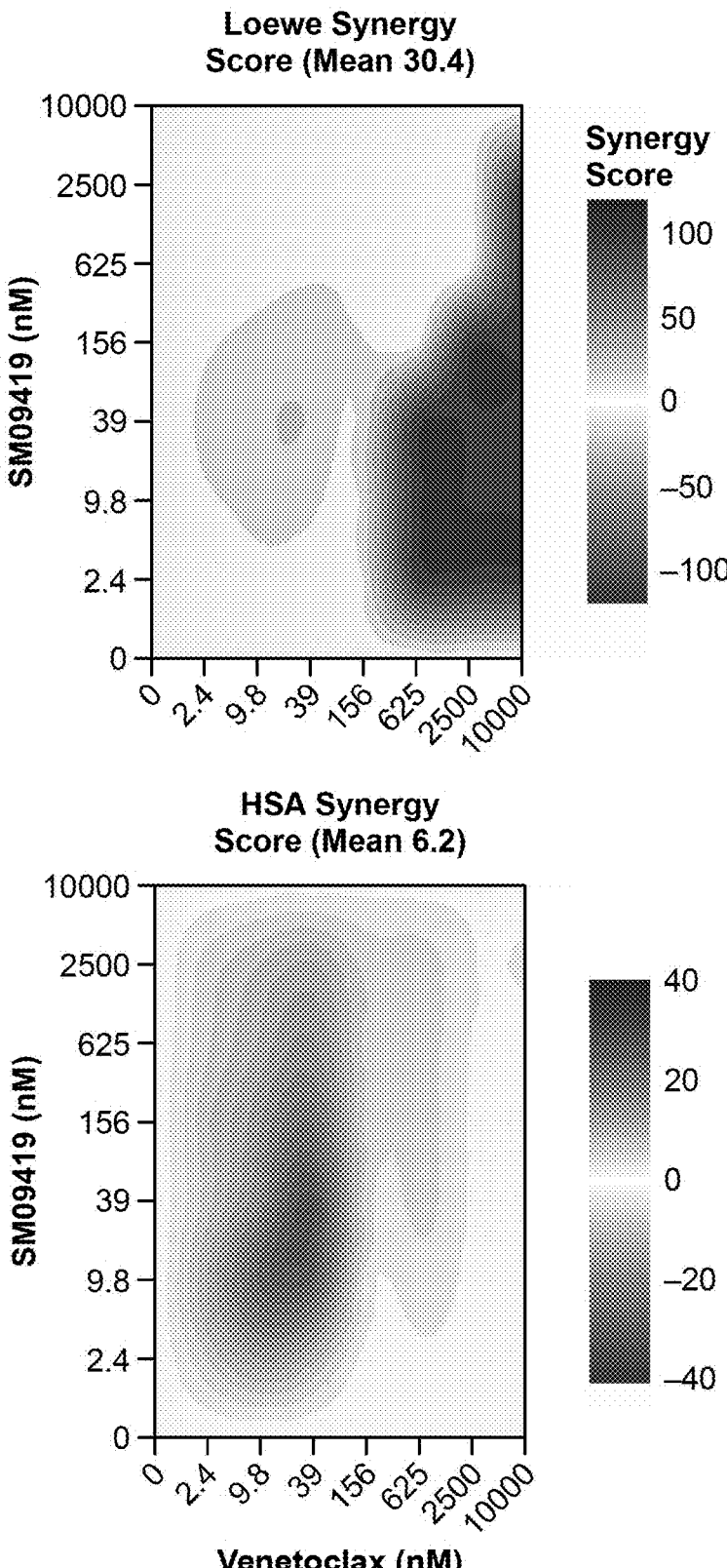
Figure 6I:
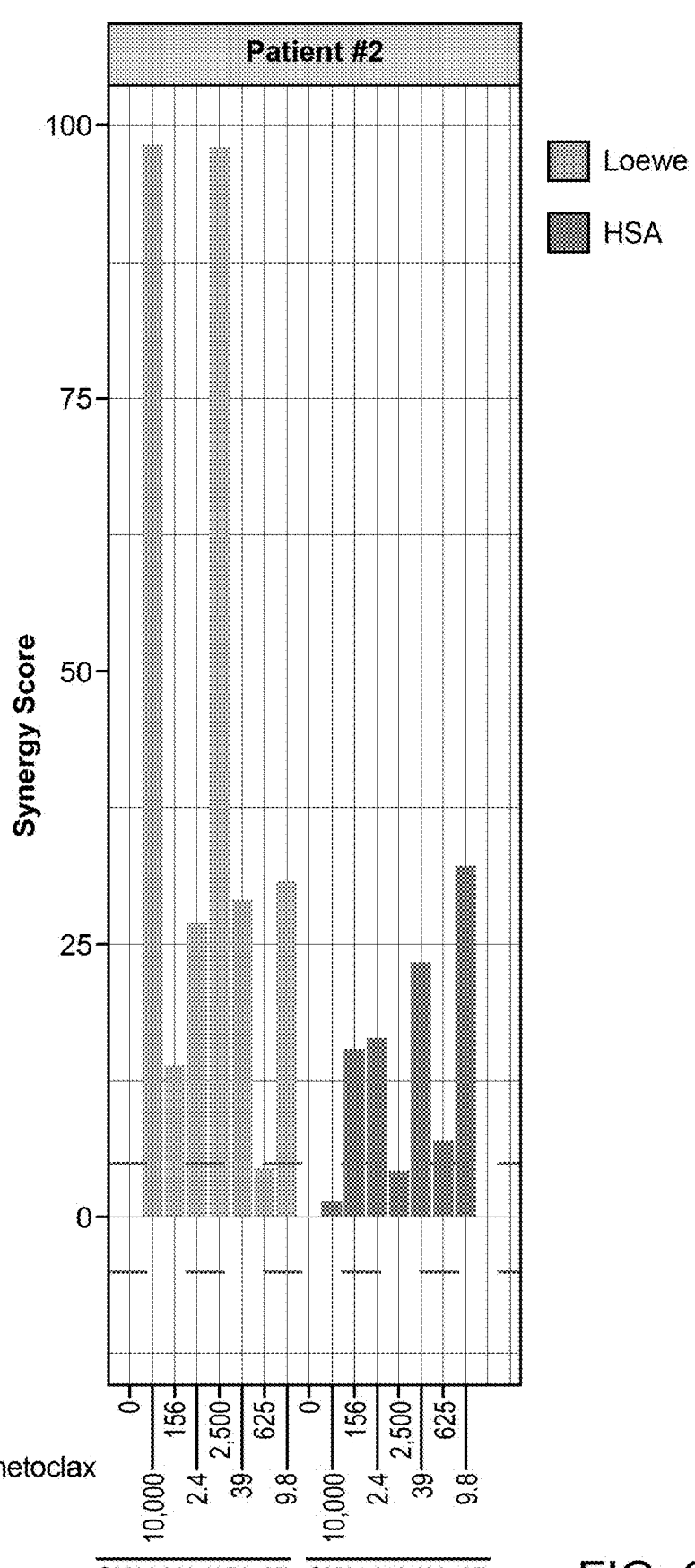
Figure 6I:
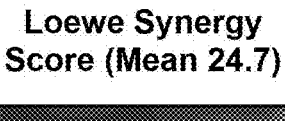
Figure 6I:
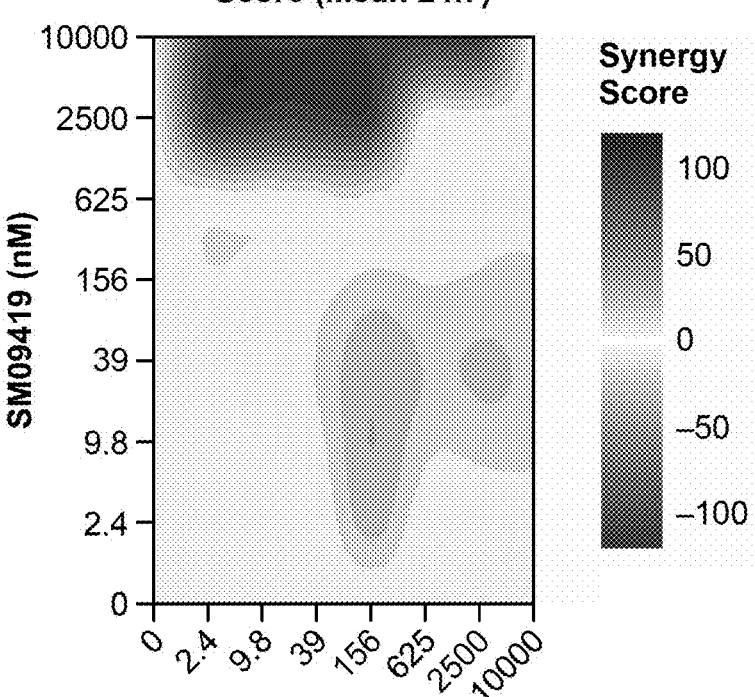
Figure 6I:
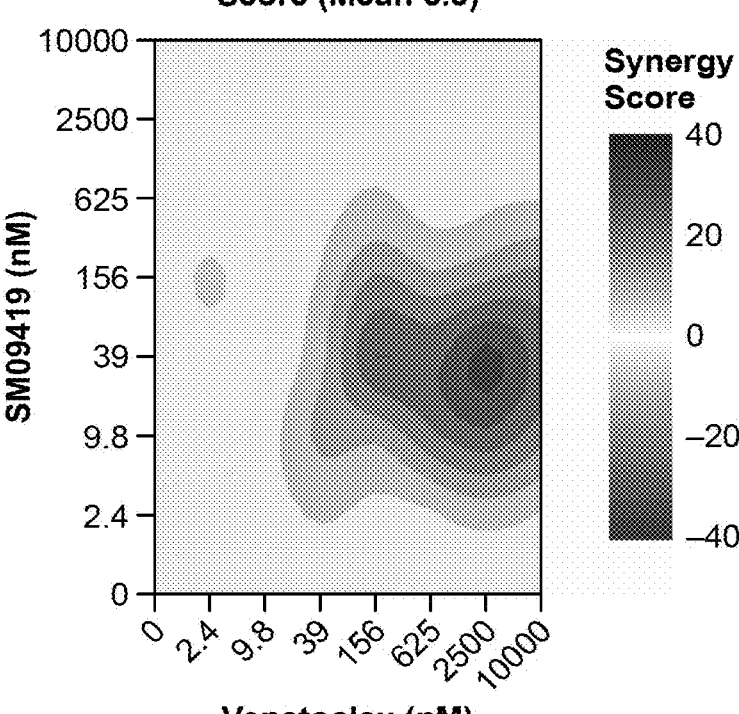

The efficacy of SM09419 across a spectrum of human AML cell lines was tested. SM09419 treatment resulted in broad anti-leukemic effects with potent inhibitory activity across AML subtypes, including cell lines that were highly resistant to venetoclax treatment (FIG. 6A). Based on these data, the ability of SM09419 to overcome venetoclax resistance was evaluated. Three independent venetoclax-resistant MOLM-13 cell lines following continuous exposure to venetoclax for 3 weeks were developed. Dose-response curves after drug selection confirmed that venetoclax-resistant cell lines displayed a high inhibitory effect concentration ($IC_{50}$>99 nM) approximately six times greater than parental cells ($IC_{50}$=~15 nM) (FIG. 6B). Whole-exome sequencing (WES) and targeted capture sequencing (MSKCC-IMPACT) did not reveal any known genomic alterations that may cause venetoclax resistance. SM09419 as single agent led to approximately equally potent inhibitory activity against venetoclax-resistant AML cells as parental, venetoclax sensitive cells (FIG. 6B). Moreover, addition of venetoclax and SM09419 led to synergistic effects in venetoclax-resistant MOLM-13 cells (FIG. 4I and FIG. 10D). Consistent with previous findings in MOLM-13 parental cells, downregulation of essential apoptotic proteins (XIAP, MCL-1), splicing factors (RBM5, U2AF2), and the tyrosine kinase FLT3 was observed in venetoclax-resistant MOLM-13 and KG-1a cells (FIG. 5H and FIG. 12E). These findings were further extended to patient-derived xenograft (PDX) models of AML from patients with de novo resistance to venetoclax combination regimens (5-azacytidine or low-dose cytarabine) (FIGS. 6C-6D). Following xenotransplantation from two individual venetoclax-resistant patients into NSGS mice, disease engraftment with >10% human $hCD45^+ hCD34^+ hCD38^+$ cells was detected and mice were exposed to SM09419 (25 mg/kg) or vehicle administered orally and daily for 3 weeks. SM09419 resulted in significant reduction of hCD45 AML cells in the peripheral blood and bone marrow of mice treated with SM09419 when compared to vehicle control (FIGS. 6D-6F). Moreover, ex vivo culturing of these AML patient samples demonstrated single-agent potency of SM09419 as well as synergistic effects when combined with venetoclax (FIGS. 6G-6H). Collectively, these findings demonstrate the in vivo efficacy of SM09419 to overcome resistance to venetoclax-based therapies.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

REFERENCES

1. Addin En.Reflist Ferrara, F., and Schiffer, C. A. (2013). Acute myeloid leukaemia in adults. Lancet 381, 484-495. 10.1016/S0140-6736(12)61727-9.

2. Short, N. J., Konopleva, M., Kadia, T. M., Borthakur, G., Ravandi, F., DiNardo, C. D., and Daver, N. (2020). Advances in the Treatment of Acute Myeloid Leukemia: New Drugs and New Challenges. Cancer Discov 10, 506-525. 10.1158/2159-8290.CD-19-1011.

3. Ganzel, C., Sun, Z., Cripe, L. D., Fernandez, H. F., Douer, D., Rowe, J. M., Paietta, E. M., Ketterling, R., O'Connell, M. J., Wiernik, P. H., et al. (2018). Very poor long-term survival in past and more recent studies for relapsed AML patients: The ECOG-ACRIN experience. Am J Hematol 93, 1074-1081. 10.1002/ajh.25162.

4. Breems, D. A., Van Putten, W. L., Huijgens, P. C., Ossenkoppele, G. J., Verhoef, G. E., Verdonck, L. F., Vellenga, E., De Greef, G. E., Jacky, E., Van der Lelie, J., et al. (2005). Prognostic index for adult patients with acute myeloid leukemia in first relapse. J Clin Oncol 23, 1969-1978. 10.1200/JCO.2005.06.027.

5. Nechiporuk, T., Kurtz, S. E., Nikolova, O., Liu, T., Jones, C. L., D'Alessandro, A., Culp-Hill, R., d'Almeida, A., Joshi, S. K., Rosenberg, M., et al. (2019). The TP53 Apoptotic Network Is a Primary Mediator of Resistance to BCL2 Inhibition in AML Cells. Cancer Discov 9, 910-925. 10.1158/2159-8290.CD-19-0125.

6. Zhang, H., Nakauchi, Y., Kohnke, T., Stafford, M., Bottomly, D., Thomas, R., Wilmot, B., McWeeney, S. K., Majeti, R., and Tyner, J. W. (2020). Integrated analysis of patient samples identifies biomarkers for venetoclax efficacy and combination strategies in acute myeloid leukemia. Nat Cancer 1, 826-839. 10.1038/s43018-020-0103-x.

7. Zuber, J., Radtke, I., Pardee, T. S., Zhao, Z., Rappaport, A. R., Luo, W., McCurrach, M. E., Yang, M. M., Dolan, M. E., Kogan, S. C., et al. (2009). Mouse models of human AML accurately predict chemotherapy response. Genes Dev 23, 877-889. 10.1101/gad.1771409.

8. Blombery, P., Lew, T. E., Dengler, M. A., Thompson, E. R., Lin, V. S., Chen, X., Nguyen, T., Panigrahi, A., Handunnetti, S. M., Carney, D. A., et al. (2022). Clonal hematopoiesis, myeloid disorders and BAX-mutated myelopoiesis in patients receiving venetoclax for CLL. Blood 139, 1198-1207. 10.1182/blood.2021012775.

9. Kandoth, C., McLellan, M. D., Vandin, F., Ye, K., Niu, B., Lu, C., Xie, M., Zhang, Q., McMichael, J. F., Wyczalkowski, M. A., et al. (2013). Mutational landscape and significance across 12 major cancer types. Nature 502, 333-339. 10.1038/nature12634.

10. Li, S., Garrett-Bakelman, F. E., Chung, S. S., Sanders, M. A., Hricik, T., Rapaport, F., Patel, J., Dillon, R., Vijay, P., Brown, A. L., et al. (2016). Distinct evolution and dynamics of epigenetic and genetic heterogeneity in acute myeloid leukemia. Nat Med 22, 792-799. 10.1038/nm.4125.

11. Fennell, K. A., Vassiliadis, D., Lam, E. Y. N., Martelotto, L. G., Balic, J. J., Hollizeck, S., Weber, T. S., Semple, T., Wang, Q., Miles, D. C., et al. (2021). Non-genetic determinants of malignant clonal fitness at single-cell resolution. Nature. 10.1038/s41586-021-04206-7.

12. Konopleva, M., Pollyea, D. A., Potluri, J., Chyla, B., Hogdal, L., Busman, T., McKeegan, E., Salem, A. H., Zhu, M., Ricker, J. L., et al. (2016). Efficacy and Biological Correlates of Response in a Phase II Study of Venetoclax Monotherapy in Patients with Acute Myelogenous Leukemia. Cancer Discov 6, 1106-1117. 10.1158/2159-8290.CD-16-0313.

13. Minn, A. J., Rudin, C. M., Boise, L. H., and Thompson, C. B. (1995). Expression of bcl-xL can confer a multidrug resistance phenotype. Blood 86, 1903-1910.

14. Jones, C. L., Stevens, B. M., Pollyea, D. A., Culp-Hill, R., Reisz, J. A., Nemkov, T., Gehrke, S., Gamboni, F., Krug, A., Winters, A., et al. (2020). Nicotinamide Metabolism Mediates Resistance to Venetoclax in Relapsed Acute Myeloid Leukemia Stem Cells. Cell Stem Cell 27, 748-764 e744. 10.1016/j.stem.2020.07.021.

15. Jones, C. L., Stevens, B. M., D'Alessandro, A., Reisz, J. A., Culp-Hill, R., Nemkov, T., Pei, S., Khan, N., Adane, B., Ye, H., et al. (2018). Inhibition of Amino Acid Metabolism Selectively Targets Human Leukemia Stem Cells. Cancer Cell 34, 724-740 e724. 10.1016/j.ccell.2018.10.005.

16. Chen, X., Glytsou, C., Zhou, H., Narang, S., Reyna, D. E., Lopez, A., Sakellaropoulos, T., Gong, Y., Kloetgen, A., Yap, Y. S., et al. (2019). Targeting Mitochondrial Structure Sensitizes Acute Myeloid Leukemia to Venetoclax Treatment. Cancer Discov 9, 890-909. 10.1158/2159-8290. CD-19-0117.

17. Fong, C. Y., Gilan, O., Lam, E. Y., Rubin, A. F., Ftouni, S., Tyler, D., Stanley, K., Sinha, D., Yeh, P., Morison, J., et al. (2015). BET inhibitor resistance emerges from leukaemia stem cells. Nature 525, 538-542. 10.1038/nature14888.

18. Rathert, P., Roth, M., Neumann, T., Muerdter, F., Roe, J. S., Muhar, M., Deswal, S., Cerny-Reiterer, S., Peter, B., Jude, J., et al. (2015). Transcriptional plasticity promotes primary and acquired resistance to BET inhibition. Nature 525, 543-547. 10.1038/nature14898.

19. Rini, B. I., Plimack, E. R., Stus, V., Gafanov, R., Hawkins, R., Nosov, D., Pouliot, F., Alekseev, B., Soulieres, D., Melichar, B., et al. (2019). Pembrolizumab plus Axitinib versus Sunitinib for Advanced Renal-Cell Carcinoma. N Engl J Med 380, 1116-1127. 10.1056/NEJMoa1816714.

20. Baselga, J., Cortes, J., Kim, S. B., Im, S. A., Hegg, R., Im, Y. H., Roman, L., Pedrini, J. L., Pienkowski, T., Knott, A., et al. (2012). Pertuzumab plus trastuzumab plus docetaxel for metastatic breast cancer. N Engl J Med 366, 109-119. 10.1056/NEJMoa1113216.

21. DiNardo, C. D., Pratz, K. W., Letai, A., Jonas, B. A., Wei, A. H., Thirman, M., Arellano, M., Frattini, M. G., Kantarjian, H., Popovic, R., et al. (2018). Safety and preliminary efficacy of venetoclax with decitabine or azacitidine in elderly patients with previously untreated acute myeloid leukaemia: a non-randomised, open-label, phase 1b study. Lancet Oncol 19, 216-228. 10.1016/S1470-2045(18)30010-X.

22. DiNardo, C. D., Jonas, B. A., Pullarkat, V., Thirman, M. J., Garcia, J. S., Wei, A. H., Konopleva, M., Dohner, H., Letai, A., Fenaux, P., et al. (2020). Azacitidine and Venetoclax in Previously Untreated Acute Myeloid Leukemia. N Engl J Med 383, 617-629. 10.1056/NEJMoa2012971.

23. Schwerk, C., and Schulze-Osthoff, K. (2005). Regulation of apoptosis by alternative pre-mRNA splicing. Mol Cell 19, 1-13. 10.1016/j.molcel.2005.05.026.

24. Sanson, K. R., Hanna, R. E., Hegde, M., Donovan, K. F., Strand, C., Sullender, M. E., Vaimberg, E. W., Goodale, A., Root, D. E., Piccioni, F., and Doench, J. G. (2018). Optimized libraries for CRISPR-Cas9 genetic screens with multiple modalities. Nat Commun 9, 5416. 10.1038/s41467-018-07901-8.

25. Gu, X., Tohme, R., Tomlinson, B., Sakre, N., Hasipek, M., Durkin, L., Schuerger, C., Grabowski, D., Zidan, A. M., Radivoyevitch, T., et al. (2021). Decitabine- and 5-azacytidine resistance emerges from adaptive responses of the pyrimidine metabolism network. Leukemia 35, 1023-1036. 10.1038/s41375-020-1003-x.

26. Sripayap, P., Nagai, T., Uesawa, M., Kobayashi, H., Tsukahara, T., Ohmine, K., Muroi, K., and Ozawa, K. (2014). Mechanisms of resistance to azacitidine in human leukemia cell lines. Exp Hematol 42, 294-306 e292. 10.1016/j.exphem.2013.12.004.

27. Wang, E., Lu, S. X., Pastore, A., Chen, X., Imig, J., Chun-Wei Lee, S., Hockemeyer, K., Ghebrechristos, Y. E., Yoshimi, A., Inoue, D., et al. (2019). Targeting an RNA-Binding Protein Network in Acute Myeloid Leukemia. Cancer Cell 35, 369-384 e367. 10.1016/j.cell.2019.01.010.

28. Zhou, Y., Han, C., Wang, E., Lorch, A. H., Serafin, V., Cho, B. K., Guttierrez Diaz, B. T., Calvo, J., Fang, C., Khodadadi-Jamayran, A., et al. (2020). Posttranslational regulation of the exon skipping machinery controls aberrant splicing in leukemia. Cancer Discov. 10.1158/2159-8290. CD-19-1436.

29. Wang, E., Zhou, H., Nadorp, B., Cayanan, G., Chen, X., Yeaton, A. H., Nomikou, S., Witkowski, M. T., Narang, S., Kloetgen, A., et al. (2021). Surface antigen-guided CRISPR screens identify regulators of myeloid leukemia differentiation. Cell Stem Cell 28, 718-731 e716. 10.1016/j.stem.2020.12.005.

30. Witkowski, M. T., Lee, S., Wang, E., Lee, A. K., Talbot, A., Ma, C., Tsopoulidis, N., Brumbaugh, J., Zhao, Y., Roberts, K. G., et al. (2022). NUDT21 limits CD19 levels through alternative mRNA polyadenylation in B cell acute lymphoblastic leukemia. Nat Immunol. 10.1038/s41590-022-01314-y.

31. Han, C., Khodadadi-Jamayran, A., Lorch, A. H., Jin, Q., Serafin, V., Zhu, P., Politanska, Y., Sun, L., Gutierrez-Diaz, B. T., Pryzhkova, M. V., et al. (2022). SF3B1 homeostasis is critical for survival and therapeutic response in T cell leukemia. Sci Adv 8, eabj8357. 10.1126/sciadv.abj8357.

32. Lachowiez, C. A., Loghavi, S., Furudate, K., Montalban-Bravo, G., Maiti, A., Kadia, T., Daver, N., Borthakur, G., Pemmaraju, N., Sasaki, K., et al. (2021). Impact of splicing mutations in acute myeloid leukemia treated with hypomethylating agents combined with venetoclax. Blood Adv 5. 2173-2183. 10.1182/bloodadvances.2020004173.

33. Shi, J., Wang, E., Milazzo, J. P., Wang, Z., Kinney, J. B., and Vakoc, C. R. (2015). Discovery of cancer drug targets by CRISPR-Cas9 screening of protein domains. Nat Biotechnol 33, 661-667. 10.1038/nbt.3235.

34. Sugimoto, K., Toyoshima, H., Sakai, R., Miyagawa, K., Hagiwara, K., Ishikawa, F., Takaku, F., Yazaki, Y., and Hirai, H. (1992). Frequent mutations in the p53 gene in human myeloid leukemia cell lines. Blood 79, 2378-2383.

35. Hart, T., Chandrashekhar, M., Aregger, M., Steinhart, Z., Brown, K. R., MacLeod, G., Mis, M., Zimmermann, M., Fradet-Turcotte, A., Sun, S., et al. (2015). High-Resolution CRISPR Screens Reveal Fitness Genes and Genotype-Specific Cancer Liabilities. Cell 163, 1515-1526. 10.1016/j.cell.2015.11.015.

36. Collins, K. M., Kainov, Y. A., Christodolou, E., Ray, D., Morris, Q., Hughes, T., Taylor, I. A., Makeyev, E. V., and Ramos, A. (2017). An RRM-ZnF RNA recognition module targets RBM10 to exonic sequences to promote exon exclusion. Nucleic Acids Res 45, 6761-6774. 10.1093/nar/gkx225.

37. Van Nostrand, E. L., Pratt, G. A., Shishkin, A. A., Gelboin-Burkhart, C., Fang, M. Y., Sundararaman, B., Blue, S. M., Nguyen, T. B., Surka, C., Elkins, K., et al. (2016). Robust transcriptome-wide discovery of RNA-binding protein binding sites with enhanced CLIP (eCLIP). Nat Methods 13, 508-514. 10.1038/nmeth.3810.

38. Shiozaki, E. N., Chai, J., Rigotti, D. J., Riedl, S. J., Li, P., Srinivasula, S. M., Alnemri, E. S., Fairman, R., and Shi, Y. (2003). Mechanism of XIAP-mediated inhibition of caspase-9. Mol Cell 11, 519-527. 10.1016/s1097-2765 (03)00054-6.

39. Srinivasula, S. M., Hegde, R., Saleh, A., Datta, P., Shiozaki, E., Chai, J., Lee, R. A., Robbins, P. D., Fernandes-Alnemri, T., Shi, Y., and Alnemri, E. S. (2001). A conserved XIAP-interaction motif in caspase-9 and Smac/DIABLO regulates caspase activity and apoptosis. Nature 410, 112-116. 10.1038/35065125.

40. Huang, Y., Park, Y. C., Rich, R. L., Segal, D., Myszka, D. G., and Wu, H. (2001). Structural basis of caspase inhibition by XIAP: differential roles of the linker versus the BIR domain. Cell 104, 781-790.

41. Riedl, S. J., Renatus, M., Schwarzenbacher, R., Zhou, Q., Sun, C., Fesik, S. W., Liddington, R. C., and Salvesen, G. S. (2001). Structural basis for the inhibition of caspase-3 by XIAP. Cell 104, 791-800. 10.1016/s0092-8674(01)00274-4.

42. Hashimoto, M., Saito, Y., Nakagawa, R., Ogahara, I., Takagi, S., Takata, S., Amitani, H., Endo, M., Yuki, H., Ramilowski, J. A., et al. (2021). Combined inhibition of XIAP and BCL2 drives maximal therapeutic efficacy in genetically diverse aggressive acute myeloid leukemia. Nature Cancer 2, 340-356. 10.1038/s43018-021-00177-w.

43. Tyner, J. W., Tognon, C. E., Bottomly, D., Wilmot, B., Kurtz, S. E., Savage, S. L., Long, N., Schultz, A. R., Traer, E., Abel, M., et al. (2018). Functional genomic landscape of acute myeloid leukaemia. Nature 562, 526-531. 10.1038/s41586-018-0623-z.

44. Gui, J. F., Tronchere, H., Chandler, S. D., and Fu, X. D. (1994). Purification and characterization of a kinase specific for the serine- and arginine-rich pre-mRNA splicing factors. Proc Natl Acad Sci USA 91, 10824-10828. 10.1073/pnas.91.23.10824.

45. Aubol, B. E., Wu, G., Keshwani, M. M., Movassat, M., Fattet, L., Hertel, K. J., Fu, X. D., and Adams, J. A. (2016). Release of SR Proteins from CLK1 by SRPK1: A Symbiotic Kinase System for Phosphorylation Control of Pre-mRNA Splicing. Mol Cell 63, 218-228. 10.1016/j.molcel.2016.05.034.

46. Colwill, K., Feng, L. L., Yeakley, J. M., Gish, G. D., Caceres, J. F., Pawson, T., and Fu, X. D. (1996). SRPK1 and Clk/Sty protein kinases show distinct substrate specificities for serine/arginine-rich splicing factors. J Biol Chem 271, 24569-24575. 10.1074/jbc.271.40.24569.

47. Prasad, J., Colwill, K., Pawson, T., and Manley, J. L. (1999). The protein kinase Clk/Sty directly modulates SR protein activity: both hyper- and hypophosphorylation inhibit splicing. Mol Cell Biol 19, 6991-7000. 10.1128/MCB.19.10.6991.

48. Qian, W., Liang, H., Shi, J., Jin, N., Grundke-Iqbal, I., Iqbal, K., Gong, C. X., and Liu, F. (2011). Regulation of the alternative splicing of tau exon 10 by SC35 and Dyrk1A. Nucleic Acids Res 39, 6161-6171. 10.1093/nar/gkr195.

49. Shi, J., Zhang, T., Zhou, C., Chohan, M. O., Gu, X., Wegiel, J., Zhou, J., Hwang, Y. W., Iqbal, K., Grundke-Iqbal, I., et al. (2008). Increased dosage of Dyrk1A alters alternative splicing factor (ASF)-regulated alternative splicing of tau in Down syndrome. J Biol Chem 283, 28660-28669. 10.1074/jbc. M802645200.

50. de Graaf, K., Czajkowska, H., Rottmann, S., Packman, L. C., Lilischkis, R., Luscher, B., and Becker, W. (2006). The protein kinase DYRK1A phosphorylates the splicing factor SF3b1/SAP155 at Thr434, a novel in vivo phosphorylation site. BMC Biochem 7, 7. 10.1186/1471-2091-7-7.

51. Meyers, R. M., Bryan, J. G., McFarland, J. M., Weir, B. A., Sizemore, A. E., Xu, H., Dharia, N. V., Montgomery, P. G., Cowley, G. S., Pantel, S., et al. (2017). Computational correction of copy number effect improves specificity of CRISPR-Cas9 essentiality screens in cancer cells. Nat Genet 49, 1779-1784. 10.1038/ng.3984.

52. Duwel, M., Welteke, V., Oeckinghaus, A., Baens, M., Kloo, B., Ferch, U., Darnay, B. G., Ruland, J., Marynen, P., and Krappmann, D. (2009). A20 negatively regulates T cell receptor signaling to NF-kappaB by cleaving Malt1 ubiquitin chains. J Immunol 182, 7718-7728. 10.4049/jimmunol.0803313.

53. Zuber, J., Rappaport, A. R., Luo, W., Wang, E., Chen, C., Vaseva, A. V., Shi, J., Weissmueller, S., Fellmann, C., Taylor, M. J., et al. (2011). An integrated approach to dissecting oncogene addiction implicates a Myb-coordinated self-renewal program as essential for leukemia maintenance. Genes Dev 25, 1628-1640. 10.1101/gad.17269211.

54. Zuber, J., Shi, J., Wang, E., Rappaport, A. R., Herrmann, H., Sison, E. A., Magoon, D., Qi, J., Blatt, K., Wunderlich, M., et al. (2011). RNAi screen identifies Brd4 as a therapeutic target in acute myeloid leukaemia. Nature 478, 524-528. 10.1038/nature10334.

55. Sykes, D. B., Kfoury, Y. S., Mercier, F. E., Wawer, M. J., Law, J. M., Haynes, M. K., Lewis, T. A., Schajnovitz, A., Jain, E., Lee, D., et al. (2016). Inhibition of Dihydroorotate Dehydrogenase Overcomes Differentiation Blockade in Acute Myeloid Leukemia. Cell 167, 171-186 e115. 10.1016/j.cell.2016.08.057.

56. Kim, J., Woo, A. J., Chu, J., Snow, J. W., Fujiwara, Y., Kim, C. G., Cantor, A. B., and Orkin, S. H. (2010). A Myc network accounts for similarities between embryonic stem and cancer cell transcription programs. Cell 143, 313-324. 10.1016/j.cell.2010.09.010.

57. Somervaille, T. C., Matheny, C. J., Spencer, G. J., Iwasaki, M., Rinn, J. L., Witten, D. M., Chang, H. Y., Shurtleff, S. A., Downing, J. R., and Cleary, M. L. (2009). Hierarchical maintenance of MLL myeloid leukemia stem cells employs a transcriptional program shared with embryonic rather than adult stem cells. Cell Stem Cell 4, 129-140. 10.1016/j.stem.2008.11.015.

58. Aird, D., Teng, T., Huang, C. L., Pazolli, E., Banka, D., Cheung-Ong, K., Eifert, C., Furman, C., Wu, Z. J., Seiler, M., et al. (2019). Sensitivity to splicing modulation of BCL2 family genes defines cancer therapeutic strategies for splicing modulators. Nat Commun 10, 137. 10.1038/s41467-018-08150-5.

59. Ten Hacken, E., Valentin, R., Regis, F. F. D., Sun, J., Yin, S., Werner, L., Deng, J., Gruber, M., Wong, J., Zheng, M., et al. (2018). Splicing modulation sensitizes chronic lymphocytic leukemia cells to venetoclax by remodeling mitochondrial apoptotic dependencies. JCI Insight 3. 10.1172/jci.insight.121438.

60. Hong, D. S., Kurzrock, R., Naing, A., Wheler, J. J., Falchook, G. S., Schiffman, J. S., Faulkner, N., Pilat, M. J., O'Brien, J., and LoRusso, P. (2014). A phase I, open-label, single-arm, dose-escalation study of E7107, a precursor messenger ribonucleic acid (pre-mRNA) spliceosome inhibitor administered intravenously on days 1 and 8 every 21 days to patients with solid tumors. Invest New Drugs 32, 436-444. 10.1007/s10637-013-0046-5.

61. Eskens, F. A., Ramos, F. J., Burger, H., O'Brien, J. P., Piera, A., de Jonge, M. J., Mizui, Y., Wiemer, E. A., Carreras, M. J., Baselga, J., and Tabernero, J. (2013). Phase I pharmacokinetic and pharmacodynamic study of the first-in-class spliceosome inhibitor E7107 in patients with advanced solid tumors. Clin Cancer Res 19, 6296-6304. 10.1158/1078-0432. CCR-13-0485.

62. Seiler, M., Yoshimi, A., Darman, R., Chan, B., Keaney, G., Thomas, M., Agrawal, A. A., Caleb, B., Csibi, A., Sean, E., et al. (2018). H3B-8800, an orally available small-molecule splicing modulator, induces lethality in spliceosome-mutant cancers. Nat Med 24, 497-504. 10.1038/nm.4493.

63. Lindberg, M. F., and Meijer, L. (2021). Dual-Specificity, Tyrosine Phosphorylation-Regulated Kinases (DYRKs) and cdc2-Like Kinases (CLKs) in Human Disease, an Overview. Int J Mol Sci 22. 10.3390/ijms22116047.

64. Martin Moyano, P., Nemec, V., and Paruch, K. (2020). Cdc-Like Kinases (CLKs): Biology, Chemical Probes, and Therapeutic Potential. Int J Mol Sci 21. 10.3390/ijms21207549.

65. Alvarez, M., Estivill, X., and de la Luna, S. (2003). DYRK1A accumulates in splicing speckles through a novel targeting signal and induces speckle disassembly. J Cell Sci 116, 3099-3107. 10.1242/jcs.00618.

66. Aubol, B. E., Plocinik, R. M., Hagopian, J. C., Ma, C. T., McGlone, M. L., Bandyopadhyay, R., Fu, X. D., and Adams, J. A. (2013). Partitioning RS domain phosphorylation in an SR protein through the CLK and SRPK protein kinases. J Mol Biol 425, 2894-2909. 10.1016/j.jmb.2013.05.013.

67. Kamachi, M., Le, T. M., Kim, S. J., Geiger, M. E., Anderson, P., and Utz, P. J. (2002). Human autoimmune sera as molecular probes for the identification of an autoantigen kinase signaling pathway. J Exp Med 196, 1213-1225. 10.1084/jem.20021167.

68. Chalfant, C. E., Ogretmen, B., Galadari, S., Kroesen, B. J., Pettus, B. J., and Hannun, Y. A. (2001). FAS activation induces dephosphorylation of SR proteins; dependence on the de novo generation of ceramide and activation of protein phosphatase 1. J Biol Chem 276, 44848-44855. 10.1074/jbc. M106291200.

69. Tolcher, A., Babiker, H. M., Chung, V., Kim, E., Moser, J., Karim, R., Vandross, A., Sommerhalder, D., Scott, A. J., Fakih, M., et al. (2021). Abstract CT112: Initial results from a Phase 1 trial of a first-in-class pan-CDC-like kinase inhibitor (SM08502) with proof of mechanism in subjects with advanced solid tumors. Cancer Research 81, CT112-CT112. 10.1158/1538-7445. Am2021-ct112.

70. Scott, A., Call, J. A., Chandana, S., Borazanci, E., Falchook, G. S., Bordoni, R., Richey, S., Starodub, A., Chung, V., Lakhani, N. J., et al. (2022). 451O Preliminary evidence of clinical activity from phase I and Ib trials of the CLK/DYRK inhibitor cirtuvivint (CIRT) in subjects with advanced solid tumors. Annals of Oncology 33, S742-S743. 10.1016/j.annonc.2022.07.580.

71. Shimizu, T., Yonemori, K., Koyama, T., Katsuya, Y., Sato, J., Fukuhara, N., Yokoyama, H., Iida, H., Ando, K., Fukuhara, S., et al. (2022). A first-in-human phase I study of CTX-712 in patients with advanced, relapsed or refractory malignant tumors. Journal of Clinical Oncology 40, 3080-3080. 10.1200/JCO.2022.40.16_suppl.3080.

72. Wang, Y., Gogol-Doring, A., Hu, H., Frohler, S., Ma, Y., Jens, M., Maaskola, J., Murakawa, Y., Quedenau, C., Landthaler, M., et al. (2013). Integrative analysis revealed the molecular mechanism underlying RBM10-mediated splicing regulation. EMBO Mol Med 5, 1431-1442. 10.1002/emmm.201302663.

73. Witkiewicz, A. K., McMillan, E. A., Balaji, U., Baek, G., Lin, W. C., Mansour, J., Mollaee, M., Wagner, K. U., Koduru, P., Yopp, A., et al. (2015). Whole-exome sequencing of pancreatic cancer defines genetic diversity and therapeutic targets. Nat Commun 6, 6744. 10.1038/ncomms7744.

74. Cancer Genome Atlas Research, N. (2014). Comprehensive molecular profiling of lung adenocarcinoma. Nature 511, 543-550. 10.1038/nature 13385.

75. Giannakis, M., Mu, X. J., Shukla, S. A., Qian, Z. R., Cohen, O., Nishihara, R., Bahl, S., Cao, Y., Amin-Mansour, A., Yamauchi, M., et al. (2016). Genomic Correlates of Immune-Cell Infiltrates in Colorectal Carcinoma. Cell Rep 15, 857-865. 10.1016/j.celrep.2016.03.075.

76. Gripp, K. W., Hopkins, E., Johnston, J. J., Krause, C., Dobyns, W. B., and Biesecker, L. G. (2011). Long-term survival in TARP syndrome and confirmation of RBM10 as the disease-causing gene. Am J Med Genet A 155A, 2516-2520. 10.1002/ajmg.a.34190.

77. Bisaillon, R., Moison, C., Thiollier, C., Krosl, J., Bordeleau, M. E., Lehnertz, B., Lavallee, V. P., MacRae, T., Mayotte, N., Labelle, C., et al. (2020). Genetic characterization of ABT-199 sensitivity in human AML. Leukemia 34, 63-74. 10.1038/s41375-019-0485-x.

78. Obeng, E. A., Chappell, R. J., Seiler, M., Chen, M. C., Campagna, D. R., Schmidt, P. J., Schneider, R. K., Lord, A. M., Wang, L., Gambe, R. G., et al. (2016). Physiologic Expression of Sf3b1 (K700E) Causes Impaired Erythropoiesis, Aberrant Splicing, and Sensitivity to Therapeutic Spliceosome Modulation. Cancer Cell 30, 404-417. 10.1016/j.ccell.2016.08.006.

79. Lee, S. C., and Abdel-Wahab, O. (2016). Therapeutic targeting of splicing in cancer. Nat Med 22, 976-986. 10.1038/nm.4165.

80. Cheng, D. T., Mitchell, T. N., Zehir, A., Shah, R. H., Benayed, R., Syed, A., Chandramohan, R., Liu, Z. Y., Won, H. H., Scott, S. N., et al. (2015). Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology. J Mol Diagn 17, 251-264. 10.1016/j.jmoldx.2014.12.006.

81. Zehir, A., Benayed, R., Shah, R. H., Syed, A., Middha, S., Kim, H. R., Srinivasan, P., Gao, J., Chakravarty, D., Devlin, S. M., et al. (2017). Mutational landscape of metastatic cancer revealed from prospective clinical sequencing of 10,000 patients. Nat Med 23, 703-713. 10.1038/nm.4333.

82. Doench, J. G., Fusi, N., Sullender, M., Hegde, M., Vaimberg, E. W., Donovan, K. F., Smith, I., Tothova, Z., Wilen, C., Orchard, R., et al. (2016). Optimized sgRNA design to maximize activity and minimize off-target effects of CRISPR-Cas9. Nat Biotechnol 34, 184-191. 10.1038/nbt.3437.

83. Demidenko, E., and Miller, T. W. (2019). Statistical determination of synergy based on Bliss definition of drugs independence. PLOS One 14, e0224137. 10.1371/journal.pone.0224137.

84. Metz, K. S., Deoudes, E. M., Berginski, M. E., Jimenez-Ruiz, I., Aksoy, B. A., Hammerbacher, J., Gomez, S. M., and Phanstiel, D. H. (2018). Coral: Clear and Customizable Visualization of Human Kinome Data. Cell Syst 7, 347-350 e341. 10.1016/j.cels.2018.07.001.

85. Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21. 10.1093/bioinformatics/bts635.

86. Liao, Y., Smyth, G. K., and Shi, W. (2014). feature-Counts: an efficient general purpose program for assigning sequence reads to genomic features. Bioinformatics 30, 923-930.

87. Meyer, L. R., Zweig, A. S., Hinrichs, A. S., Karolchik, D., Kuhn, R. M., Wong, M., Sloan, C. A., Rosenbloom, K. R., Roe, G., Rhead, B., et al. (2013). The UCSC Genome Browser database: extensions and updates 2013. Nucleic Acids Res 41, D64-69. 10.1093/nar/gks1048.

88. Flicek, P., Ahmed, I., Amode, M. R., Barrell, D., Beal, K., Brent, S., Carvalho-Silva, D., Clapham, P., Coates, G., Fairley, S., et al. (2013). Ensembl 2013. Nucleic Acids Res 41, D48-55. 10.1093/nar/gks1236.

89. Katz, Y., Wang, E. T., Airoldi, E. M., and Burge, C. B. (2010). Analysis and design of RNA sequencing experiments for identifying isoform regulation. Nat Methods 7, 1009-1015. 10.1038/nmeth.1528.

90. Li, B., and Dewey, C. N. (2011). RSEM: accurate transcript quantification from RNA-Seq data with or without a reference genome. BMC Bioinformatics 12, 323. 10.1186/1471-2105-12-323.

91. Langmead, B., Trapnell, C., Pop, M., and Salzberg, S. L. (2009). Ultrafast and memory-efficient alignment of short DNA sequences to the human genome. Genome Biol 10, R25. 10.1186/gb-2009-10-3-r25.

92. Robinson, M. D., and Oshlack, A. (2010). A scaling normalization method for differential expression analysis of RNA-seq data. Genome Biol 11, R25. 10.1186/gb-2010-11-3-r25.

93. Trapnell, C., Pachter, L., and Salzberg, S. L. (2009). TopHat: discovering splice junctions with RNA-Seq. Bioinformatics 25, 1105-1111. 10.1093/bioinformatics/btp120.

94. Huber, W., Carey, V. J., Gentleman, R., Anders, S., Carlson, M., Carvalho, B. S., Bravo, H. C., Davis, S., Gatto, L., Girke, T., et al. (2015). Orchestrating high-throughput genomic analysis with Bioconductor. Nat Methods 12, 115-121. 10.1038/nmeth.3252.

95. Conway, J. R., Lex, A., and Gehlenborg, N. (2017). UpSetR: an R package for the visualization of intersecting sets and their properties. Bioinformatics 33, 2938-2940. 10.1093/bioinformatics/btx364.

96. Huppertz, I., Perez-Perri, J. I., Mantas, P., Sekaran, T., Schwarzl, T., Russo, F., Ferring-Appel, D., Koskova, Z., Dimitrova-Paternoga, L., Kafkia, E., et al. (2022). Ribo-regulation of Enolase 1 activity controls glycolysis and embryonic stem cell differentiation. Mol Cell 82, 2666-2680 e2611. 10.1016/j.molcel.2022.05.019.

97. Lawrence, M., Huber, W., Pages, H., Aboyoun, P., Carlson, M., Gentleman, R., Morgan, M. T., and Carey, V. J. (2013). Software for computing and annotating genomic ranges. PLOS Comput Biol 9, e1003118. 10.1371/journal.pcbi.1003118.

98. Ignatiadis, N., Klaus, B., Zaugg, J. B., and Huber, W. (2016). Data-driven hypothesis weighting increases detection power in genome-scale multiple testing. Nat Methods 13, 577-580. 10.1038/nmeth.3885.

What is claimed is:

1. A method for treating leukemia in a subject in need thereof comprising administering to the subject a synergistically effective amount of a CLK/DYRK inhibitor and a BCL2 inhibitor, wherein the CLK/DYRK inhibitor is selected from cirtuvivint (SM08502) or SM09419, wherein the BCL2 inhibitor is selected from venetoclax (ABT-199), navitoclax (ABT-263), or obatoclax (GX15-070), wherein the CLK/DYRK inhibitor and the BCL2 inhibitor are administered simultaneously and orally.

2. A method for treating leukemia in a subject in need thereof comprising administering to the subject a synergistically effective amount of cirtuvivint (SM08502) and venetoclax, wherein cirtuvivint (SM08502) and venetoclax are administered simultaneously and orally.

3. A method for treating leukemia in a subject in need thereof comprising administering to the subject a synergistically effective amount of SM09419 and venetoclax, wherein SM09419 and venetoclax are administered simultaneously and orally.

4. The method of claim 1, wherein the subject is resistant to BCL2 inhibitor therapy.

5. The method of claim 2, wherein the subject is resistant to venetoclax therapy.

6. The method of claim 3, wherein the subject is resistant to venetoclax therapy.

7. The method of claim 1, wherein the subject is resistant to combination therapy with a BCL2 inhibitor and a pyrimidine analog.

8. The method of claim 2, wherein the subject is resistant to combination therapy with venetoclax and a pyrimidine analog.

9. The method of claim 3, wherein the subject is resistant to combination therapy with venetoclax and a pyrimidine analog.

10. The method of claim 7, wherein the pyrimidine analog is 5-azacytidine, cytarabine, 5-fluorouracil, floxuridine, capecitabine, decitabine, or gemcitabine.

11. The method of claim 8, wherein the pyrimidine analog is 5-azacytidine, cytarabine, 5-fluorouracil, floxuridine, capecitabine, decitabine, or gemcitabine.

12. The method of claim 9, wherein the pyrimidine analog is 5-azacytidine, cytarabine, 5-fluorouracil, floxuridine, capecitabine, decitabine, or gemcitabine.

13. The method of claim 1, wherein the subject harbors acquired mutations in BAX, PMAIP, or TP53.

14. The method of claim 2, wherein the subject harbors acquired mutations in BAX, PMAIP, or TP53.

15. The method of claim 3, wherein the subject harbors acquired mutations in BAX, PMAIP, or TP53.

16. The method of claim 1, wherein the leukemia is chronic lymphocytic leukemia (CLL) or acute myeloma leukemia (AML).

17. The method of claim 2, wherein the leukemia is chronic lymphocytic leukemia (CLL) or acute myeloma leukemia (AML).

18. The method of claim 3, wherein the leukemia is chronic lymphocytic leukemia (CLL) or acute myeloma leukemia (AML).

19. The method of claim 1, wherein the subject is a child or an adult.

* * * * *